(12) United States Patent
Hartmann et al.

(10) Patent No.: US 9,884,839 B2
(45) Date of Patent: Feb. 6, 2018

(54) INHIBITORS OF 17BETA-HYDROXYSTEROID DEHYDROGENASES TYPE 1 AND TYPE 2

(71) Applicant: ElexoPharm GmbH, Saarbruecken (DE)

(72) Inventors: Rolf Hartmann, Saarbruecken (DE); Martin Frotscher, Sulzbach (DE); Ahmed Saad Abdelsamie Ahmed, Bahteem (EG); Emmanuel Bey, Colmar (FR); Chris J. van Koppen, Kleve (DE); Sandrine Oberwinkler-Marchais, Marburg (DE); Carsten Börger, Saarbruecken (DE); Lorenz Siebenbürger, Saarbruecken (DE); Victor Hernández Olmos, Saarbruecken (DE)

(73) Assignee: ElexoPharm GmbH, Saarbruecken (DE)

( * ) Notice: Subject to any disclaimer, the term of this patent is extended or adjusted under 35 U.S.C. 154(b) by 0 days.

(21) Appl. No.: 15/109,271

(22) PCT Filed: Jan. 5, 2015

(86) PCT No.: PCT/EP2015/050062
§ 371 (c)(1),
(2) Date: Jun. 30, 2016

(87) PCT Pub. No.: WO2015/101670
PCT Pub. Date: Jul. 9, 2015

(65) Prior Publication Data
US 2016/0318895 A1  Nov. 3, 2016

(30) Foreign Application Priority Data

Jan. 3, 2014  (EP) .................................... 14150140

(51) Int. Cl.
C07D 333/22 (2006.01)
C07D 333/28 (2006.01)
C07D 409/04 (2006.01)
C07D 409/10 (2006.01)
C07D 409/12 (2006.01)

(52) U.S. Cl.
CPC ......... *C07D 333/22* (2013.01); *C07D 333/28* (2013.01); *C07D 409/04* (2013.01); *C07D 409/10* (2013.01); *C07D 409/12* (2013.01)

(58) Field of Classification Search
CPC .. C07D 333/22; C07D 333/28; C07D 409/04; C07D 409/10; C07D 409/12
USPC ..................................................... 514/231.5
See application file for complete search history.

(56) References Cited

U.S. PATENT DOCUMENTS

| | | | | |
|---|---|---|---|---|
| 4,197,309 | A * | 4/1980 | Thuillier .............. | C07D 333/22 514/438 |
| 5,817,691 | A | 10/1998 | Barnes et al. | |
| 8,609,622 | B2 * | 12/2013 | Yang ....................... | C07H 7/04 514/23 |
| 9,434,670 | B2 * | 9/2016 | Deliencourt-Godefroy .............. | C07C 43/225 |
| 2005/0038053 | A1 | 2/2005 | Hirvelae et al. | |
| 2005/0228038 | A1 | 10/2005 | Vander Jagt et al. | |

FOREIGN PATENT DOCUMENTS

| | | | |
|---|---|---|---|
| DE | 102007040243 A1 | 2/2009 | |
| EP | 0801058 A1 | 10/1997 | |
| WO | 2004110459 A1 | 12/2004 | |
| WO | 2005037845 A1 | 4/2005 | |
| WO | 2005123671 A1 | 12/2005 | |
| WO | 2006063615 A1 | 6/2006 | |
| WO | 2008116920 A2 | 10/2008 | |
| WO | 2009002746 A1 | 12/2008 | |
| WO | 2011079772 A1 | 7/2011 | |
| WO | 2012025638 A1 | 3/2012 | |
| WO | WO 2012025638 A1 * | 3/2012 | ........... C07D 277/24 |
| WO | 2012117097 A1 | 9/2012 | |

OTHER PUBLICATIONS

Allan et al., "Novel inhibitors of 17β-hydroxysteroid dehydrogenase type 1: Templates for design", Bioorg. Med. Chem., 2008, vol. 16, pp. 4438-4456.

Bagi et al., "Effect of 17β-hydroxysteroid dehydrogenase type 2 inhibitor on bone strength in ovariectomized cynomolgus monkeys", J. Musculoskelet. Neuronal Interact., 2008, vol. 8:3, pp. 267-280.

Berube et al., "Preparation of 16β-Estradiol Derivative Libraries as Bisubstrate Inhibitors of 17β-Hydroxysteroid Dehydrogenase Type 1 Using the Multidetachable Sulfamate Linker", Molecules, 2010, vol. 15, pp. 1590-1631.

Bey et al., "New Insights into the SAR and Binding Modes of Bis(hydroxyphenyl)thiophenes and -benzenes: Influence of Additional Substituents on 17β-Hydroxysteroid Dehydrogenase Type 1 (17β-HSD1) Inhibitory Activity and Selectivity", J. Med. Chem., 2009, vol. 52, pp. 6724-6743.

Bulun et al., "Role of aromatase in endometrial disease", J. Steroid Biochem. Mol. Biol., 2001, vol. 79, pp. 19-25.

(Continued)

*Primary Examiner* — Yevegeny Valenrod

(74) *Attorney, Agent, or Firm* — The Webb Law Firm

(57) ABSTRACT

Provided herein are non-steroidal 17beta-hydroxysteroid dehydrogenase type 1 and type 2 (17β-HSD1 and 17β-HSD2) inhibitors, their production and use, especially for the treatment and for prophylaxis of hormone-related diseases.

14 Claims, No Drawings

(56) References Cited

OTHER PUBLICATIONS

Bydal et al., "Steroidal lactones as inhibitors of 17β-hydroxysteroid dehydrogenase type 5: Chemical synthesis, enzyme inhibitory activity, and assessment of estrogenic and androgenic activities", Eur. J. Med. Chem., 2009, vol. 44, pp. 632-644.
Cook et al., "4,5-Disubstituted cis-pyrrolidinones as inhibitors of 17β-hydroxysteroid dehydrogenase II. Part 1: Synthetic approach", Tetrahedron Letters, 2005, vol. 46, pp. 1525-1528.
Elo et al., "Characterization of 17β-Hydroxysteroid Dehydrogenase Isoenzyme Expression in Benign and Malignant Human Prostate", Int. J. Cancer, 1996, vol. 66, pp. 37-41.
Fink et al., "Association of Testosterone and Estradiol Deficiency with Osteoporosis and Rapid Bone Loss in Older Men", J. Clin. Endocrinol. Metab., 2006, vol. 91:10, pp. 3908-3915.
Geisler et al., "Aromatase inhibitors as adjuvant treatment of breast cancer", Crit. Rev. Oncol. Hematol., 2006, vol. 57, pp. 53-61.
Gunn et al., "4,5-Disubstituted cis-pyrrolidinones as inhibitors of type II 17β-hydroxysteroid dehydrogenase. Part 2. SAR", Bioorg. Med. Chem. Lett., 2005, vol. 15, pp. 3053-3057.
Haller et al., "Molecular Framework of Steroid/Retinoid Discrimination in 17β-Hydroxysteroid Dehydrogenase Type 1 and Photoreceptor-associated Retinol Dehydrogenase", J. Mol. Biol., 2010, vol. 399, pp. 255-267.
Hanson et al., "Sulfatases: Structure, Mechanism, Biological Activity, Inhibition, and Synthetic Utility", Angew. Chem. Int. Ed., 2004, vol. 43, pp. 5736-5763.
Hughes et al., "1,25-Dihydroxyvitamin D3 Regulates Estrogen Metabolism in Cultured Keratinocytes", Endocrinology, 1997, vol. 138:9, pp. 3711-3718.
Labrie, "At the Cutting Edge Intracrinology", Mol. Cell. Endocrinol., 1991, vol. 78, pp. C113-C118.
Lawrence et al., "Novel and Potent 17β-Hydroxysteroid Dehydrogenase Type 1 Inhibitors", J. Med. Chem., 2005, vol. 48, pp. 2759-2762.
Lilienkampf et al., "Synthesis and Biological Evaluation of 17β-Hydroxysteroid Dehydrogenase Type 1 (17β-HSD1) Inhibitors Based on a Thieno[2,3-d]pyrimidin-4(3H)-one Core", J. Med. Chem., 2009, vol. 52, pp. 6660-6671.
Marhais-Oberwinkler et al., "Structural Optimization of 2,5-Thiophene Amides as Highly Potent and Selective 17β-Hydroxysteroid Dehydrogenase Type 2 Inhibitors for the Treatment of Osteoporosis", J. Med. Chem., 2013, vol. 56, pp. 167-181.
Marchais-Oberwinkler et al., "Substituted 6-Phenyl-2-naphthols. Potent and Selective Nonsteroidal Inhibitors of 17β-Hydroxysteroid Dehydrogenase Type 1 (17β-HSD1): Design, Synthesis, Biological Evaluation, and Pharmacokinetics", J. Med. Chem., 2008, vol. 51, pp. 4685-4698.
Messinger et al., "New inhibitors of 17β-hydroxysteroid dehydrogenase type 1", Mol. Cell. Endocrinol., 2006, vol. 248, pp. 192-198.
Miyoshi et al., "Involvement of Up-Regulation of 17β-Hydroxysteroid Dehydrogenase Type 1 in Maintenance of Intratumoral High Estradiol Levels in Postmenopausal Breast Cancers", Int. J. Cancer, 2001, vol. 94, pp. 685-689.
Oster et al., "Bicyclic Substituted Hydroxyphenylmethanones as Novel Inhibitors of 17β-Hydroxysteroid Dehydrogenase Type 1 (17β-HSD1) for the Treatment of Estrogen-Dependent Diseases", J. Med. Chem., 2010, vol. 53, pp. 8176-8186.
Oster et al., "Novel estrone mimetics with high 17β-HSD1 inhibitory activity", Bioorg. Med. Chem., 2010, vol. 18, pp. 3494-3505.
Pasqualini, "The selective estrogen enzyme modulators in breast cancer: a review", Biochim. Biophys. Acta, 2004, vol. 1654, pp. 123-143.
Perspicace et al., "Novel N-methylsulfonamide and retro-N-methylsulfonamide derivatives as 17β-hydroxysteroid dehydrogenase type 2 (17β-HSD2) inhibitors with good ADME-related physicochemical parameters", Eur. J. Med. Chem., 2013, vol. 69, pp. 201-215.
Perspicace et al., "Synthesis and Biological Evaluation of Thieno[3,2-d]-pyrimidinones, Thieno[3,2-d]pyrimidines and Quinazolinones: Conformationally Restricted 17β-Hydroxysteroid Dehydrogenase Type 2 (17β-HSD2) Inhibitors", Molecules, 2013, vol. 18, pp. 4487-4509.
Poirier et al., "Inhibitors of type II 17β-hydroxysteroid dehydrogenase", Mol. Cell, Endocrinol., 2001, vol. 171, pp. 119-128.
Saloniemi et al., "Novel Hydroxysteroid (17β) Dehydrogenase 1 Inhibitors Reverse Estrogen-Induced Endometrial Hyperplasia in Transgenic Mice", Am. J. Pathol., 2010, vol. 176:3, pp. 1443-1451.
Sam et al., "Steroidal Spiro-γ-lactones That Inhibit 17β-Hydroxysteroid Dehydrogenase Activity in Human Placental Microsomes", J. Med. Chem., 1995, vol. 38, pp. 4518-4528.
Santner et al., "In Situ Estrogen Production via the Estrone Sulfatase Pathway in Breast Tumors: Relative Importance versus the Aromatase Pathway", J. Clin. Endocrinol. Metab., 1984, vol. 59:1, pp. 29-33.
Schuster et al., "Discovery of Nonsteroidal 17β-Hydroxysteroid Dehydrogenase 1 Inhibitors by Pharmacophore-Based Screening of Virtual Compound Libraries", J. Med. Chem., 2008, vol. 51, pp. 4188-4199.
Starcevic et al., "Synthesis and Biological Evaluation of (6- and 7-Phenyl) Coumarin Derivatives as Selective Nonsteroidal Inhibitors of 17β-Hydroxysteroid Dehydrogenase Type 1", J. Med. Chem., 2011, vol. 54, pp. 248-261.
Takayama et al., "Pyrrole derivatives as potent inhibitors of lymphocyte-specific kinase: Struture, synthesis, and SAR", Bioorg. Med. Chem. Lett., 2010, vol. 20, pp. 108-111.
Thakar et al., "Synthesis and Antifungal Activity of 3-Furyl and 3-Thienyl-substituted-1,2-benzisoxazoles", J. Indian Chem. Soc., 1984, vol. LXI, pp. 715-716.
Vihko et al., "Structure and function of 17β-hydroxysteroid dehydrogenase type 1 and type 2", Mol. Cell. Endocrinol., 2001, vol. 171, pp. 71-76.
Wetzel et al., "Introduction of an Electron Withdrawing Group on the Hydroxyphenylnaphthol Scaffold Improves the Potency of 17β-Hydroxysteroid Dehydrogenase Type 2 (17β-HSD2) Inhibitors", J. Med. Chem., 2011, vol. 54, pp. 7547-7557.
Wetzel et al., "17β-HSD2 inhibitors for the treatment of osteoporosis: Identification of a promising scaffold", Bioorg. Med. Chem., 2011, vol. 19, pp. 807-815.
Wood et al., "4,5-Disubstituted cis-pyrrolidinones as inhibitors of type II 17β-hydroxysteroid dehydrogenase. Part 3. Identification of lead candidate", Bioorg. Med. Chem. Lett., 2006, vol. 16, pp. 4965-4968.
Xie et al., "Identification of small-molecule inhibitors of the Aβ-ABAD interaction", Bioorg. Med. Chem. Lett., 2006, vol. 16, pp. 4657-4660.
Xu et al., "Triazole ring-opening leads to the discovery of potent nonsteroidal 17β-hydroxysteroid dehydrogenase type 2 inhibitors", Eur. J. Med. Chem., 2011, vol. 46, pp. 5978-5990.

* cited by examiner

INHIBITORS OF 17BETA-HYDROXYSTEROID DEHYDROGENASES TYPE 1 AND TYPE 2

CROSS-REFERENCE TO RELATED APPLICATIONS

This application is the United States national phase of International Application No. PCT/EP2015/050062 filed Jan. 5, 2015, and claims priority to European Patent Application No. 14150140.3 filed Jan. 3, 2014, the disclosures of which are hereby incorporated in their entirety by reference.

The invention relates to non-steroidal 17beta-hydroxysteroid dehydrogenase type 1 and type 2 (17β-HSD1 and 17β-HSD2) inhibitors, their production and use, especially for the treatment and for prophylaxis of hormone-related diseases.

BACKGROUND OF THE INVENTION

General Aspects and Inhibition of 17β-HSD1: Steroid hormones are important chemical carriers of information serving for the longterm and global control of cellular functions. They control the growth and the differentiation and function of many organs. On the other hand, they may also have negative effects and favor the pathogenesis and proliferation of diseases in the organism, such as mammary and prostate cancers (Deroo, B J. et al., J. Clin. Invest., 116: 561-570 (2006); Fernandez, S. V. et al., Int. J. Cancer, 118: 1862-1868 (2006)).

The biosynthesis of steroids takes place in the testes or ovaries, where sex hormones are produced. In addition, the production of glucocorticoids and mineral corticoids takes place in the adrenal glands. Moreover, individual synthetic steps also occur outside the glands, namely in the brain or in the peripheral tissue, e.g., adipose tissue (Bulun, S. E. et al., J. Steroid Biochem. Mol. Biol., 79: 19-25 (2001); Gangloff, A. et al., Biochem. J., 356: 269-276 (2001)). In this context, Labrie coined the term "intracrinology" in 1988 (Labrie, C. et al., Endocrinology, 123: 1412-1417 (1988); Labrie, F. et al., Ann. Endocrinol. (Paris), 56: 23-29 (1995); Labrie, F. et al., Horm. Res., 54: 218-229 (2000)). Attention was thus focused on the synthesis of steroids that are formed locally in peripheral tissues and also display their action there without getting into the blood circulation. The intensity of the activity of the hormones is modulated in the target tissue by means of various enzymes.

Thus, it could be shown that the 17β-hydroxysteroid dehydrogenase type 1 (17β-HSD1), which catalyzes the conversion of estrone (E1) to estradiol (E2), is more abundant in endometriotic tissue and breast cancer cells while there is a deficiency in 17β-HSD type 2, which catalyzes the reverse reaction (Bulun, S. E. et al., J. Steroid Biochem. Mol. Biol., 79: 19-25 (2001); Miyoshi, Y. et al., Int. J. Cancer, 94: 685-689 (2001)).

A major class of steroid hormones is formed by the estrogens, the female sex hormones, whose biosynthesis takes place mainly in the ovaries and reaches its maximum immediately before ovulation. However, estrogens also occur in the adipose tissue, muscles and some tumors. Their main functions include a genital activity, i.e., the development and maintenance of the female sexual characteristics as well as an extragenital lipid-anabolic activity leading to the development of subcutaneous adipose tissue. In addition, they are involved in the pathogenesis and proliferation of estrogen-related diseases, such as endometriosis, endometrial carcinoma, adenomyosis, breast cancer and endometrial hyperplasia (Bulun, S. E. et al., J. Steroid Biochem. Mol. Biol., 79: 19-25 (2001); Miyoshi, Y. et al., Int. J. Cancer, 94: 685-689 (2001); Gunnarsson, C. et al., Cancer Res., 61: 8448-8451 (2001); Kitawaki, J., Journal of Steroid Biochemistry & Molecular Biology, 83: 149-155 (2003); Vihko, P. et al., J. Steroid. Biochem. Mol. Biol., 83: 119-122 (2002); Vihko, P. et al., Mol. Cell. Endocrinol., 215: 83-88 (2004); Saloniemi T. et al., Am. J. Pathol. 176: 1443-1451 (2010)), ovarian cancer, prostate cancer (Elo et al J. Cancer 66: 37 (1996)), acne (Odlind et al., Clin. Endocrinol. 16: 243-249 (1982)), androgen-dependent hair loss and psoriasis (Hughes et al. Endocrinology 138: 3711 (1997)).

The most potent estrogen is E2, which is formed in premenopausal females, mainly in the ovaries. On an endocrine route, it arrives at the target tissues, where it displays its action by means of an interaction with the estrogen receptor (ER) α. After the menopause, the plasma E2 level decreases to 1/10 of the E2 level found in premenopausal females (Santner, S. J. et al., J. Clin. Endocrinol. Metab., 59: 29-33 (1984)). E2 is mainly produced in the peripheral tissue, e.g., breast tissue, endometrium, adipose tissue and skin, from inactive precursors, such as estrone sulfate -EI-S), dehydroepiandrosterone (DHEA) and DHEA-S. These reactions occur with the participation of various steroidogenic enzymes (hydroxysteroid dehydrogenases, aromatase), which are in part more abundantly produced in the peripheral tissue, where these active estrogens display their action. As a consequence of such intracrine mechanism for the formation of E2-, its concentration in the peripheral tissue, especially in estrogen-related diseases, is higher than that in the healthy tissue. Above all, the growth of many breast cancer cell lines is stimulated by a locally increased E2 concentration. Further, the occurrence and progress of diseases such as endometriosis, leiomyosis, adenomyosis, menorrhagia, metrorrhagia and dysmenorrhea is dependent on a significantly increased -E2 level in accordingly diseased tissue.

Endometriosis is an estrogen-related disease affecting about 5 to 10% of all females of childbearing age (Kitawaki, J., Journal of Steroid Biochemistry & Molecular Biology, 83: 149-155 (2003)). From 35 to 50% of the females suffering from abdominal pain and/or sterility show signs of endometriosis (Urdl, W., J. Reproduktionsmed. Endokrinol., 3: 24-30 (2006)). This disease is defined as a histologically detected ectopic endometrial glandular and stromal tissue. In correspondingly severe cases, this chronic disease, which tends to relapse, leads to pain of different intensities and variable character and possibly to sterility. Three macroscopic clinical pictures are distinguished: peritoneal endometriosis, retroperitoneal deep-infiltrating endometriosis including adenomyosis uteri, and cystic ovarial endometriosis. There are various explanatory theories for the pathogenesis of endometriosis, e.g., the metaplasia theory, the transplantation theory and the theory of autotraumatization of the uterus as established by Leyendecker (Leyendecker, G. et al., Hum. Reprod., 17: 2725-2736 (2002)).

According to the metaplasia theory (Meyer, R., Zentralbl. Gynakol., 43: 745-750 (1919); Nap, A. W. et al., Best Pract. Res. Clin. Obstet. Gynaecol., 18: 233-244 (2004)), pluripotent coelomic epithelium is supposed to have the ability to differentiate and form endometriotic foci even in adults under certain conditions. This theory is supported by the observation that endometrioses, in part severe ones, can occur in females with lacking uterus and gynastresy. Even in males who were treated with high estrogen doses due to a prostate carcinoma, an endometriosis could be detected in singular cases.

According to the theory postulated by Sampson (Halme, J. et al., Obstet. Gynecol., 64: 151-154 (1984); Sampson, J., Boston Med. Surg. J., 186: 445-473 (1922); Sampson, J., Am. J. Obstet. Gynecol., 14: 422-469 (1927)), retrograde menstruation results in the discharge of normal endometrial cells or fragments of the eutopic endometrium into the abdominal cavity with potential implantation of such cells in the peritoneal space and further development to form endometriotic foci. Retrograde menstruation could be detected as a physiological event. However, not all females with retrograde menstruation become ill with endometriosis, but various factors, such as cytokines, enzymes, growth factors (e.g., matrix metalloproteinases), play a critical role.

The enhanced autonomous non-cyclical estrogen production and activity as well as the reduced estrogen inactivation are typical peculiarities of endometriotic tissue. This enhanced local estrogen production and activity is caused by a significant overexpression of aromatase, expression of 17β-HSD1 and reduced inactivation of potent E2 due to a lack of 17β-HSD2, as compared to the normal endometrium (Bulun, S. E. et al., J. Steroid Biochem. Mol. Biol., 79: 19-25 (2001); Kitawaki, J., Journal of Steroid Biochemistry & Molecular Biology, 83: 149-155 (2003); Karaer, O. et al., Acta. Obstet. Gynecol. Scand., 83: 699-706 (2004); Zeitoun, K. et al., J. Clin. Endocrinol. Metab., 83: 4474-4480 (1998)).

The polymorphic symptoms caused by endometriosis include any pain symptoms in the minor pelvis, back pain, dyspareunia, dysuria and defecation complaints.

One of the therapeutic measures employed most frequently in endometriosis is the surgical removal of the endometriotic foci (Urdl, W., J. Reproduktionsmed. Endokrinol., 3: 24-30 (2006)). Despite new therapeutic concepts, medicamental treatment remains in need of improvement. The purely symptomatic treatment of dysmenorrhea is effected by means of non-steroidal anti-inflammatory drugs (NSAID), such as acetylsalicylic acid, indomethacine, ibuprofen and diclofenac. Since a COX2 overexpression could be observed both in malignant tumors and in the eutopic endometrium of females with endometriosis, a therapy with the selective COX2 inhibitors, such as celecoxib, suggests itself (Fagotti, A. et al., Hum. Reprod. 19: 393-397 (2004); Hayes, E. C. et al., Obstet. Gynecol. Surv., 57: 768-780 (2002)). Although they have a better gastro-intestinal side effect profile as compared to the NSAID, the risk of cardiovascular diseases, infarction and stroke is increases, especially for patients with a predamaged cardiovascular system (Dogne, J. M. et al., Curr. Pharm. Des., 12: 971-975 (2006)). The causal medicamental theory is based on estrogen deprivation with related variable side effects and a generally contraceptive character. The gestagens with their anti-estrogenic and antiproliferative effect on the endometrium have great therapeutic significance. The most frequently employed substances include medroxyprogesterone acetate, norethisterone, cyproterone acetate. The use of danazole is declining due to its androgenie side effect profile with potential gain of weight, hirsutism and acne. The treatment with GnRH analogues is of key importance in the treatment of endometriosis (Rice, V.; Ann. NY Acad. Sei., 955: 343-359 (2001)); however, the duration of the therapy should not exceed a period of 6 months since a longer term application is associated with irreversible damage and an increased risk of fracture. The side effect profile of the GnRH analogues includes hot flushes, amenorrhea, loss of libido and osteoporosis, the latter mainly within the scope of a long term treatment.

Another therapeutic approach involves the steroidal and non-steroidal aromatase inhibitors. It could be shown that the use of the non-steroidal aromatase inhibitor letrozole leads to a significant reduction of the frequency and severity of dysmenorrheal and dyspareunia and to a reduction of the endometriosis marker CA125 level (Soysal, S. et al., Hum. Reprod., 19: 160-167 (2004)). The side effect profile of aromatase inhibitors ranges from hot flushes, nausea, fatigue to osteoporosis and cardiac diseases. Long term effects cannot be excluded. All the possible therapies mentioned herein are also employed in the combatting of diseases such as leiomyosis, adenomyosis, menorrhagia, metrorrhagia and dysmenorrhea.

Every fourth cancer disease in the female population falls under the category of mammary cancers. This disease is the main cause of death in the western female population at the age of from 35 to 54 years (Nicholls, P. J., Pharm. J., 259: 459-470 (1997)). Many of these tumors exhibit an estrogen-dependent growth and are referred to as so-called HDSC (hormone dependent breast cancer). A distinction is made between ER+ and ER− tumors. The classification criteria are important to the choice of a suitable therapy. About 50% of the breast cancer cases in premenopausal females and 75% of the breast cancer cases in postmenopausal females are ER+ (Coulson, C., Steroid biosynthesis and action, $2^{nd}$ edition, 95-122 (1994); Lower, E. et al., Breast Cancer Res. Treat., 58: 205-211 (1999)), i.e., the growth of the tumor is promoted by as low as physiological concentrations of estrogens in the diseased tissue.

The therapy of choice at an early stage of breast cancer is surgical measures, if possible, breast-preserving surgery. Only in a minor number of cases, mastectomy is performed. In order to avoid relapses, the surgery is followed by radiotherapy, or else radiotherapy is performed first in order to reduce a larger tumor to an operable size. In an advanced state, or when metastases occur in the lymph nodes, skin or brain, the objective is no longer to heal the disease, but to achieve a palliative control thereof.

The therapy of the mammary carcinoma is dependent on the hormone receptor status of the tumor, on the patient's hormone status and on the status of the tumor (Paepke, S. et al., Onkologie, 26 Suppl., 7: 4-10 (2003)). Various therapeutical approaches are available, but all are based on hormone deprivation (deprivation of growth-promoting endogenous hormones) or hormone interference (supply of exogenous hormones). However, a precondition of such responsiveness is the endocrine sensitivity of the tumors, which exists with HDSC ER+ tumors. The drugs employed in endocrine therapy include GnRH analogues, anti-estrogens and aromatase inhibitors. GnRH analogues, such as gosereline, will bind to specific membrane receptors in the target organ, the pituitary gland, which results in an increased secretion of FSH and LH. These two hormones in turn lead to a reduction of GnRH receptors in a negative feedback loop in the pituitary cells. The resulting desensitization of the pituitary cells towards GnRH leads to an inhibition of FSH and LH secretion, so that the steroid hormone feedback loop is interrupted. The side effects of such therapeutic agents include hot flushes, sweats and osteoporosis.

Another therapeutic option is the use of anti-estrogens, antagonists at the estrogen receptor. Their activity is based on the ability to competitively bind to the ER and thus avoid the specific binding of the endogenous estrogen. Thus, the natural hormone is no longer able to promote tumor growth. Today, therapeutic use involves so-called SERM (selective estrogen receptor modulators), which develop estrogen agonism in tissues such as bones or liver, but have antagonistic andjor minimal agonistic effects in breast tissue or uterus (Holzgrabe, U., Pharm. Unserer Zeit, 33: 357-359 (2004); Pasqualini, J. R., Biochim. Biophys. Acta., 1654: 123-143 (2004); Sexton, M. J. et al., Prim Care Update Ob Gyns, 8: 25-30 (2001)). Thus, these compounds are not only effective in combatting breast cancer, but also increase the bone density and reduce the risk of osteoporosis in postmenopausal females. The use of the SERM tamoxifen is most widely spread. However, after about 12-18 months of treatment, there is development of resistance, an increased risk of endometrial cancers and thrombo-embolic diseases due to the partial agonistic activity at the ER (Goss, P. E. et al., Clin. Cancer Res., 10: 5717-5723 (2004); Nunez, N. P. et al., Clin. Cancer Res., 10: 5375-5380 (2004)).

The enzymatically catalyzed estrogen biosynthesis may also be influenced by selective enzyme inhibitors. The enzyme aromatase, which converts C19 steroids to C18 steroids, was one of the first targets for lowering the E2 level. This enzyme complex, which belongs to the cytochrome P-450 enzymes, catalyzes the aromaticzation of the androgenic A ring to form estrogens. The methyl group at position 10 of the steroid is thereby cleaved off. The first aromatase inhibitor employed for the therapy of breast cancer was aminoglutethimide. However, aminoglutethimide affects several enzymes of the cytochrome P-450 superfamily and thus inhibits a number of other biochemical conversions. For example, among others, the compound interferes with the steroid production of the adrenal glands so heavily that a substitution of both glucocorticoids and mineralocorticoids may be necessary. In the meantime, more potent and more selective aromatase inhibitors, which can be subdivided into steroidal and non-steroidal compounds, are on the market. The steroidal inhibitors include, for example, exemestane, which has a positive effect on the bone density, which is associated with its affinity for the androgen receptor (Goss, P. E. et al., Clin. Cancer Res., 10: 5717-5723 (2004)). However, this type of compounds is an irreversible inhibitor that also has a substantial number of side effects, such as hot flushes, nausea, fatigue. However, there are also non steroidal compounds that are employed therapeutically, for example, letrozole. The advantage of these compounds resides in the lesser side effects, they do not cause uterine hypertrophy, but have no positive effect on the bone density and result in an increase of LDL (low density lipoprotein), cholesterol and triglyceride levels (Goss, P. E. et al., Clin. Cancer Res., 10: 5717-5723 (2004); Nunez, N. P. et al., Clin. Cancer Res., 10: 5375-5380 (2004)). Today, aromatase inhibitors are predominantly employed as second-line therapeutic agents. In the meantime, however, the equivalence or even superiority of aromatase inhibitors to SERM, such as tamoxifene, has been proven in clinical studies (Geisler, J. et al., Crit. Rev. Oncol. Hematol., 57: 53-61 (2006); Howell, A. et al., Lancet, 365: 60-62 (2005)). Thus, the use of aromatase inhibitors also as first-line therapeutical agents is substantiated.

However, the estrogen biosynthesis in the peripheral tissue also includes other pathways for the production of E1 and the more potent E2 by avoiding the enzyme aromatase that is locally present in the target tissue, for example, breast tumors. Two pathways for the production of estrogens in breast cancer tissue are postulated (Pasqualini, J. R., Biochim. Biophys. Acta., 1654: 123-143 (2004)), the aromatase pathway (Abul-Hajj, Y J. et al., Steroids, 33: 205-222 (1979); Lipton, A. et al., Cancer, 59: 779-782 (1987)) and the sulfatase pathway (Perei, E. et al., J. Steroid. Biochem., 29: 393-399 (1988)). The aromatase pathway includes the production of estrogens from androgens with participation of the enzyme aromatase. The sulfatase pathway is the pathway for the production of E1/E2 by means of the enzyme steroid sulfatase, an enzyme that catalyzes the conversion of E1 sulfate and DHEA-S to estrone and DHEA. In this way, 10 times as much E1 is formed in the target tissue as compared to the aromatase pathway (Santner, S. J. et al., J. Clin. Endocrinol. Metab., 59: 29-33 (1984)). E1 is then reduced by means of the enzyme 17β-HSD1 to form E2, the most potent estrogen. Steroid sulfatase and 17β-HSD1 are new targets in the battle against estrogen-related diseases, especially for the development of therapeutic agents for mammary carcinomas (Pasqualini, J. R., Biochim. Biophys. Acta., 1654: 123-143 (2004)).

Numerous steroidal sulfatase inhibitors could be found, including the potent irreversible inhibitor EMATE, which exhibited an agonistic activity at the estrogen receptor, however (Ciobanu, L. C. et al., Cancer Res., 63: 6442-6446 (2003); Hanson, S. R. et al., Angew. Chem. Int. Ed. Engl., 43: 5736-5763 (2004)). Some potent non-steroidal sulfatase inhibitors could also be found, such as COUMATE and derivatives as weil as numerous sulfamate derivatives of tetrahydronaphthalene, indanone and tetralone (Hanson, S. R. et al., Angew. Chem. Int. Ed. Engl., 43: 5736-5763 (2004)). Recently, one sulfatase inhibitor has completed a phase I clinical trial in postmenopausal women with breast cancer (Foster, P. A. et al., Anticancer Agents Med Chem. 8(7):732-8 (2008).

The inhibition of 17β-HSD1, a key enzyme in the biosynthesis of E2, the most potent estrogen, could suggest itself as an option in the therapy of estrogen-related diseases in both premenopausal and postmenopausal females (Kitawaki, J., Journal of Steroid Biochemistry & Molecular Biology, 83: 149-155 (2003); Allan, G. M. et al., Mol. Cell Endocrinol., 248: 204-207 (2006); Penning, T. M., Endocr. Rev., 18: 281-305 (1997); Sawicki, M. W. et al., Proc. Natl. Acad. Sci. USA, 96: 840-845 (1999); Vihko, P. et al., Mol. Cell. Endocrinol., 171: 71-76 (2001)). An advantage of this approach is the fact that the intervention is effected in the last step of estrogen biosynthesis, i.e., the conversion of E1 to the highly potent E2 is inhibited. The intervention is effected in the biosynthetic step occurring in the peripheral tissue, so that a reduction of E2 production takes place locally in the diseased tissue. The use of correspondingly selective inhibitors would probably be associated with little side effects since the synthesis of other steroids would remain unaffected. To achieve a selective effect, it would be important that such inhibitors exhibit no or only very little agonistic activity at the ER, especially at the ER α, since agonistic binding is accompanied by an activation and thus proliferation and differentiation of the target cell. In contrast, an antagonistic activity of such compounds at the ER would be tolerated since the inhibitor would prevent the natural substrates from binding at the receptor which in turn will result in a further reduction of the proliferation of the target cells. The use of selective 17β-HSD1 inhibitors for the therapy of numerous estrogen-dependent diseases is discussed, for example, for breast cancer, tumors of the ovaries, prostate carcinoma, endometrial carcinoma, endometriosis, adenomyosis, endometrial hyperplasia, acne, psoriasis, and androgen-dependent hair loss. Highly interesting and completely novel is the proposal to employ selective inhibitors of 17β-HSD1 for prevention when there is a genetic disposition for breast cancer (Miettinen, M. et al., J. Mammary Gland. Biol. Neoplasia, 5: 259-270 (2000)).

Hydroxysteroid dehydrogenases (HSD) can be subdivided into different classes. The 11β-HSD modulate the activity of glucocorticoids, 3β-HSD catalyzes the reaction of Δ5-3β-hydroxysteroids (DHEA or 5-androstene-3β,17β- diol) to form Δ5-3β-ketosteroids (androstenedione or testosterone). 17β-HSDs convert the less active 17-ketosteroids to the corresponding highly active 17-hydroxy compounds (androstenedione to testosterone and E1 to E2) or conversely (Payne, A. H. et al., Endocr. Rev., 25: 947-970 (2004); Peltoketo, H. et al., J. Mol. Endocrinol., 23: 1-11 (1999); Suzuki, T. et al., Endocr. Relat. Cancer, 12: 701-720 (2005)). Thus, the HSD play a critical role in both the activation and the inactivation of steroid hormones. Depending on the cell's need for steroid hormones, they alter the potency of the sex hormones (Penning, T. M., Endocr. Rev., 18: 281-305 (1997)), for example, Ei is converted to the highly potent E2 by means of 17β-HSD1, while E2 is converted to the less potent E1 by means of 17β-HSD2; 17β-HSD2 inactivates E2 while 17β-HSD1 activates E1.

To date, fourteen different mammalian 17β-HSDs have been identified (Haller, F. et al., J. Mol. Biol. doi: 10.1016jj.jmb.2010.04.002 (2010); Zhongyi, S. et al., Endocrinology 148 3827-3836 (2007); Miyoshi, T. et al., Int. J. Cancer 94 (2001) 685-689), and twelve of these enzymes could be cloned (Suzuki, T. et al., Endocr. Relat. Cancer, 12: 701-720 (2005)). They all belong to the so-called short chain dehydrogenasejreductase (SDR) family, with the exception of 17β-HSD5, which is a ketoreductase. The amino acid identity between the different 17β-HSDs is as low as 20-30% (Luu-The, V., J. Steroid Biochem. Mol. Biol., 76: 143-151 (2001)), and they are membrane-bound or soluble enzymes. The X-ray structure of 6 human subtypes is known (Ghosh, D. et al., Structure, 3: 503-513 (1995); Kissinger, C. R. et al., J. Mol. Biol., 342: 943-952 (2004); Zhou, M. et al., Acta Crystallogr. D. Biol. Crystallogr., 58: 1048-1050 (2002). The 17β-HSDs are NAD(H)-dependent and NADP(H)-dependent enzymes. They play a critical role in the hormonal regulation in humans. The enzymes are distinguished by their tissue distribution, catalytic preference (oxidation or reduction), substrate specificity and subcellular localization. The same HSD subtype was found in different tissues. It is likely that all 17β-HSDs are expressed in the different estrogen-dependent tissues, but in different concentrations. In diseased tissue, the ratio between the different subtypes is altered as compared to healthy tissue, some subtypes being overexpressed while others may be absent. This may cause an increase or decrease of the concentration of the corresponding steroid. Thus, the 17β-HSDs play an extremely important role in the regulation of the activity of the sex hormones. Further, they are involved in the development of estrogen-sensitive diseases, such as breast cancer, ovarian, uterine and endometrial carcinomas, weil as androgenrelated diseases, such as prostate carcinoma, benign prostate hyperplasia, acne, hirsutism etc. It has been shown that some 17β-HSDs are also involved in the development of further diseases, e.g., pseudohermaphrodism (17β-HSD3 (Geissler, W. M. et al., Nat. Genet., 7: 34-39 (1994))), bifunctional enzyme deficiency (17β-HSD4 (van Grunsven, E. G. et al., Proc. Natl. Acad. Sci. USA, 95: 2128-2133 (1998))), polycystic kidney diseases (17β-HSD8 (Maxwell, M. M. et al., J. Biol. Chem., 270: 25213-25219 (1995))) and Alzheimer's (17β-HSD10 (Kissinger, C. R. et al., J. Mol. Biol., 342: 943-952 (2004); He, X. Y. et al., J. Biol. Chem., 274: 15014-15019 (1999); He, X. Y. et al., Mol. Cell Endocrinol., 229: 111-117 (2005); He, X. Y. et al., J. Steroid Biochem. Mol. Biol., 87: 191-198 (2003); Yan, S. D. et al., Nature, 389: 689-695 (1997))). The best characterized member of the 17β-HSDs is the type 1 17β-HSD. The 17β-HSD1 is an enzyme from the SDR family, also referred to as human placenta E2 dehydrogenase (Gangloff, A. et al., Biochem. J., 356 269-276 (2001); Jomvall, H. et al., Biochemistry, 34 6003-6013 (1995)). Its designation as assigned by the enzyme commission is E.C.1.1.1.62.

Engel et al. (Langer, L. J. et al., J. Biol. Chem., 233: 583-588 (1958)) were the first to describe this enzyme in the 1950's. In the 1990's, first crystallization attempts were made, so that a total of 20 crystallographic structures can be recurred to today in the development of inhibitors (Negri, M. et al. PLoS ONE 5(8): e12026. doi: 10.1371/journal-.pone.0012026 (2010)). Available are X-ray structures of the enzyme alone, but also of binary and ternary complexes of the enzyme with its substrate and other ligands or substrate/ligand and cofactor.

17β-HSD1 is a soluble cytosolic enzyme. NADPH serves as a cofactor. 17β-HSD1 is encoded by a 3.2 kb gene consisting of 6 exons and 5 introns that is converted to a 2.2 kb transcript (Luu-The, V., J. Steroid Biochem. Mol. Biol., 76: 143-151 (2001); Labrie, F. et al., J. Mol. Endocrinol., 25: 1-16 (2000)). It is constituted by 327 amino acids. The molecular weight of the monomer is 34.9 kDa (Penning, T. M., Endocr. Rev., 18: 281-305 (1997)). 17β-HSD1 is expressed in the placenta, liver, ovaries, endometrium, prostate gland, peripheral tissue, such as adipose tissue and breast cancer cells (Penning, T. M., Endocr. Rev., 18: 281-305 (1997)). It was isolated for the first time from human placenta (Jarabak, J. et al., J. Biol. Chem., 237: 345-357 (1962)). The main function of 17β-HSD1 is the conversion of the less active E1 to the highly potent E2. However, it also catalyzes to a lesser extent the reaction of dehydroepiandrosterone (DHEA) to 5-androstene-3β,17β-diol, an androgen showing estrogenic activity (Labrie, F., Mol. Cell. Endocrinol., 78: CI13-118 (1991); Poirier, D., Curr. Med. Chem., 10: 453-477 (2003); Poulin, R. et al., Cancer Res., 46: 4933-4937 (1986)). In vitro, the enzyme catalyzes the reduction and oxidation between E1 and E2 while it catalyzes only the reduction under physiological conditions. These bisubstrate reactions proceed according to a random catalytic mechanism, i.e., either the steroid or the cofactor is first to bind to the enzyme (Negri, et al. PLoS ONE 5(8): e12026. doi:10.1371/journal.pone.0012026 (2010)). The enzyme consists of a substrate binding site and a channel that opens into the cofactor binding site. The substrate binding site is a hydrophobie tunnel having a high complementarity to the steroid. The 3-hydroxy and 17-hydroxy groups in the steroid form four hydrogen bonds to the amino acid residues His221, Glu282, Ser142 and Tyr155. The hydrophobie van der Waals interactions seem to form the main interactions with the steroid while the hydrogen bonds are responsible for the specificity of the steroid for the enzyme (Labrie, F. et al., Steroids, 62: 148-158 (1997)). Like with all the other enzymes of this family, what is present as a cofactor binding site is the Rossmann fold, which is a region consisting of ex-helices and β-sheets (β-α-β-α-β)$_2$, a generally occurring motif Gly-Xaa-Xaa-Xaa-Gly-Xaa-Gly, and a nonsense region Tyr-Xaa-Xaa-Xaa-Lys within the active site. What is important to the activity is a catalytic tetrade consisting of Tyr155-Lys159-Ser142-Asn114, which stabilize the steroid and the ribose in the nicotinamide during the hydride transfer (Alho-Richmond, S. et al., Mol. Cell Endocrinol., 248: 208-213 (2006); Labrie, F. et al., Steroids, 62: 148-158 (1997); Nahoum, V. et al., Faseb. J., 17: 1334-1336 (2003)).

The gene encoding 17β-HSD1 is linked with the gene for mammary and ovarian carcinomas that is very susceptible to mutations and can be inherited, the BRCA1 gene, on chromosome 17q11-q21 (Labrie, F. et al., J. Mol. Endocrinol., 25: 1-16 (2000)). As has been demonstrated, the activity of 17β-HSD1 is higher in endometrial tissue and breast cancer cells as compared to healthy tissue, which entails high intracellular E2 levels, which in turn cause proliferation and differentiation of the diseased tissue (Bulun, S. E. et al., J.

Steroid Biochem. Mol. Biol., 79: 19-25 (2001); Miyoshi, Y. et al., Int. J. Cancer, 94: 685-689 (2001); Kitawaki, J., Journal of Steroid Biochemistry & Molecular Biology, 83: 149-155 (2003); Pasqualini, J. R., Biochim. Biophys. Acta., 1654: 123-143 (2004); Vihko, P. et al., Mol. Cell. Endocrinol., 171: 71-76 (2001); Miettinen, M. et al., Breast Cancer Res. Treat., 57: 175-182 (1999); Sasano, H. et al., J. Clin. Endocrinol. Metab., 81: 4042-4046 (1996); Yoshimura, N. et al., Breast Cancer Res., 6: R46-55 (2004)). An inhibition of 17β-HSD1 could result in the E2 level being lowered and thus lead to a regression of the estrogen-related diseases. Further, selective inhibitors of 17β-HSD1 could be used for prevention when there is a genetic disposition for breast cancer (Miettinen, M. et al., J. Mammary Gland. Biol. Neoplasia, 5: 259-270 (2000)).

Therefore, this enzyme would suggest itself as a target for the development of novel selective and non-steroidal inhibitors as therapeutic agents in the battle against estrogen-related diseases. Recently, in vivo efficacy of 17β-HSD1 inhibitors has been reported in two animal models. Immunodeficient mice were inoculated either with MCF-7 cells over-expressing human recombinant 17β-HSD1 enzyme (Husen, B. et al., Mol. Cell. Endocrinol., 248, 109-113 (2006); Husen, B. et al., Endocrinology, 147, 5333-5339 (2006)) or with T47D cells naturally expressing 17β-HSD1 (Day, J. M. et al.; Int. J. Cancer, 122, 1931-1940 (2008). In both models, the E1 induced tumor growth was reduced by 17β-HSD1 inhibitors, validating 17β-HSD1 as a novel target for the treatment of estrogen dependent diseases. Up to date however, no 17β-HSD1 inhibitor has entered clinical trials.

In the literature, only a few compounds have been described as inhibitors of 17βHSD1 (D. Poirier, Anticancer Agents Med. Chem. 9 642-660 (2009); Day, J. M. et al., Minerva Endocrinol., 35(2), 87-108 (2010); D. Poirier, Expert Opin Ther Pat., doi:10.1517/13543776.2010.505604 (2010)). Most inhibitors are steroidal compounds obtained by different variations of the estrogen skeleton (Rouillard, F. et al., Open Enzyme Inhib. J., 1 61-71 (2008); D. Poirier, Anticancer Agents Med. Chem. 9 642-660 (2009); Mazumdar M. et al.; Biochem J., 424(3):357-366 (2009); Möller G et al. Bioorg Med Chem Lett., 19(23): 6740-6744 (2009); Berube M. et al. Molecules 15 1590-1631 (2010)).

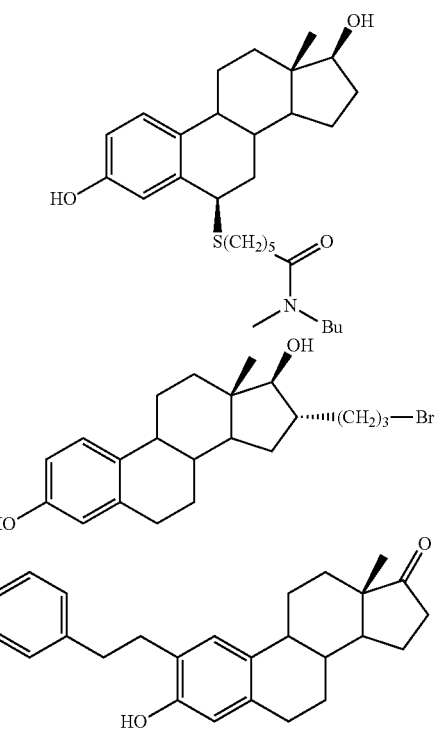

Another class of compounds which has been described is the so-called hybrid inhibitors (Berube, M. et al., Can. J. Chem. 87 1180-1199 (2009)), compounds that, due to their molecular structure, not only attack at the substrate binding site, but also undergo interactions with the cofactor binding site. The inhibitors have the following structure:
- adenosine moiety or simplified derivatives that can interact with the cofactor binding site;
- E2 or E1 moiety, which interacts with the substrate binding site; and
- a spacer of varying length as a linking element between the two moieties.

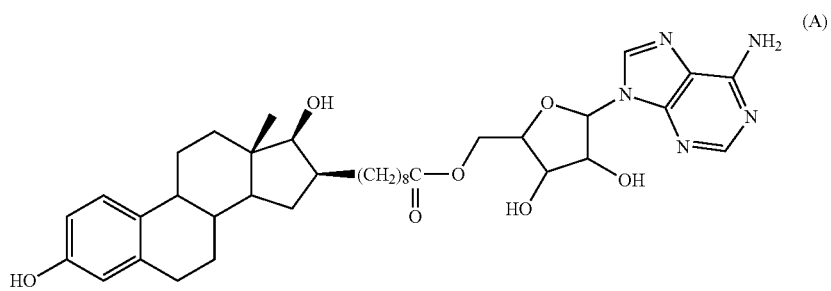

EM1745 Ki = 3.0 ± 0.8 nM

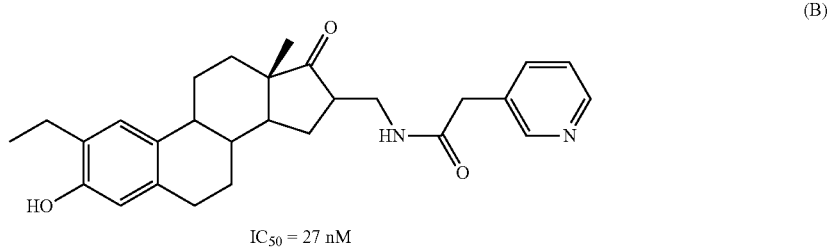

IC$_{50}$ = 27 nM

Among these compounds, inhibitors have been synthesized that exhibit a good inhibition of the enzyme and a good selectivity for 17β-HSD2 (compound B (Lawrence, H. R. et al., J. Med. Chem., 48: 2759-2762 (2005)). In addition, the inventors consider that a small estrogenic effect can be achieved by a substitution at the C2 of the steroid skeleton (Cushman, M. et al., J. Med. Chem., 38: 2041-2049 (1995); Leese, M. P. et al., J. Med. Chem., 48: 5243-5256 (2005)); however, this effect has not yet been demonstrated in tests.

However, a drawback of these steroidal compounds may be a low selectivity. With steroids, there is a risk that the compounds will also interfere with other enzymes of the steroid biosynthesis, which would lead to side effects. In addition, due to their steroidal structure, they may have an affinity for steroid receptors and function as agonists or antagonists.

Among the phytoestrogens, which have affinity for the estrogen receptor and act as estrogens or anti-estrogens depending on the physiological conditions, flavones, isoflavones and lignans have been tested for an inhibitory activity (Makela, S. et al., Proc. Soc. Exp. Biol. Med., 217: 310-316 (1998); Makela, S. et aL, Proc. Soc. Exp. Biol. Med., 208: 51-59 (1995); Brooks, J. D. et al., J. Steroid Biochem. Mol. Biol., 94: 461-467 (2005)). Coumestrol was found to be particularly potent, but of course showed estrogenic activity (Nogowski, L., J. Nutr. Biochem., 10: 664-669 (1999)). Gossypol derivatives were also synthesized as inhibitors (US2005/0228038). In this case, however, the cofactor binding site rather than the substrate binding site is chosen as the target site (Brown, W. M. et al., Chem. Biol. Interact., 143-144, 481-491 (2003)), which might entail problems in selectivity with respect to other enzymes utilizing NAD(H) or NADP(H).

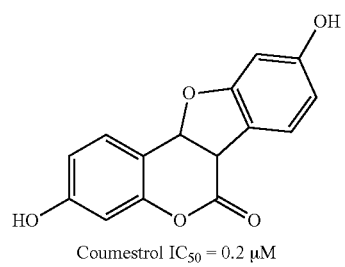 [SMILES: O=C1Oc2cc(O)ccc2C2Oc3cc(O)ccc3C12]

Coumestrol IC$_{50}$ = 0.2 μM

In addition to diketones, such as 2,3-butanedione and glyoxal, which were used for studies on the enzyme, suicide inhibitors were also tested. However, these were found not to be therapeutically utilizable since the oxidation rate of the alcohols to the corresponding reactive form, namely the ketones, was too weak (Poirier, D., Curr. Med. Chem., 10: 453-477 (2003)).

In other studies, Jarabak et al. (Jarabak, J. et al., Biochemistry, 8: 2203-2212 (1969)) examined various non-steroidal inhibitors for their inhibitory effect, U-11-100A having been found as the most potent compound in this group. However, as compared to other non steroidal compounds, U-II-100A is a weak inhibitor of 17βHSD1.

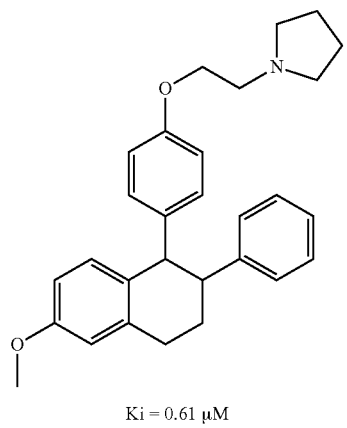

U-11-100A

Ki = 0.61 μM

Recently, using a pharmacophore model for 17β-HSD1 inhibitors Schuster et al. identified some compounds with 17β-HSD1 inhibitory activity in the micromolar range (Schuster, D. et al., J Med Chem. 51:4188-4199 (2008)). Regarding additional non steroidal 17β-HSD1 inhibitors, 5 templates reveal interesting biological activities: A. Thiophenepyrimidinones (US2005/038053; Messinger, J. et al., Mol. Cell. Endocrinol., 248: 192-198 (2006); W02004jll0459; Lilienkampf, A. et al., J. Med. Chem. 52: 6660-6671 (2009)); B. Biphenyl ethanones (Allan, G. M. et al. Bioorg. Med. Chem. 16: 4438-4456 (2008)); C. Hydroxyphenylnaphtols (WO/08EP/53672; Marchais-Oberwinkler S. et al., J. Med. Chem., 51: 4685-4698 (2008)) Marchais-Oberwinkler, S. et al., J. Med. Chem., 54: 534-547, 2011); D. Heterocyclic substituted biphenylols (Oster, A. et al., Bioorg. Med. Chem., 18: 3494-3505 (2010)); E. Bis(hydroxyphenyl) arenes (W02009/02746; Bey, E. et al., J. Med. Chem., 52: 6724-6743 (2009)).

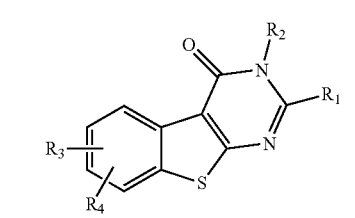

A

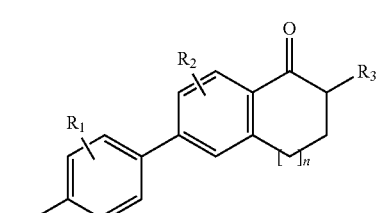

B

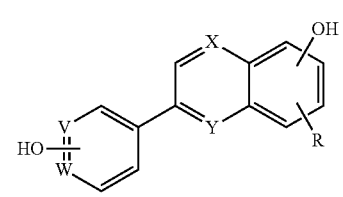

C

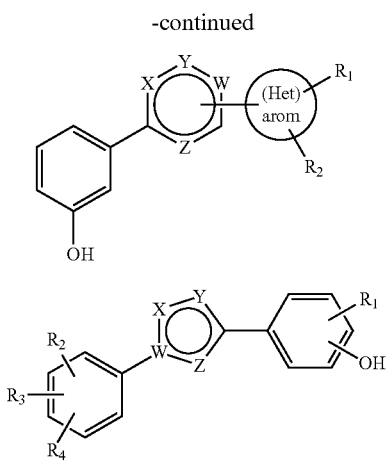

D

E

Most of those classes showed high potency at the protein level (IC50<20 nM; WO2004/53424) but a limited inhibitory activity (IC50>200 nM) in cell-based 17β-HSD1 assays (Messinger J. et al, Mol. Cell. Endocrinol., 248: 192-198 (2006) and Bey E. et al, J. Med. Chem., 52: 6724-6743 (2009)), which might be due to poor cell membrane permeability.

Recently described coumarins display only moderate inhibition of 17β-HSD1 (Starčević et al, J. Med. Chem. 54: 248-261 (2011)), whereas bicyclic substituted hydroxyphenylmethanones have been described as potent inhibitors (Oster et al., J. Med. Chem. 53: 8176-8186 (2010)).

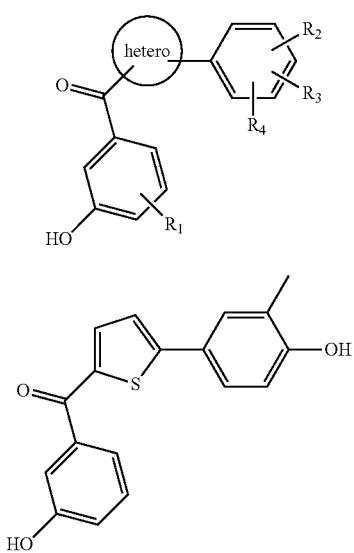

F

F1

Inhibitors with hydroxybenzothiazole core (Spadaro et al. PLoS ONE 7: e29252. doi:10.1371/journal.pone.0029252; J. Med. Chem. 55: 2469-2473 (2012)) are potent but show poor pharmacokinetics. Further, 2-benzoylbenzothiazole derivatives having lipid lowering activity are known from EP-A-735029, and N-(benzothiazol-2-yl)arylcarboxamide and 1-(benzothiazol-2-yl)-3-(aryl)urea derivatives and their use for the inhibition of ubiquitination are known from WO2005/037845. Similar N-(benzothiazol-2-yl)arylcarboxamide and 1-(benzothiazol-2-yl)-3-(aryl)urea derivatives including frentizole (1-(6-methoxy-1,3-benzothiazol-2-yl)-3-phenylurea) are also known to interact with amyloid beta (Aβ) peptide and/or (Aβ)-binding alcohol dehydrogenase and are potential anti-Alzheimer agent (Xie, Y. et al., Bioorg. & Med. Chem. Lett. 16: 4657-60 (2006)).

Finally, selective 17β-HSD1 inhibitors with (phenylthiazolyl)(phenyl)methanone (phenylthienyl)(phenyl)methanone and (benzothiazolyl)(phenyl)methanone structure are known from WO2012/025638, and selective 17β-HSD1 inhibitors with (phenyl-1,3-thiazol-4-yl)phenol and (phenylthienyl)phenol structure are known from DE102007040243A1.

17Beta-Hydroxysteroid Dehydrogenase Type 2 Inhibitors: Estrogens and androgens play a crucial role in the development, growth and function of all tissues involved in reproduction and fertility. It is also well known, that E2 and testosterone/dihydrotestosterone (T/DHT) the most active estrogen and androgen, respectively, can be involved in a series of hormone-sensitive diseases. For example estrogens or androgens are often responsible for the development of breast cancer or prostate cancer, respectively, via stimulation of cell proliferation in the corresponding tissues (Travis, R. C. et al., Breast Cancer Res., 5: 239-247 (2003); Wilding, G., Cancer Surv., 14113-14130 (1992)) or insufficient levels of E2 and T/DHT predispose the human skeleton to osteoporosis in both men and women (Pietschmann, P. et al., Gerontology, 55:3-12 (2008)).

Osteoporosis is a systemic skeletal disease characterized by deterioration of bone tissue and low bone mass, resulting in increased fragility of the bone and higher risk of fractures of the hip, spine and wrist. Osteoporotic fractures lead to pain, occasional disability and more important, they increase mortality (Cree, M. et al., J. Am. Geriatr. Soc., 48:283-288 (2000)).

In healthy individuals, bone mass is maintained by a balance between bone resorption and bone formation performed by the osteoclasts (OCs) and osteoblasts (OBs), respectively. This process of bone remodelling facilitates repair of microdamage, provides calcium uptake and therefore brings stability and strength to the bone.

Bone loss is, however, accelerated in post-menopausal women and in elderly men. The mechanisms by which elderly people, both men and women, lose bone are not fully understood and remain under investigation. Decreased quantity of sex hormones is one important factor causing bone loss. In women at menopause, estrogen deficiency (Cree, M. et al., J. Am. Geriatr. Soc., 48:283-288 (2000)) and in older men, estrogen and androgen insufficiency (Fink, H. A. et al., J. Clin. Endocrinol. Metab., 91:3908-3915 (2006); Meier, C. et al., Arch. Intern. Med., 168:47-54 (2008)) result in a disproportionate increase in bone loss as compared with bone formation and often lead to osteoporosis.

Since OBs and OCs express estrogen receptors (Hoyland, J. A. et al., Bone, 20:87-92 (1997)) and respond to estrogen treatments, the most potent estrogen, E2 must have a direct effect on maintenance of bone mineral density. There are also substantial evidence that androgens like testosterone (T) and dihydrotestosterone (DHT) may as well be involved in bone formation, increasing OB activity and therefore protecting the bones against osteoporosis (Vanderschueren, D. et al., Endocr. Rev., 25:389-425 (2004), Vanderschueren, D. et al., Curr. Opin. Endocrinol. Diabetes Obes., 15:250-254 (2008)). T and DHT might act via activation of the androgen receptor (AR) which is present in the OBs (Bland, R., Clin. Sci., 98:217-240 (2000)) or could be the precursor of estrogens (the enzyme aromatase, responsible for the transformation of androgens in estrogens has been identified in the OBs). Controlled increase of E2 and T in bones of osteoporotic patients will simultaneously lower bone resorption (effect of E2) and raise bone formation (effect of T) improving bone loss and osteoporotic fractures. Augmentation of E2 and T levels in bones might be achieved by inhibition of the enzyme 17β-hydroxysteroid dehydrogenase type 2 (17β-HSD2) which has been identified in OBs (Dong, Y. et al., J. Bone Miner. Res., 13:1539-1546 (1998); Feix, M. et al., Mol. Cell. Endocrinol., 171:163-164 (2001); Janssen, J. M et al., J. Cell. Biochem., 75:528-37 (1999)). A restricted increase in E2 and T in OCs and OBs is important to avoid unwanted side-effects such as induction of breast cancer or prostate cancer. This might be achieved via an intracrine mechanism (Labrie, F., Mol. Cell. Endocrinol. 78:C113-118 (1991)), i.e., the transformation of E2 and T in inactive precursors should be blocked dominantly in the bone cells 17β-HSD2 (Wu, L. et al., J. Biol. Chem., 268:12964-12969 (1993); Lu, M., J. Biol. Chem., 277:22123-22130 (2002)) belongs to the hydroxysteroid dehydrogenase (HSD) superfamily. The HSD enzymes play pivotal roles not only in the activation but also in the inactivation of steroid hormones. Depending on the need of the cell, they modulate the potency of the sex hormones (Penning, T. M. et al., Endocr. Rev., 18:281-305 (1997)). For example, 17β-HSD1 activates E1 into the very potent E2, while 17β-HSD2 oxidizes E2 into E1 thus decreasing the action of the potent E2. It is therefore believed that in physiology 17β-HSD2 protects the cell against excessive level of active estrogen. To date, fourteen different 17β-HSDs have been identified (Lukacik, P. et al., Mol. Cell. Endocrinol. 248:61-71 (2006); Luu-The, V. et al., Best Pract. Res. Clin. Endocrinol. Metab., 22:207-221 (2008)) and twelve different subtypes have been cloned from human tissues. They all belong to the Short-Chain Dehydrogenase/Reductase family (except type 5). The 17β-HSDs show little amino acid identity (20-30%) and are membrane-bound or soluble enzymes. The X-ray structures of six human subtypes (type 1, 4, 8, 10, 11, 14) are known (Moeller, G. et al., Mol. Cell. Endocrinol. 301:7-19 (2009)). All of them are NAD(H)- or NADP(H)-dependent. The 17β-HSDs play therefore a key role in hormonal regulation and function in humans. They differ in tissue distribution, catalytic preference (oxidation or reduction), substrate specificity and subcellular localisation. It is likely that all 17β-HSDs, modulating estrogen and androgen action, are expressed in the different estrogen/androgen-dependent tissues but certainly at different concentrations. In diseased tissues, the ratio between the different subtypes is changed compared to healthy tissues: one enzyme subtype might be overexpressed or completely absent, leading to higher/lower concentrations of the specific steroids. Selective inhibition of one subtype could therefore be a good strategy to influence the level in estrogen and androgen in hormone sensitive diseases. 17β-HSD2 (EC 1.1.1.51) is a transmembrane protein localized in the endoplasmic reticulum (Wu, L. et al., J. Biol. Chem., 268:12964-12969 (1993); Lu, M., J. Biol. Chem., 277:22123-22130 (2002)). Its 3D-structure remains unknown. 17β-HSD2 shows a broad tissue distribution in adult: it is expressed in liver, small intestine, endometrium, urinary tracts and bone osteoblastic (Dong, Y. et al., J. Bone Miner. Res., 13:1539-1546 (1998); Feix, M. et al., Mol. Cell. Endocrinol., 171:163-164 (2001); Eyre, L. J. et al., J. Bone Miner. Res., 13:996-1004 (1998)) and osteoclastic (van der Eerden, B. C. J. et al., J. Endocrinol., 180:457-467 (2004)) cells. It has a predominant oxidative activity on hydroxy groups at the position C17 of the steroids: it converts the highly active 17β-hydroxysteroid estrogen E2 as well as the 17β-hydroxysteroid androgens T and DHT into their inactive keto forms using the cofactor $NAD^+$. The broad tissue distribution together with the oxidative activity of 17β-HSD2 suggests that this enzyme may play an essential role in the inactivation of highly active estrogens and androgens, resulting in diminished sex hormone action in target tissues.

Relatively few inhibitors of 17β-HSD2 have been described. Sam, K. M., J. Med. Chem., 38:4518-4528 (1995); Poirier, D. et al., Mol. Cell. Endocrinol., 171:119-128 (2001); Bydal, P. et al., Eur. J. Med. Chem., 44:632-644 (2009)) reported on the potent steroidal C17-spirolactone 1 (inhibitory activity of 70% at 1 μM and 40% at 100 nM). Cook et al. (Cook, J. H. et al., Tetrahedron Letters, 46:1525-1528 (2005); Gunn, D., Bioorg. Med. Chem. Lett., 15:3053-3057 (2005); Wood, J. et al., Bioorg. Med. Chem. Lett., 16:4965-4968 (2006)) found, using high through-put screening methods, the first new class of potent non-steroidal inhibitors of 17β-HSD2: the 4,5-disubstituted cis-pyrrolidines. The most active compound described is 2 ($IC_{50}$=10 nM). It has been recently proven in monkeys, using an osteoporosis model for in vivo evaluation of the 17β-HSD2 inhibitor 3, that inhibition of this enzyme helps to maintain a sufficient local level of E2 and T in bones when the level of circulating active sex steroid drops (Bagi, C. M. et al., J. Musculoskelet. Neuronal Interact., 8:267-280 (2008)).

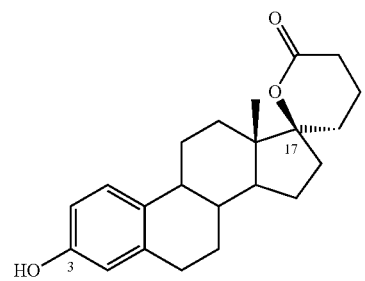

1

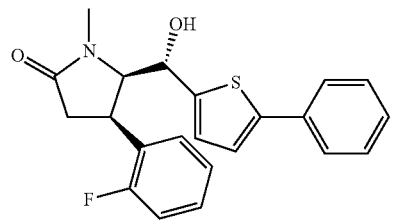

2

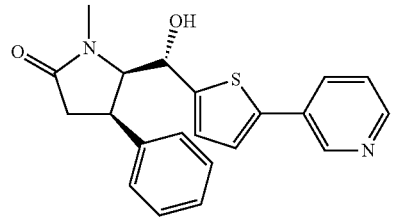

3

This modulation of steroid levels might be useful for a variety of indications like prevention and treatment of diseases caused by a misbalance of OB/OC activity like osteoporosis, osteopenia and impaired bone fracture healing (Undsay, R. et al., Obst. Gynecol., 76:290-295 (1990); Turner, R. T. et al., Endocr. Rev., 16:275-300 (1994); Meczekalski, B. et al., Gynecol. Endocrinol., 26:652-657 (2010)), postmenopausal symptoms, vaginal atrophy (Klingsberg S. A. et al., Int J Women's Health, 1: 105-111 (2009); Mac Bride, M. B., Mayo Clin. Proc., 85:87-94 (2010); Smith, A. L et al., Discov. Med., 10:500-510

(2010)); colon cancer (Oduwole O. O. et al., J. Steroid. Biochem. Mol. Biol. 87:133-140 (2003)), neuronal diseases (Behl, C. et al., Biochem. Biophys. Res. Commun., 216: 473-482 (1995)) like Alzheimer (Pike, C. J., Front Neuroendocrinol., 30:239-258 (2009)) and Parkinson's disease (Bourque, M. et al., Front Neuroendocrinol., 30:142-157 (2009)), depression (Schmidt, P. J. et al., Ann. N.Y. Acad. Sci., 179:70-85 (2009)) anxiety, hypercholesterolemia (Karjalainen, A. et al., Arterioscler. Thromb. Vasc. Biol., 4:1101-1106 (2000)), cardiovascular diseases (Traish, A. M. et al., J. Androl., 30:477-494 (2009); Xing D. et al., Arteriosder. Thromb. Vasc. Biol., 29:289-295 (2009)); hair loss (Mooradian, A. D. et al., Endocr. Rev., 8:1-28 (1987); Georgala S. et al., Dermatology 208:178-9 (2004)), non-insulin-dependent diabetes mellitus (Ferrara A. et al., Diabetes Care 25: 1144-1150 (2001)), rheumatic diseases and inflammatory diseases (Cutolo, M. et al., Ann. N.Y. Sci., 1193:36-42 (2010); Islander U. et al., Mol. Cell. Endocrinol. Doi: 10.1016/j.mce. 2010.05.018 (2010)). More recently, non-steroidal 17β-HSD2 inhibitors from different compound classes have been described (Wetzel M. et al., Bioorg. Med. Chem., 19: 807-815 (2011); Wetzel M. et al., J. Med. Chem., 54: 7547-7557 (2011). Wetzel M. et al., Eur. J. Med. Chem., 47:1-17 (2012). Xu K. et al., Eur. J. Med. Chem., 46: 5978-5990 (2011); Xu K. et al., Letters in Drug Design & Discovery, 8: 406-421 (2011); Al-Soud Y. A. et al, Arch. Pharm. (Weinheim), 345: 610-621 (2012); Marchais-Oberwinkler et al. S., J. Med. Chem., 56:167-181 (2013); Perspicace E. et al., Eur. J. Med. Chem., 69:201-215 (2013); Perspicace E. et al., Molecules, 18: 4487-4509 (2013)). Further, selective 17bHSD1 inhibitors with N-benzyl-N-methyl(phenyl)thiophene-carboxamide, N-benzyl-N-methyl-(phenyl)-1,3-thiazole-carboxamide and N-benzyl-N-methyl-biphenyl-3-carboxamide structure are known from WO2012117097.

Related Structures: Thakar K. A. and Padhye A. M., J. Ind. Chem. Soc. LXI: 715-716 (1984) discloses certain mono- and dihalogeno-hydroxyphenyl-furyl-ketones, and mono- and di-halogeno-hydroxyphenyl-thienyl-ketones in the synthesis of furyland thienyl-substituted benzisoxazoles.

Takayama T. et al., Bioorg. & Med. Chem. Lett. 20: 108-111 (2010) and WO2005/123671 disclose (3-amino-4-carboxamido-5-(4'-phenoxy)phenyl-pyrrol-2-yl)-phenyl-ketone derivatives that are inhibitors of lymphocyte-specific kinase and are useful as immunsuppresive agents, e.g. for the treatment of inflammatory diseases and of organ transplant rejection.

EP0801058A1 and U.S. Pat. No. 5,817,691 disclose arylthio-, arylsulfinyl- and arylsulfonylpyrrole compounds having insecticidal activity.

WO2011/079772 discloses the one-pot synthesis of certain 2,5-disubstituted thienes.

SUMMARY OF THE INVENTION

A new series of non-steroidal inhibitors has been identified. The compounds are structurally derived from the bicyclic substituted hydroxyphenylmethanones (Oster et al., J. Med. Chem. 53: 8176-8186 (2010)) mentioned above, but display clearly improved properties: They show greatly enhanced potency toward human 17β-HSD1 and 17β-HSD2, respectively, at the protein level. The compounds are the most potent inhibitors of 17β-HSD1 and 17β-HSD2 ever described. This high potency was achieved by the introduction of halogen (fluorine) atoms. Selectivity for the type 1 or the type 2 enzyme can be adjusted by the substitution pattern. The compounds are active towards the rodent enzyme (mouse and rat) which is crucial for proof of principle studies. In particular, the introduction of two and three fluorine atoms, respectively, on the benzoyl moiety led to a dramatic increase in potency towards murine 17beta-HSD1 and 2 by up to 100-fold; in case of the human enzymes, the achieved potencies increase 5-1000-fold. The strong beneficial effects exerted by multiple halogenation of the benzoyl moiety on human and rodent 17beta-HSD1 and 2 inhibition are documented by a direct comparison of inhibitory activities displayed by compounds with different degrees of halogenation, see section "Comparative Data". The examples given there also illustrate the fact that difluorination in general leads to a slight-to-good human 17beta-HSD1 selectivity whereas trifluorination favours human 17beta-HSD2 selectivity. Both the strong increase in potency and the modulation of selectivity are surprising in light of WO 2012/025638: The monofluorinated compounds 7 and 9 of WO 2012/025638 show insignificant differences in potency toward human 17beta-HSD1 and are less selective compared to their non-fluorinated analogs 1 and 4 (numbering refers to WO 2012/025638). Compounds with more than one fluorine atom attached to the benzoyl moiety are not described in WO 2012/025638. Thus, the data did not allow the condusion that introduction of two or three fluorine atoms increases potencies dramatically. Furthermore, due to the different architectures of the substrate binding sites (which are supposed to be the inhibitor binding sites as well) of human 17beta-HSD1/2 in comparison to murine 17beta-HSD1/2, the strong inhibition of the murine enzymes is unexpected.

Moreover, the new inhibitors display improved pharmacokinetic parameters such as solubility and metabolic stability. The invention thus provides:

(1) A compound (with 17beta-hydroxysteroid dehydrogenase type 1 (17β-HSD1) or type 2 (17β-HSD2) inhibitory activity) having the formula (I)

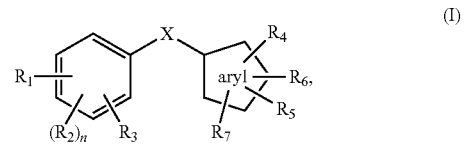

wherein

R1 represents H, OH, alkoxy or acyloxy;

n represents an integer of 1 or 2;

R2 at each occurrence independently represents a halogen atom;

R3 represents alkyl, haloalkyl or halogen atom;

R4 represents H; OH; an alkyl or an alkoxy group, each of which may carry phenyl and halogen substituents (wherein said phenyl substituents may carry up to 3 substituents independently selected from —OH, alkyl, haloalkyl, alkoxy, halogen, amino, —CN and —NO$_2$); a 6-membered aromatic group which may carry 1 to 3 substituents independently selected from —R, haloalkyl, halogen, —NO$_2$, —OR', —SR', —CH$_2$R, —COR', —NR'R', —CN, —COOR', —NR'SO$_2$R, —SO$_2$NR'R', —NR'COR, —CONR'R', —OC(O)R', —CH$_2$NR'R', —CH$_2$OR', —SO$_2$R and —SOR (wherein R is an alkyl group, a heterocyclic ring, an aromatic or non aromatic ring that may be condensed or linked with a 5- or 6-membered, aliphatic or aromatic heterocyclic ring, a benzyl group, or an aliphatic or aromatic heterocyclic group that may be condensed or linked with a benzene ring, each of said groups may be substituted with up to 5 substituents independently selected from halogen, lower alkyl, lower haloalkyl, OH, —NO$_2$, lower alkoxy, lower haloalkoxy, —NH$_2$, phenyl, —CN, —COR", —NHCOR", —CONHR", —NHSO$_2$R" and SO$_2$NHR" (wherein R" is H, lower alkyl, lower haloalkyl or phenyl), and R' at each occurrence is independently selected from the groups of R above and H), or two of said substituents, together with the adjacent carbon atoms of the 6-membered aromatic group, may form a 5- or 6-membered, aliphatic or aromatic, homocyclic or heterocyclic ring condensed to said 6-membered aromatic group, wherein the heterocyclic ring carries up to 3 heteroatoms independently selected from N, S and O, and the third substituent may be located on the 6-membered aromatic group or on the ring condensed thereto; or a 5 or 6-membered aliphatic or aromatic heterocyclic group which carries up to 3 heteroatoms independently selected from N, S and O and may carry 1 to 3 substituents independently selected from —R, haloalkyl, halogen, —NO$_2$, —OR', —SR', —CH$_2$R, —COR', —NR'R', —CN, —COOR', —NR'SO$_2$R, —SO$_2$NR'R', —NR'COR', —NRCOR', —CONR'R', —OC(O)R', —CH$_2$NR'R', —CH$_2$OR', —SO$_2$R and —SOR (wherein R and R' is as defined above) or two of said substituents, together with the adjacent carbon atoms of the 5 or 6-membered aliphatic or aromatic heterocyclic group, may form a 6-membered, aliphatic or aromatic ring condensed to said 5 or 6-membered aromatic group, and the third substituent may be present on the 5 or 6-membered aromatic group or on the ring condensed thereto; and said substituent R3 being directly or through a phenylen group bound to the aryl ring;

R5, R6 and R7 independently represent H, —R, haloalkyl, halogen, —NO$_2$, —OR', —SR', —CH$_2$R', —COR', —NR'R', —CN, —COOR', —NHSO$_2$R', —NRSO$_2$R' —SO$_2$NRR', —NHCOR', —NRCOR', —CONRR', —OC(O)R', —CH$_2$NRR', —CH$_2$OR', —SO$_2$R' or —SOR' (wherein R and R' is as defined above), X represents

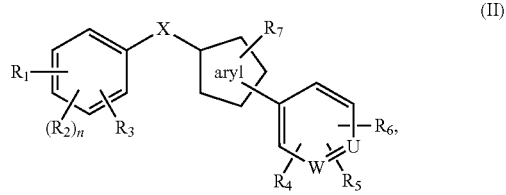

(wherein Y, if present, represents O or S, and R8 represents H or lower alkyl); and the aryl ring is a 5-membered heteroaromatic ring which carries up to 3 heteroatoms independently selected from N, S and O, including, but not limited to, a thiadiazole, triazole, oxadiazole, isothiadiazole, isooxadiazole, thiazole, oxazole, imidazole, pyrazole, isoxazole, isothiazole, furane, pyrrole or thiophene (thiene); or a pharmaceutically acceptable salt thereof.

(2) In a preferred embodiment of (1) above, the compound has the formula (II)

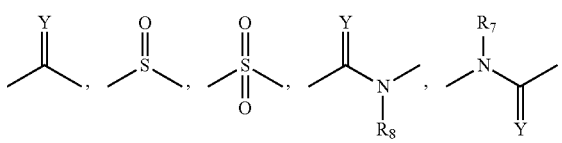

(II)

wherein R1, R2, R3, R4, R5, R6, R7, X and n have the same meaning as in (1) above, the aryl ring is a heterocyclic aromatic ring, which carries up to 3 heteroatoms independently selected from N, S and O, W and U represent independently CH or N, preferably the compound has the formula (IIa)

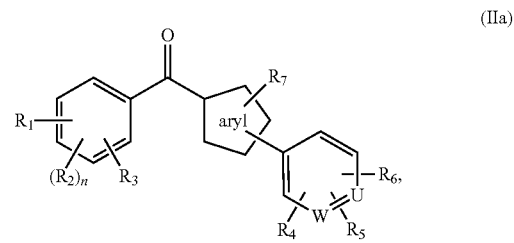

(IIa)

wherein all the variables are as defined for formula (II) above.

(3) In a preferred embodiment of (2) above, the compound has the formula (III)

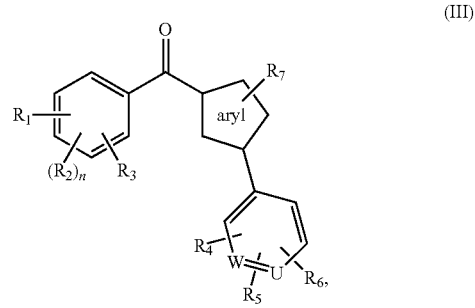

(III)

wherein all the variables are as defined in (2) above.

(4) In a preferred embodiment of (1) to (3) above, the compound is a compound with 17β-HSD1 inhibitory activity, wherein in the formulas (I)-(III) n is 1 and R2 and R3 independently represent halogen atoms.

(5) In a preferred embodiment of (1) to (3) above, the compound is a compound with 17β-HSD2 inhibitory activity, wherein in the formulas (I)-(III)
(i) n is 1, R2 is a halogen atom and R3 represents alkyl or haloalkyl (preferably R3 represents CH$_3$ or CF$_3$); or
(ii) n is 2, R2 and R3 at each occurrence independently represent halogen atoms.

(6) A compound (with 17β-HSD1 or 17β-HSD2 inhibitory activity) having the formula (I)

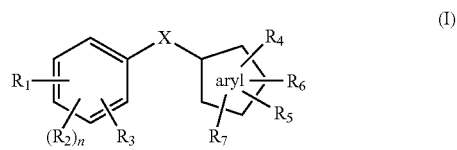

(I)

as defined in any one of (1) to (5) above, for use in the treatment and prophylaxis of hormone-related diseases in a mammal.

(7) A method for the production of the compound of any one of (1) o (5) above or a pharmaceutically acceptable salt thereof, which comprises condensing aromatic precursor compounds of formula (I).

(8) A pharmaceutical composition or medicament comprising at least one compound of any one of (1) to (5), or a pharmaceutically acceptable salt thereof, and optionally one or more suitable carriers and/or excipients.

(9) Use of a compound of any one of (1) to (5) above, or a pharmaceutically acceptable salt thereof for preparing a medicament for the treatment and prophylaxis of hormone-related diseases in a mammal.

(10) A method for the treatment and prophylaxis of hormone-related diseases in a mammal, such as estrogen-related diseases, which comprises administering a compound of any one of (1) to (5) above, or a pharmaceutically acceptable salt thereof to the mammal (i.e., the patient) in need of such treatment or prophylaxis.

(11) In a preferred embodiment of (6) and (8) to (10) above, the compound, pharmaceutical composition, medicament or method is for the treatment and prophylaxis of estrogen-related diseases in a mammal, preferably comprises (i) a compound having 17β-HSD1 inhibitory activity, e.g. as defined in (4) above, and is for use in the treatment and prophylaxis of endometriosis, endometrial carcinoma, endometrial hyperplasia, adenomyosis, breast cancer, prostate cancer, acne, androgen-dependent hair loss, psoriasis, prostate cancer, acne, androgen-dependent hair loss, psoriasis and ovarian carcinoma; or (ii) a compound having 17β-HSD2 inhibitory activity, e.g. as defined in (5) above, and is for use in the treatment and prophylaxis of osteoporosis, osteopenia, impaired bone fracture healing, hair loss, colon cancer, vaginal atrophy, hypercholesterolemia, and non-insulin-dependent diabetes mellitus.

(12) In a preferred embodiment of the compound of (1) to (5) and (11) above, (i) the compound of formula (I) is not 2,4-dichloro-6-hydroxyphenyl-furyl-ketone, 2,4-dibromo-6-hydroxyphenyl-furyl-ketone, 4-chloro-2-hydroxy-6-methylphenyl-furyl-ketone, 4-chloro-2-hydroxy-5-methylphenyl-furyl-ketone, 2,4-dichloro-6-hydroxyphenyl-thienyl-ketone or 4-chloro-2-hydroxy-6-methylphenyl-thienyl-ketone;

(ii) when in the compound of formula (I) the aryl ring is 3-amino-4-carboxamido-5-(4'-phenoxy)phenyl-pyrrol-2-yl, and X is —CO—, then the phenyl moiety carrying R1-R3 is not 2,6-difluorophenyl, 2,4,6-trifluorophenyl, 2,6-difluoro-3-methylphenyl, 2,5-difluorophenyl, 3-fluoro-2-methylphenyl, 2,3-difluorophenyl, 2,3-dichlorophenyl, 2,4-dichlorophenyl, 3,5-dichlorophenyl, 2,5-dichlorophenyl, 3-chloro-2-methylphenyl, 3,4-dichlorophenyl or 3-bromo-2-methylphenyl;

(iii) when in the compound of formula (I) the phenyl moiety carrying R1-R3 is 2,6-difluorophenyl and X is —CO—, then the aryl ring is not a 3-amino-4-carboxamido-5-(4'-substituted)phenyl-pyrrol-2-yl, in which the substituent is methoxy, 2-pyrimidinyloxy, benzyloxy, 2,6-dichlorobenzyloxy, amino, benzoylamido, benzylamino, cyclohexylmethylamino, 2,6-dichlorobenzylamino, N-(2,6-dichlorobenzyl)-N-methylamino, 2,5-dichlorobenzylamino, 2-chloro-6-methlbenzylamino, 3-phenylpropylamino, 4-trifluoromethylbenzylamino, 2-pyridylmethoxy, 2-(4-methyl-piperazin-1-yl)ethyloxy, 5-tifluoromethylpyridin-2-yloxy, piperidin-2-yloxy, 4,6-dimethylpiperidin-2-yloxy, piperidin-2-yloxy, 4,6-dimethoxypiperidin-2-yloxy, 3-phenylpropionoylamido, 2-pyridinylcarbamido, 3-(3-pyridinyl)propionoylamido, 2-chloro-6-fluorobenzylamino, 2-trifluoromethylbenzylamino, 2-methylbenzylamino, 2,6-difluorobenzylamino, 2,4,6-trimethylbenzylamino, 2,3,5,6-tetramethylbenzylamino, 2,3,5,6-tetrafluorobenzylamino, 2,4,6-trichlorobenzylamino, 2,4,6-triisopropylbenzylamino, 2,4,6-trifluorobenzylamino, 2,6-dimethoxybenzylamino, 2,6-dichloro-3-nitrobenzylamino, 3-chloro-2,6-difluorobenzylamino, 2-chloro-6-methylbenzylamino, 2-chloro-6-fluoro-5-methylbenzylamino, 4-bromo-2,6-fluorobenzylamino, 2-chloro-3,6-difluorobenzylamino, 2,5-dichlorobenzylamino, 2-bromo-6-methylbenzylamino, 2,6-difluoro-3-methylbenzylamino, 2-bromo-6-chlorobenzylamino, 2-fluoro-6-methoxybenzylamino, 2,6-dimethyl-4-fluorobenzylamino, 2-chloro-6-methoxybenzylamino, 2-chloro-6-fluoro-5-methylbenzylamino, 2-(2-(N,N-dimethylamino)ethyloxy)phenyloxy or 3-(2-(N,N-dimethylamino)ethyloxy)phenyloxy;

(iv) when in the compound of formula (I) the aryl ring is N-methyl-3-amino-4-carboxamido-5-(4'-phenoxy)phenyl-pyrrol-2-yl, and X is —CO—, then the phenyl moiety carrying R1-R3 is not 2,6-dichlorophenyl;

(v) when in the compound of formula (I) the aryl is a pyrrol and R4 is a phenyl residue substituted with 1 to 3 substituents independently selected from halogen, —NO$_2$, CN, C$_{1-4}$alkyl, C$_{1-4}$haloalkyl and C$_{1-4}$alkoxy, and the phenyl moiety carrying R1-R3 is a phenyl substituted with 2 to 4 substituents selected from halogen, —NO$_2$, CN, C$_{1-4}$alkyl, C$_{1-4}$haloalkyl and C$_{1-4}$alkoxy, then X is not —SO— or —SO$_2$—; and (vi) when in the compound of formula (I) the aryl is a thiene, R4 is an aryl group, unsaturated monocyclic heterocyclic ring or unsaturated fused heterobicyclic ring, each of which may be substituted with 1 to 3 substituents independently selected from halogen, —NO$_2$, amino, cyano, hydroxy, mercapto, carboxyl, C$_{1-4}$ alkyl, C$_{1-4}$haloalkyl, C$_{1-4}$alkoxy, benzyloxy, C$_{1-4}$alkylthio, C$_{1-4}$ hydroxyalkyl, C$_{1-4}$alkyl amino, bis(C$_{1-4}$alkyl)amino, C$_{1-4}$acylamino, carbamoyl, C$_{1-4}$alkoxycarbonyl, and C$_{1-4}$ alkylsulfonyl, R5 and R6 are hydrogen, and the phenyl moiety is a phenyl substituted with 2 to 3 substituents selected from halogen, hydroxy, C$_{1-4}$ alkyl, C$_{1-4}$ haloalkyl and C$_{1-4}$alkoxy, then X is not —CO—.

(13) In another preferred embodiment of the compound of (1) to (5) and (11) above, (i) when in the compound of formula (I) the aryl ring is a furyl or thiene, R3 is methyl or a halogen and X is —CO—, then one of R1 and R4 to R7 is not H;

(ii) in the compound of formula (I) the aryl ring is a not pyrrol carrying an —NH$_2$ and a —CONH$_2$ group in its positions 3 and 4;

(iii) when in the compound of formula (I) the aryl ring is a pyrrol, then X is not —SO— or —SO$_2$—; and (iv) when in the compound of formula (I) the aryl ring is a thiene and X is —CO—, then R2 and R3 are halogen atoms, preferably R2 and R3 are F and n is 2.

(14) In a preferred embodiment of the composition or medicament of (8) and (11) above, (i) when in the compound of formula (I) the aryl ring is 3-amino-4-carboxamido-5-(4'-phenoxy)phenyl-pyrrol-2-yl, and X is —CO—, then the phenyl moiety carrying R1-R3 is not 2,6-difluorophenyl, 2,4,6-trifluorophenyl, 2,6-difluoro- 3-methylphenyl, 2,5-difluorophenyl, 3-fluoro-2-methylphenyl, 2,3-difluorophenyl, 2,3-dichlorophenyl, 2,4-dichlorophenyl, 3,5-dichlorophenyl, 2,5-dichlorophenyl, 3-chloro-2-methylphenyl, 3,4-dichlorophenyl or 3-bromo-2-methylphenyl;

(ii) when in the compound of formula (I) the phenyl moiety carrying R1-R3 is 2,6-difluorophenyl and X is —CO—, then the aryl ring is not a 3-amino-4-carboxamido-5-(4'-substituted)phenyl-pyrrol-2-yl, in which the substituent is methoxy, 2-pyrimidinyloxy, benzyloxy, 2,6-dichlorobenzyloxy, amino, benzoylamido, benzylamino, cydohexylmethylamino, 2,6-dichlorobenzylamino, N-(2,6-dichlorobenzyl)-N-methylamino, 2,5-dichlorobenzylamino, 2-chloro-6-methlbenzylamino, 3-phenylpropylamino, 4-trifluoromethylbenzylamino, 2-pyridylmethoxy, 2-(4-methylpiperazin-1-yl)ethyloxy, 5-tifluoromethylpyridin-2-yloxy, piperidin-2-yloxy, 4,6-dimethylpiperidin-2-yloxy, piperidin-2-yloxy, 4,6-dimethoxypiperidin-2-yloxy, 3-phenylpropionoylamido, 2-pyridinylcarbamido, 3-(3-pyridinyl)propionoylamido, 2-chloro-6-fluorobenzylamino, 2-trifluoromethylbenzylamino, 2-methylbenzylamino, 2,6-difluorobenzylamino, 2,4,6-trimethylbenzylamino, 2,3,5,6-tetramethylbenzylamino, 2,3,5,6-tetrafluorobenzylamino, 2,4,6-trichlorobenzylamino, 2,4,6-triisopropylbenzylamino, 2,4,6-trifluorobenzylamino, 2,6-dimethoxybenzylamino, 2,6-dichloro-3-nitrobenzylamino, 3-chloro-2,6-difluorobenzylamino, 2-chloro-6-methylbenzylamino, 2-chloro-6-fluoro-5-methylbenzylamino, 4-bromo-2,6-fluorobenzylamino, 2-chloro-3,6-difluorobenzylamino, 2,5-dichlorobenzylamino, 2-bromo-6-methylbenzylamino, 2,6-difluoro-3-methylbenzylamino, 2-bromo-6-chlorobenzylamino, 2-fluoro-6-methoxybenzylamino, 2,6-dimethyl-4-fluorobenzylamino, 2-chloro-6-methoxybenzylamino, 2-chloro-6-fluoro-5-methylbenzylamino, 2-(2-(N,N-dimethylamino)ethyloxy)phenyloxy or 3-(2-(N,N-dimethylamino)ethyloxy)phenyloxy; and (iii) when in the compound of formula (I) the aryl ring is N-methyl-3-amino-4-carboxamido-5-(4'-phenoxy)phenyl-pyrrol-2-yl, and X is —CO—, then the phenyl moiety carrying R1-R3 is not 2,6-dichlorophenyl.

(15) In another preferred embodiment of the composition or medicament of (8) and (11) above, in the compound of formula (I) the aryl ring is a not pyrrol carrying an —NH$_2$ and a —CONH$_2$ group in its positions 3 and 4.

DETAILED DESCRIPTION OF THE INVENTION

In the compounds of formulas (I) to (III) of the invention, the variables and the terms used for their characterization have the following meanings:

"Alkyl" and "alkoxy" residues within the meaning of the invention may be straight-chain, branched-chain or cyclic, and saturated or (partially) unsaturated. Preferable alkyl residues and alkoxy residues are saturated or have one or more double and/or triple bonds. Of straight-chain or branched-chain alkyl residues, preferred are those having from 1 to 10 carbon atoms, more preferably those having from 1 to 6 carbon atoms, even more preferably those having from 1 to 3 carbon atoms. Of the cyclic alkyl residues, more preferred are mono- or bicyclic alkyl residues having from 3 to 15 carbon atoms, especially monocyclic alkyl residues having from 3 to 8 carbon atoms.

"Lower alkyl" and "lower alkoxy" residues within the meaning of the invention are straight-chain, branched-chain or cyclic saturated lower alkyl residues and lower alkoxy residues or those having a double or triple bond. Of the straight-chain ones, those having from 1 to 6 carbon atoms, especially 1 to 3 carbon atoms, are particularly preferred.

"Aryls" and "homocyclic aromatic groups" within the meaning of the present invention include, if not specified otherwise, mono-, bi- and tricyclic aryl residues having from 3 to 18 ring atoms, which may optionally be anellated with one or more saturated rings. Particularly preferred are anthracenyl, dihydronaphthyl, fluorenyl, hydrindanyl, indanyl, indenyl, naphthyl, naphthenyl, phenanthrenyl, phenyl and tetralinyl.

Unless stated otherwise, "heteroaryl" residues and "heterocyclic groups" are mono- or bicyclic heteroaryl residues having from 3 to 12 ring atoms and preferably having from 1 to 5 heteroatoms selected from nitrogen, oxygen and sulfur, which may be anellated with one or more saturated rings. The preferred monocyclic and bicyclic heteroaryls include benzimidazolyl, benzothiazolyl, benzoxazolyl, benzisoxazolyl, quinazolinyl, quinolyl, quinoxalinyl, cinnolinyl, dihydroindolyl, dihydroisoindolyl, dihydropyranyl, dithiazolyl, furyl, homopiperidinyl, imidazolidinyl, imidazolinyl, imidazolyl, indazolyl, indolyl, isoquinolyl, isoindolyl, isothiazolidinyl, isothiazolyl, isoxazolidinyl, isoxazolyl, morpholinyl, oxadiazolyl, oxazolidinyl, oxazolyl, phthalazinyl, piperazinyl, piperidyl, pteridinyl, purinyl, pyrazolidinyl, pyrazinyl, pyrazolyl, pyrazolinyl, pyridazinyl, pyridyl, pyrimidyl, pyrrolidinyl, pyrrolidin-2-onyl, pyrrolinyl, pyrrolyl, tetrazinyl, tetrazolyl, tetrahydropyrrolyl, thiadiazolyl, thiazinyl, thiazolidinyl, thiazolyl, triazinyl, triazolyl and thiophenyl.

"Arylenes" and "phenylenes" within the meaning of this invention include the bivalent equivalents of the above defined aryl residues.

"Halogen" includes fluorine, chlorine, bromine and iodine.

"Halo-", "halogenated" or "optionally halogenated" residues within the meaning of the present invention include any residues in which one to all H atoms have been replaced by the above mentioned halogen atoms or combinations of such halogen atoms.

"Pharmaceutically acceptable salts" and "salts" within the meaning of the present invention include salts of the compounds with organic acids (such as lactic acid, acetic acid, amino acids, oxalic acid etc.), inorganic acids (such as HCl, HBr, phosphoric acid etc.), and, if the compounds have acid substituents, also with organic or inorganic bases including amino acids. Preferred are salts with HCl.

"Pharmacologically suitable carriers" within the meaning of the present invention are selected by the skilled person, depending on the desired dosage form.

In a preferred embodiment of the compound of aspects (1) to (3) above, the aryl ring, is a thiadiazole, triazole, oxadiazole, isothiadiazole, isooxadiazole, thiazole, oxazole, imidazole, pyrazole, isoxazole, isothiazole, furane, pyrrole or thiene (thiophene);

R1 is —H, OH or lower alkoxy; W and U (if present) are independently selected from CH or N; R2 represents halogen; R3 represents lower alkyl, lower haloalkyl or halogen; R7 represents H or lower alkyl;

R5 represent H, —R, haloalkyl, halogen, —NO$_2$, —CH$_2$R, —OR', —NR'R', —CN, —NR'SO$_2$R, —SO$_2$NR'R', —NR'COR' or —CONR'R', (wherein R is alkyl, aryl, benzyl, an aliphatic or aromatic heterocyclic group, an aliphatic cyclic or heterocyclic ring, each of which may be substituted with up to 5 substituents independently selected from halogen, lower alkyl, lower haloalkyl, OH, —NO$_2$, lower alkoxy, —NH$_2$, phenyl, —CN, —COR", —NHCOR", —CONHR", —NHSO$_2$R" and SO$_2$NHR" (wherein R" is —H, lower alkyl, lower haloalkyl or phenyl); and R' is R or H);

R6 is selected from H, OH, lower alkyl, lower alkoxy, lower haloalkoxy and halogen; and/or R4 represents H, OH, an alkyl or an alkoxy group, each of which may carry phenyl and halogen substituents, wherein said phenyl substituents may carry up to 3 substituents independently selected from —OH, alkyl, haloalkyl, alkoxy, halogen, amino, —CN and —NO$_2$, —CH$_2$R, —NHSO$_2$R and —NHCOR', (wherein R and R' is as defined above), a 6-membered aromatic or hetero aromatic group which may carry 1 to 3 substituents independently selected from —R, haloalkyl, halogen, —NO$_2$, —OR', —NR'R', —CN, —NR'SO$_2$R, —SO$_2$NR'R', —NR'COR', —CONR'R' (wherein R and R' is as defined above) or two of said substituents, together with the adjacent carbon atoms of the 6-membered aromatic group, may form a 5- or 6-membered aliphatic or aromatic, homocyclic or heterocyclic ring condensed to said 6-membered aromatic group, wherein the heterocyclic ring carries up to 3 heteroatoms independently selected from N, S and O, and wherein the third substituent may be located on the 6-membered aromatic group or on the ring condensed thereto, or a 5 or 6-membered, aliphatic or aromatic heterocyclic group which carries up to 3 heteroatoms independently selected from N, S and O and may carry 1 to 3 substituents independently selected from —R, haloalkyl, halogen, —NO$_2$, —OR', —NR'R', —CN, —NR'SO$_2$R, —SO$_2$NR'R', —NR'COR', —CONR'R', (wherein R and R' is as defined above) or two of said substituents, together with the adjacent carbon atoms of the 5 or 6-membered aliphatic or aromatic heterocyclic group, may form a 6-membered, aliphatic or aromatic ring condensed to said 5 or 6-membered aromatic group.

In a particularly preferred embodiment of aspects (1) to (3) above, the aryl ring represents a thiophene; R1 is OH; n is 1 or 2; R2 is F; R3 is lower alkyl, lower kaloalkyl or F; W and U (if present) are independently selected from CH and N; R4 represents H, OH, an alkoxy group, which may carry up to 3 halogen substituents, —CH$_2$R, —SO$_2$R, —NHSO$_2$R and —NRSO$_2$R', (wherein R and R' is as defined above); R7 is selected from H and alkyl; and/or R5 and R6 are independently selected from H, OH, —CN, alkyl, alkoxy and halogen.

In a further preferred embodiment of aspects (1) to (3) above, R1 is a hydroxy group in the meta position relative to the —CO— junction, n is 1 or 2, R2 is F and R3 is CH$_3$, CF$_3$ or F.

In a particularly preferred embodiment of aspects (1) to (5) above, the compounds are selected from the following compounds (1) to (79):

[5-(3-Aminophenyl)thiophen-2-yl](2,6-difluoro-3-hydroxyphenyl)methanone (1).

4-Bromo-N-{3-[5-(2,6-difluoro-3-hydroxybenzoyl)thiophen-2-yl]-phenyl}-2-trifluoromethoxybenzenesulfonamide (2).

N-{3-[5-(2,6-Difluoro-3-hydroxybenzoyl)thiophen-2-yl]phenyl}-2-trifluoromethoxybenzene-sulfonamide (3).

N-{3-[5-(2,6-Difluoro-3-hydroxybenzoyl)thiophen-2-yl]phenyl}-2-trifluoromethylbenzene-sulfonamide (4).

Pyridine-3-sulfonic acid {3-[5-(2,6-difluoro-3-hydroxybenzoyl)-thiophen-2-yl]-phenyl}-amide (5).

1-Methyl-1H-imidazole-4-sulfonic acid {3-[5-(2,6-difluoro-3-hydroxy-benzoyl)thiophen-2-yl]-phenyl}-amide (6).

Cyclopropanesulfonic acid {3-[5-(2,6-difluoro-3-hydroxybenzoyl)-thiophen-2-yl]-phenyl}-amide (7).

(2,6-Difluoro-3-hydroxy-phenyl)-(5-pyridin-4-yl-thiophen-2-yl)-methanone (8).

2,6-Difluoro-3-hydroxy-phenyl)-(5-pyridin-3-yl-thiophen-2-yl)-methanone (9).

(2,6-Difluoro-3-hydroxy-phenyl)-[5-(2,4-difluoro-phenyl)-thiophen-2-yl]-methanone (10).

[5-(3-Chloro-phenyl)-thiophen-2-yl]-(2,6-difluoro-3-hydroxy-phenyl)-methanone (11).

[5-(3-Chloro-4-methoxy-phenyl)-thiophen-2-yl]-(2,6-difluoro-3-hydroxy-phenyl)methanone (12).

[5-(3-Chloro-4-methoxy-phenyl)-4-methyl-thiophen-2-yl]-(2,6-difluoro-3-hydroxy-phenyl)-methanone (13).

[5-(3-Chloro-2-methoxy-phenyl)-thiophen-2-yl]-(2,6-difluoro-3-hydroxy-phenyl)methanone (14).

[5-(3,5-Dichloro-4-methoxy-phenyl)-thiophen-2-yl]-(2,6-difluoro-3-hydroxy-phenyl)-methanone (15).

(2,6-Difluoro-3-hydroxy-phenyl)-[5-(4-methoxy-3,5-dimethyl-phenyl)-thiophen-2-yl]-methanone (16).

(2,6-Difluoro-3-hydroxy-phenyl)-[5-(4-difluoromethoxy-3,5-difluoro-phenyl)thiophen-2-yl]-methanone (17).

5-[5-(2,6-Difluoro-3-hydroxy-benzoyl)-thiophen-2-yl]-2-isopropoxy-benzonitrile (18).

(2,6-Difluoro-3-hydroxy-phenyl)-{5-[4-methoxy-3-(morpholine-4-sulfonyl)phenyl]-thiophen-2-yl}-methanone (19).

[5-(3-Chloro-4-hydroxy-phenyl)-thiophen-2-yl]-(2,6-difluoro-3-hydroxy-phenyl)methanone (20).

[5-(3-Chloro-4-hydroxy-phenyl)-4-methyl-thiophen-2-yl]-(2,6-difluoro-3-hydroxy-phenyl)-methanone (21).

[5-(3-Chloro-2-hydroxy-phenyl)-thiophen-2-yl]-(2,6-difluoro-3-hydroxy-phenyl)methanone (22).

[5-(3,5-Dichloro-4-hydroxy-phenyl)-thiophen-2-yl]-(2,6-difluoro-3-hydroxy-phenyl)-methanone (23).

(2,6-Difluoro-3-hydroxy-phenyl)-[5-(4-hydroxy-3,5-dimethyl-phenyl)-thiophen-2-yl]-methanone (24).

5-[5-(2,6-Difluoro-3-hydroxy-benzoyl)-thiophen-2-yl]-2-hydroxy-benzonitrile (25).

[5-(3-Chloro-4-methoxy-5-methyl-phenyl)-thiophen-2-yl]-(2,6-difluoro-3-hydroxy-phenyl)-methanone (26).

[5-(3-Chloro-4-hydroxy-5-methyl-phenyl)-thiophen-2-yl]-(2,6-difluoro-3-hydroxy-phenyl)-methanone (27).

1-(4-{3-Chloro-5-[5-(2,6-difluoro-3-hydroxy-benzoyl)-thiophen-2-yl]-2-methoxy-benzyl}-piperazin-1-yl)-ethanone (28).

1-(4-{3-Chloro-5-[5-(2,6-difluoro-3-hydroxy-benzoyl)-thiophen-2-yl]-2-hydroxy-benzyl}-piperazin-1-yl)-ethanone (29).

[5-(3-Chloro-4-methoxy-5-piperazin-1-ylmethyl-phenyl)-thiophen-2-yl]-(2,6-difluoro-3-hydroxy-phenyl)-methanone (30).

[5-(3-Chloro-4-methoxy-5-[1,2,3]triazol-1-ylmethyl-phenyl)-thiophen-2-yl]-(2,6-difluoro-3-hydroxy-phenyl)-methanone (31).

[5-(3-Chloro-4-hydroxy-5-[1,2,3]triazol-1-ylmethyl-phenyl)-thiophen-2-yl]-(2,6-difluoro-3-hydroxy-phenyl)-methanone (32).

Cyclopropanesulfonic acid {3-[5-(2,6-difluoro-3-hydroxy-benzoyl)-thiophen-2-yl]-5-methyl-phenyl}-amide (33).

Cyclopropanesulfonic acid {3-[5-(2,6-difluoro-3-hydroxy-benzoyl)-thiophen-2-yl]-5-methyl-phenyl}-methyl-amide (34).

[5-(3-Aminophenyl)thiophen-2-yl](2,4,5-trifluoro-3-hydroxyphenyl)methanone (35).

4-Bromo-N-{3-[5-(2,4,5-trifluoro-3-hydroxybenzoyl)thiophen-2-yl]phenyl}-2-trifluoromethoxybenzenesulfonamide (36).

N-{3-[5-(2,4,5-Trifluoro-3-hydroxybenzoyl)thiophen-2-yl]phenyl}-2-trifluoro-methoxybenzenesulfonamide (37).

N-{3-[5-(2,4,5-Trifluoro-3-hydroxybenzoyl)thiophen-2-yl]phenyl}-2-trifluoro-methylbenzenesulfonamide (38).

[5-(5-Fluoro-pyridin-3-yl)-thiophen-2-yl]-(2,4,5-trifluoro-3-hydroxy-phenyl)methanone (39).

[5-(2,4-Difluoro-phenyl)-thiophen-2-yl]-(2,4,5-trifluoro-3-hydroxy-phenyl)-methanone (40).

(5-(3-Chloro-4-hydroxyphenyl)thiophen-2-yl)(2,4,5-trifluoro-3-hydroxyphenyl)methanone (41).

(5-(3-Fluoro-4-hydroxyphenyl)thiophen-2-yl)(2,4,5-trifluoro-3-hydroxyphenyl)methanone (42).

(5-(1H-Indol-6-yl)thiophen-2-yl)(2,4,5-trifluoro-3-hydroxyphenyl)methanone (43).

3-(5-(2,4,5-Trifluoro-3-hydroxybenzoyl)thiophen-2-yl)benzamide (44).

(5-(3,5-Dichloro-4-methoxyphenyl)thiophen-2-yl)(2,4,5-trifluoro-3-hydroxyphenyl)methanone (45).

(5-(4-Methoxy-3,5-dimethylphenyl)thiophen-2-yl)(2,4,5-trifluoro-3-hydroxyphenyl)methanone (46).

(5-(3-(Hydroxymethyl)phenyl)thiophen-2-yl)(2,4,5-trifluoro-3-hydroxyphenyl)methanone (47).

1-Methyl-N-(3-(5-(2,4,5-trifluoro-3-hydroxybenzoyl)thiophen-2-yl)phenyl)-1H-imidazole-4-sulfonamide (48).

(5-(3,5-Dichloro-4-hydroxyphenyl)thiophen-2-yl)(2,4,5-trifluoro-3-hydroxyphenyl)methanone (49).

(5-(4-Hydroxy-3,5-dimethylphenyl)thiophen-2-yl)(2,4,5-trifluoro-3-hydroxyphenyl)methanone (50).

(5-(4-Methoxyphenyl)thiophen-2-yl)(2,4,5-trifluoro-3-hydroxyphenyl)methanone (51).

(5-(3-Methoxyphenyl)thiophen-2-yl)(2,4,5-trifluoro-3-hydroxyphenyl)methanone (52).

(5-(2-Methoxyphenyl)thiophen-2-yl)(2,4,5-trifluoro-3-hydroxyphenyl)methanone (53).

N-(3-(5-(2,4,5-Trifluoro-3-hydroxybenzoyl)thiophen-2-yl)phenyl)acetamide (54).

(5-(2-Aminophenyl)thiophen-2-yl)(2,4,5-trifluoro-3-hydroxyphenyl)methanone (55).

(5-Phenylthiophen-2-yl)(2,4,5-trifluoro-3-hydroxyphenyl)methanone (56).

(5-(3-Amino-4-methylphenyl)thiophen-2-yl)(2,4,5-trifluoro-3-hydroxyphenyl)methanone (57).

(5-(3-Amino-2-methylphenyl)thiophen-2-yl)(2,4,5-trifluoro-3-hydroxyphenyl)methanone (58).

(5-(3-Amino-4-hydroxyphenyl)thiophen-2-yl)(2,4,5-trifluoro-3-hydroxyphenyl)methanone (59).

(5-(3-Amino-4-methoxyphenyl)thiophen-2-yl)(2,4,5-trifluoro-3-hydroxyphenyl)methanone (60).

(5-(1H-Indol-5-yl)thiophen-2-yl)(2,4,5-trifluoro-3-hydroxyphenyl)methanone (61).

(5-(1H-Indol-4-yl)thiophen-2-yl)(2,4,5-trifluoro-3-hydroxyphenyl)methanone (62).

N-(3-(5-(2,4,5-trifluoro-3-hydroxybenzoyl)thiophen-2-yl)phenyl)methanesulfonamide (63).

N-(4-(5-(2,4,5-trifluoro-3-hydroxybenzoyl)thiophen-2-yl)phenyl)acetamide (64).

(5-(Pyridin-3-yl)thiophen-2-yl)(2,4,5-trifluoro-3-hydroxyphenyl)methanone (65).

(5-(Quinolin-7-yl)thiophen-2-yl)(2,4,5-trifluoro-3-hydroxyphenyl)methanone (66).

(5-(1H-Benzo[d]imidazol-5-yl)thiophen-2-yl)(2,4,5-trifluoro-3-hydroxyphenyl)methanone (67).

(5-(4-Hydroxyphenyl)thiophen-2-yl)(2,4,5-trifluoro-3-hydroxyphenyl)methanone (68).

(5-(3-Hydroxyphenyl)thiophen-2-yl)(2,4,5-trifluoro-3-hydroxyphenyl)methanone (69).

(5-(2-Hydroxyphenyl)thiophen-2-yl)(2,4,5-trifluoro-3-hydroxyphenyl)methanone (70).

(5-(4-Hydroxy-3,5-dimethylphenyl)thiophen-2-yl)(5-fluoro-3-hydroxy-2-methyl-phenyl)methanone (71).

(4,5-Difluoro-3-hydroxy-2-methylphenyl)(5-(4-hydroxy-3,5-dimethylphenyl)thiophen-2-yl)methanone (72).

(5-Methylthiophen-2-yl)(2,4,5-trifluoro-3-hydroxyphenyl)methanone (73).

4-(5-(2,4,5-Trifluoro-3-hydroxybenzoyl)thiophen-2-yl)phenyl sulfamate (74).

4-(5-(2,6-Difluoro-3-hydroxybenzoyl)thiophen-2-yl)benzenesulfonamide (75).

3-(5-(2,6-Difluoro-3-hydroxybenzoyl)thiophen-2-yl)benzenesulfonamide (76).

(6-Chloro-2-fluoro-3-hydroxyphenyl)(5-(3,5-dichloro-4-methoxyphenyl)thiophen-2-yl)methanone (77).

(2-Chloro-6-fluoro-3-hydroxyphenyl)(5-(3,5-dichloro-4-methoxyphenyl)thiophen-2-yl)methanone (78).

(2-Chloro-3-hydroxyphenyl)(5-(4-hydroxy-3,5-dimethylphenyl)thiophen-2-yl)methanone (79).

Pharmaceutically acceptable a salts of said compounds (1) to (79).

The compound for use in a mammal in the treatment and/or prophylaxis of hormone-related diseases in a mammal of aspect (6) above, the pharmaceutical composition or medicament of aspect (8) above, the medicament of aspect (9) above and the method for the treatment and/or prophylaxis of hormone-related diseases in a mammal of aspect (10) above, all of which include the compounds of aspects (1) to (5) above and the particular compounds (1) to (79) as defined above, are particularly suitable for the prophylaxis and/or treatment of estrogen-related diseases in a mammal, notably diseases in which a modulation of the estradiol level is required, such as the treatment and/or prophylaxis of endometriosis, endometrial carcinoma, endometrial hyperplasia, adenomyosis, breast cancer, ovarian carcinoma, osteoporosis, osteopenia, impaired bone fracture healing, prostate cancer, psoriasis, acne, (androgen-dependent) hair loss, colon cancer, vaginal atrophy, hypercholesterolemia, and non-insulin-dependent diabetes mellitus.

The treatment and/or prophylaxis of hormone-related diseases in a mammal as referred to in of aspects (6) and (8) to (11) above includes the treatment and/or prophylaxis of all types of mammals, such as primates (human beings, apes etc.), farm animals (cattle, pig, horse, goat, rabbit etc.), companion animals (dog, cat guinea pig, hamster etc.), rodents (mice, rats etc.) and the like, wherein the treatment and/or prophylaxis of human beings is particularly preferred.

In the following the chemical structures of the particularly preferred inhibitors (1) to (79) of the invention (hereinafter also "title compounds") are shown.

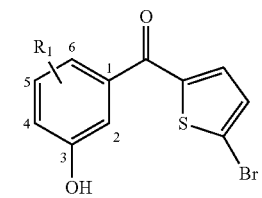

1e, 1g

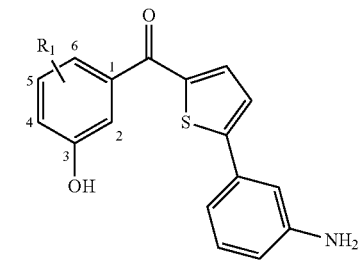

1, 35

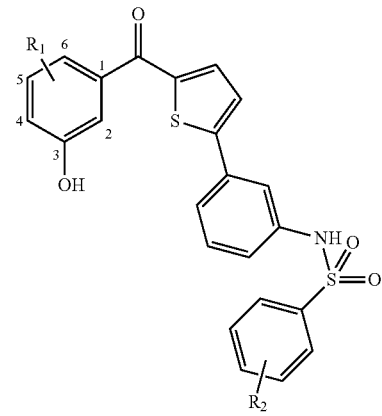

2-4, 36-38

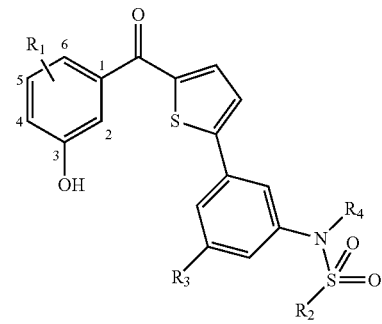

5-7, 33, 34, 48, 63

| Compound | $R_1$ | $R_2$ | $R_3$ | $R_4$ |
|---|---|---|---|---|
| 1e | 2,6-di-F | — | — | — |
| 1g | 2,4,5-tri-F | — | — | — |
| 1 | 2,6-di-F | — | — | — |
| 2 | 2,6-di-F | 4-Br—2-OCF$_3$ | — | — |
| 3 | 2,6-di-F | 2-OCF$_3$ | — | — |
| 4 | 2,6-di-F | 2-CF$_3$ | — | — |

-continued

| Compound | R₁ | R₂ | R₃ | R₄ |
|---|---|---|---|---|
| 5 | 2,6-di-F | 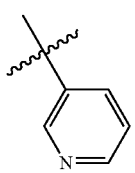 [SMILES: *c1cccnc1] | H | H |
| 6 | 2,6-di-F | 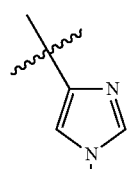 | H | H |
| 7 | 2,6-di-F | 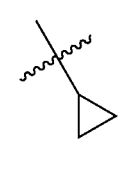 | H | H |
| 33 | 2,6-di-F | 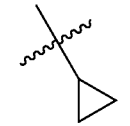 | $CH_3$ | H |
| 34 | 2,6-di-F | 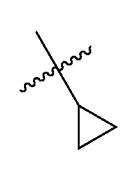 | $CH_3$ | $CH_3$ |
| 35 | 2,4,5-tri-F | — | — | — |
| 36 | 2,4,5-tri-F | 4-Br—2-$OCF_3$ | — | — |
| 37 | 2,4,5-tri-F | 2-$OCF_3$ | — | — |
| 38 | 2,4,5-tri-F | 2-$CF_3$ | — | — |
| 48 | 2,4,5-tri-F | 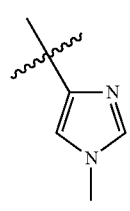 [SMILES: *c1cn(C)cn1] | H | H |
| 63 | 2,4,5-tri-F | $CH_3$ | H | H |

8-10, 39, 40, 65

-continued 11-27, 41-42, 44-47, 49-60, 64, 68-72, 74-79

| Compound | R₁ | R₂ | R₃ | R₄ | R₅ | R₆ |
|---|---|---|---|---|---|---|
| 8 | 2,6-di-F | H | CH | CH | N | H |
| 9 | 2,6-di-F | H | CH | N | CH | H |
| 10 | 2,6-di-F | H | CF | CH | CF | H |
| 11 | 2,6-di-F | H | H | Cl | H | H |
| 12 | 2,6-di-F | H | H | Cl | $OCH_3$ | H |
| 13 | 2,6-di-F | $CH_3$ | H | Cl | $OCH_3$ | H |
| 14 | 2,6-di-F | H | $OCH_3$ | Cl | H | H |
| 15 | 2,6-di-F | H | H | Cl | $OCH_3$ | Cl |
| 16 | 2,6-di-F | H | H | $CH_3$ | $OCH_3$ | $CH_3$ |
| 17 | 2,6-di-F | H | H | F | $OCHF_2$ | F |
| 18 | 2,6-di-F | H | H | CN | $OCH(CH_3)_2$ | H |
| 19 | 2,6-di-F | H | H | —$SO_2$-4-morpholine | $OCH_3$ | H |
| 20 | 2,6-di-F | H | H | Cl | OH | H |
| 21 | 2,6-di-F | $CH_3$ | H | Cl | OH | H |
| 22 | 2,6-di-F | H | OH | Cl | H | H |
| 23 | 2,6-di-F | H | H | Cl | OH | Cl |
| 24 | 2,6-di-F | H | H | $CH_3$ | OH | $CH_3$ |
| 25 | 2,6-di-F | H | H | CN | OH | H |
| 26 | 2,6-di-F | H | H | Cl | $OCH_3$ | $CH_3$ |
| 27 | 2,6-di-F | H | H | Cl | OH | $CH_3$ |
| 39 | 2,4,5-tri-F | H | CH | N | CH | CF |
| 40 | 2,4,5-tri-F | H | CF | CH | CF | CH |
| 41 | 2,4,5-tri-F | H | H | Cl | OH | H |
| 42 | 2,4,5-tri-F | H | H | F | OH | H |
| 44 | 2,4,5-tri-F | H | H | $CONH_2$ | H | H |
| 45 | 2,4,5-tri-F | H | H | Cl | $OCH_3$ | Cl |
| 46 | 2,4,5-tri-F | H | H | $CH_3$ | $OCH_3$ | $CH_3$ |
| 47 | 2,4,5-tri-F | H | H | $CH_2OH$ | H | H |
| 49 | 2,4,5-tri-F | H | H | Cl | OH | Cl |
| 50 | 2,4,5-tri-F | H | H | $CH_3$ | OH | $CH_3$ |
| 51 | 2,4,5-tri-F | H | H | H | $OCH_3$ | H |
| 52 | 2,4,5-tri-F | H | H | $OCH_3$ | H | H |
| 53 | 2,4,5-tri-F | H | $OCH_3$ | H | H | H |
| 54 | 2,4,5-tri-F | H | H | $NHCOCH_3$ | H | H |
| 55 | 2,4,5-tri-F | H | $NH_2$ | H | H | H |
| 56 | 2,4,5-tri-F | H | H | $NH_2$ | H | H |
| 57 | 2,4,5-tri-F | H | H | $NH_2$ | $CH_3$ | H |
| 58 | 2,4,5-tri-F | H | $CH_3$ | $NH_2$ | H | H |
| 59 | 2,4,5-tri-F | H | H | $NH_2$ | OH | H |
| 60 | 2,4,5-tri-F | H | H | $NH_2$ | $OCH_3$ | H |
| 64 | 2,4,5-tri-F | H | H | H | $NHCOCH_3$ | H |
| 65 | 2,4,5-tri-F | H | C | N | C | C |
| 68 | 2,4,5-tri-F | H | H | H | OH | H |
| 69 | 2,4,5-tri-F | H | H | OH | H | H |
| 70 | 2,4,5-tri-F | H | OH | H | H | H |
| 71 | 5-F,2-$CH_3$ | H | H | $CH_3$ | OH | $CH_3$ |
| 72 | 4,5-di-F, 2-$CH_3$ | H | H | $CH_3$ | OH | $CH_3$ |
| 74 | 2,4,5-tri-F | H | H | H | $OSO_2NH_2$ | H |
| 75 | 2,6-di-F | H | H | H | $SO_2NH_2$ | H |
| 76 | 2,6-di-F | H | H | $SO_2NH_2$ | H | H |
| 77 | 6-Cl,2-F | H | H | Cl | OMe | Cl |
| 78 | 2-Cl,6-F | H | H | Cl | OMe | Cl |
| 79 | 2-Cl | H | H | Me | OH | Me |

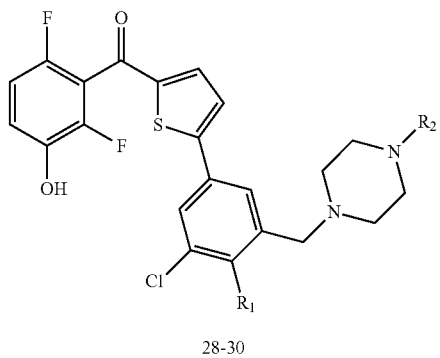

28-30

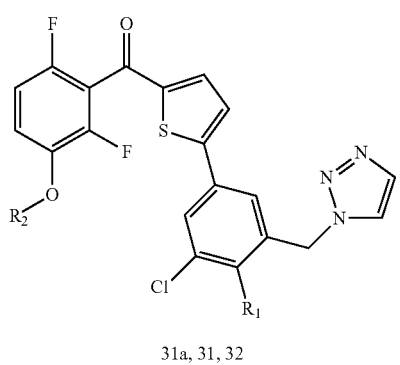

31a, 31, 32

| Compound | R₁ | R₂ |
|---|---|---|
| 28 | OCH₃ | COCH₃ |
| 29 | OH | COCH₃ |
| 30 | OCH₃ | H |
| 31a | OCH₃ | COCH₃ |
| 31 | OCH₃ | H |
| 32 | OH | H |

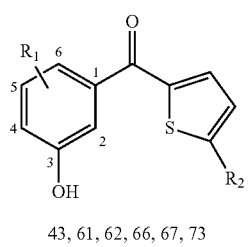

43, 61, 62, 66, 67, 73

| Compound | R₁ | R₂ |
|---|---|---|
| 43 | 2,4,5-tri-F | 1H-indol-6-yl |
| 61 | 2,4,5-tri-F | 1H-indol-5-yl |
| 62 | 2,4,5-tri-F | 1H-indol-4-yl |
| 66 | 2,4,5-tri-F | quinolin-7-yl |
| 67 | 2,4,5-tri-F | 1H-benzo[d]imidazol-5-yl |
| 73 | 2,4,5-tri-F | CH₃ |

Scheme 1: General synthesis of compounds having formula I[a]

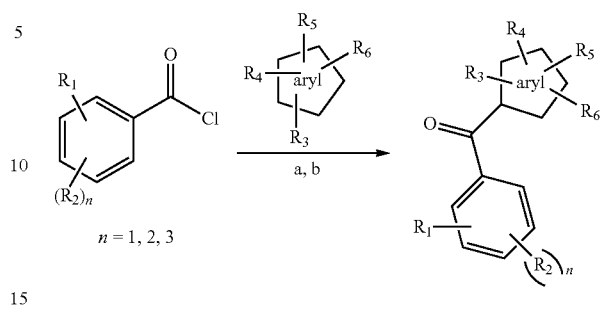

[a]Reagents and conditions:
a method A, AlCl₃, anhydrous CH₂Cl₂, 0° C., 0.5 h and then rt, 3 h.
b method B, BBr₃, CH₂Cl₂, -78° C. to rt, overnight.

Scheme 2: General synthesis of compounds having formula II[a]

[a]Reagents and conditions:
a method A, AlCl₃, anhydrous CH₂Cl₂, 0° C., 0.5 h and then rt, 3 h.
b method C₁, Cs₂CO₃, Pd(PPh₃)₄, DME/water (1:1), reflux, 4 h; or method C2, Na₂CO₃ (2M), Pd(PPh₃)₄, toluene/ethanol (1:1), reflux, overnight.
c method B, BBr₃, CH₂Cl₂, -78° C. to rt, overnight.
d method D, pyridine, corresponding sulfonyl chloride, rt, overnight.
e HCl 6M, reflux, 2 h.
f NaH, DMF, MeI, 0° C. to rt, 0.5 h.

Scheme 3: Synthesis of compounds 1e, 1g, 1-25, 35-78[a]
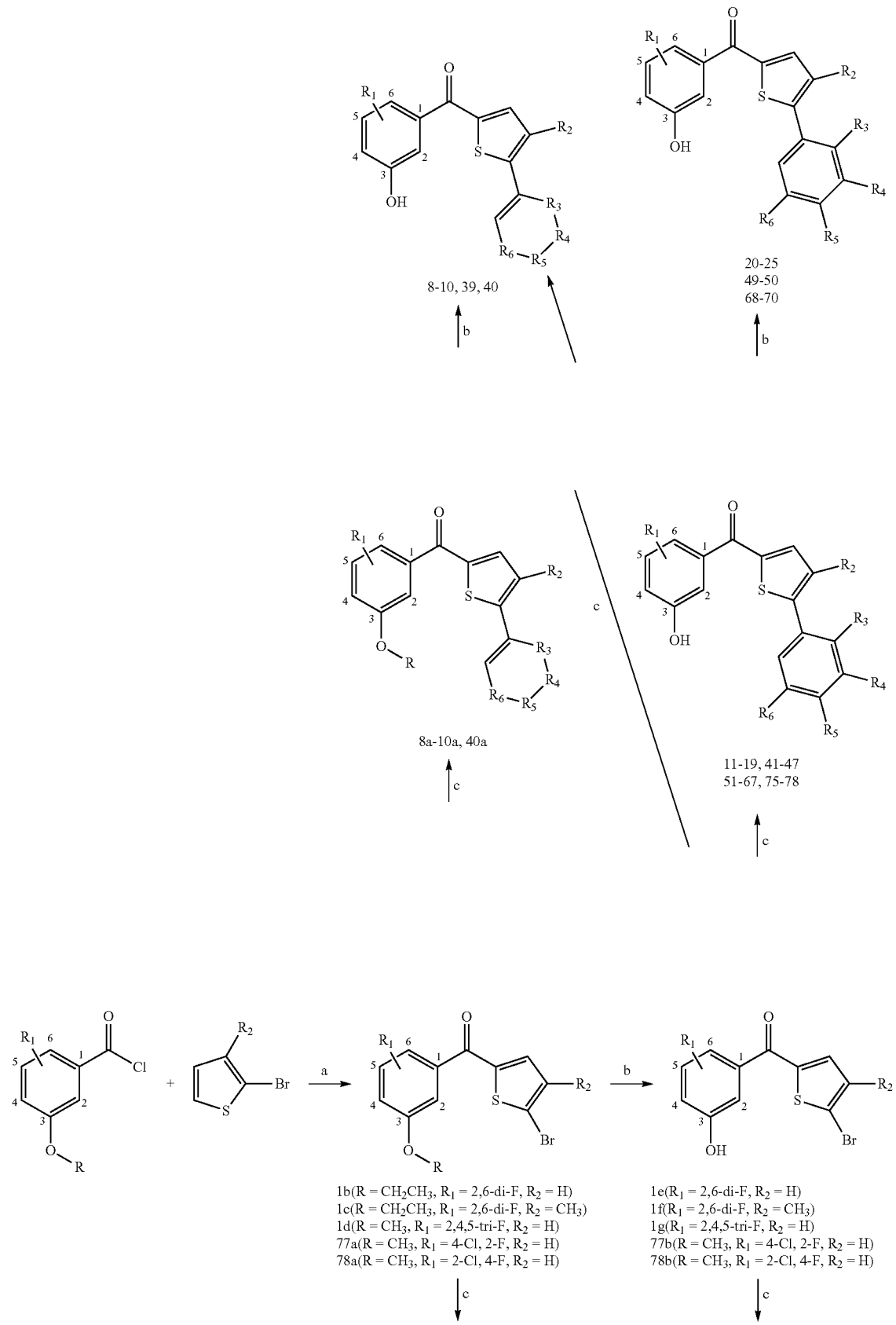

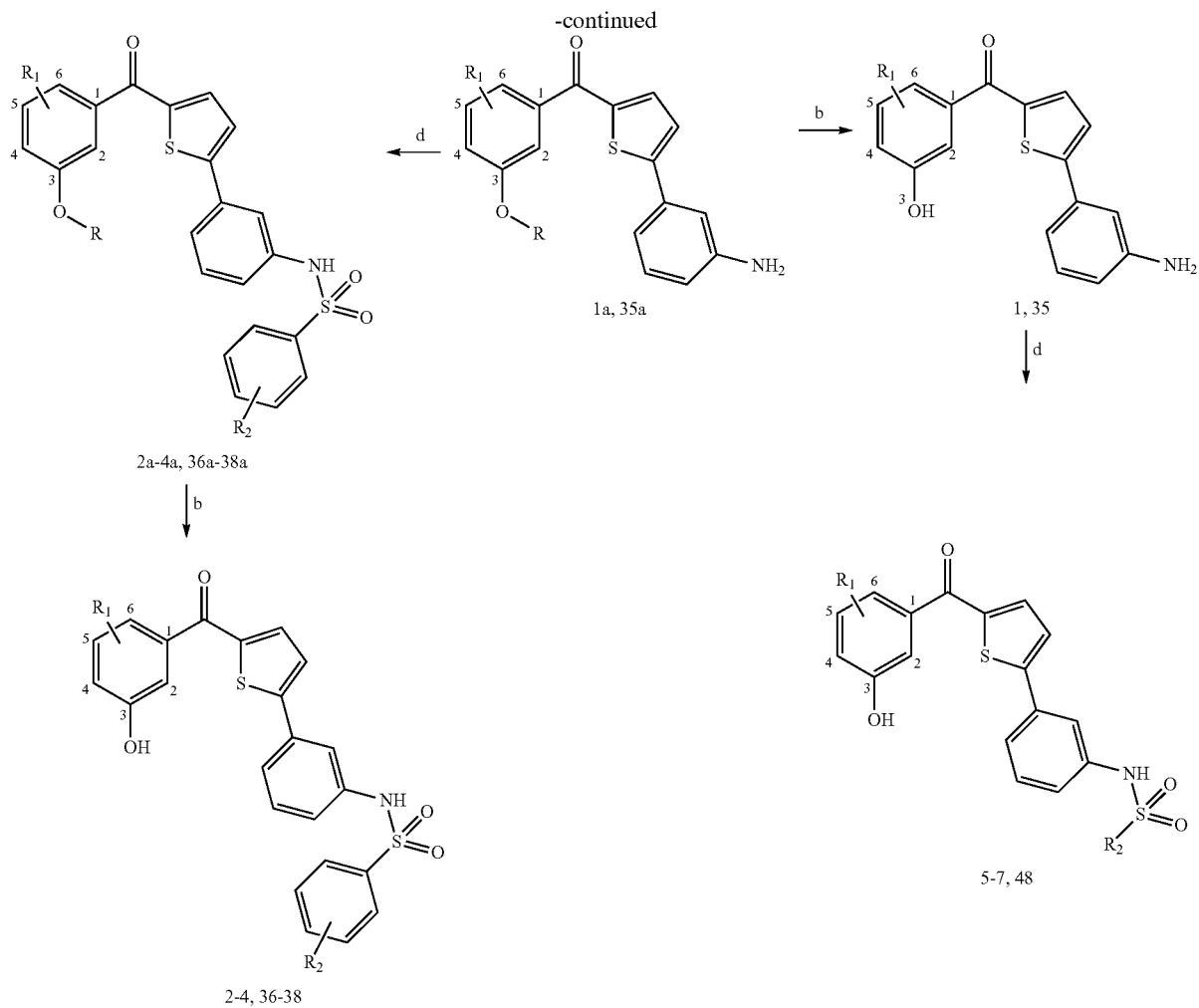

*Reagents and conditions:
a method A, AlCl₃, anhydrous CH₂Cl₂, 0° C., 0.5 h and then rt, 3 h.
b method B, BBr₃, CH₂Cl₂, -78° C. to rt, overnight.
c method C1, corresponding boronic acid for (1, 1a, 10-19), Cs₂CO₃, Pd(PPh₃)₄, DME/water (1:1), reflux, 4 h; method C2, 4-pyridinylboronic acid pinacol ester for (8a), 3-pyridinylboronic acid for (9a), 5- fluoro-3-pyridinylboronic acid for (39), (7-(4,4,5,5-tetramethyl-1,3,2-dioxaborolan-2-yl)quinolone (66a) for (66), Na₂CO₃ (2M), Pd(PPh₃)₄, toluene/ethanol (1:1), reflux, overnight; method C3, corresponding boronic acid for (41-47, 51-67, 75-78), Cs₂CO₃, Pd(PPh₃)₄, toluene/DME/water (0.7:0.9:2), 85° C., 16 h.
d method D1, pyridine, corresponding su;fonyl chloride, rt, overnight; method D2, pyridine, corrseponding sulfonyl chloride, CH₂Cl₂, rt, overnight.

Scheme 4: Synthesis of compounds 27-30ᵃ

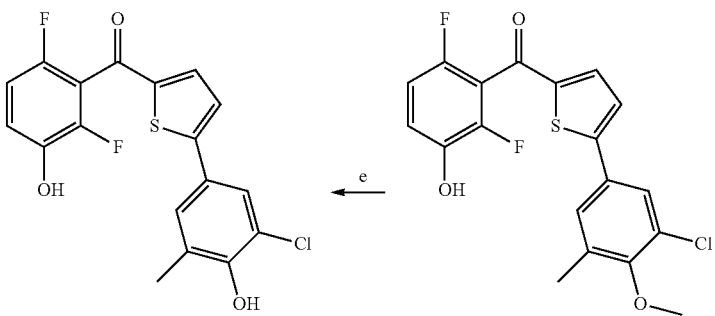

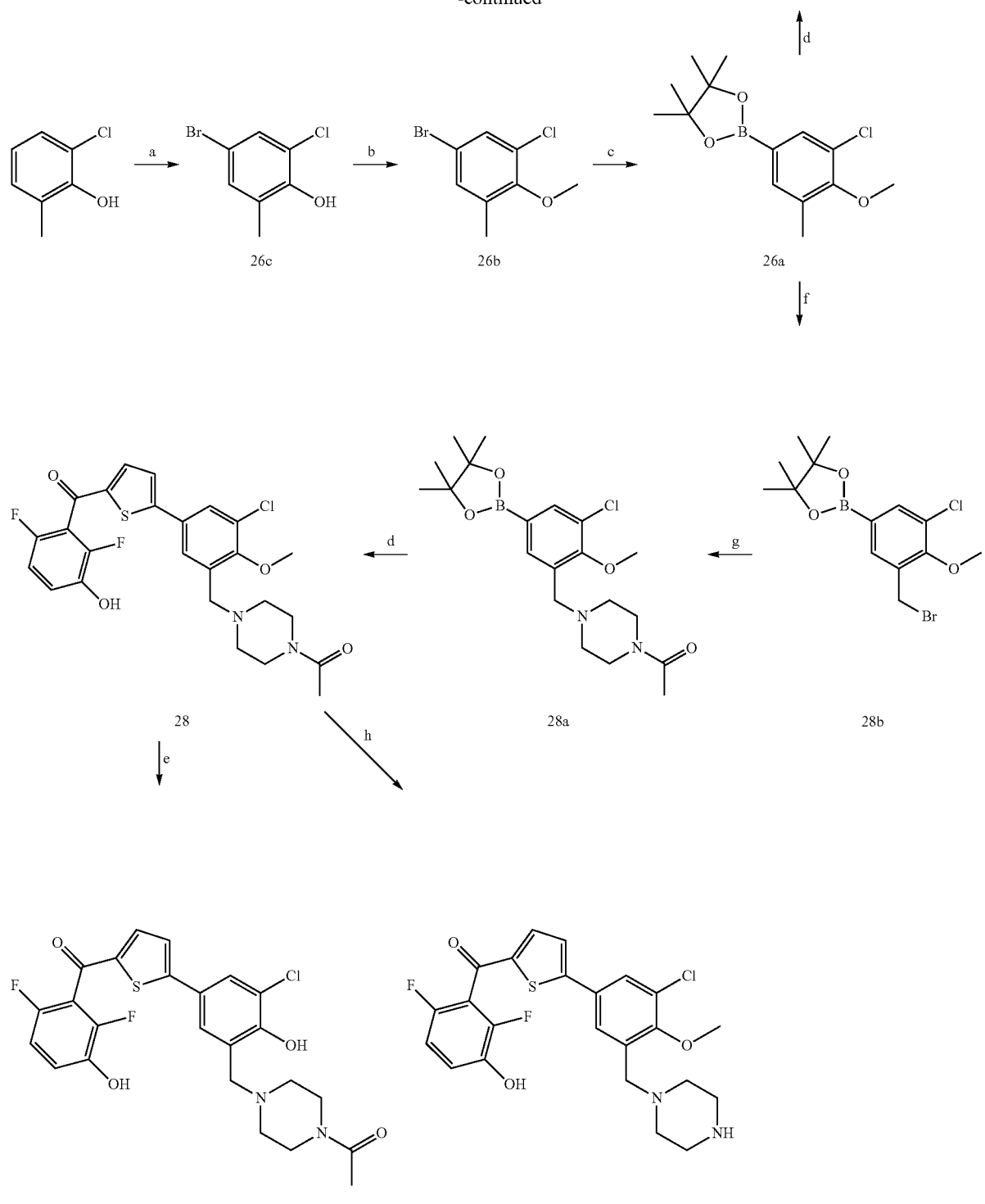
-continued
$^a$Reagents and conditions:
a NBS, AcOH, rt, overnight.
b CH$_3$I, K$_2$CO$_3$, DMF, rt, overnight.
c bispinocolato diborane, PddppCl$_2$, KOAc/DMSO, 2 h.
d method C$_1$, 1e, Cs$_2$CO$_3$, Pd(PPh$_3$)$_4$, DME/water (1:1), reflux, overnight.
e method B, BBr$_3$, CH$_2$Cl$_2$, -78° C. to rt, overnight.
f NBS, DBPO, CCl$_4$, reflux, 2 h.
g NEt$_3$, 1-piperazine-1-yl-ethanone.
h HCl 6M, reflux, 2 h.

Scheme 5: Synthesis of compounds 31a, 31, 32[a]
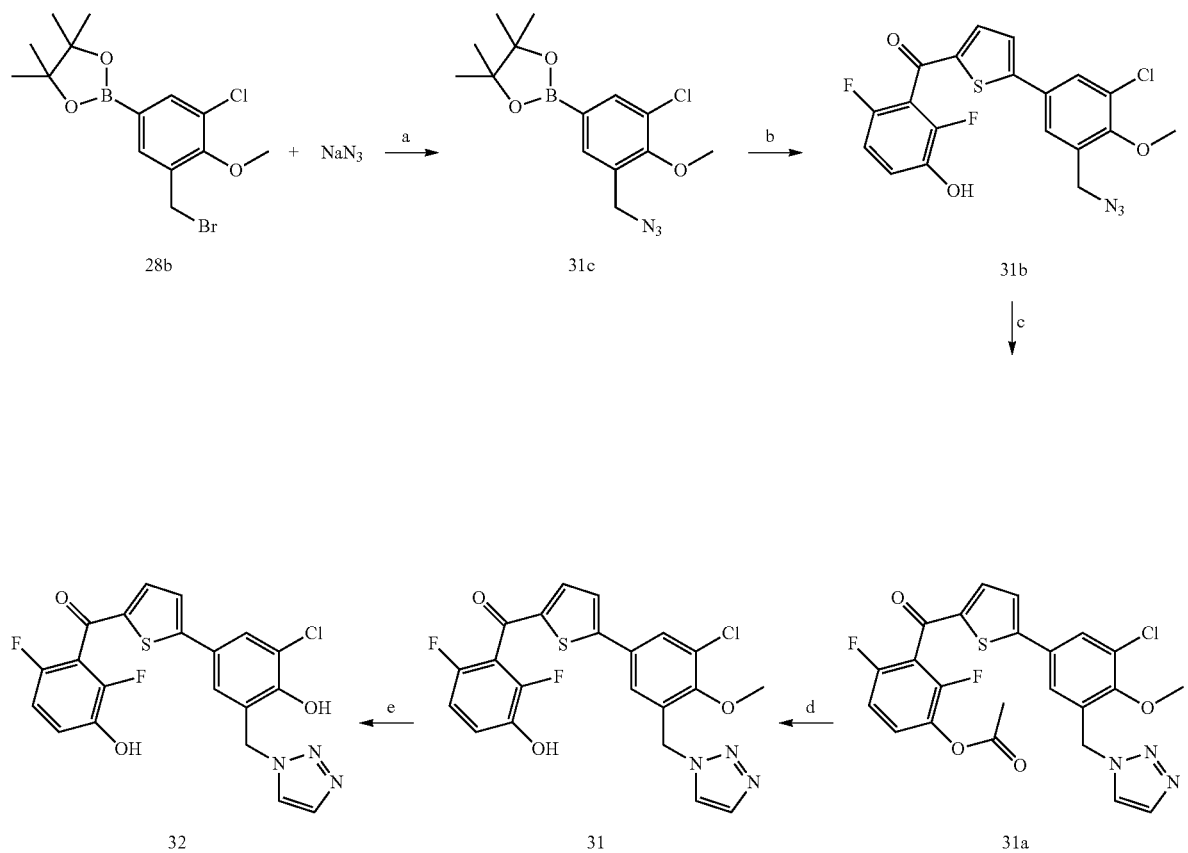
[a] Reagents and conditions:
a DMF, rt, overnight.
b method C1, 1e, Cs$_2$CO$_3$, Pd(PPh$_3$)$_4$, DME/water (1:1), reflux, overnight.
c CH$_3$COOCH═CH$_2$, microwave, 120° C.,
d 2M NaOH, THF, rt, 2 h.
e method B, BBr$_3$, CH$_2$Cl$_2$, -78° C. to rt, overnight.
Scheme 6: Synthesis of compounds 33, 34[a]
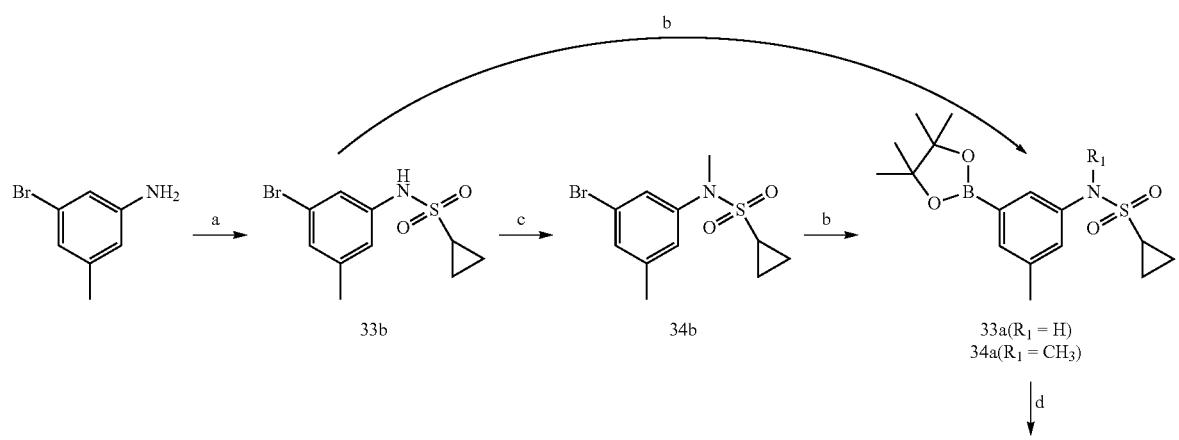

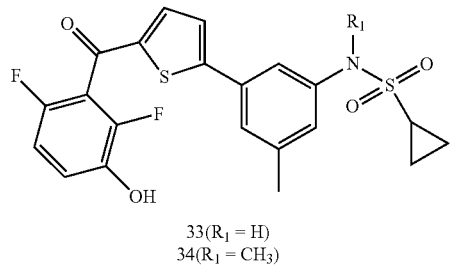

33($R_1$ = H)
34($R_1$ = $CH_3$)

[a]Reagents and conditions:
a method D, pyridine, cyclopropanesulfonyl chloride, rt, overnight.
b bispinacolato diborane, Pd(dppf)$Cl_2$, KOAc/DMSO, 2 h.
c NaH, DMF, MeI, 0° C. to rt, 0.5 h.
d method C1, 1e, $Cs_2CO_3$, Pd($PPh_3$)$_4$, DME/water (1:1), reflux, 3 days.

Scheme 7: Synthesis of compounds 58a, 59a, 60a, 62a, 66a, 76a[a]

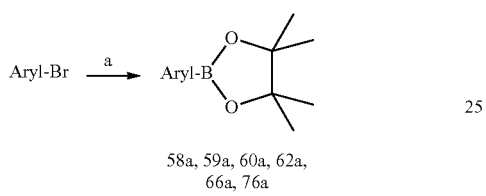

58a, 59a, 60a, 62a, 66a, 76a

[a]Reagents and conditions:
a bispinacolato diborane, Pd(dppf)$Cl_2$, KOAc/DMSO or Dioxane, 40 to 80° C., 30 min to 72 h.

Scheme 8: Synthesis of compound 71[a]

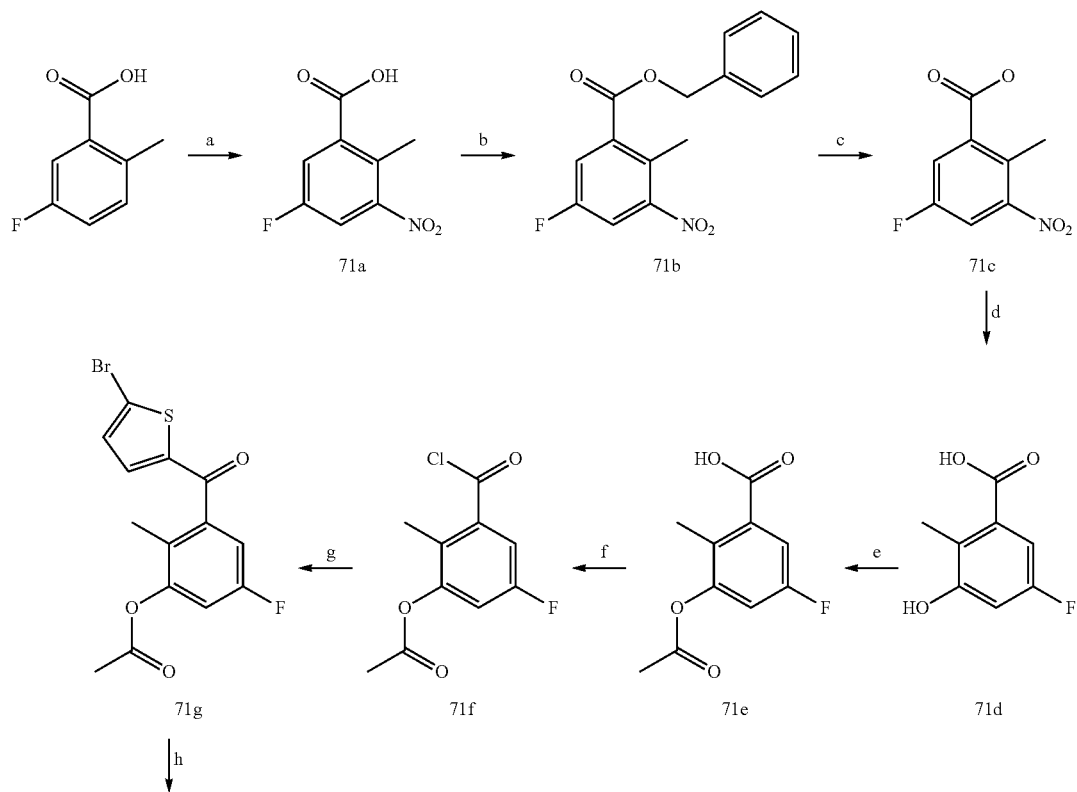

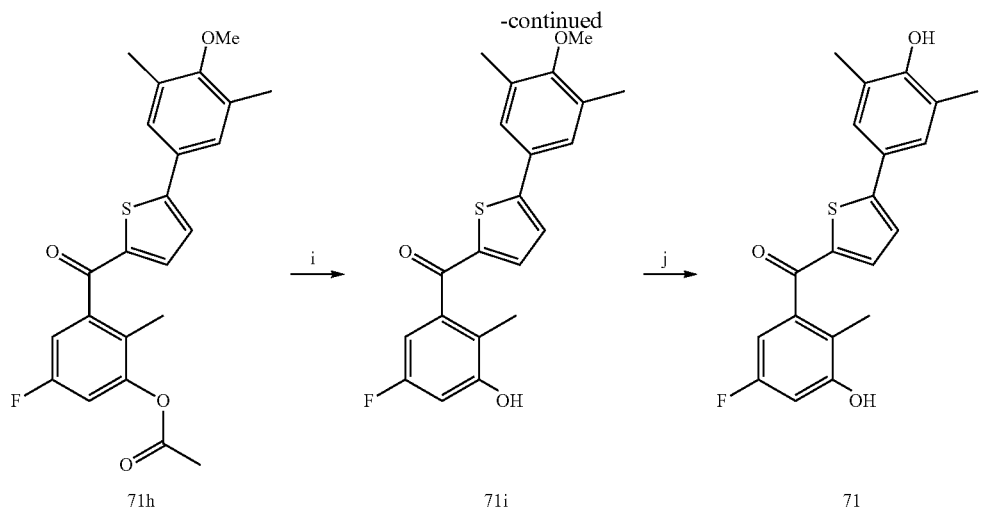
71h, 71i, 71
<sup>a</sup>Reagents and conditions:
a H₂SO₄, HNO₃, 0° C., 1 h.
b BnBr, K₂CO₃, DMF, 50° C., 1.5 h.
c H₂, Pd/C, MeOH, rt, 41.5 h.
d NaNO₂, H₂O, H₂SO₄, 0° C., 2 h then reflux, 15 min.
e Ac₂O, DMAP, rt, 15 h,
f SOCl₂, rt, 14 h then 80° C., 1 h.
g 2-bromothiophene, AlCl₃, DCM, 0° C., 1 h, rt, 4 h.
h method C3.
i NaOH, THF, methanol, water, rt, overnight.
j Method B.
Scheme 9: Synthesis of compound 72<sup>a</sup>
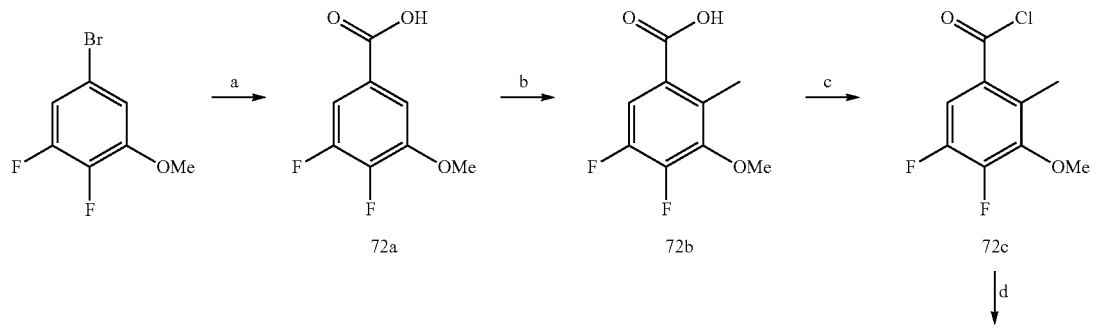
72a, 72b, 72c

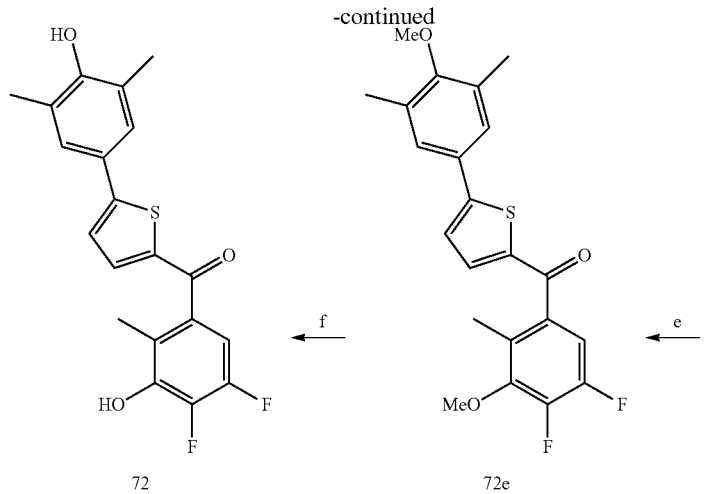

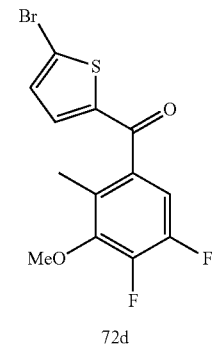

*Reagents and conditions:
a Mg, Et$_2$O, reflux, 2 h, then CO$_2$, THF, 10° C., 4 h.
b n-BuLi, 2,2,6,6-tetramethylmpiperidine, THF, −78° C., 15 min then 0° C., 1 h, MeI, 0° C., 20 min then 40° C., 1.5 h.
c SOCl$_2$, rt, 14 h.
d method A.
e method C3.
f method B.

Scheme 10: Synthesis of compound 73$^a$

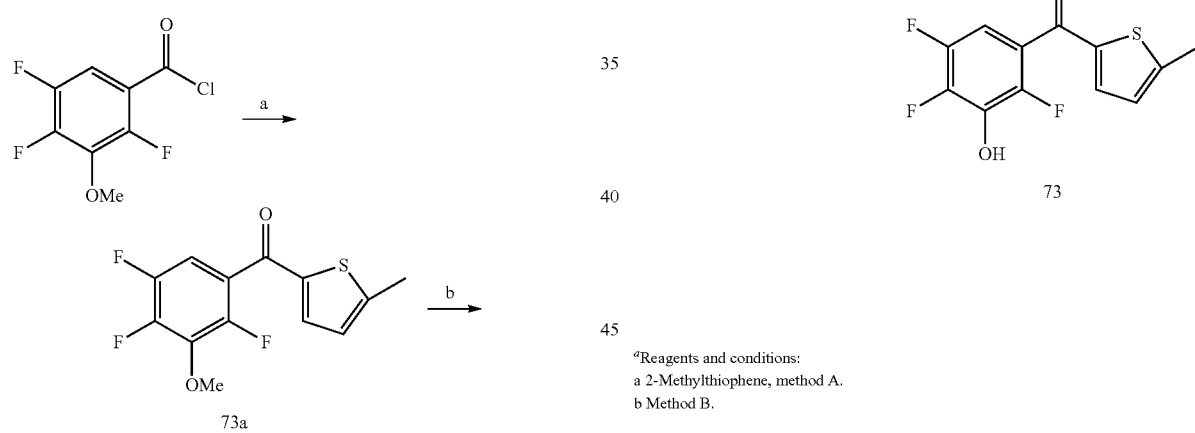

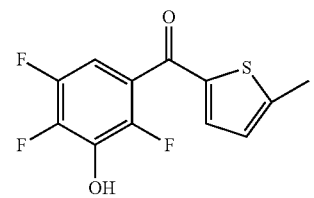

*Reagents and conditions:
a 2-Methylthiophene, method A.
b Method B.

Scheme 11: Synthesis of compound 74$^a$

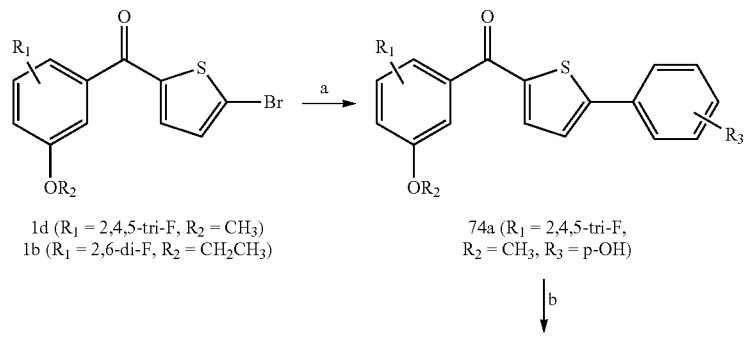

1d (R$_1$ = 2,4,5-tri-F, R$_2$ = CH$_3$)
1b (R$_1$ = 2,6-di-F, R$_2$ = CH$_2$CH$_3$)

74a (R$_1$ = 2,4,5-tri-F,
R$_2$ = CH$_3$, R$_3$ = p-OH)

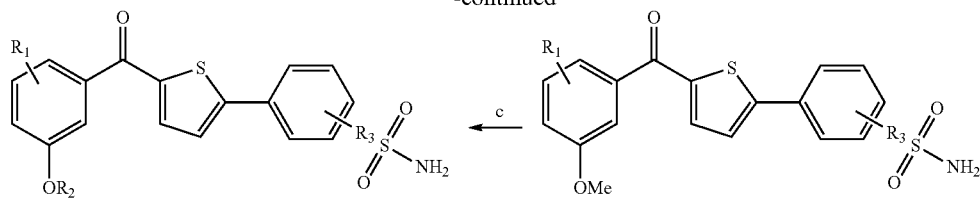

74 (R₁ = 2,4,5-tri-F, R₂ = CH₃, R₃ = p-OH)  74b (R₁ = 2,4,5-tri-F, R₂ = CH₃, R₃ = p-OH)

[a] Reagents and conditions:
a Method C3.
b Sulfamoyl chloride, N,N-dimethylacetamide, 0° C., 2 h.
c Method B.

Scheme 12: Synthesis of compound 79[a]

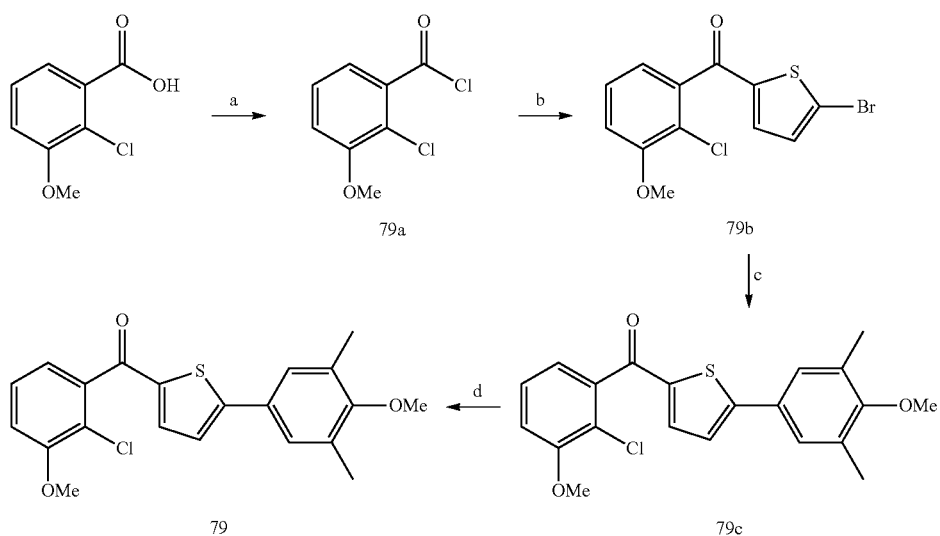

[a]Reagents and conditions:
a SOCl₂, reflux, 1 h.
b Method A.
c Method C1.
d Method B.

The invention is further described and illustrated in the following examples, which are however not to be construed as limiting the invention.

EXAMPLES

Chemical Methods: Chemical names follow IUPAC nomenclature. Starting materials were purchased from Aldrich, Acros, Lancaster, Maybridge, Combi Blocks, Merk, or Fluka and were used without purification.

Column chromatography (CC) was performed on silica gel (70-200 μm), reaction progress was monitored by thin layer chromatography (TLC) on Alugram SIL G UV$_{254}$ (Macherey-Nagel).

In case of preparative HPLC purification the compounds were purified using a setup produced by Waters Corporation containing a 2767 Sample Manager, a 2545 binary gradient pump, a 2998 PDA detector and a 3100 electron spray mass spectrometer. The system has been used for a part of the analytical analysis as well as the preparative separation. In the latter case after separation the solvent flow has been split using a flow splitter and a 515 HPLC pump for makeup flow. Water containing 0.1% formic acid and acetonitrile containing 0.1% formic acid were used as solvents for the analysis and separation. A Waters X-Bridge column (C18, 150×4.6 mm, 5 μM) has been used with a flow of 1 ml/min for the analysis and a Waters X-Bridge column (C18, 150×19 mm, 5 μM) has been used with a flow of 20 ml/min for the separation.

All microwave irradiation experiments were carried out in a CEM-Discover monomode microwave apparatus.

$^1$H NMR and $^{13}$C NMR spectra were measured on a Bruker AM500 spectrometer (500 MHz) at 300 K or on a Bruker Fourier300 (300 MHz) at 295.5 K. Chemical shifts are reported in δ (parts per million: ppm), by reference to the hydrogenated residues of deuteriated solvent as internal standard (CDCl3: δ=7.24 ppm ($^1$H NMR) and δ=77 ppm ($^{13}$C NMR), CD$_3$OD: δ=3.35 ppm ($^1$H NMR) and δ=49.3 ppm ($^{13}$C NMR), CD$_3$COCD$_3$: δ=2.05 ppm ($^1$H NMR) and δ=29.9 ppm ($^{13}$C NMR), CD$_3$SOCD$_3$ δ=2.50 ppm ($^1$H NMR) and δ=39.5 ppm ($^{13}$C NMR)). Signals are described as s, br. s, d, t, dd, ddd, m, dt, q, sep for singlet, broad singlet, doublet, triplet, doublet of doublets, doublet of doublets of doublets, multiplet, doublet of triplets, quadruplet, and septet respectively. All coupling constants (3) are given in hertz (Hz).

Mass spectra (ESI) has been recorded on a TSQ Quantum (Thermo Finnigan) instrument or on the system mentioned above.

Tested compounds are >95% chemical purity as measured by HPLC.

Example 1

Preparation of the Title Compounds

General Procedure for Friedel-Crafts Acylation. Method A: An ice-cooled mixture of monosubstituted thiophene derivate (1 or 1.5 equiv), arylcarbonyl chloride (1 equiv), and aluminumtrichloride (1 equiv) in anhydrous dichloromethane was warmed to room temperature and stirred for 2-4 h. 1M HCl was used to quench the reaction. The aqueous layer was extracted with ethyl acetate. The combined organic layers were washed with brine, dried over magnesium sulfate, filtered, and concentrated to dryness. The product was purified by CC.

General Procedure for Ether Cleavage. Method B: To a solution of methoxybenzene derivative (1 equiv) in anhydrous dichloromethane at -78 OC (dry ice/acetone-d6 bath), boron tribromide in dichloromethane (1M, 3 equiv per methoxy function) was added dropwise. The reaction mixture was stirred overnight at room temperature under nitrogen atmosphere. Water was added to quench the reaction, and the aqueous layer was extracted with ethyl acetate. The combined organic layers were washed with brine, dried over magnesium sulfate, filtered, and concentrated to dryness. The product was purified by CC.

General Procedure for Suzuki Coupling. Method C1: A mixture of arylbromide (1 equiv), boronic acid derivative (1.2 equiv), cesium carbonate (4 equiv) and tetrakis(triphenylphosphine) palladium (0.01 equiv) was suspended in an oxygen-free DME/water (1:1) solution and refluxed under nitrogen atmosphere. The reaction mixture was cooled to room temperature. The aqueous layer was extracted with ethyl acetate. The combined organic layers were washed with brine, dried over magnesium sulfate, filtered and concentrated to dryness. The product was purified by CC.

Method C2: A mixture of arylbromide (1 equiv), boronic acid derivative (1.2 equiv), sodium carbonate (2 equiv) and tetrakis(triphenylphosphine) palladium (0.01 equiv) was suspended in an oxygen-free toluene/ethanol (1:1) solution was refluxed for 20 h under nitrogen atmosphere. The aqueous layer was extracted with ethyl acetate. The combined organic layers were washed with brine, dried over magnesium sulfate, filtered and concentrated to dryness. The product was purified by CC.

Method C3: A mixture of arylbromide (1 equiv), boronic acid derivative (1.1 equiv), cesium carbonate (3.5 equiv) and tetrakis(triphenylphosphine) palladium (0.035 equiv) was suspended in an oxygen-free toluene/DME/water (0.7:0.9:2) solution and heated under argon atmosphere to 85° C. for 16 h. The reaction mixture was cooled to room temperature. Water was added and the aqueous layer was extracted with ethyl acetate three times. The combined organic layers were dried over magnesium sulfate, filtered and concentrated to dryness. The product was purified by preparative HPLC.

General Procedure for Sulfonamide/Amide Coupling. Method D1: The amino phenyl derivative (1 equiv) was dissolved in pyridine absolute and was spiked with sulfonyl chloride/acid chloride (1.5 equiv). The reaction mixture was stirred overnight at rt (refluxed in case of amide coupling). The reaction was quenched by adding 10 ml of 2N HCl and extracted with ethyl acetate. The organic layers were washed with saturated sodium hydrogenocarbonate and brine, dried over magnesium sulfate, filtered and concentrated to dryness. The product was purified by CC.

Method D2: The amino phenyl derivative (1 equiv) and absolute pyridine (3 equiv) was dissolved in dichloromethane and was spiked with sulfonyl chloride (1.1 equiv). The reaction mixture was stirred for 24 h at rt and 4 h at reflux. The reaction was quenched by adding water and extracted three times with ethyl acetate. The organic layers were dried over magnesium sulfate, filtered and concentrated to dryness. The product was purified by preparative HPLC.

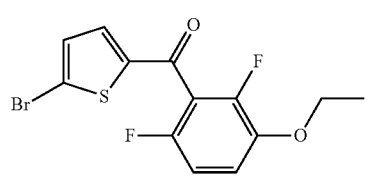

1b

5-Bromo-thiophen-2-yl)-(3-ethoxy-2,6-difluoro-phenyl)-methanone (1b): The title compound was prepared by reaction of 2-bromothiophene (2217 mg, 13.60 mmol), 2,6-difluoro-4-ethoxybenzoyl chloride (3000 mg, 13.60 mmol) and aluminum chloride (1813 mg, 13.60 mmol) according to method A. The product was purified by CC (hexane/ethyl acetate 97:3); yield: 79% (3740 mg). $^1$H NMR (300 MHz, acetone-d$^6$) δ 7.34 (dd, J=4.1, 0.9 Hz, 1H), 7.20-7.22 (m, 2H), 6.98 (td, J=9.0, 2.0 Hz, 1H), 4.05 (q, J=7.0 Hz, 2H), 1.27 (t, J=7.0 Hz, 3H); $^{13}$C NMR (75 MHz, acetone-d$^6$) δ 179.03, 153.83, 153.76, 150.63, 145.09, 136.88, 132.66, 128.96, 124.50, 117.19, 117.06, 65.44, 14.08; $^{13}$C NMR (75 MHz, Acetone-d$^6$) δ 179.03, 152.19 (dd, J=242.2, 5.8 Hz), 148.69 (dd, J=250.5, 7.4 Hz), 145.09, 143.94 (dd, J=10.6, 3.3 Hz), 136.88, 132.66, 128.96, 124.50, 117.11 (dd, J=9.3, 3.2 Hz), 111.26 (dd, J=22.6, 4.1 Hz), 65.44, 14.08; MS (ESI): 448.64 (M+H)$^+$.

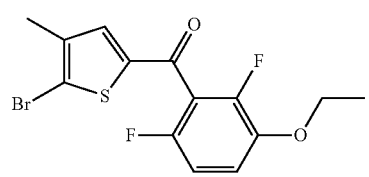

1c (5-Bromo-4-methyl-thiophen-2-yl)-(3-ethoxy-2,6-difluoro-phenyl)-methanone (1c): The title compound was prepared by reaction of 2-bromo-3-methoxy-thiophene (1204 mg, 6.80 mmol), 2,6-difluoro-4-ethoxybenzoyl chloride (1000 mg, 4.53 mmol) and aluminum chloride (604 mg, 4.53 mmol) according to method A. The product was purified by CC (hexane/ethyl acetate 97:3); 49% (800 mg). MS (ESI): 362.09 (M+H)$^+$.

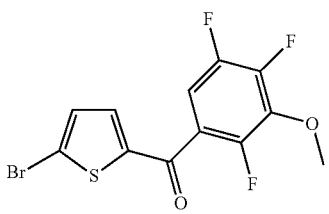

1d

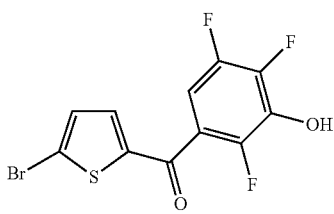

1g (5-Bromo-thiophen-2-yl)-(2,4,5-trifluoro-3-methoxy-phenyl)-methanone (1d): A mixture of 2-bromothiophene (3000 mg, 18.4 mmol), 2,4,5-trifluoro-3-methoxybenzoyl chloride (4132 mg, 18.4 mmol) and aluminium chloride (2453 mg, 18.4 mmol) in anhydrous dichloromethane was stirred at 0° C. for 30 min. The reaction mixture was warmed to rt and stirred for 1 h. HCl 1M was used to quench the reaction. The aqueous layer was extracted with ethyl acetate. The combined organic layers were washed with brine, dried over magnesium sulfate, filtered and concentrated to dryness. The product was purified by CC (hexan/ethyl acetate 97:3), yield 75% (5845 mg); $^1$H NMR (300 MHz, acetone-$d^6$) δ 7.41 (dd, J=4.1, 1.9 Hz, 1H), 7.28-7.19 (m, 2H), 3.97 (t, J=1.2 Hz, 3H); $^{13}$C NMR (75 MHz, acetone-$d^6$) δ 180.99, 151.02, 149.48, 147.76, 144.68, 136.99, 136.95, 132.45, 124.04, 110.44, 110.12, 61.86.

(5-Bromo-thiophen-2-yl)-(2,4,5-trifluoro-3-hydroxy-phenyl)-methanone (1g): The title compound was prepared by reaction of (5-bromothiophen-2-yl)(2,4,5-trifluoro-3-methoxyphenyl)methanone (1d) (3000 mg, 8.64 mmol) and boron tribromide (43.2 mmol) according to method B. The product was purified by CC (hexan/ethyl-acetate 9:1); yield: 84% (2310 mg). $^1$H NMR (300 MHz, acetone-$d^6$) δ 9.85 (s, 1H, OH), 7.40 (dd, J=4.1, 1.8 Hz, 1H), 7.23 (t, J=4.4 Hz, 1H), 6.99 (ddd, J=10.0, 8.1, 5.6 Hz, 1H); $^{13}$C NMR (75 MHz, acetone-$d^6$) δ 181.29, 148.81 (dd, J=11.1, 3.1 Hz), 148.37 (dd, J=16.2, 2.3 Hz), 144.80, 144.64 (dd, J=6.6, 2.3 Hz), 141.26 (dd, J=15.9, 5.8 Hz), 136.83 (d, J=2.3 Hz), 136.20 (dd, J=30.7, 3.2 Hz), 132.40, 123.83, 106.16 (dd, J=21.2, 3.0 Hz).

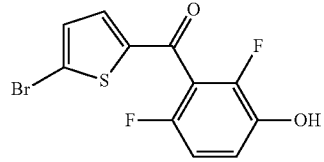

1e

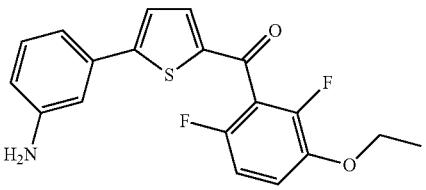

1a (5-Bromo-thiophen-2-yl)-(2,6-difluoro-3-hydroxy-phenyl)-methanone (1e): The title compound was prepared by reaction of 5-bromo-thiophen-2-yl)-(3-ethoxy-2,6-difluoro-phenyl)-methanone (1b) (3000 mg, 8.64 mmol) and boron tribromide (43.20 mmol, 5 equiv) according to method B. The product was purified by CC (hexane/ethyl acetate 90:10); yield: 84% (2310 mg). MS (ESI): 320.12 (M+H)$^+$. The product was used in the next steps without any characterisation.

[5-(3-Aminophenyl)thiophen-2-yl](3-ethoxy-2,6-difluorophenyl)methanone (1a): The title compound was prepared by reaction of (5-bromothiophen-2-yl)(3-ethoxy-2,6-difluorophenyl)methanone (1b) (450 mg, 1.30 mmol) and 3-aminophenyl-boronic acid (213 mg, 1.55 mmol), cesium carbonate (1689 mg, 5.18 mmol) and tetrakis(triphenylphosphine) palladium (20 mg, 16 μmol) according to method C1. The product was used directly in the subsequent reaction without any characterisation; yield: 88% (410 mg).

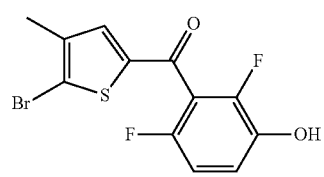

1f

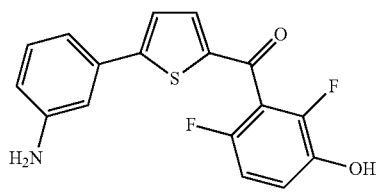

1

(5-Bromo-4-methyl-thiophen-2-yl)-(2,6-difluoro-3-hydroxy-phenyl)-methanone (1f): The title compound was prepared by reaction of (5-bromo-4-methyl-thiophen-2-yl)-(3-ethoxy-2,6-difluoro-phenyl)-methanone (1c) (850 mg, 2.35 mmol) and boron tribromide (11.76 mmol, 5 equiv) according to method B. The product was used in the next step without further purification and characterisation; yield: 77% (600 mg).

[5-(3-Aminophenyl)thiophen-2-yl](2,6-difluoro-3-hydroxyphenyl)methanone (1): The title compound was prepared by reaction of [5-(3-aminophenyl)thiophen-2-yl]-(3-ethoxy-2,6-difluorophenyl)methanone (1a) (440 mg, 1.22 mmol) and boron tribromide (3.7 mmol) according to method B. The product was purified by CC (dichloromethane/methanol 99.5:0.5); yield: 50% (200 mg). $^1$H NMR (500 MHz, acetone-$d^6$) δ 9.02 (br. s, 1H), 7.45 (dd, J=7.1, 2.9 Hz, 1H), 7.33 (d, J=4.1 Hz, 1H), 7.10 (dd, J=41.1, 6.5 Hz, 2H), 7.00-6.85 (m, 3H), 6.62 (ddd, J=8.0, 2.1, 0.8 Hz, 1H), 4.75

(br. s, 2H, NH₂); ¹³C NMR (125 MHz, acetone-d⁶) δ 179.48, 155.98, 152.23 (dd, J=241.6, 6.1 Hz), 149.34, 148.66 (dd, J=249.5, 7.7 Hz), 143.90 (dd, J=10.7, 3.2 Hz), 137.34, 133.47, 129.97, 125.13, 124.46, 121.00, 116.62 (dd, J=9.3, 3.0 Hz), 115.73, 114.65, 111.62, 111.13 (dd, J=22.7, 4.1 Hz); MS (ESI): 332.12 (M+H)⁺.

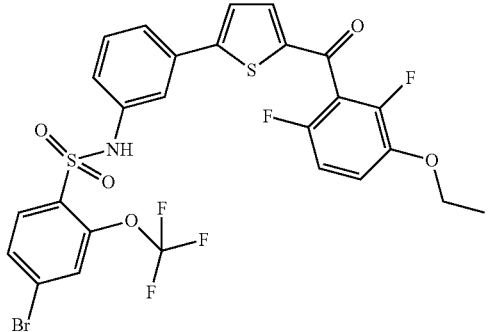

2a

4-Bromo-N-{3-[5-(3-ethoxy-2,6-difluorobenzoyl)thiophen-2-yl]phenyl}-2-trifluoro-methoxy-benzenesulfonamide (2a): The title compound was prepared by reaction of [5-(3-aminophenyl)thiophen-2-yl](3-ethoxy-2,6-difluorophenyl)methanone (1a) (210 mg, 0.58 mmol) and 4-bromo-2-trifluoromethoxybenzenesulfonyl chloride (198 mg, 0.58 mmol) according to method D1.; yield: 65% (250 mg). The product was used in the next steps without any characterisation.

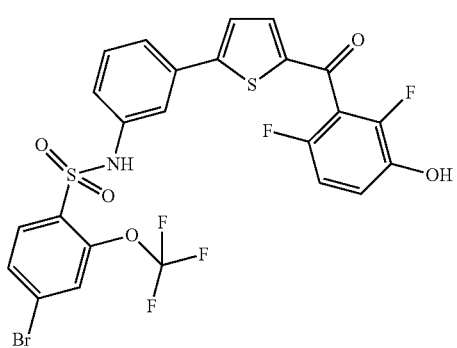

2

4-Bromo-N-{3-[5-(2,6-difluoro-3-hydroxybenzoyl)thiophen-2-yl]-phenyl}-2-trifluoromethoxybenzenesulfonamide (2):The title compound was prepared by reaction of 4-bromo-N-{3-[5-(3-ethoxy-2,6-difluorobenzoyl-thiophen-2-yl]phenyl}-2-trifluoromethoxy-benzenesulfonamide (2a) (250 mg, 0.38 mmol) and boron tribromide (2.3 mmol) according to method B. The product was purified by CC (dichloromethane/methanol 99.5:0.5); yield: 75% (180 mg). ¹H NMR (500 MHz, acetone-d⁶) δ 9.35 (br. s, 1H), 8.58 (br. s, 1H), 8.03 (d, J=8.5 Hz, 1H), 7.76 (dd, J=8.5, 1.8 Hz, 1H), 7.73 (m, 1H), 7.68-7.65 (m, 1H), 7.62 (dt, J=4.1, 0.9 Hz, 1H), 7.54 (ddd, J=7.7, 1.8, 1.0 Hz, 1H), 7.52 (d, J=4.1 Hz, 1H), 7.42-7.37 (m, 1H), 7.32 (ddd, J=8.1, 2.2, 1.0 Hz, 1H), 7.19-721 (m, 1H), 7.03 (ddd, J=9.1, 8.6, 1.9 Hz, 1H); ¹³C NMR (125 MHz, acetone-d⁶) δ 180.68, 154.32, 152.55 (dd, J=240.6, 5.8 Hz), 148.43 (dd, J=245.8, 7.7 Hz), 146.95 (d, J=1.8 Hz), 143.55, 142.66 (dd, J=13.0, 3.2 Hz), 138.85, 138.17, 134.88, 133.83, 131.81, 131.47, 131.34, 129.12, 126.34, 124.92 (d, J=1.9 Hz), 123.59, 122.15, 120.39 (dd, J=9.1, 3.8 Hz), 120.08, 118.80, 118.01 (dd, J=24.0, 19.7 Hz), 112.44 (dd, J=22.8, 3.9 Hz); MS (ESI): 635.43 (M+H)⁺.

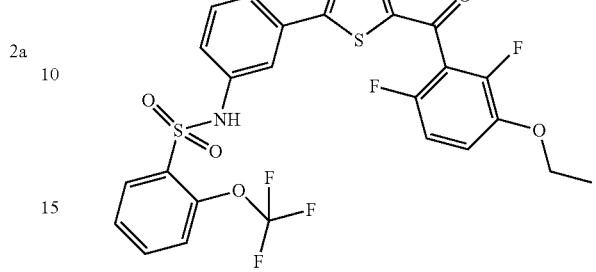

3a

N-{3-[5-(3-Ethoxy-2,6-difluorobenzoyl)thiophen-2-yl]phenyl}-2-trifluoromethoxy-benzene-sulfonamide (3a): The title compound was prepared by reaction of [5-(3-aminophenyl)thiophen-2-yl](3-ethoxy-2,6-difluorophenyl)methanone (1a) (210 mg, 0.58 mmol) and 2-trifluoromethoxybenzenesulfonyl chloride (152 mg, 0.58 mmol) according to method D1. The product was sufficiently pure for use in the subsequent reaction; yield: 66% (225 mg; yellow oil).

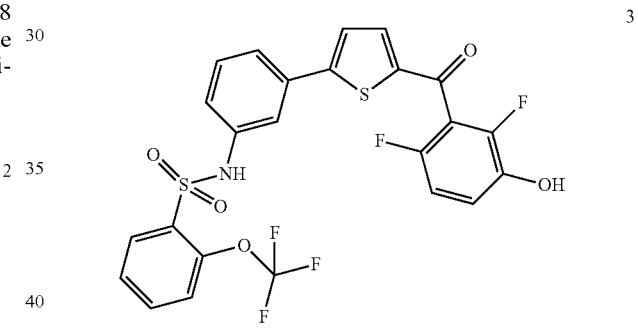

3

N-{3-[5-(2,6-Difluoro-3-hydroxybenzoyl)thiophen-2-yl]phenyl}-2-trifluoromethoxy-benzene-sulfonamide (3): The title compound was prepared by reaction of N-{3-[5-(3-ethoxy-2,6-difluorobenzoyl)thiophen-2-yl]phenyl}-2-trifluoromethoxybenzene-sulfonamide (3a) (225 mg, 0.39 mmol) and boron tribromide (2.3 mmol) according to method B. The product was purified by CC (dichloromethane/methanol 99.5:0.5); yield: 44% (142 mg). ¹H NMR (500 MHz, acetone-d⁶) δ 9.50 (br. s, 1H), 9.04 (br. s, 1H), 8.14-8.09 (m, 1H), 7.77 (ddd, J=8.4, 7.5, 1.7 Hz, 1H), 7.68-7.65 (m, 1H), 7.62 (dt, J=4.0, 0.8 Hz, 1H), 7.57-7.51 (m, 3H), 7.51-7.50 (m, 1H), 7.38 (tt, J=4.6, 2.3 Hz, 1H), 7.34-7.30 (m, 1H), 7.25-7.17 (m, 1H), 7.03 (ddd, J=10.5, 6.9, 1.9 Hz, 1H); ¹³C NMR (125 MHz, acetone-d⁶) δ 180.69, 154.44, 152.55 (dd, J=240.6, 5.8 Hz), 148.43 (dd, J=245.9, 7.8 Hz), 146.82 (d, J=1.7 Hz), 143.48, 142.66 (dd, J=12.9, 3.2 Hz), 139.17, 138.18, 136.37, 134.77, 132.58, 132.25, 131.25, 128.02, 126.26, 123.28, 124.49-120.18 (m), 121.95, 121.53 (d, J=1.8 Hz), 120.39 (dd, J=9.1, 3.8 Hz), 118.50, 118.02 (dd, J=23.9, 19.7 Hz), 112.45 (dd, J=22.8, 3.9 Hz); MS (ESI): 555.17 (M)⁺.

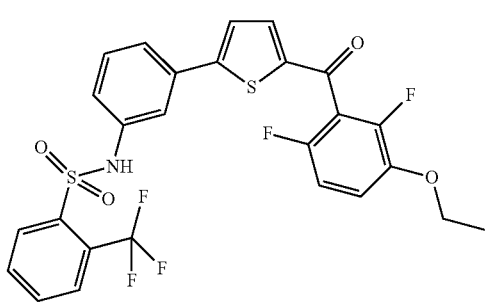

4a

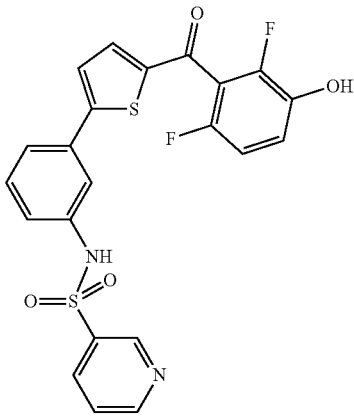

5

N-{3-[5-(3-Ethoxy-2,6-difluorobenzoyl)thiophen-2-yl]phenyl}-2-trifluoromethyl-benzene-sulfonamide (4a). The title compound was prepared by reaction of [5-(3-aminophenyl)thiophen-2-yl](3-ethoxy-2,6-difluorophenyl)methanone (1a) (210 mg, 0.58 mmol) and 2-trifluoromethylbenzenesulfonyl chloride (143 mg, 0.58 mmol) according to method D1 yield: 68% (225 mg). The product was used in the next steps without any characterisation.

Pyridine-3-sulfonic acid {3-[5-(2,6-difluoro-3-hydroxybenzoyl)-thiophen-2-yl]-phenyl}-amide (5): The title compound was prepared by reaction of [5-(3-aminophenyl)thiophen-2-yl](2,6-difluoro-3-hydroxyphenyl)methanone (1) (100 mg, 0.30 mmol) and pyridine-3-sulfonyl chloride hydrochloride (96 mg, 0.45 mmol) according to method D1. The product was purified by CC (dichloromethane/methanol 95:5); yield: 35% (50 mg). $^1$H NMR (500 MHz, acetone-d$^6$) δ 8.28 (dd, J=2.4, 0.8 Hz, 1H), 8.10 (dd, J=4.7, 1.6 Hz, 1H), 7.52-7.49 (m, 1H), 6.96-6.94 (m, 1H), 6.94-6.91 (m, 1H), 6.88 (d, J=4.1 Hz, 1H), 6.83 (d, J=7.6 Hz, 1H), 6.82-6.80 (m, 1H), 6.71 (t, J=7.9 Hz, 1H), 6.55-6.47 (m, 2H), 6.41 (td, J=9.0, 1.6 Hz, 1H); $^{13}$C NMR (125 MHz, acetone-d$^6$) δ 180.8, 154.6, 154.4, 148.7, 143.6, 139.3, 138.3, 137.0, 135.9, 135.0, 131.5, 126.5, 125.1, 123.8, 122.8, 120.4, 119.4, 112.6, 112.4; MS (ESI): 473.28 (M+H)$^+$.

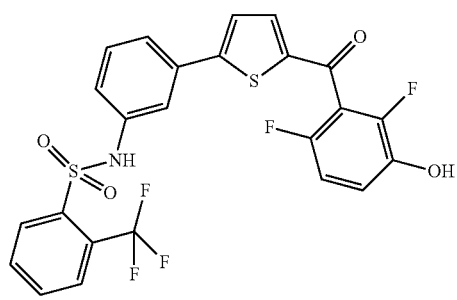

4

N-{3-[5-(2,6-Difluoro-3-hydroxybenzoyl)thiophen-2-yl]phenyl}-2-trifluoromethyl-benzene-sulfonamide (4): The title compound was prepared by reaction of N-{3-[5-(3-ethoxy-2,6-difluorobenzoyl)thiophen-2-yl]phenyl}-2-trifluoromethylbenzenesulfonamide (4a) (230 mg, 0.41 mmol) and boron tribromide (2.4 mmol) according to method B. The product was purified by CC (dichloromethane/methanol 99.5:0.5); yield: 48% (165 mg). $^1$H NMR (500 MHz, acetone-d$^6$) δ 9.39 (br. s, 1H), 9.00 (br. s, 1H), 8.30-8.25 (m, 1H), 8.03-7.98 (m, 1H), 7.87-7.82 (m, 2H), 7.68-7.65 (m, 1H), 7.62 (dt, J=4.1, 0.9 Hz, 1H), 7.55-7.51 (m, 2H), 7.42-7.37 (m, 1H), 7.32 (ddd, J=8.1, 2.2, 1.0 Hz, 1H), 7.19-7.21 (m, 1H), 7.06-7.00 (m, 1H); $^{13}$C NMR (125 MHz, acetone-d$^6$) δ 180.69, 152.54 (dd, J=240.6, 5.8 Hz), 148.42 (dd, J=245.8, 7.8 Hz), 143.51, 142.66 (dd, J=12.9, 3.2 Hz), 139.14, 139.11, 138.17, 134.83, 134.47, 133.86, 132.78, 131.32, 129.56 (q, J=6.4 Hz), 128.41, 128.15, 126.32, 125.06, 123.37, 122.88, 122.14, 120.39 (dd, J=9.1, 3.8 Hz), 118.73, 118.02 (dd, J=24.0, 19.6 Hz); MS (ESI): 539.32 (M)$^+$.

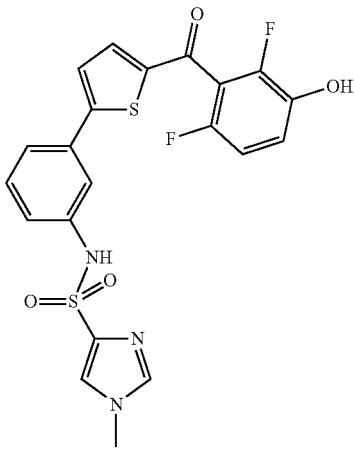

6

1-Methyl-1H-imidazole-4-sulfonic acid {3-[5-(2,6-difluoro-3-hydroxy-benzoyl)-thiophen-2-yl]-phenyl}-amide (6): The title compound was prepared by reaction of [5-(3-aminophenyl)thiophen-2-yl](2,6-difluoro-3-hydroxyphenyl)methanone (1) (100 mg, 0.30 mmol) and 1-methyl-1H-imidazole-4-sulfonyl chloride (81 mg, 0.45 mmol) according to method D1. The product was purified by CC (dichloromethane/methanol 95:5); yield: 72% (103 mg). $^1$H NMR (500 MHz, acetone-d$^6$) δ 9.17 (s, 1H), 9.01 (s, 1H), 7.75-7.72 (m, 2H), 7.64-7.61 (m, 2H), 7.54 (d, J=4.1 Hz, 1H), 7.50-7.43 (m, 1H), 7.39-7.34 (m, 2H), 7.21 (td, J=9.4, 5.5 Hz, 1H), 7.04 (td, J=8.8, 1.9 Hz, 1H), 3.76 (s, 3H); $^{13}$C NMR (125 MHz, acetone-d$^6$) δ 180.7, 155.1, 153.6, 151.6, 149.5, 147.5, 143.3, 142.7, 140.7, 140.1, 138.3, 134.5, 130.9, 126.2, 122.5, 121.9, 1204, 118.4, 112.6, 112.4, 34.2; MS (ESI): 476.21 (M+H)$^+$.

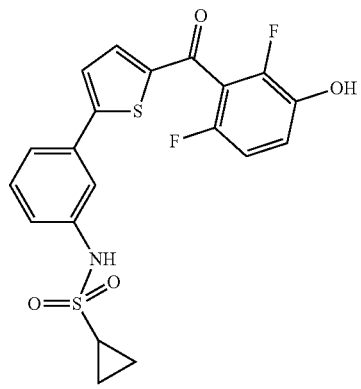

7

Cyclopropanesulfonic acid {3-[5-(2,6-difluoro-3-hydroxy-benzoyl)-thiophen-2-yl]-phenyl}-amide (7): The title compound was prepared by reaction of [5-(3-aminophenyl)thiophen-2-yl](2,6-difluoro-3-hydroxyphenyl)methanone (1) (100 mg, 0.30 mmol) and cyclopropanesulfonyl chloride (1M in dichloromethane) (63 mg, 0.45 mmol) according to method D1. The product was purified by CC (dichloromethane/methanol 95:5); yield: 56% (73 mg). $^1$H NMR (500 MHz, acetone-d$^6$) δ 9.01 (s, 1H), 8.77 (s, 1H), 7.80-7.78 (m, 1H), 7.65 (dt, J=4.1, 0.9 Hz, 1H), 7.61-7.58 (m, 2H), 7.54-7.44 (m, 2H), 7.21 (td, J=9.5, 5.4 Hz, 1H), 7.04 (td, J=9.0, 1.9 Hz, 1H), 2.73-2.67 (m, 1H), 1.07-0.96 (m, 4H); $^{13}$C NMR (125 MHz, acetone-d$^6$) δ 188.7, 154.8, 143.5, 140.6, 138.3 134.9, 131.3, 126.3, 123.1, 122.6, 120.4, 119.2, 112.6, 112.4, 32.4, 5.8; MS (ESI): 436.25 (M+H)$^+$.

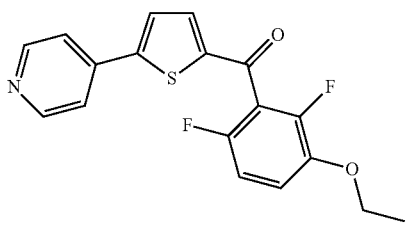

8a (3-Ethoxy-2,6-difluoro-phenyl)-(5-pyridin-4-yl-thiophen-2-yl)-methanone (8a): The title compound was prepared by reaction of 5-bromo-thiophen-2-yl)-(3-ethoxy-2,6-difluoro-phenyl)-methanone (1b) (300 mg, 0.86 mmol), pyridine-4-boronic acid pinacol ester (355 mg, 1.73 mmol), sodium carbonate (2.5 ml, 2 M) and tetrakis(triphenylphosphine) palladium (5 µmol) according to method C2. The product was purified by CC (dichloromethane/methanol 99.5:0.5); yield: 91% (450 mg). The product was used in the next steps without any characterisation.

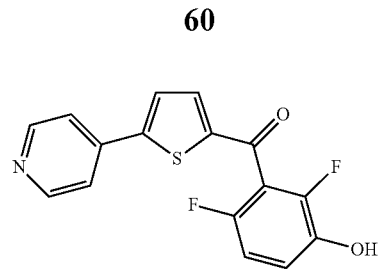

8

(2,6-Difluoro-3-hydroxy-phenyl)-(5-pyridin-4-yl-thiophen-2-yl)-methanone (8): The title compound was prepared by reaction of (3-Ethoxy-2,6-difluoro-phenyl)-(5-pyridin-4-yl-thiophen-2-yl)-methanone (8a) (450 mg, 1.30 mmol) and boron tribromide (7.8 mmol, 6.0 equiv) according to method B. The product was purified by CC (dichloromethane/methanol 90:10); yield: 24% (100 mg). $^1$H NMR (500 MHz, DMSO-d$^6$) δ 10.40 (br. s, 1H), 8.64 (d, J=6.1 Hz, 2H), 7.91 (d, J=4.1 Hz, 1H), 7.77 (dd, J=4.6, 1.5 Hz, 2H), 7.69 (d, J=4.0 Hz, 1H), 7.16 (td, J=9.4, 5.6 Hz, 1H), 7.08 (t, J=8.6 Hz, 1H); $^{13}$C NMR (125 MHz, DMSO-d$^6$) δ 180.32, 150.66, 150.49, 150.46 (dd, J=239.7, 5.6 Hz), 146.88 (dd, J=246.7, 7.5 Hz), 143.06, 141.92 (dd, J=11.8, 2.9 Hz), 139.04, 137.82, 128.13, 120.19, 119.81 (dd, J=8.9, 3.9 Hz), 116.22 (dd, J=23.4, 19.0 Hz), 111.75 (dd, J=22.3, 3.5 Hz); MS (ESI): 317.94 (M)$^+$.

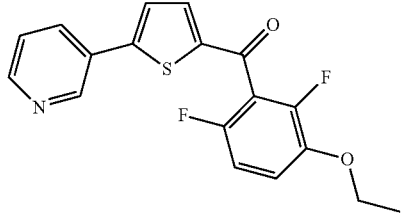

9a (3-Ethoxy-2,6-difluoro-phenyl)-(5-pyridin-3-yl-thiophen-2-yl)-methanone (9a): The title compound was prepared by reaction of 5-bromo-thiophen-2-yl)-(3-ethoxy-2,6-difluoro-phenyl)-methanone (1b) (400 mg, 1.15 mmol), pyridine-3-boronic acid (170 mg, 1.38 mmol), sodium carbonate (2.5 ml, 2 M) and tetrakis(triphenylphosphine) palladium (5 µmol) according to method C2. The product was purified by CC (dichloromethane/methanol 99.5:0.5); yield: 50% (200 mg). $^1$H NMR (300 MHz, acetone-d$^6$) δ 8.90 (d, J=2.2 Hz, 1H), 8.50 (dd, J=4.8, 1.4 Hz, 1H), 8.04 (ddd, J=8.0, 2.3, 1.7 Hz, 1H), 7.59 (d, J=4.1 Hz, 1H), 7.55 (dd, J=4.0, 0.7 Hz, 1H), 7.37 (ddd, J=8.0, 4.8, 0.6 Hz, 1H), 7.22 (td, J=9.3, 5.3 Hz, 1H), 6.99 (td, J=8.9, 2.0 Hz, 1H), 4.06 (q, J=7.0 Hz, 2H), 1.28 (t, J=7.0 Hz, 3H); $^{13}$C NMR (75 MHz, acetone-d$^6$) δ 179.71, 152.23 (dd, J=241.8, 5.9 Hz), 150.81, 148.70 (dd, J=241.8, 5.9 Hz), 147.16, 143.95 (dd, J=10.6, 3.3 Hz), 143.20, 137.35, 133.48, 128.92, 126.24, 124.03, 117.40 (dd, J=22.9, 3.2 Hz), 116.88 (dd, J=9.3, 3.1 Hz), 111.22 (dd, J=22.6, 4.2 Hz), 65.44 (s), 14.10 (s); MS (ESI): 346.05 (M)$^+$.

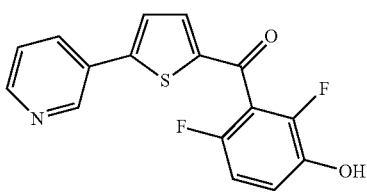

9

(2,6-Difluoro-3-hydroxy-phenyl)-(5-pyridin-3-yl-thiophen-2-yl)-methanone (9): The title compound was prepared by reaction of (3-ethoxy-2,6-difluoro-phenyl)-(5-pyridin-3-yl-thiophen-2-yl)-methanone (9a) (200 mg, 0.58 mmol) and boron tribromide (3.47 mmol, 6.0 equiv) according to method B. The product was purified by CC (dichloromethane/methanol 90:10); yield: 17% (31 mg). $^1$H NMR (500 MHz, DMSO-d$^6$) δ 10.28 (s, 1H, OH), 9.06 (s, 1H), 8.64 (d, J=4.2 Hz, 1H), 8.23 (ddd, J=8.0, 2.4, 1.5 Hz, 1H), 7.81 (d, J=4.1 Hz, 1H), 7.71 (d, J=4.1 Hz, 1H), 7.53 (dd, J=8.0, 4.8 Hz, 1H), 7.16 (td, J=9.4, 5.7 Hz, 1H), 7.10 (td, J=8.9, 1.4 Hz, 1H); $^{13}$C NMR (125 MHz, DMSO-d$^6$) δ 180.06, 150.52 (dd, J=239.6, 5.7 Hz), 150.43, 150.25, 146.90 (dd, J=246.5, 7.6 Hz), 146.86, 142.30, 141.88 (dd, J=11.9, 3.0 Hz), 137.98, 133.83, 128.41, 126.98, 124.25, 119.60 (dd, J=9.1, 4.0 Hz), 116.43 (dd, J=23.5, 19.4 Hz), 111.71 (dd, J=22.4, 3.6 Hz); MS (ESI): 317.92 (M)$^+$.

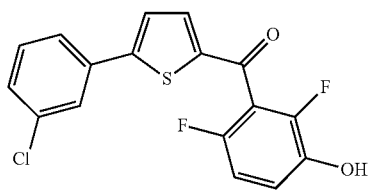

10a

[5-(2,4-Difluoro-phenyl)-thiophen-2-yl]-(3-ethoxy-2,6-difluoro-phenyl)-methanone (10a): The title compound was prepared by reaction of 5-bromo-thiophen-2-yl)-(3-ethoxy-2,6-difluoro-phenyl)-methanone (1b) (300 mg, 0.86 mmol), 2,4-difluorophenylboronic acid (164 mg, 1.04 mmol), cesium carbonate (1126 mg, 3.5 mmol) and tetrakis(triphenylphosphine) palladium (5 µmol) according to method C1; yield: 91% (300 mg). The product was used in the next steps without any characterisation.

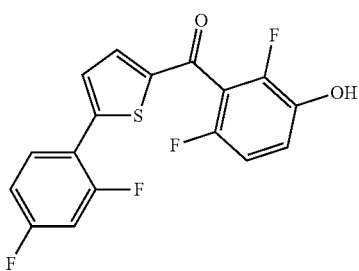

10

(2,6-Difluoro-3-hydroxy-phenyl)-[5-(2,4-difluoro-phenyl)-thiophen-2-yl]-methan-one (10): The title compound was prepared by reaction of [5-(2,4-difluoro-phenyl)-thiophen-2-yl]-(3-ethoxy-2,6-difluoro-phenyl)-methanone (10a) (300 mg, 0.79 mmol) and boron tribromide (3.9 mmol, 5.0 equiv) according to method B. The product was purified by CC (dichloromethane/methanol 99.75:0.25); yield: 72% (280 mg). $^1$H NMR (500 MHz, acetone-d$^6$) δ 8.99 (s, 1H), 7.96 (td, J=8.8, 6.3 Hz, 1H), 7.68 (ddd, J=4.0, 1.9, 0.9 Hz, 1H), 7.65 (dd, J=4.1, 0.9 Hz, 1H), 7.29-7.23 (m, 1H), 7.23-7.16 (m, 2H), 7.02-7.04 (m, 1H); $^{13}$C NMR (125 MHz, acetone-d$^6$) δ 180.88 (s), 164.18 (dd, J=251.5, 12.7 Hz), 160.45 (dd, J=253.6, 12.6 Hz), 152.56 (dd, J=240.6, 5.8 Hz), 148.43 (dd, J=245.8, 7.7 Hz), 145.46 (dd, J=361.6, 3.6 Hz), 142.65 (dd, J=12.9, 3.2 Hz), 137.39, 131.60 (dd, J=9.8, 4.4 Hz), 128.62, 128.59, 120.41 (dd, J=9.1, 3.9 Hz), 118.40 (dd, J=12.7, 4.1 Hz), 118.04 (dd, J=24.0, 19.6 Hz), 113.46 (dd, J=21.1, 4.5 Hz), 112.46 (dd, J=22.8, 3.9 Hz), 105.76 (t, J=26.4 Hz); MS (ESI): 352.88 (M)$^+$.

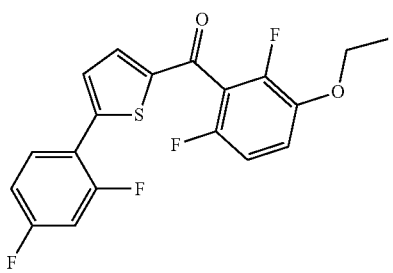

11

[5-(3-Chloro-phenyl)-thiophen-2-yl]-(2,6-difluoro-3-hydroxy-phenyl)-methanone (11): The title compound was prepared by reaction of (5-bromo-thiophen-2-yl)-(2,6-difluoro-3-hydroxy-phenyl)-methanone (1e) (430 mg, 1.35 mmol), 3-chloro-phenylboronic acid (253 mg, 1.62 mmol), cesium carbonate (1756 mg, 5.39 mmol) and tetrakis(triphenylphosphine) palladium (5 µmol) according to method C1. The product was purified by CC (hexane/ethyl acetate 9:1); yield: 74% (350 mg). 1H NMR (500 MHz, acetone-d$^6$) δ 9.02 (s, 1H, OH), 7.84 (tt, J=2.4, 1.2 Hz, 1H), 7.74-7.76 (m, 1H), 7.69 (d, J=4.1 Hz, 1H), 7.66 (dt, J=4.1, 0.9 Hz, 1H), 7.50-7.52 (m, 1H), 7.47 (ddd, J=8.0, 2.0, 1.1 Hz, 1H), 7.19-7.21 (m, 1H), 7.02-7.04 (m, 1H); $^{13}$C NMR (125 MHz, acetone-d$^6$) δ 180.77, 153.31, 152.56 (dd, J=240.6, 5.8 Hz), 148.44 (dd, J=245.9, 7.7 Hz), 143.92, 142.68 (dd, J=12.9, 3.2 Hz), 138.12, 135.80, 135.69, 131.92, 130.20, 126.96, 126.90, 125.81, 120.42 (dd, J=9.1, 3.9 Hz), 117.97 (dd, J=23.9, 19.7 Hz), 112.47 (d, J=22.8 Hz); MS (ESI): 350.63 (M)$^+$.

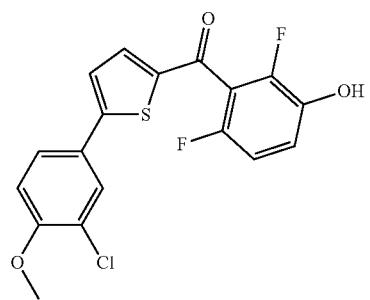

12

[5-(3-Chloro-4-methoxy-phenyl)-thiophen-2-yl]-(2,6-difluoro-3-hydroxy-phenyl)-methanone (12): The title compound was prepared by reaction of (5-bromo-thiophen-2-yl)-(2,6-difluoro-3-hydroxy-phenyl)-methanone (1e) (445 mg, 1.71 mmol), 3-chloro-4-methoxy-phenylboronic acid (382 mg, 2.05 mmol), cesium carbonate (2226 mg, 6.83 mmol) and tetrakis(triphenylphosphine) palladium (5 µmol) according to method C1. The product was purified by CC (petroleum ether/ethyl acetate 8:2); yield: 69% (450 mg). $^1$H NMR (500 MHz, acetone-d$^6$) δ 8.99 (s, 1H, OH), 7.84 (d, J=2.3 Hz, 1H), 7.73 (dd, J=8.6, 2.3 Hz, 1H), 7.60 (dd, J=3.0, 2.0 Hz, 1H), 7.55 (d, J=4.1 Hz, 1H), 7.23-7.17 (m, 2H), 7.02 (ddd, J=9.1, 8.6, 1.9 Hz, 1H), 3.97 (s, 3H); $^{13}$C NMR (125 MHz, acetone-d$^6$) δ 180.50, 157.07, 154.01, 152.57 (dd, J=240.4, 5.8 Hz), 148.43 (dd, J=245.7, 7.8 Hz), 142.81, 142.63 (dd, J=13.0, 3.2 Hz), 138.32, 128.60, 127.29, 127.28, 125.60, 123.74, 120.27 (dd, J=9.1, 3.9 Hz), 118.12 (dd, J=24.0, 19.7 Hz), 113.93, 112.41 (dd, J=22.8, 3.9 Hz); MS (ESI): 380.67 (M)$^+$.

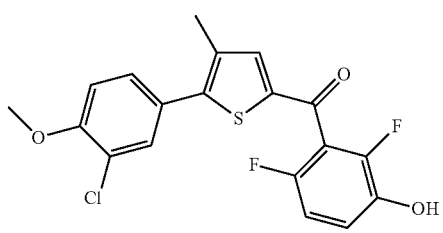

13

[5-(3-Chloro-4-methoxy-phenyl)-4-methyl-thiophen-2-yl]-(2,6-difluoro-3-hydroxy-phenyl)-methanone (13): The title compound was prepared by reaction of (5-bromo-4-methyl-thiophen-2-yl)-(2,6-difluoro-3-hydroxy-phenyl)-methanone (1f) (600 mg, 1.81 mmol), 3-chloro-4-methoxy-phenylboronic acid (507 mg, 2.72 mmol), cesium carbonate (2347 mg, 7.20 mmol) and tetrakis(triphenylphosphine) palladium (5 µmol) according to method C1. The product was purified by CC (dichloromethane); yield: 80% (570 mg). $^1$H NMR (500 MHz, acetone-d$^6$) δ 8.98 (s, 1H), 7.62 (d, J=2.2 Hz, 1H), 7.54 (dd, J=8.5, 2.3 Hz, 1H), 7.52-7.50 (m, 1H), 7.27 (d, J=8.6 Hz, 1H), 7.17-7.19 (m, 1H), 7.02 (ddd, J=9.1, 8.6, 1.9 Hz, 1H), 3.99 (s, 3H), 2.32-2.32 (m, 3H); 13C NMR (125 MHz, acetone-d$^6$) δ 180.54 (s), 156.53 (s), 152.54 (dd, J=240.3, 5.9 Hz), 148.39 (dd, J=245.4, 7.9 Hz), 148.32 (s), 142.60 (dd, J=13.1, 3.0 Hz), 141.34 (s), 140.62 (s), 136.43 (s), 130.96 (s), 129.76 (s), 127.35 (s), 123.27 (s), 120.14 (dd, J=9.2, 3.8 Hz), 118.23 (dd, J=24.1, 20.1 Hz), 113.71 (s), 112.37 (dd, J=22.8, 3.9 Hz), 56.75 (s), 14.96 (s); MS (ESI): 396.72 (M+2H)$^+$.

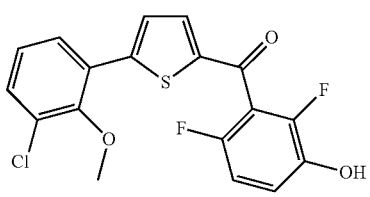

14

[5-(3-Chloro-2-methoxy-phenyl)-thiophen-2-yl]-(2,6-difluoro-3-hydroxy-phenyl)-methanone (14): The title compound was prepared by reaction of (5-bromo-thiophen-2-yl)-(2,6-difluoro-3-hydroxy-phenyl)-methanone (1e) (300 mg, 0.94 mmol), 3-chloro-2-methoxy-phenylboronic acid (210 mg, 1.12 mmol), cesium carbonate (1225 mg, 3.76 mmol) and tetrakis(triphenylphosphine) palladium (5 µmol) according to method C1; yield: 39% (140 mg). The product was used in the next steps without any characterisation.

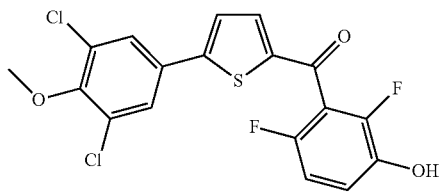

15

[5-(3,5-Dichloro-4-methoxy-phenyl)-thiophen-2-yl]-(2,6-difluoro-3-hydroxy-phen-yl)-methanone (15): The title compound was prepared by reaction of (5-bromo-thiophen-2-yl)-(2,6-difluoro-3-hydroxy-phenyl)-methanone 1e) (300 mg, 0.94 mmol), 3,5-dichloro-4-methoxy-phenylboronic acid (249 mg, 1.13 mmol), cesium carbonate (1225 mg, 3.76 mmol) and tetrakis(triphenylphosphine) palladium (5 µmol) according to method C1. The product was purified by CC (dichloro-methane/petroleum ether 90:10) followed by washing with petroleum ether; yield: 90% (350 mg). $^1$H NMR (500 MHz, acetone-d$^6$) δ 8.99 (s, 1H; OH), 7.83 (s, 2H), 7.67 (d, J=4.1 Hz, 1H), 7.64 (d, J=4.1 Hz, 1H), 7.21 (td, J=9.4, 5.4 Hz, 1H), 7.03 (td, J=8.9, 1.8 Hz, 1H), 3.93 (s, 3H); 13C NMR (125 MHz, acetone-d$^6$) δ 180.74 (s), 153.85 (s), 152.57 (dd, J=240.7, 5.7 Hz), 151.51 (s), 148.44 (dd, J=246.0, 7.7 Hz), 144.21 (s), 142.66 (dd, J=12.9, 3.2 Hz), 138.06 (s), 131.62 (s), 130.85 (s), 127.68 (s), 127.35 (s), 120.48 (dd, J=9.1, 3.9 Hz), 117.89 (dd, J=23.8, 19.6 Hz), 112.47 (dd, J=22.8, 3.9 Hz), 61.32 (s); MS (ESI): 414.73 (M)$^+$.

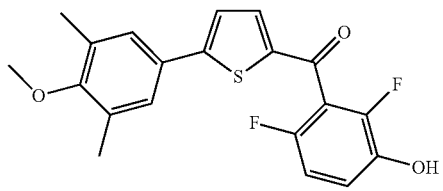

16

(2,6-Difluoro-3-hydroxy-phenyl)-[5-(4-methoxy-3,5-dimethyl-phenyl)-thiophen-2-yl]-methanone (16): The title compound was prepared by reaction of (5-bromo-thiophen-2-yl)-(2,6-difluoro-3-hydroxy-phenyl)-methanone (1e) (500 mg, 1.57 mmol), 4-methoxy-3,5-dimethyl phenylboronic acid (338 mg, 1.88 mmol), cesium carbonate (2042 mg, 6.27 mmol) and tetrakis(triphenylphosphine) palladium (5 µmol) according to method C1. The product was purified by CC (hexane/ethyl acetate 8:2); yield: 78% (460 mg). $^1$H NMR (500 MHz, acetone-d$^6$) δ 8.83 (s, 1H, OH), 7.48-7.46 (m, 1H), 7.37 (d, J=4.2 Hz, 3H), 7.06 (td, J=9.4, 5.4 Hz, 1H), 6.89 (td, J=8.8, 1.8 Hz, 1H), 3.62 (s, 3H), 2.18 (s, 6H); $^{13}$C NMR (75 MHz, acetone-d$^6$) δ 179.53, 158.58, 154.86, 150.08 (dd, J=240.5, 5.9 Hz), 145.81 (dd, J=245.2, 7.9 Hz), 141.72 (dd, J=10.9, 5.4 Hz), 141.65, 137.32, 131.90, 128.40, 126.85, 124.37, 119.27 (dd, J=9.0, 3.8 Hz), 117.15 (dd, J=30.8, 11.1 Hz), 111.47 (dd, J=22.9, 3.8 Hz), 59.09, 15.27; MS (ESI): 374.69 (M)$^+$.

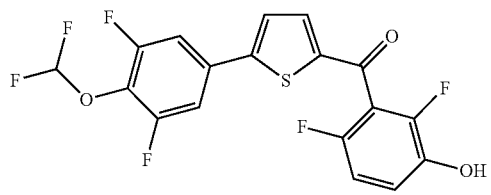

17

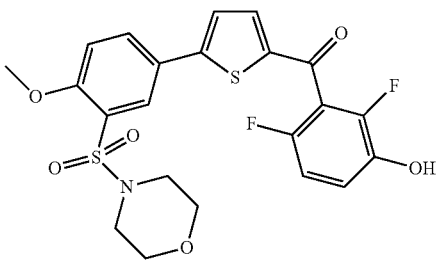

19

(2,6-Difluoro-3-hydroxy-phenyl)-[5-(4-difluoromethoxy-3,5-difluoro-phenyl)-thiophen-2-yl]-methanone (17): The title compound was prepared by reaction of (5-bromo-thiophen-2-yl)-(2,6-difluoro-3-hydroxy-phenyl)-methanone (1e) (460 mg, 1.44 mmol), 4-difluoromethoxy-3,5-diflouro-phenylboronic acid (387 mg, 1.73 mmol), cesium carbonate (1877 mg, 5.77 mmol) and tetrakis(triphenylphosphine) palladium (5 μmol) according to method C1. The product was purified by CC (DCM); yield: 84% (505 mg). $^1$H NMR (500 MHz, acetone-d$^6$) δ 9.01 (s, 1H, OH), 7.75 (d, J=4.1 Hz, 1H), 7.72-7.65 (m, 1H), 7.24-7.19 (m, 1H), 7.11-7.10 (m, 1H), 7.07-7.02 (m, 1H); $^{13}$C NMR (125 MHz, acetone-d$^6$) δ 180.88 (s), 157.04 (dd, J=251.3, 4.6 Hz), 152.56 (dd, J=240.8, 5.7 Hz), 151.23 (t, J=2.8 Hz), 148.43 (dd, J=246.1, 7.6 Hz), 144.71, 142.68 (dd, J=12.9, 3.2 Hz), 138.02, 133.47 (t, J=9.6 Hz), 128.01, 120.54 (dd, J=9.1, 3.9 Hz), 117.79 (dd, J=23.6, 19.5 Hz), 117.36 (t, J=264.6 Hz), 112.50 (dd, J=22.7, 3.9 Hz), 111.64 (d, J=5.4 Hz), 111.49 (d, J=5.4 Hz); MS (ESI): 418.72 (M)$^+$.

(2,6-Difluoro-3-hydroxy-phenyl)-{5-[4-methoxy-3-(morpholine-4-sulfonyl)-phen-yl]-thiophen-2-yl}-methanone (19): The title compound was prepared by reaction of (5-bromo-thiophen-2-yl)-(2,6-difluoro-3-hydroxy-phenyl)-methanone (1e) (460 mg, 1.44 mmol), 4-methoxy-3-(morpholine-4-sulfonyl)-phenylboronic acid (521 mg, 1.73 mmol), cesium carbonate (1877 mg, 5.77 mmol) and tetrakis (triphenylphosphine) palladium (5 μmol) according to method C1. The product was purified by CC (dichloromethane/methanol 99.5:0.5); yield: 56% (400 mg). $^1$H NMR (500 MHz, acetone-d$^6$) δ 9.01 (br. s, 1H), 8.18 (d, J=2.4 Hz, 1H), 8.05 (dd, J=8.7, 2.5 Hz, 1H), 7.64 (dt, J=4.1, 0.9 Hz, 1H), 7.60 (d, J=4.1 Hz, 1H), 7.39 (d, J=8.7 Hz, 1H), 7.22-7.20 (m, 1H), 7.03 (ddd, J=9.1, 8.6, 1.9 Hz, 1H), 4.06 (s, 3H), 3.67-3.64 (m, 4H), 3.25-3.22 (m, 4H); $^{13}$C NMR (125 MHz, acetone-d$^6$) δ 180.52, 158.93, 153.70, 152.55 (dd, J=240.5, 5.8 Hz), 148.42 (dd, J=245.7, 7.7 Hz), 143.06, 142.65 (dd, J=12.9, 3.2 Hz), 138.33, 133.37, 129.86, 128.17, 126.22, 125.93, 120.33 (dd, J=9.1, 3.9 Hz), 118.07 (dd, J=24.0, 19.6 Hz), 114.83, 112.43 (dd, J=22.8, 3.9 Hz), 67.27, 56.86, 47.01; MS (ESI): 495.74 (M)$^+$.

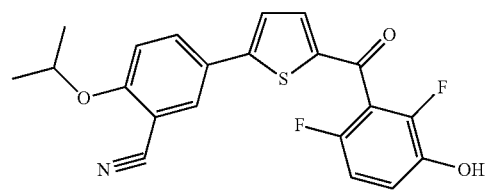

18

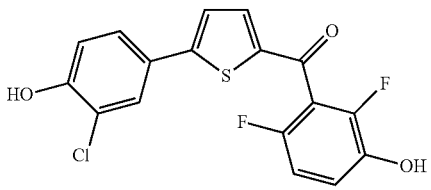

20

5-[5-(2,6-Difluoro-3-hydroxy-benzoyl)-thiophen-2-yl]-2-isopropoxy-benzonitrile (18): The title compound was prepared by reaction of (5-bromo-thiophen-2-yl)-(2,6-difluoro-3-hydroxy-phenyl)-methanone (1e) (460 mg, 1.44 mmol), 3-cyano-4-isopropoxyphenylboronic acid (387 mg, 1.73 mmol), cesium carbonate (1877 mg, 5.77 mmol) and tetrakis (triphenylphosphine) palladium (5 μmol) according to method C1. The product was purified by CC (dichloromethane/methanol 99.5:0.5); yield: 52% (300 mg). $^1$H NMR (500 MHz, acetone-d$^6$) δ 8.99 (s, 1H, OH), 8.13 (d, J=2.5 Hz, 1H), 8.03 (dd, J=8.9, 2.4 Hz, 1H), 7.65-7.62 (m, 2H), 7.36 (d, J=9.1 Hz, 1H), 7.24-7.17 (m, 1H), 7.03 (td, J=8.9, 1.9 Hz, 1H), 4.92 (sep, J=6.0 Hz, 1H), 1.41 (d, J=6.0 Hz, 6H); $^{13}$C NMR (125 MHz, acetone-d$^6$) δ 180.58, 161.32 (s), 153.11 (s), 152.56 (dd, J=240.7, 5.7 Hz), 148.42 (dd, J=245.8, 7.9 Hz), 143.18, 142.64 (dd, J=13.0, 3.1 Hz), 138.32, 133.34, 132.42, 126.74, 126.07, 120.33 (dd, J=9.0, 3.9 Hz), 118.04 (dd, J=24.0, 19.8 Hz), 116.29, 115.60, 112.43 (dd, J=22.8, 3.8 Hz), 104.38, 73.09, 22.03; MS (ESI): 399.75 (M)$^+$.

[5-(3-Chloro-4-hydroxy-phenyl)-thiophen-2-yl]-(2,6-difluoro-3-hydroxy-phenyl)-methanone (20): The title compound was prepared by reaction of [5-(3-chloro-4-methoxy-phenyl)-thiophen-2-yl]-(2,6-difluoro-3-hydroxy-phenyl)-methanone (12) (340 mg, 0.89 mmol) and boron tribromide (4.46 mmol, 5.0 equiv) according to method B. The product was purified by CC (dichloromethane/methanol 99.5:0.5); yield: 74% (241 mg). $^1$H NMR (500 MHz, acetone-d$^6$) δ 9.33 (s, 1H, OH), 8.99 (d, J=1.4 Hz, 1H, OH), 7.82 (t, J=2.9 Hz, 1H), 7.62 (dd, J=8.5, 2.3 Hz, 1H), 7.60-7.59 (m, 1H), 7.52 (d, J=4.1 Hz, 1H), 7.19 (ddd, J=9.6, 9.2, 5.4 Hz, 1H), 7.12 (d, J=8.5 Hz, 1H), 7.06-6.96 (m, 1H). $^{13}$C NMR (125 MHz, acetone-d$^6$) δ 180.47, 155.24, 154.39, 152.56 (dd, J=240.4, 5.8 Hz), 148.43 (dd, J=245.6, 7.8 Hz), 142.63 (dd, J=13.1, 3.2 Hz), 142.55, 138.36, 128.67, 127.32, 126.79, 125.30, 122.15, 120.24 (dd, J=9.1, 3.8 Hz), 118.33, 118.10 (dd, J=23.8, 19.6 Hz), 112.39 (dd, J=22.8, 3.9 Hz); MS (ESI): 366.47 (M)$^+$.

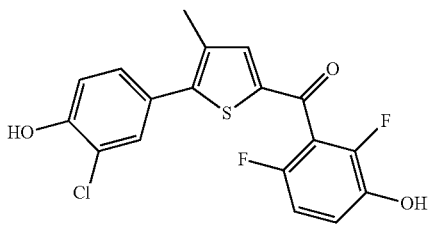

21

[5-(3-Chloro-4-hydroxy-phenyl)-4-methyl-thiophen-2-yl]-(2,6-difluoro-3-hydroxy-phenyl)-methanone (21): The title compound was prepared by reaction of [5-(3-chloro-4-methoxy-phenyl)-4-methyl-thiophen-2-yl]-(2,6-difluoro-3-hydroxy-phen-yl)-methanone (13) (520 mg, 1.32 mmol) and boron tribromide (6.58 mmol, 5.0 equiv) according to method B. The product was purified by CC (dichloromethane/methanol 99.75:0.25); yield: 82% (413 mg). $^1$H NMR (500 MHz, acetone-d$^6$) δ 9.25 (s, 1H, OH), 8.97 (d, J=1.4 Hz, 1H), 7.58 (d, J=2.3 Hz, 1H), 7.50-7.48 (m, 1H), 7.41 (dd, J=8.4, 2.2 Hz, 1H), 7.21-7.17 (m, 1H), 7.15 (d, J=8.4 Hz, 1H), 7.04-6.98 (m, 1H), 2.34-2.29 (m, 3H); $^{13}$C NMR (125 MHz, acetone-d$^6$) δ 180.52, 154.61, 152.54 (dd, J=240.2, 5.9 Hz), 148.69, 148.40 (dd, J=245.5, 7.8 Hz), 142.60 (dd, J=13.0, 3.2 Hz), 141.12, 140.65, 136.21, 130.99, 129.72, 126.78, 121.68, 120.12 (dd, J=9.1, 3.8 Hz), 118.22 (dd, J=32.7, 28.5 Hz), 118.05, 112.36 (dd, J=22.8, 3.9 Hz), 15.00; MS (ESI): 380.74 (M)$^+$.

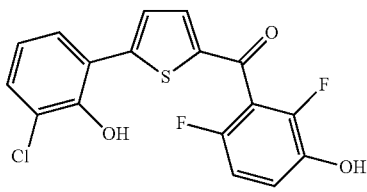

22

[5-(3-Chloro-2-hydroxy-phenyl)-thiophen-2-yl]-(2,6-difluoro-3-hydroxy-phenyl)-methanone (22): The title compound was prepared by reaction of [5-(3-chloro-2-methoxy-phenyl)-thiophen-2-yl]-(2,6-difluoro-3-hydroxy-phenyl)-methanone (14) (140 mg, 0.37 mmol) and boron tribromide (1.84 mmol, 5.0 equiv) according to method B. The product was purified by CC (dichloromethane/methanol 99.75:0.25); yield: 76% (102 mg). $^1$H NMR (500 MHz, acetone-d$^6$) δ 9.32 (s, 1H; OH), 9.11 (d, J=0.9 Hz, 1H, OH), 7.80 (dd, J=8.0, 1.4 Hz, 1H), 7.77 (d, J=4.2 Hz, 1H), 7.62 (d, J=4.2 Hz, 1H), 7.45 (dd, J=8.0, 1.4 Hz, 1H), 7.19 (td, J=9.4, 5.4 Hz, 1H), 7.06-6.98 (m, 2H); $^{13}$C NMR (125 MHz, acetone-d$^6$) δ 181.04, 152.52 (dd, J=240.2, 5.9 Hz), 150.46, 150.17, 148.43 (dd, J=245.6, 7.8 Hz), 143.71, 142.68 (dd, J=12.9, 3.2 Hz), 136.63, 131.00, 128.18, 128.00, 123.22, 122.89, 122.13, 120.14 (dd, J=9.1, 3.9 Hz), 118.45 (dd, J=24.2, 19.9 Hz), 112.34 (dd, J=22.8, 3.9 Hz); MS (ESI): 368.86 (M+2H)$^+$.

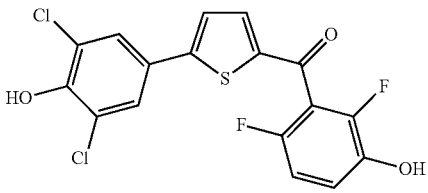

23

[5-(3,5-Dichloro-4-hydroxy-phenyl)-thiophen-2-yl]-(2,6-difluoro-3-hydroxy-phen-yl)-methanone (23): The title compound was prepared by reaction of [5-(3,5-dichloro-4-methoxy-phenyl)-thiophen-2-yl]-(2,6-difluoro-3-hydroxy-phenyl)-methanone (15) (350 mg, 0.84 mmol) and boron tribromide (4.12 mmol, 5.0 equiv) according to method B. The product was purified by CC (dichloromethane/methanol 99.75:0.25); yield: 84% (285 mg). $^1$H NMR (500 MHz, acetone-d$^6$) δ 9.28 (s, 1H), 8.98 (s, 1H), 7.79 (s, 2H), 7.62 (dt, J=4.1, 0.8 Hz, 1H), 7.60 (d, J=4.1 Hz, 1H), 7.20 (ddd, J=9.6, 9.2, 5.4 Hz, 1H), 7.02 (ddd, J=9.1, 8.6, 1.9 Hz, 1H); $^{13}$C NMR (125 MHz, acetone-d$^6$) δ 180.58, 152.56 (dd, J=240.6, 5.8 Hz), 152.50, 151.05, 148.43 (dd, J=245.8, 7.8 Hz), 143.32, 142.64 (dd, J=13.0, 3.2 Hz), 138.19, 127.32, 127.22, 126.30, 123.61, 120.36 (dd, J=9.1, 3.8 Hz), 118.01 (dd, J=23.9, 19.7 Hz), 112.43 (dd, J=22.8, 3.9 Hz); MS (ESI): 402.59 (M+H)$^+$.

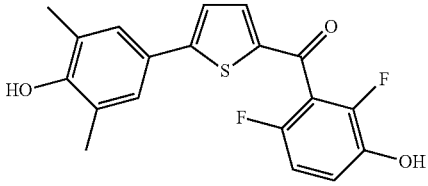

24

(2,6-Difluoro-3-hydroxy-phenyl)-[5-(4-hydroxy-3,5-dimethyl-phenyl)-thiophen-2-yl]-methanone (24): The title compound was prepared by reaction of (2,6-difluoro-3-hydroxy-phenyl)-[5-(4-methoxy-3,5-dimethyl-phenyl)-thiophen-2-yl]-methanone (16) (400 mg, 1.07 mmol) and boron tribromide (5.34 mmol, 5.0 equiv) according to method B. The product was purified by CC (dichloromethane/methanol 99.5:0.5); yield: 69% (266 mg). $^1$H NMR (500 MHz, acetone-d$^6$) δ 8.82 (br. s, 1H), 7.65 (br. s, 1H), 7.41 (d, J=4.1 Hz, 1H), 7.32-7.28 (m, 3H), 7.05 (td, J=9.4, 5.4 Hz, 1H), 6.87 (td, J=8.8, 1.8 Hz, 1H), 2.16 (s, 6H); $^{13}$C NMR (125 MHz, acetone-d$^6$) δ 179.30, 155.99, 155.18, 151.66 (dd, J=240.2, 5.9 Hz), 147.52 (dd, J=245.3, 7.9 Hz), 141.69 (dd, J=13.1, 3.3 Hz), 140.66, 137.47, 126.63, 124.95, 124.42, 123.22, 119.14 (dd, J=9.1, 3.8 Hz), 117.57-117.07 (m), 111.42 (dd, J=22.9, 3.9 Hz), 15.66; MS (ESI): 360.91 (M)$^+$.

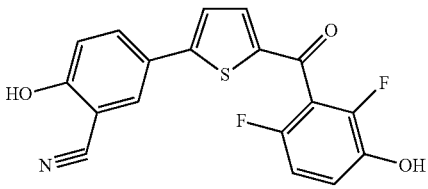

25

5-[5-(2,6-Difluoro-3-hydroxy-benzoyl)-thiophen-2-yl]-2-hydroxy-benzonitrile (25): The title compound was prepared by reaction of 5-[5-(2,6-difluoro-3-hydroxy-benzoyl)-thiophen-2-yl]-2-isopropoxy-benzonitrile (18) (220 mg, 0.55 mmol) and boron tribromide (2.75 mmol, 5.0 equiv) according to method B. The product was purified by CC (dichloromethane/methanol 99.25:0.75); yield: 59% (115 mg). $^1$H NMR (500 MHz, acetone-d$^6$) δ 9.67 (br. s, 1H), 8.12-8.07 (m, 1H), 7.93 (dd, J=8.7, 2.4 Hz, 1H), 7.62 (d, J=4.1 Hz, 1H), 7.60 (d, J=4.1 Hz, 1H), 7.24-7.17 (m, 2H), 7.03 (td, J=8.9, 1.9 Hz, 1H); $^{13}$C NMR (125 MHz, acetone-d$^6$) δ 180.56, 161.47, 153.44, 152.56 (dd, J=240.4, 5.8 Hz), 148.42 (dd, J=245.7, 7.8 Hz), 142.98, 142.63 (dd, J=13.0, 3.2 Hz), 138.33, 133.37, 132.07, 126.34, 125.82, 120.31 (dd, J=9.1, 3.9 Hz), 118.08, 118.07 (d, J=43.7 Hz), 116.41, 112.42 (dd, J=22.8, 3.9 Hz), 101.91; MS (ESI): 357.81 (M)$^+$.

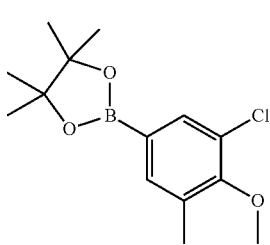

26a 2-(3-Chloro-4-methoxy-5-methyl-phenyl)-4,4,5,5-tetramethyl-[1,3,2]dioxaborolane (26a): 5-bromo-1-chloro-2-methoxy-3-methylbenzene (5.00 g, 20.2 mmol, 1.00 equiv), bis(pinacolato)diboron (8.09 g, 31.8 mmol, 1.50 equiv), potassium acetate (5.95 g, 60.6 mmol, 3.00 equiv) and Pd(dppf)Cl$_2$ (739 mg, 1.01 mmol, 0.05 equiv) were dissolved under N$_2$ in 40 ml dry DMSO and the mixture was stirred at 80° C. for 2 h. The reaction was quenched with water, diluted with diethyl ether and filtered over celite. The phases were separated and the aqueous layer was extracted two times with diethyl ether. The combined organic layers were washed three times with water; one time with brine, dried over magnesium sulfate, filtered and concentrated under reduced pressure. The crude product was purified by cc (hexane/ethyl acetate 85:15); yield: 88% (4.71 g). $^1$H NMR (500 MHz, acetone-d$^6$) δ 7.54-7.56 (m, 1H), 7.48-7.50 (m, 1H), 3.82 (s, 3H), 2.31 (t, J=0.6 Hz, 3H), 1.33 (s, 12H).

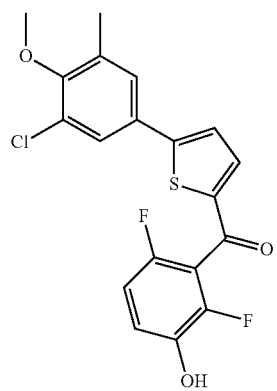

26

[5-(3-Chloro-4-methoxy-5-methyl-phenyl)-thiophen-2-yl]-(2,6-difluoro-3-hydroxy-phenyl)-methanone (26): The title compound was prepared by reaction of 2-(3-chloro-4-methoxy-5-methyl-phenyl)-4,4,5,5-tetramethyl-[1,3,2]dioxaborolane (26a) (1000 mg, 3.53 mmol), (5-bromo-thiophen-2-yl)-(2,6-difluoro-3-hydroxy-phenyl)-methanone (1e) (1000 mg, 3.13 mmol), cesium carbonate (4000 mg, 12.5 mmol) and tetrakis(triphenylphosphine) palladium (18 mg, 0.02 mmol) according to method C1. The product was purified by CC (hexane/ethyl acetate 8:2); yield: 82% (1000 mg). $^1$H NMR (500 MHz, acetone-d$^6$) δ 8.98 (s, 1H), 7.72 (dd, J=2.2, 0.6 Hz, 1H), 7.65-7.60 (m, 2H), 7.60 (d, J=4.1 Hz, 1H), 7.20 (td, J=9.4, 5.2 Hz, 1H), 7.03 (td, J=8.8, 1.9 Hz, 1H), 3.86 (s, 3H), 2.38 (s, 3H); $^{13}$C NMR (125 MHz, acetone-d$^6$) δ 180.7, 156.4, 153.6, 151.7, 149.5, 149.5, 147.5, 143.5, 142.8, 142.7, 138.3, 135.5, 130.7, 129.3, 128.8, 126.5, 120.4, 112.6, 112.4, 60.7, 16.5; MS (ESI): 395.28 (M+H)$^+$.

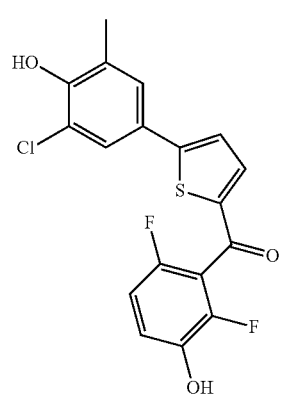

27

[5-(3-Chloro-4-hydroxy-5-methyl-phenyl)-thiophen-2-yl]-(2,6-difluoro-3-hydroxy-phenyl)-methanone (27): The title compound was prepared by reaction of [5-(3-chloro-4-methoxy-5-methyl-phenyl)-thiophen-2-yl]-(2,6-difluoro-3-hydroxy-phen-yl)-methanone (26) (104 mg, 0.26 mmol) and boron tribromide (1.05 mmol, 4.0 equiv) according to method B. The product was purified by CC (hexane/ethyl acetate 7:3); yield: 82% (84 mg). $^1$H NMR (500 MHz, acetone-d$^6$) δ 8.96 (d, J=1.3 Hz, 1H), 8.50 (s, 1H), 7.68-7.66 (m, 1H), 7.60-7.55 (m, 2H), 7.53 (d, J=4.1 Hz, 1H), 7.19 (td, J=9.4, 5.5 Hz, 1H), 7.02 (td, J=8.8, 1.9 Hz, 1H), 2.34 (s, 3H); $^{13}$C NMR (125 MHz, acetone-d$^6$) δ 180.5, 154.6, 153.6, 153.2, 151.7, 149.5, 147.5, 142.7, 138.4, 128.7, 128.6, 126.5, 125.8, 125.3, 121.8, 120.3, 118.4, 118.2, 112.5, 112.4, 16.8; MS (ESI): 381.06 (M+H)$^+$.

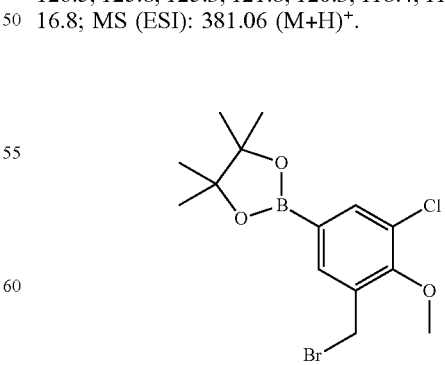

28b 2-(3-Bromomethyl-5-chloro-4-methoxy-phenyl)-4,4,5,5-tetramethyl-[1,3,2]dioxaborolane (28b): 2-(3-chloro-4-methoxy-5-methylphenyl)-4,4,5,5-tetramethyl-1,3,2-dioxaborolane (26a) (200 mg, 0.71 mmol, 1.00 equiv) and N-bromo-succinimide (113 mg, 0.63 mmol, 0.90 equiv) were dissolved under N₂ in 17 ml CCl₄, followed by a catalytic amount of dibenzoyl peroxide. The mixture was stirred under reflux for 1 h. The reaction was quenched with water and extracted three times with dichloromethane. The combined organic layers were washed two times with water, one time with brine, dried over sodium sulfate, filtered and concentrated under reduced pressure. The crude product was purified by CC (hexane/ethyl acetate 85:15); yield: 70% (180 mg). $^1$H NMR (500 MHz, acetone-d$^6$) δ 7.75 (d, J=1.5 Hz, 1H), 7.68 (d, J=1.5 Hz, 1H), 4.71 (s, 2H), 4.00 (s, 3H), 1.33-1.35 (m, 12H).

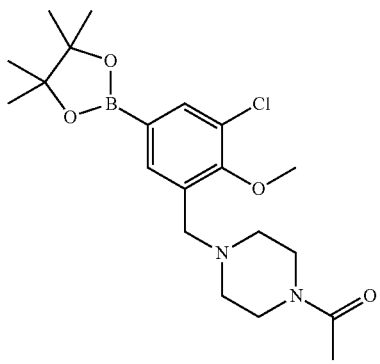

28a

1-{4-[3-Chloro-2-methoxy-5-(4,4,5,5-tetramethyl-[1,3,2]dioxaborolan-2-yl)-benzyl]-piperazin-1-yl}-ethanone (28a): 2-(3-(bromomethyl)-5-chloro-4-methoxyphenyl)-4,4,5,5-tetramethyl-1,3,2-dioxaborolane (28b) (180 mg, 0.50 mmo, 1.00 equiv) was dissolved under N₂ in 1 ml dry THF and 1-acetylpiperazine was added. The mixture was stirred for 1 h under reflux. The reaction was quenched with water and extracted three times with ethyl acetate. The combined organic layers were washed two times with water, one time with brine, dried over MgSO₄, filtered and concentrated under reduced pressure. The crude product was purified by cc (ethyl acetate/ethanol 8:2), to give the desired product as yellow solid; yield: 70% (198 mg). $^1$H NMR (500 MHz, acetone-d$^6$) δ 7.69 (d, J=1.5 Hz, 1H), 7.65 (d, J=1.5 Hz, 1H), 3.90 (s, 3H), 3.57 (s, 3H), 2.77 (t, J=5.2 Hz, 2H), 2.70 (t, J=5.2 Hz, 2H), 2.47 (t, J=5.2 Hz, 2H), 2.42 (t, J=5.2 Hz, 2H), 2.00 (s, 3H), 1.34 (s, 12H).

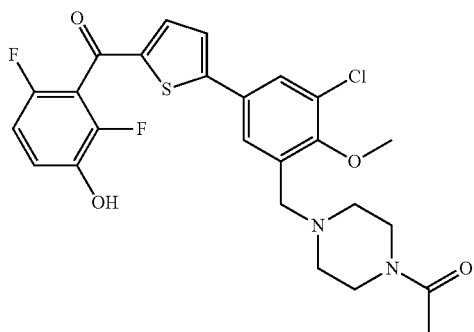

28

1-(4-{3-Chloro-5-[5-(2,6-difluoro-3-hydroxy-benzoyl)-thiophen-2-yl]-2-methoxy-benzyl}-piperazin-1-yl)-ethanone (28): The title compound was prepared by reaction of 1-(4-(3-chloro-2-methoxy-5-(4,4,5,5-tetramethyl-1,3,2-dioxaborolan-2-yl)benzyl)piperazin-1-yl)ethanone (28a) (100 mg, 0.24 mmol, 1.00 equiv), (5-bromothiophen-2-yl)(2,6-difluoro-3-hydroxyphenyl)-methanone (1e) (77 mg, 0.24 mmol, 1.00 equiv), cesium carbonate (156 mg, 0.48 mmol) and tetrakis(triphenylphosphine) palladium (1 mg, 0.001 mmol, 0.005 equiv) according to method C1. The product was purified by CC (ethyl acetate/ethanol 8:2); yield: 98% (55 mg). $^1$H NMR (500 MHz, DMSO-d$^6$) δ 9.53 (br. s., 1H), 8.28-8.26 (m, 2H), 8.10-8.03 (m, 2H), 7.66 (td, J=9.4, 5.3 Hz, 1H), 7.48 (td, J=8.9, 2.0 Hz, 1H), 4.38 (s, 3H), 4.10 (s, 2H), 4.03-3.94 (m, 4H), 2.99 (t, J=5.0 Hz, 2H), 2.93 (t, J=5.0 Hz, 2H), 2.46 (s, 3H). $^{13}$C NMR (125 MHz, DMSO-d$^6$) δ 180.7, 169.0, 156.7, 153.5, 151.6, 149.4, 147.4, 143.5, 142.7, 138.2, 135.8, 130.6, 129.6, 128.3, 127.7, 126.5, 120.4, 118.0, 112.5, 112.3, 61.8, 57.1, 54.0, 53.7, 46.9, 42.0, 21.3; MS (ESI): 521.41 (M+H)$^+$.

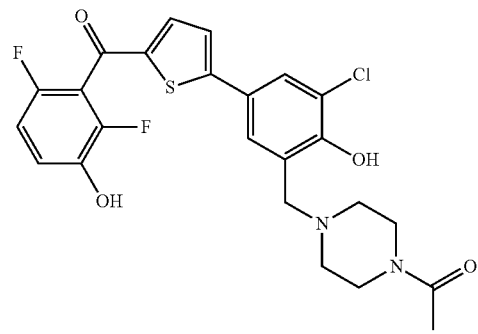

29

1-(4-{3-Chloro-5-[5-(2,6-difluoro-3-hydroxy-benzoyl)-thiophen-2-yl]-2-hydroxy-benzyl}-piperazin-1-yl)-ethanone (29): The title compound was prepared by reaction of 1-(4-{3-Chloro-5-[5-(2,6-difluoro-3-hydroxy-benzoyl)-thiophen-2-yl]-2-methoxy-benzyl}-piperazin-1-yl)-ethanone (28) (150 mg, 0.29 mmol) and boron tribromide (0.87 mmol, 3.0 equiv) according to method B. The product was purified by using preparative TLC (dichloromethane/methanol 95:5); yield: 12% (16 mg). $^1$H NMR (500 MHz, acetone-d$^6$) δ 7.86-7.80 (m, 1H), 7.75 (d, J=2.2 Hz, 1H), 7.65-7.56 (m, 1H), 7.54-7.49 (m, 1H), 7.24-7.18 (m, 1H), 7.06-6.99 (m, 1H), 3.70-3.60 (m, 4H), 2.71-2.52 (m, 4H), 2.04 (s, 3H); $^{13}$C NMR (125 MHz, acetone-d$^6$) δ 180.7, 169.9, 156.0, 154.6, 153.5, 153.5, 151.6, 149.5, 147.5, 142.8, 142.5, 138.4, 127.7, 126.7, 125.8, 125.3, 124.9, 122.1, 120.2, 118.2, 112.5, 112.4, 61.1, 53.5, 52.9, 46.6, 41.8, 21.3; MS (ESI): 506.89 (M+H)$^+$.

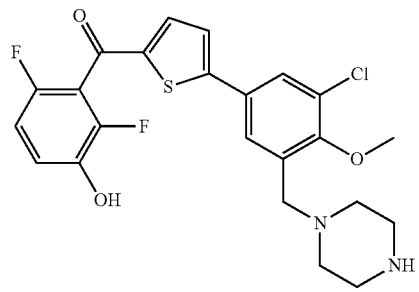

30

[5-(3-Chloro-4-methoxy-5-piperazin-1-ylmethyl-phenyl)-thiophen-2-yl]-(2,6-difluoro-3-hydroxy-phenyl)-methanone (30): 1-(4-(3-chloro-5-(5-(2,6-difluoro-3-hydroxybenzoyl)-thiophen-2-yl)-2-methoxybenzyl)piperazine-1-yl)ethanone (28) (150 mg, 0.29 mmol, 1.00 equiv) was dissolved in 20 ml 3 M aqueous HCl and heated to 80° C. for 3 h. The reaction was washed two times with ethyl acetate, the aqueous layer was basified to pH 10 with 2 M NaOH and washed two times with ethyl acetate. The aqueous layer was neutralized with 2 M HCl and extracted three times with ethyl acetate. The combined organic layers were washed one time with water, one time with brine, dried over MgSO$_4$, filtered and concentrated under reduced pressure to give the desired pure product in 40% yield as pale yellow solid. $^1$H NMR (500 MHz, acetone-d$^6$) δ 7.83-7.79 (m, 2H), 7.67-7.60 (m, 2H), 7.19 (m, 1H), 7.00 (td, J=9.0, 1.9 Hz, 1H), 3.92 (s, 3H), 3.59 (s, 2H), 2.89-2.81 (m, 4H), 2.53-2.45 (m, 4H); $^{13}$C NMR (125 MHz, acetone-d$^6$) δ 180.8, 156.8, 153.3, 151.5, 149.4, 147.5, 143.6, 142.9, 142.7, 138.2, 135.4, 130.7, 129.6, 128.4, 127.9, 126.7, 120.5, 118.1, 112.3, 112.2, 62.0, 56.9, 50.4, 44.3; MS (ESI): 479.22 (M+H)$^+$.

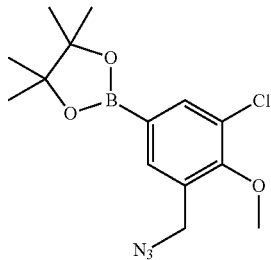

31c 2-(3-Azidomethyl-5-chloro-4-methoxy-phenyl)-4,4,5,5-tetramethyl-[1,3,2]dioxaborolane (31c): 2-(3-(bromomethyl)-5-chloro-4-methoxyphenyl)-4,4,5,5-tetramethyl-1,3,2-dioxaborolane (28b) (800 mg, 2.19 mmol, 1.00 equiv) was dissolved under N$_2$ in 8 ml dry DMF and sodium azide (143 mg, 2.19 mmol, 1.00 equiv) was added. The mixture was stirred at room temperature overnight. The mixture was quenched with water and extracted three times with ethyl acetate. The combined organic layers were washed two times with water, one time with brine, dried over magnesium sulfate, filtered and concentrated under reduced pressure. The crude product was purified by CC (hexane/ethyl acetate 8:2); yield: 71% (503 mg). $^1$H NMR (500 MHz, acetone-d$^6$) δ 7.72 (d, J=1.6 Hz, 1H), 7.69 (d, J=1.6 Hz, 1H), 4.55 (s, 2H), 3.93 (s, 3H), 1.34 (s, 12H).

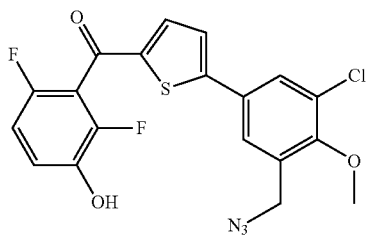

31b

[5-(3-Azidomethyl-5-chloro-4-methoxy-phenyl)-thiophen-2-yl]-(2,6-difluoro-3-hydroxy-phenyl)-methanone (31b): The title compound was prepared by reaction of 2-(3-Azidomethyl-5-chloro-4-methoxy-phenyl)-4,4,5,5-tetramethyl-[1,3,2]dioxaborolane (31c) (683 mg, 2.16 mmol, 1.00 equiv), (5-bromothiophen-2-yl)(2,6-difluoro-3-hydroxyphenyl)methanone (1e) (700 mg, 2.16 mmol, 1.00 equiv), cesium carbonate (2000 mg, 6.44 mmol, 3 equiv) and tetrakis(triphenylphosphine) palladium (13 mg, 0.01 mmol, 0.005 equiv) according to method C1; yield: 84% (785 mg); The product was used in the next steps without any characterisation.

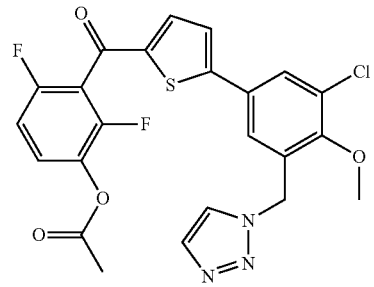

31a

Acetic acid 3-[5-(3-chloro-4-methoxy-5-[1,2,3]triazol-1-ylmethyl-phenyl)-thiophene-2-carbonyl]-2,4-difluoro-phenylester (31a): (5-(3-(azidomethyl)-5-chloro-4-methoxyphenyl)-thiophen-2-yl)(2,6-difluoro-3-hydroxyphenyl)methanone (31b) (50 mg, 0.11 mmol, 1.00 equiv), was dissolved in 106 µl vinyl acetate and the reaction was heated at 120° C. under microwave for 10 h. The reaction was concentrated under reduced pressure and purified by CC using ethyl acetate as eluent; yield: 27% (15 mg). $^1$H NMR (500 MHz, DMSO-d$^6$) δ 8.11 (d, J=0.9 Hz, 1H), 7.92 (d, J=2.5 Hz, 1H), 7.70 (d, J=0.9 Hz, 1H), 7.68-7.66 (m, 1H), 7.64-7.61 (m, 2H), 7.53 (td, J=8.9, 5.5 Hz, 1H), 7.26 (td, J=8.8, 1.9 Hz, 1H), 5.78 (s, 2H), 3.89 (s, 3H), 2.34 (s, 3H); MS (ESI): 504.12 (M+H)$^+$.

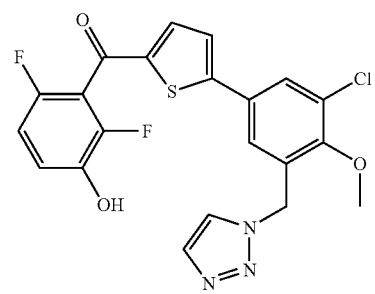

31

[5-(3-Chloro-4-methoxy-5-[1,2,3]triazol-1-ylmethyl-phenyl)-thiophen-2-yl]-(2,6-difluoro-3-hydroxy-phenyl)-methanone (31): Acetic acid 3-[5-(3-chloro-4-methoxy-5-[1,2,3]triazol-1-ylmethyl-phenyl)-thiophene-2-carbonyl]-2,4-difluoro-phenylester (31a) (110 mg, 0.24 mmol, 1.00 equiv) was dissolved under N$_2$ in a degased mixture of 5 ml THF and 600 µl of 2M NaOH. The mixture was stirred for 2 h at room temperature. The reaction was acidified to pH 6 with 1 M HCl and extracted three times with ethyl acetate. The combined organic layers were washed two times with water, one time with brine, dried over magnesium sulfate, filtered and concentrated under reduced pressure to give the desired product; yield: 95% (90 mg). $^1$H NMR (500 MHz, acetone-d$^6$) δ 9.05 (br. s, 1H), 8.11 (d, J=0.9 Hz, 1H), 7.91 (d, J=2.2

Hz), 7.70 (d, J=0.9 Hz, 1H), 7.67 (d, J=2.2 Hz, 1H), 7.65-7.62 (m, 1H), 7.61-7.58 (m, 1H), 7.21 (td, J=8.9, 5.5 Hz, 1H), 7.03 (td, J=8.8, 1.9 Hz, 1H), 5.78 (s, 2H), 3.89 (s, 3H); MS (ESI): 462.15 (M+H)+.

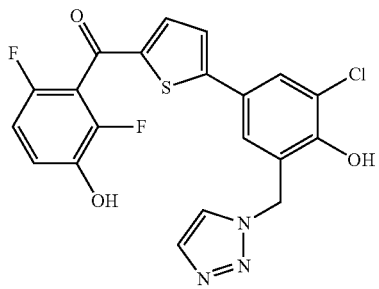

32

[5-(3-Chloro-4-hydroxy-5-[1,2,3]triazol-1-ylmethyl-phenyl)-thiophen-2-yl]-(2,6-difluoro-3-hydroxy-phenyl)-methanone (32): The title compound was prepared by reaction of [5-(3-Chloro-4-methoxy-5-[1,2,3]triazol-1-ylmethyl-phenyl)-thiophen-2-yl]-(2,6-difluoro-3-hydroxy-phenyl)-methanone (31) (80 mg, 0.16 mmol) and boron tribromide (800 μl, 0.80 mmol, 5.0 equiv) according to method B. The product was purified by CC (ethyl acetate/ethanol 9:1); yield: 32% (23 mg). $^1$H NMR (500 MHz, acetone-d[6]) δ 8.74 (d, J=1.3 Hz, 1H), 8.43 (s, 1H), 8.03-7.90 (m, 2H), 7.68-7.54 (m, 2H), 7.30 (td, J=8.8, 5.5 Hz, 1H), 7.01 (td, J=8.8, 1.9 Hz, 1H), 6.05 (s, 2H); $^{13}$C NMR (125 MHz, acetone-d[6]) δ 180.7, 153.3, 143.2, 138.3, 130.7, 129.3, 129.2, 128.8, 127.3, 126.1, 124.6, 123.0, 120.3, 112.4, 52.0; MS (ESI): 448.12 (M+H)+.

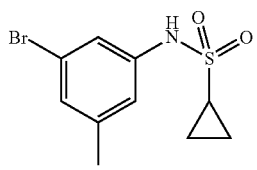

33b

Cyclopropanesulfonic acid (3-bromo-5-methyl-phenyl)-amide (33b): The title compound was prepared by reaction of 3-bromo-5-methylaniline (1000 mg, 5.38 mmol, 1 equiv) and cyclopropanesulfonyl chloride (1013 mg, 8.07 mmol, 1.5 equiv) according to method D. The product was purified by CC (hexane/ethyl acetate 8:2); yield: 77% (1200 mg). $^1$H NMR (500 MHz, acetone-d[6]) δ 8.62 (br. s, 1H), 7.35 (s, 1H), 7.15 (s, 1H), 7.13 (s, 1H), 2.65-2.61 (m, 1H), 2.30 (s, 3H), 1.00-0.95 (m, 4H).

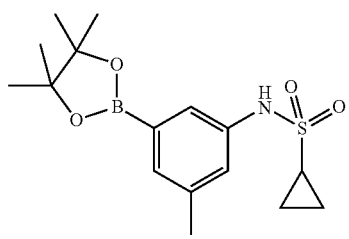

33a

Cyclopropanesulfonic acid [3-methyl-5-(4,4,5,5-tetramethyl-[1,3,2]dioxaborolan-2-yl)-phenyl]-amide (33a): Cyclopropanesulfonic acid (3-bromo-5-methyl-phenyl)-amide (33b) (800 mg, 2.76 mmol, 1 equiv) was dissolved in 10 ml dry dimethyl sulfoxide under N₂ atmosphere. Bispinacolatodiborone (1050 mg, 4.14 mmol, 1.5 equiv), potassium acetate (8.28 mmol, 3 equiv) and Pd(dppf)Cl₂ (0.14 mmol, 0.05 equiv) were added. The reaction mixture was heated to 80° C. overnight. Reaction mixture was cooled down to room temperature, quenched with water and diethyl ether, filtered over celite, extracted three times with diethyl ether, washed three times with water, washed with brine, dried over magnesium sulfate, filtered and evaporated under reduced pressure. Purified with flash chromatography (dichloromethane pure to dichloromethane/methanol 8:2); yield: 16% (150 mg).

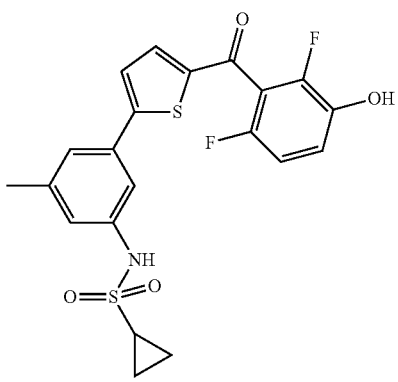

33

Cyclopropanesulfonic acid {3-[5-(2,6-difluoro-3-hydroxy-benzoyl)-thiophen-2-yl]-5-methyl-phenyl}-amide (33): cyclopropanesulfonic acid [3-methyl-5-(4,4,5,5-tetramethyl-[1,3,2]dioxaborolan-2-yl)-phenyl]-amide (33a) (0.45 mmol, 1.20 equiv), (5-bromo-2-thienyl)(2,4-difluoro-3-hydroxyphenyl)-methanone 1e (0.37 mmol, 1.00 equiv), ceasium carbonate (1.11 mmol, 3.00 equiv) and Pd(PPh₃)₄ (0.002 mmol, 0.005 equiv) were suspended in a degased mixture of 5 ml DME and 5 ml water. The mixture was heated to reflux for 3 days under N₂ atmosphere. The mixture was cooled down to room temperature, quenched with water, filtered over celite, extracted three times with ethyl acetate, washed one time with water, one time with brine, dried over sodium sulphate, filtered and evaporated under reduced pressure. The product was purified by mPLC (0% ethyl acetate to 100% ethyl acetate) followed by preparative TLC (hexane/ethyl acetate 5:5); yield: 18% (30 mg). $^1$H NMR (500 MHz, acetone-d[6]) δ 8.98 (s, 1H), 8.68 (s, 1H), 7.61 (d, J=4.0 Hz, 1H), 7.57 (s, 1H), 7.55 (d, J=4.0 Hz, 1H), 7.41 (s, 1H), 7.26 (s, 1H), 7.21-7.15 (m, 1H), 7.01 (td, J=8.8, 1.8 Hz, 1H), 2.70-2.65 (m, 1H), 2.38 (s, 3H), 1.02-0.96 (m, 4H); $^{13}$C NMR (125 MHz, acetone-d[6]) δ 180.6, 155.0, 143.2, 141.3, 140.4, 138.1, 134.6, 126.1, 123.7, 123.1, 120.3, 116.4, 112.3, 29.7, 21.4, 5.7; MS (ESI): 449.76 (M+H)+.

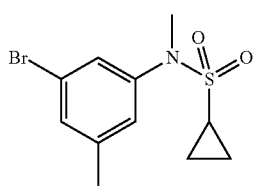

34b

Cyclopropanesulfonic acid (3-bromo-5-methyl-phenyl)-methyl-amide (34b): Cyclo-propane-sulfonic acid (3-bromo-5-methyl-phenyl)-amide (33b) (100 mg, 0.345 mmol, 1 equiv) was dissolved in 1 ml anhydrous dimethyl formamide and cooled to 0° C. under $N_2$ atmosphere. Sodium hydride (10 mg, 0.414 mmol, 1.2 equiv) was added and the solution was stirred for 10 min. Methyl iodide (54 mg, 0.024 ml, 0.380 mmol, 1.1 equiv) was added slowly, the mixture warmed up to room temperature and stirred over night. The mixture was quenched with water, extracted three times with diethyl ether, washed 5 times with water, and subsequently with brine, dried over sodium sulphate, filtered and evaporated under reduced pressure. The product was used in the next steps without further purification; yield: 81% (85 mg). $^1$H NMR (500 MHz, acetone-$d^6$) δ 7.44 (s, 1H), 7.29 (s, 1H), 7.16 (s, 1H), 3.31 (s, 3H), 2.56-2.54 (m, 1H), 2.33 (s, 3H), 0.99-0.96 (m, 4H).

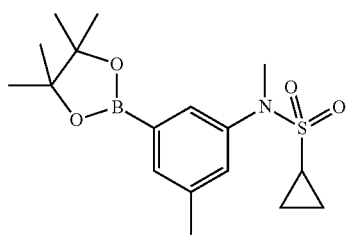

34a

Cyclopropanesulfonic acid methyl-[3-methyl-5-(4,4,5,5-tetramethyl-[1,3,2]dioxaborolan-2-yl)-phenyl]-amide (34a): Cyclopropanesulfonic acid (3-bromo-5-methyl-phenyl)-amide (34b) (260 mg, 0.86 mmol, 1 equiv) was dissolved in 3 ml dry dimethyl sulfoxide under $N_2$ atmosphere. Bispinacolatodiborone (326 mg, 1.28 mmol, 1.5 equiv), potassium acetate (2.57 mmol, 3 equiv) and Pd(dppf)Cl$_2$ (0.04 mmol, 0.05 equiv) were added. The reaction mixture was heated to 80° C. overnight. Reaction mixture was cooled down to room temperature, quenched with water and diethyl ether, filtered over celite, extracted three times with diethyl ether, washed three times with water and subsequently with brine, dried over magnesium sulphate, filtered and evaporated under reduced pressure. Purified with flash chromatography (dichloromethane pure to dichloromethane/methanol 8:2); yield: 50% (150 mg).

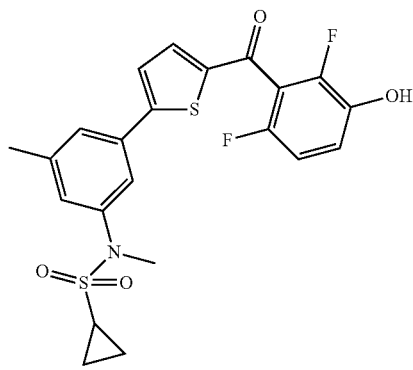

34

Cyclopropanesulfonic acid {3-[5-(2,6-difluoro-3-hydroxy-benzoyl)-thiophen-2-yl]-5-methyl-phenyl}-methyl-amide (34): cyclopropanesulfonic acid methyl-[3-methyl-5-(4,4,5,5-tetramethyl-[1,3,2]dioxaborolan-2-yl)-phenyl]-amide (34a) (0.86 mmol, 1.00 equiv), (5-bromo-2-thienyl) (2,4-difluoro-3-hydroxyphenyl)-methanone 1e (0.86 mmol, 1.00 equiv), cesium carbonate (3.42 mmol, 4.00 equiv) and Pd(PPh$_3$)$_4$ (0.004 mmol, 0.005 equiv) were suspended in a degased mixture of 5 ml DME and 5 ml water. The mixture was heated to reflux for 3 days under $N_2$ atmosphere. The mixture was cooled down to room temperature, quenched with water, filtered over celite, extracted three times with ethyl acetate, washed one time with water, one time with brine, dried over sodium sulphate, filtered and evaporated under reduced pressure. The product was purified by CC (hexane/ethyl acetate 8:2 to 5:5) followed by preparative TLC (dichloromethane/methanol 99:1); yield: 6% (25 mg). $^1$H NMR (500 MHz, acetone-$d^6$) δ 9.04 (s, 1H), 7.71 (s, 1H), 7.65-7.63 (m, 2H), 7.58 (s, 1H), 7.30 (s, 1H), 7.23-7.18 (m, 1H), 7.04 (dt, J=9.0, 1.9 Hz, 1H), 3.41 (s, 3H), 2.68-2.65 (m, 1H), 2.43 (s, 3H), 1.01-0.90 (m, 4H); $^{13}$C NMR (125 MHz, acetone-$d^6$) δ 180.7, 154.7, 144.2, 140.9, 138.1, 134.4, 129.3, 126.4, 122.5, 112.4, 38.7, 21.2, 4.9; MS (ESI): 463.87 (M)$^+$.

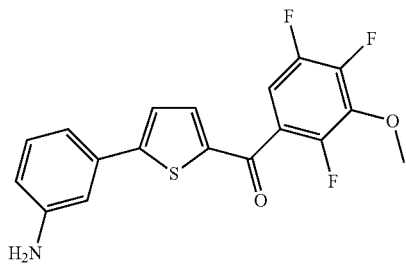

35a 5-(3-Aminophenyl)-thiophen-2-yl](2,4,5-trifluoro-3-methoxyphenyl)methanone (35a): The title compound was prepared by reaction of (5-bromothiophen-2-yl) (2,4,5-trifluoro-3-methoxyphenyl)methanone (1d) (1000 mg, 2.85 mmol) and 3-aminophenylboronic acid (468 mg, 3.42 mmol), cesium carbonate (3711 mg, 11.39 mmol) and tetrakis(triphenylphosphine) palladium (40 mg, 33 μmol) according to method C1; yield: 90% (930 mg; yellow oil). The product was used directly in the subsequent reaction without any characterisation.

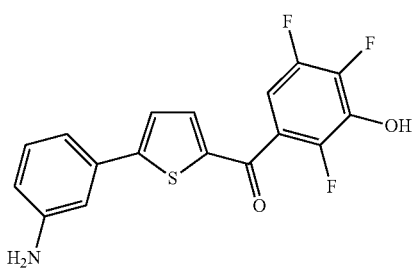

35

[5-(3-Aminophenyl)thiophen-2-yl](2,4,5-trifluoro-3-hydroxyphenyl)methanone (35): The title compound was prepared by reaction of [5-(3-aminophenyl)thiophen-2-yl](2,4,5-trifluoro-3-methoxyphenyl)methanone (35a) (930 mg, 2.56 mmol) and boron tribromide (7.7 mmol) according to method B. The product was purified by CC (dichloromethane/methanol 99.5:0.5); yield: 61.5% (550 mg; yellow oil); $^1$H NMR (500 MHz, acetone-d$^6$) δ 7.66 (ddd, J=16.9, 4.1, 1.8 Hz, 1H), 7.61-7.37 (m, 2H), 7.19-7.00 (m, 3H), 6.76 (dddd, J=8.0, 4.4, 2.1, 1.0 Hz, 1H); $^{13}$C NMR (75 MHz, acetone-d$^6$) δ 181.53 (s), 149.83 (ddd, J=14.8, 9.2, 3.3 Hz), 147.77-147.32 (m), 145.75-145.38 (m), 144.52-143.93 (m), 138.27 (ddd, J=15.8, 11.0, 2.4 Hz), 133.50, 129.94, 124.29, 123.20-122.69 (m), 120.91 (d, J=4.6 Hz), 117.16, 115.65, 114.65, 111.59, 110.16 (dd, J=20.8, 3.7 Hz), 61.85; MS (ESI): 350.18 (M+H)$^+$.

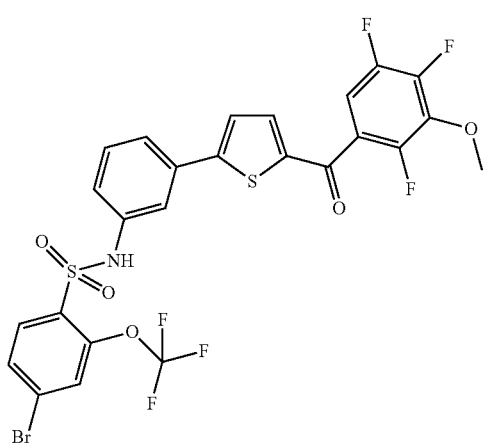

36a

4-Bromo-2-trifluoromethoxy-N-{3-[5-(2,4,5-trifluoro-3-methoxybenzoyl)thiophen-2-yl]phenyl}benzenesulfonamide (36a): The title compound was prepared by reaction of [5-(3-aminophenyl)thiophen-2-yl](2,4,5-trifluoro-3-methoxyphenyl)methanone (35a) (260 mg, 0.72 mmol) and 4-bromo-2-trifluoromethoxybenzenesulfonyl chloride (243 mg, 0.72 mmol) according to method D; yield: 65.0% (310 mg; yellow oil). The product was used directly in the subsequent reaction without any characterisation.

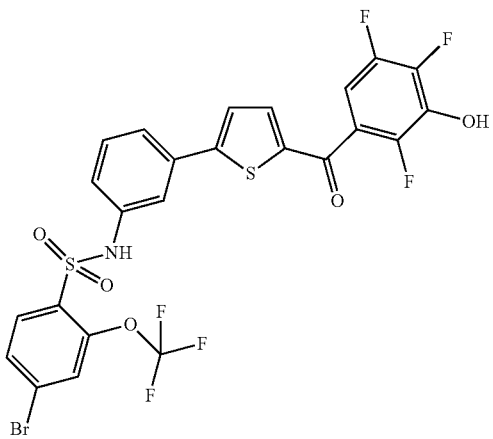

36

4-Bromo-N-{3-[5-(2,4,5-trifluoro-3-hydroxybenzoyl)thiophen-2-yl]phenyl}-2-trifluoromethoxybenzenesulfonamide (36): The title compound was prepared by reaction of 4-bromo-2-trifluoromethoxy-N-{3-[5-(2,4,5-trifluoro-3-methoxybenzoyl)thiophen-2-yl]phenyl}benzenesulfonamide (36a) (310 mg, 0.47 mmol) and boron tribromide (2.3 mmol) according to method B. The product was purified by CC (dichloromethane/methanol 99.5:0.5); yield: 72.5% (190 mg; yellow oil); $^1$H NMR (500 MHz, acetone-d$^6$) δ 9.97 (br., 1H, NH), 9.61 (br. s, 1H, OH), 8.03 (d, J=8.5 Hz, 1H), 7.77 (dd, J=8.5, 1.8 Hz, 1H), 7.74 (p, J=1.6 Hz, 1H), 7.67 (dd, J=4.1, 1.8 Hz, 1H), 7.67-7.65 (m, 1H), 7.54 (ddd, J=7.8, 1.8, 1.0 Hz, 1H), 7.52 (d, J=4.1 Hz, 1H), 7.42-7.37 (m, 1H), 7.31 (ddd, J=8.1, 2.2, 1.0 Hz, 1H), 7.12 (ddd, J=9.9, 8.1, 5.6 Hz, 1H); $^{13}$C NMR (125 MHz, acetone-d$^6$) δ 182.85, 148.56 (ddd, J=7.3, 6.5, 3.3 Hz), 146.95 (dd, J=3.2, 1.6 Hz), 146.61 (ddd, J=7.7, 6.9, 3.1 Hz), 143.65 (ddd, J=248.6, 15.8, 5.8 Hz), 143.09, 138.84, 138.25, 138.23, 137.08 (ddd, J=18.3, 12.9, 3.0 Hz), 134.94, 133.83, 131.82, 131.46, 131.32, 129.11, 126.14, 124.91 (d, J=1.9 Hz), 123.53, 123.07 (ddd, J=15.7, 6.8, 3.9 Hz), 122.07, 121.11 (q, J=260.6 Hz), 118.76, 106.96 (dd, J=21.1, 3.0 Hz); MS (ESI): 653.32 (M+H)$^+$.

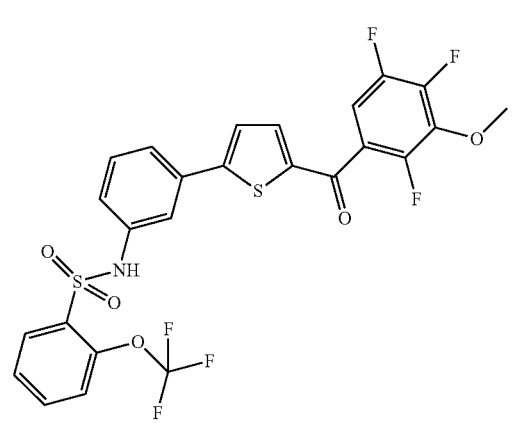

37a

2-Trifluoromethoxy-N-{3-[5-(2,4,5-trifluoro-3-methoxybenzoyl)thiophen-2-yl]phenyl}benzenesulfonamide (37a): The title compound was prepared by reaction of [5-(3-aminophenyl)thiophen-2-yl](2,4,5-trifluoro-3-methoxyphenyl)methanone (35a) (260 mg, 0.72 mmol) and 2-trifluoromethoxybenzenesulfonyl chloride (189 mg, 0.72 mmol) according to method D1; yield: 70.6% (260 mg; yellow oil). The product was used directly in the subsequent reaction without any characterisation.

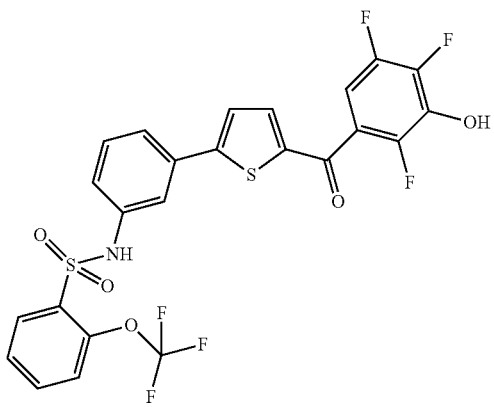

37

N-{3-[5-(2,4,5-Trifluoro-3-hydroxybenzoyl)thiophen-2-yl]phenyl}-2-trifluoromethoxybenzenesulfonamide (37): The title compound was prepared by reaction of 2-trifluoromethoxy-N-{3-[5-(2,4,5-trifluoro-3-methoxybenzoyl) thiophen-2-yl]phenyl}benzenesulfonamide (37a) (300 mg, 0.51 mmol) and boron tribromide (2.5 mmol) according to method B. The product was purified by CC (dichloromethane/methanol 99.5:0.5); yield: 52.4% (154 mg; yellow oil); $^1$H NMR (500 MHz, acetone-d$^6$) δ 9.98 (br. s, 1H, NH), 9.52 (br. s, 1H, OH), 8.13-8.09 (m, 1H), 7.78 (ddd, J=8.4, 7.5, 1.7 Hz, 1H), 7.66 (ddd, J=4.3, 3.1, 1.1 Hz, 2H), 7.58-7.53 (m, 2H), 7.52-7.50 (m, 2H), 7.38 (td, J=7.9, 0.4 Hz, 1H), 7.31 (ddd, J=8.1, 2.2, 1.0 Hz, 1H), 7.12 (ddd, J=9.9, 8.1, 5.6 Hz, 1H); $^{13}$C NMR (125 MHz, acetone-d$^6$) δ 182.85, 153.98, 148.55 (ddd, J=7.7, 7.0, 3.0 Hz), 146.81 (dd, J=3.2, 1.6 Hz), 146.61 (ddd, J=7.6, 7.1, 3.0 Hz), 143.65 (ddd, J=248.6, 15.9, 5.6 Hz), 143.03, 139.16, 138.25 (d, J=2.1 Hz), 137.09 (ddd, J=18.2, 13.1, 3.3 Hz), 136.36, 134.84, 132.57, 132.27, 131.23, 128.02, 126.06, 123.22, 123.07 (ddd, J=15.6, 6.5, 3.7 Hz), 121.85, 121.53 (d, J=1.8 Hz), 121.28 (q, J=259.2 Hz), 118.45, 106.94 (dd, J=21.1, 3.0 Hz); MS (ESI): 573.62 (M)$^+$.

The title compound was prepared by reaction of [5-(3-aminophenyl)thiophen-2-yl](2,4,5-trifluoro-3-methoxyphenyl)methanone (35a) (260 mg, 0.72 mmol) and 2-trifluoromethylbenzenesulfonyl chloride (177 mg, 0.72 mmol) according to method D1; yield: 43.5% (180 mg; yellow oil). The product was used directly in the subsequent reaction without any characterisation.

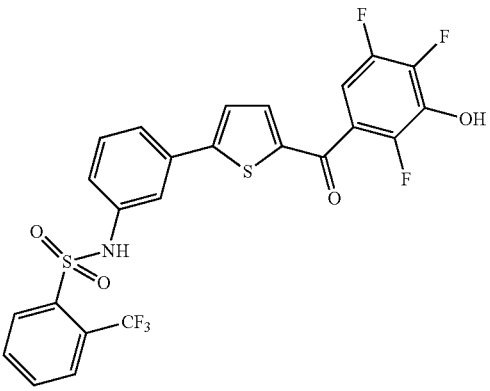

38

N-{3-[5-(2,4,5-Trifluoro-3-hydroxybenzoyl)thiophen-2-yl]phenyl}-2-trifluoromethylbenzenesulfonamide (38): The title compound was prepared by reaction of N-{3-[5-(2,4,5-trifluoro-3-methoxybenzoyl)thiophen-2-yl]phenyl}-2-trifluoromethylbenzenesulfonamide (38a) (185 mg, 0.32 mmol) and boron tribromide (1.6 mmol) according to method B. The product was purified by CC (dichloromethane/methanol 99.5:0.5); yield: 41.6% (75 mg; yellow oil); $^1$H NMR (500 MHz, acetone-d$^6$) δ 9.97 (br. s, 1H, NH), 9.40 (br. s, 1H, OH), 8.30-8.23 (m, 1H), 8.04-7.98 (m, 1H), 7.89-7.82 (m, 2H), 7.67 (dd, J=4.1, 1.8 Hz, 1H), 7.66 (t, J=1.8 Hz, 1H), 7.53 (ddd, J=7.8, 1.8, 1.0 Hz, 1H), 7.51 (d, J=4.1 Hz, 1H), 7.40 (t, J=7.9 Hz, 1H), 7.31 (ddd, J=8.1, 2.2, 1.0 Hz, 1H), 7.12 (ddd, J=9.9, 8.1, 5.6 Hz, 1H); $^{13}$C NMR (125 MHz, acetone-d$^6$) δ 182.84, 153.91, 148.57 (ddd, J=16.0, 12.3, 2.7 Hz), 146.61 (ddd, J=10.7, 9.1, 3.1 Hz), 144.89-142.31 (m), 143.06, 139.15, 138.25 (d, J=2.1 Hz), 137.05 (ddd, J=10.1, 8.0, 5.8 Hz), 134.90, 134.47, 133.86, 132.76, 131.30, 129.56 (q, J=6.4 Hz), 128.42, 128.16, 126.11, 125.05, 123.31, 122.88, 122.05, 118.69, 106.96 (dd, J=21.1, 3.0 Hz); MS (ESI): 558.02 (M+H)$^+$.

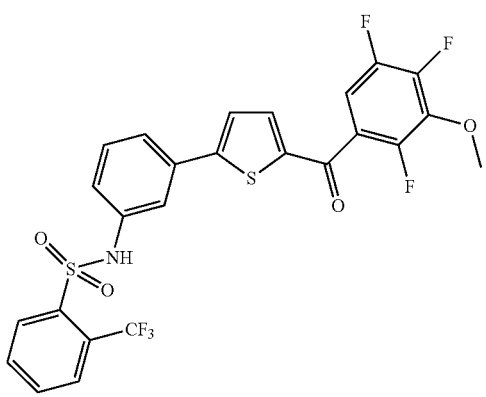

38a

N-{3-[5-(2,4,5-Trifluoro-3-methoxybenzoyl)thiophen-2-yl]phenyl}-2-trifluoromethylbenzenesulfonamide (38a):

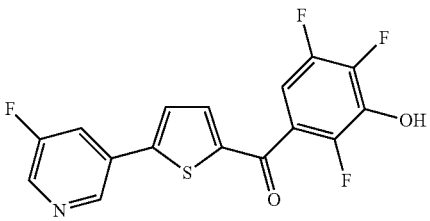

39

[5-(5-Fluoro-pyridin-3-yl)-thiophen-2-yl]-(2,4,5-trifluoro-3-hydroxy-phenyl)-methanone (39): The title compound was prepared by reaction of (5-bromo-thiophen-2-yl)-(2,4,5-trifluoro-3-hydroxy-phenyl)-methanone (1g) (650 mg, 1.93 mmol), 5-fluoro-3-pyridinylboronic acid (326 mg, 2.31 mmol), sodium carbonate (3.5 ml, 2 M) and tetrakis (triphenylphosphine) palladium (5 μmol) according to method C2. The product was purified by CC (dichloromethane/methanol 9:1); yield: 26% (180 mg). $^1$H NMR (500 MHz, DMSO-d$^6$) δ 11.39 (s, 1H), 8.93 (t, J=1.6 Hz, 1H), 8.64 (d, J=2.6 Hz, 1H), 8.27 (ddd, J=10.0, 2.6, 1.9 Hz, 1H), 7.89 (d, J=4.1 Hz, 1H), 7.76 (dd, J=4.1, 1.5 Hz, 1H), 7.23 (dd, J=14.6, 8.9 Hz, 1H). $^{13}$C NMR (126 MHz, DMSO-d$^6$) δ 182.35, 160.22, 158.19, 147.81, 147.79, 143.16, 143.13, 142.70, 138.34, 138.19, 138.15, 138.14, 137.91, 130.11, 130.08, 127.90, 121.43, 120.48, 120.32; MS (ESI): 354.35 (M+H)$^+$.

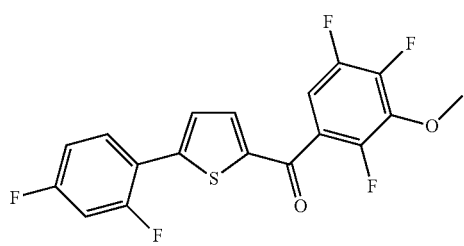

40a

[5-(2,4-Difluoro-phenyl)-thiophen-2-yl]-(2,4,5-trifluoro-3-methoxy-phenyl)-methanone (40a): The title compound was prepared by reaction of (5-Bromo-thiophen-2-yl)-(2,4,5-trifluoro-3-methoxy-phenyl)-methanone (1d) (500 mg, 1.42 mmol), 2,4-difluorophenylboronic acid (270 mg, 1.71 mmol), cesium carbonate (1856 mg, 5.70 mmol) and tetrakis(triphenylphosphine) palladium (40 mg, 33 µmol) according to method C1; yield: 86% (500 mg). The product was used in the next steps without any characterisation.

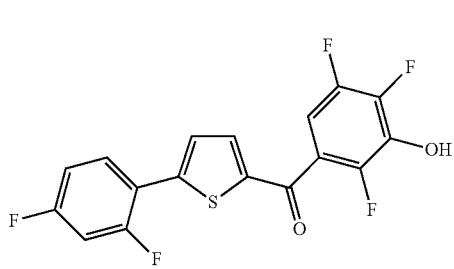

40

[5-(2,4-Difluoro-phenyl)-thiophen-2-yl]-(2,4,5-trifluoro-3-hydroxy-phenyl)-methanone (40): The title compound was prepared by reaction of [5-(2,4-Difluoro-phenyl)-thiophen-2-yl]-(2,4,5-trifluoro-3-methoxy-phenyl)-methanone (40a) (500 mg, 1.3 mmol) and boron tribromide (6.5 mmol) according to method B. The product was purified by CC (DCM/MeOH 99.5:0.5); yield: 79% (380 mg); $^1$H NMR (300 MHz, acetone-d$^6$) δ 9.79 (s, 1H, OH), 7.88-7.77 (m, 1H), 7.59 (dd, J=4.1, 0.7 Hz, 1H), 7.51 (d, J=4.1 Hz, 1H), 7.18-6.95 (m, 3H). $^{13}$C NMR (75 MHz, acetone-d$^6$) δ 182.12, 170.11, 163.21 (dd, J=251.4, 12.8 Hz), 159.51 (dd, J=253.6, 12.4 Hz), 147.81, 145.54 (dd, J=3.2, 1.7 Hz), 143.62 (dd, J=146.3, 3.6 Hz), 136.55, 136.52, 130.63 (dd, J=8.7, 5.5 Hz), 127.49 (dd, J=4.1, 1.8 Hz), 122.06, 117.66, 117.50 (dd, J=6.9, 2.3 Hz), 112.54 (dd, J=19.9, 5.7 Hz), 106.08 (dd, J=21.1, 3.1 Hz), 104.85 (t, J=26.3 Hz); MS (ESI): 370.79 (M+H)$^+$.

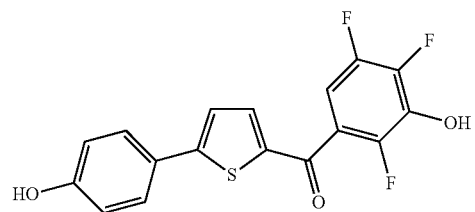

41

(5-(3-Chloro-4-hydroxyphenyl)thiophen-2-yl)(2,4,5-trifluoro-3-hydroxyphenyl)methanone (41): The title compound was prepared by reaction of (5-bromothiophen-2-yl)(2,4,5-trifluoro-3-hydroxyphenyl)methanone (1g) (96.0 mg, 0.285 mmol), (3-chloro-4-hydroxyphenyl)boronic acid (51.7 mg, 0.300 mmol), cesium carbonate (326 mg, 1.00 mmol) and tetrakis(triphenylphosphine) palladium (11.5 mg, 9.95 µmol) according to method C3. The product was purified by preparative HPLC (water with 0.1% formic acid/acetonitrile with 0.1% formic acid 60:40 to 30:70); yield: 40% (43.4 mg); $^1$H NMR (300 MHz, acetone-d$^6$) δ 9.61 (br. s, 1H), 7.82 (d, J=2.2 Hz, 1H), 7.68-7.59 (m, 2H), 7.53 (d, J=4.1 Hz, 1H), 7.13 (d, J=8.6 Hz, 1H), 7.18-7.04 (m, 1H), 7.13 (d, J=8.6 Hz, 1H); MS (ESI): 385.1 (M+H)$^+$.

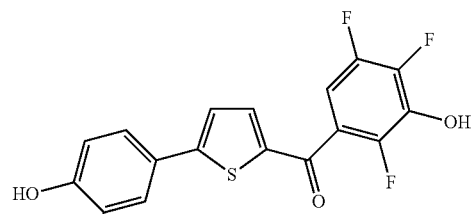

42

(5-(3-Fluoro-4-hydroxyphenyl)thiophen-2-yl)(2,4,5-trifluoro-3-hydroxyphenyl)methanone (42): The title compound was prepared by reaction of (5-bromothiophen-2-yl)(2,4,5-trifluoro-3-hydroxyphenyl)methanone (1g) (96.0 mg, 0.285 mmol), (3-fluoro-4-hydroxyphenyl)boronic acid (46.8 mg, 0.300 mmol), cesium carbonate (326 mg, 1.00 mmol) and tetrakis(triphenylphosphine) palladium (11.5 mg, 9.95 µmol) according to method C3. The product was purified by preparative HPLC (water with 0.1% formic acid/acetonitrile with 0.1% formic acid 60:40 to 30:70); yield: 29% (30.8 mg); $^1$H NMR (300 MHz, acetone-d$^6$) δ 9.55 (br. s, 1H), 7.65 (dd, J=4.1, 1.5 Hz, 1H), 7.60 (dd, J=11.9, 2.2 Hz, 1H), 7.52-7.48 (m, 1H), 7.51 (d, J=4.1 Hz, 1H), 7.14-7.06 (m, 1H), 7.11 (t, J=8.8 Hz, 1H); MS (ESI-): 367.1 (M−H)$^-$.

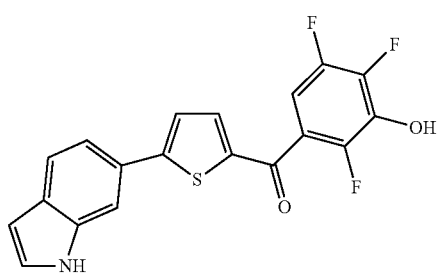

43

(5-(1H-Indol-6-yl)thiophen-2-yl)(2,4,5-trifluoro-3-hydroxyphenyl)methanone (43): The title compound was prepared by reaction of (5-bromothiophen-2-yl)(2,4,5-trifluoro-3-hydroxyphenyl)methanone (1g) (96.0 mg, 0.285 mmol), (1H-indol-6-yl)boronic acid (48.3 mg, 0.300 mmol), cesium carbonate (326 mg, 1.00 mmol) and tetrakis(triphenylphosphine) palladium (11.5 mg, 9.95 μmol) according to method C3. The product was purified by preparative HPLC (water with 0.1% formic acid/acetonitrile with 0.1% formic acid 50:50 to 20:80); yield: 81% (85.7 mg); 1H NMR (300 MHz, acetone-d$^6$) δ 10.50 (br. s, 1H), 7.91 (m, 1H), 7.67 (d, J=8.4 Hz, 1H), 7.64 (dd, J=4.1, 1.9 Hz, 1H), 7.53 (d, J=4.1 Hz, 1H), 7.51-7.46 (m, 2H), 7.13-7.05 (m, 1H), 6.56-6.52 (m, 1H); MS (ESI−): 372.1 (M−H)$^-$.

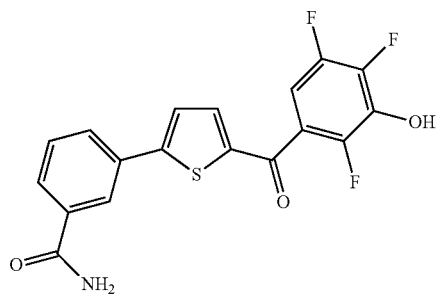

44

3-(5-(2,4,5-Trifluoro-3-hydroxybenzoyl)thiophen-2-yl)benzamide (44): The title compound was prepared by reaction of (5-bromothiophen-2-yl)-(2,4,5-trifluoro-3-hydroxyphenyl)methanone (1g) (96.0 mg, 0.285 mmol), (3-carbamoylphen-yl)boronic acid (49.5 mg, 0.300 mmol), cesium carbonate (326 mg, 1.00 mmol) and tetrakis(triphenylphosphine) palladium (11.5 mg, 9.95 μmol) according to method C3. The product was purified by preparative HPLC (water with 0.1% formic acid/acetonitrile with 0.1% formic acid 70:30 to 40:60) giving the formiate of the title compound; yield: 21% (25.7 mg); $^1$H NMR (300 MHz, DMSO-d$^6$) δ 11.35 (br. s, 1H), 8.28 (t, J=1.8 Hz, 1H), 8.16 (br. s, 1H), 8.00-7.92 (m, 2H), 7.77 (d, J=4.3 Hz, 1H), 7.73 (dd, J=4.3, 1.7 Hz, 1H), 7.66-7.50 (m, 3H), 7.28-7.20 (m, 1H); MS (ESI−): 376.1 (M−H)$^-$.

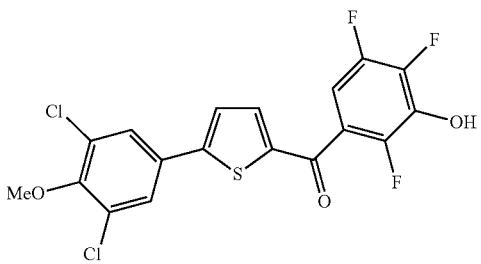

45

(5-(3,5-Dichloro-4-methoxyphenyl)thiophen-2-yl)(2,4,5-trifluoro-3-hydroxyphenyl)methanone (45): The title compound was prepared by reaction of (5-bromothiophen-2-yl) (2,4,5-trifluoro-3-hydroxyphenyl)methanone (1g) (96.0 mg, 0.285 mmol), (3,5-dichloro-4-methoxyphenyl)boronic acid (66.3 mg, 0.300 mmol), cesium carbonate (326 mg, 1.00 mmol) and tetrakis(triphenylphosphine) palladium (11.5 mg, 9.95 μmol) according to method C3. The product was purified by preparative HPLC (water with 0.1% formic acid/acetonitrile with 0.1% formic acid 40:60 to 5:95); yield: 59% (73.2 mg); $^1$H NMR (300 MHz, acetone-d$^6$) δ 7.86 (s, 2H), 7.71-7.69 (m, 2H), 7.13 (ddd, J=10.0, 8.1, 5.7 Hz, 1H), 3.95 (s, 3H); MS (ESI−): 431.0 (M−H)$^-$.

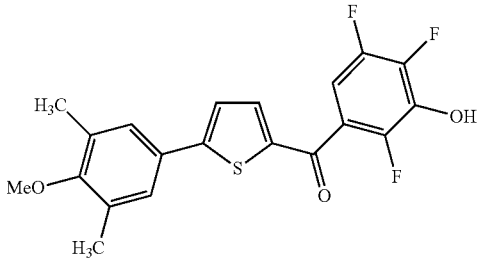

46

(5-(4-Methoxy-3,5-dimethylphenyl)thiophen-2-yl)(2,4,5-trifluoro-3-hydroxyphenyl)methanone (46): The title compound was prepared by reaction of (5-bromothiophen-2-yl) (2,4,5-trifluoro-3-hydroxyphenyl)methanone (1g) (96.0 mg, 0.285 mmol), (4-methoxy-3,5-dimethylphenyl)boronic acid (54.0 mg, 0.300 mmol), cesium carbonate (326 mg, 1.00 mmol) and tetrakis(triphenylphosphine) palladium (11.5 mg, 9.95 μmol) according to method C3. The product was purified by preparative HPLC (water with 0.1% formic acid/acetonitrile with 0.1% formic acid 40:60 to 5:95); yield: 73% (81.5 mg); $^1$H NMR (300 MHz, CDCl$_3$) δ 7.49 (dd, J=3.9, 1.7 Hz, 1H), 7.34 (s, 2H), 7.24-7.27 (m, 1H), 6.99 (td, J=8.7, 6.1 Hz, 1H), 3.76 (s, 3H), 2.38 (s, 6H); MS (ESI): 393.2 (M+H)$^+$.

47

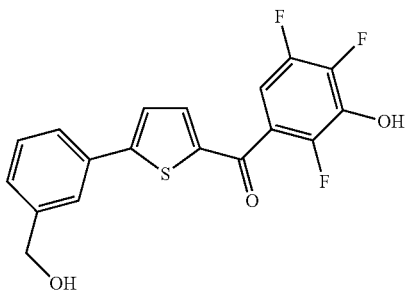

(5-(3-(Hydroxymethyl)phenyl)thiophen-2-yl)(2,4,5-trifluoro-3-hydroxyphenyl)methanone (47): The title compound was prepared by reaction of (5-bromothiophen-2-yl)(2,4,5-trifluoro-3-hydroxyphenyl)methanone (1g) (96.0 mg, 0.285 mmol), (3-(hydroxymethyl)phenyl)boronic acid (45.6 mg, 0.300 mmol), cesium carbonate (326 mg, 1.00 mmol) and tetrakis(triphenylphosphine) palladium (11.5 mg, 9.95 μmol) according to method C1. The product was purified by preparative HPLC (water with 0.1% formic acid/acetonitrile with 0.1% formic acid 70:30 to 40:60); yield: 24% (25.1 mg); $^1$H NMR (300 MHz, MeOH-d$^4$) δ 7.75 (s, 1H), 7.65 (d, J=6.7 Hz, 1H), 7.58 (dd, J=4.0, 1.8 Hz, 1H), 7.51 (d, J=4.1 Hz, 1H), 7.47-7.37 (m, 2H), 6.97 (ddd, J=9.7, 8.1, 5.7 Hz, 1H), 4.67 (s, 2H); MS (APCI-): 364.1 (M-H)$^-$.

48

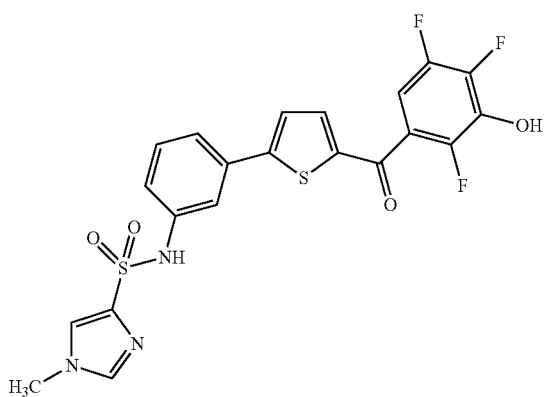

1-Methyl-N-(3-(5-(2,4,5-trifluoro-3-hydroxybenzoyl)thiophen-2-yl)phenyl)-1H-imidazole-4-sulfonamide (48): The title compound was prepared by reaction of (5-(3-aminophenyl)thiophen-2-yl)(2,4,5-trifluoro-3-hydroxyphenyl)methanone (39.4 mg, 113 μmol) and 1-methyl-1H-imidazole-4-sulfonyl chloride (29.4 mg, 124 μmol) according to method D.

49

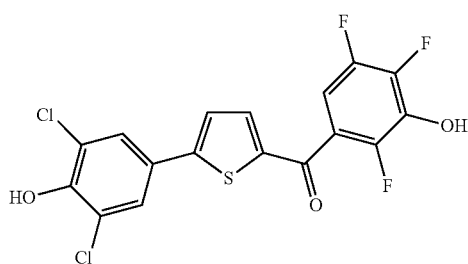

(5-(3,5-Dichloro-4-hydroxyphenyl)thiophen-2-yl)(2,4,5-trifluoro-3-hydroxyphenyl)methanone (49): The title compound was prepared by reaction of (5-(3,5-dichloro-4-methoxyphenyl)thiophen-2-yl)(2,4,5-trifluoro-3-hydroxyphenyl)methanone (45) (48 mg, 0.11 mmol) and boron tribromide (0.34 mmol, 3.0 equiv) according to method B. The product was purified by CC (hexane:ethyl acetate, 3.1→2:1); yield: quantitative (84 mg). $^1$H NMR (300 MHz, acetone-d$^6$) δ 9.92 (s, 1 H); 9.30 (s, 1 H); 7.81 (s, 2 H); 7.68 (dd, J=1.8, 4.1 Hz, 1 H); 7.65-7.61 (m, 1 H); 7.13 (ddd, J=5.6, 8.1, 10.0 Hz, 1 H); MS (ESI): 420.20 (M+H)$^+$.

50

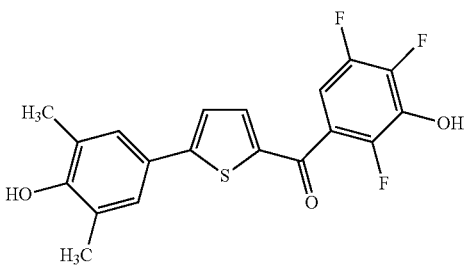

(5-(4-Hydroxy-3,5-dimethylphenyl)thiophen-2-yl)(2,4,5-trifluoro-3-hydroxyphenyl)methanone (50): The title compound was prepared by reaction of (5-(4-Methoxy-3,5-dimethylphenyl)thiophen-2-yl)(2,4,5-trifluoro-3-hydroxyphenyl)methanone (46) (51 mg, 0.13 mmol) and boron tribromide (0.39 mmol, 3.0 equiv) according to method B. The product was purified by CC (hexane:ethyl acetate, 6:4); yield: 98% (51 mg). $^1$H NMR (300 MHz, CDCl$_3$): 7.48 (dd, J=4.1, 2.0 Hz, 1H), 7.32 (br.s, 2H), 7.22 (d, J=4.1 Hz, 1H), 6.98 (ddd, J=9.6, 8.1, 5.8 Hz, 1H), 4.90 (s, 1H), 2.30 (s, 6H); MS (ESI): 379.10 (M+H)$^+$.

51

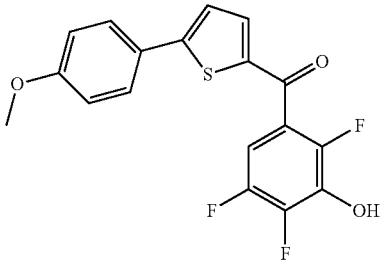

(5-(4-Methoxyphenyl)thiophen-2-yl)(2,4,5-trifluoro-3-hydroxyphenyl)methanone (51): The title compound was prepared by reaction of (5-bromothiophen-2-yl)(2,4,5-trifluoro-3-hydroxyphenyl)methanone (1g) (94.8 mg, 0.281 mmol), 4-methoxyphenylboronic acid (45.6 mg, 0.300 mmol), cesium carbonate (326 mg, 1.00 mmol) and tetrakis(triphenylphosphine) palladium (11.6 mg, 10.0 μmol) according to method C3. The product was purified by preparative HPLC (water with 0.1% formic acid/acetonitrile with 0.1% formic acid); yield: 40% (40.7 mg). 1H NMR (300 MHz, acetone-d$^6$): δ 7.81-7.70 (m, 2H), 7.64 (dd, J=4.1, 1.8 Hz, 1H), 7.48 (d, J=4.1 Hz, 1H), 7.17-6.99 (m, 3H), 3.87 (s, 3H); MS (ESI): 365.2 (M+H)$^+$.

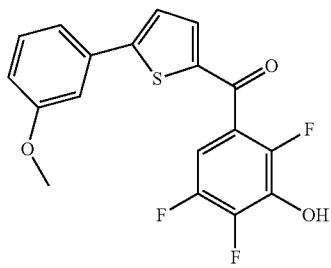

52

(5-(3-Methoxyphenyl)thiophen-2-yl)(2,4,5-trifluoro-3-hydroxyphenyl)methanone (52): The title compound was prepared by reaction of (5-bromothiophen-2-yl)(2,4,5-trifluoro-3-hydroxyphenyl)methanone (1g) (94.8 mg, 0.281 mmol), 3-methoxyphenylboronic acid (45.6 mg, 0.300 mmol), cesium carbonate (326 mg, 1.00 mmol) and tetrakis(triphenylphosphine) palladium (11.6 mg, 10.0 μmol) according to method C3. The product was purified by preparative HPLC (water with 0.1% formic acid/acetonitrile with 0.1% formic acid); yield: 43% (44.0 mg). $^1$H NMR (300 MHz, MeOH-d$^4$): δ 7.81-7.48 (m, 2H), 7.46-7.26 (m, 3H), 7.09-6.95 (m, 2H), 3.89 (s, 3H); MS (ESI): 365.2 (M+H)$^+$.

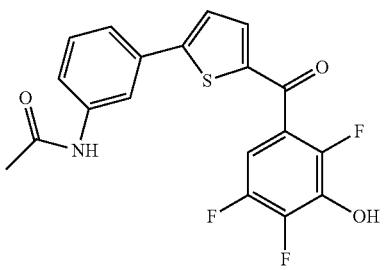

54

N-(3-(5-(2,4,5-Trifluoro-3-hydroxybenzoyl)thiophen-2-yl)phenyl)acetamide (54): The title compound was prepared by reaction of (5-bromothiophen-2-yl)(2,4,5-trifluoro-3-hydroxyphenyl)methanone (1g) (94.8 mg, 0.281 mmol), 3-acetylamidophenylboronic acid (53.7 mg, 0.300 mmol), cesium carbonate (326 mg, 1.00 mmol) and tetrakis(triphenylphosphine) palladium (11.6 mg, 10.0 μmol) according to method C3. The product was purified by preparative HPLC (water with 0.1% formic acid/acetonitrile with 0.1% formic acid); yield: 8% (8.72 mg). $^1$H NMR (300 MHz, acetone-d$^6$): δ 9.31 (br. s, 1H), 8.21-8.14 (m, 1H), 7.72-7.60 (m, 2H), 7.60-7.34 (m, 3H), 7.12 (ddd, J=10.0, 8.1, 5.6 Hz, 1H), 3.31 (s, 3H); MS (ESI): 392.3 (M+H)$^+$.

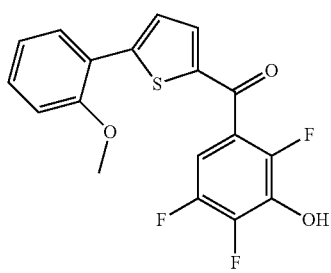

53

(5-(2-Methoxyphenyl)thiophen-2-yl)(2,4,5-trifluoro-3-hydroxyphenyl)methanone (53): The title compound was prepared by reaction of (5-bromothiophen-2-yl)(2,4,5-trifluoro-3-hydroxyphenyl)methanone (1g) (94.8 mg, 0.281 mmol), 2-methoxyphenylboronic acid (45.6 mg, 0.300 mmol), cesium carbonate (326 mg, 1.00 mmol) and tetrakis(triphenylphosphine) palladium (11.6 mg, 10.0 μmol) according to method C3. The product was purified by preparative HPLC (water with 0.1% formic acid/acetonitrile with 0.1% formic acid); yield: 68% (70.0 mg). $^1$H NMR (300 MHz, acetone-d$^6$): δ 7.87 (dd, J=7.8, 1.7 Hz, 1H), 7.71 (d, J=4.2 Hz, 1H), 7.63 (dd, J=4.2, 1.8 Hz, 1H), 7.43 (ddd, J=8.5, 7.2, 1.6 Hz, 1H), 7.24-7.19 (m, 1H), 7.15-7.05 (m, 2H), 4.03 (s, 3H); MS (ESI): 365.2 (M+H)$^+$.

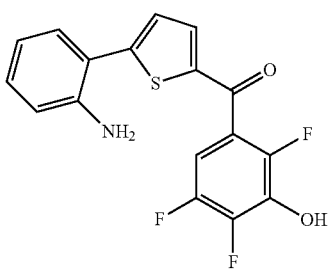

55

(5-(2-Aminophenyl)thiophen-2-yl)(2,4,5-trifluoro-3-hydroxyphenyl)methanone (55): The title compound was prepared by reaction of (5-bromothiophen-2-yl)(2,4,5-trifluoro-3-hydroxyphenyl)methanone (1g) (94.8 mg, 0.281 mmol), (2-aminophenyl)boronic acid (41.1 mg, 0.300 mmol), cesium carbonate (326 mg, 1.00 mmol) and tetrakis(triphenylphosphine) palladium (11.6 mg, 10.0 μmol) according to method C3. The product was purified by preparative HPLC (water with 0.1% formic acid/acetonitrile with 0.1% formic acid); yield: 53% (52.1 mg). $^1$H NMR (300 MHz, MeOH-d$^4$): δ 7.64 (dd, J=3.8, 1.7 Hz, 1H), 7.45-7.38 (m, 1H), 7.33 (dd, J=7.7, 1.5 Hz, 1H), 7.26-7.14 (m, 1H), 7.11-6.95 (m, 1H), 6.90 (d, J=8.1 Hz, 1H), 6.84-6.71 (m, 1H); MS (ESI): 350.2 (M+H)$^+$.

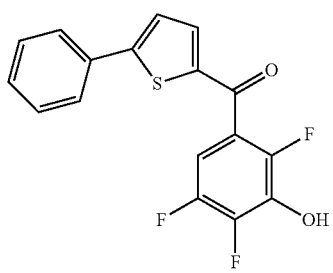

56

(5-Phenylthiophen-2-yl)(2,4,5-trifluoro-3-hydroxyphenyl)methanone (56): The title compound was prepared by reaction of (5-bromothiophen-2-yl)(2,4,5-trifluoro-3-hydroxyphenyl)methanone (1g) (94.8 mg, 0.281 mmol), phenylboronic acid (36.6 mg, 0.300 mmol), cesium carbonate (326 mg, 1.00 mmol) and tetrakis(triphenylphosphine) palladium (11.6 mg, 10.0 µmol) according to method C3. The product was purified by preparative HPLC (water with 0.1% formic acid/acetonitrile with 0.1% formic acid); yield: 51% (47.9 mg). $^1$H NMR (300 MHz, acetone-$d^6$): δ 9.91 (br. s, 1H), 7.87-7.77 (m, 2H), 7.69 (dd, J=4.1, 1.8 Hz, 1H), 7.61 (d, J=4.1 Hz, 1H), 7.55-7.39 (m, 3H), 7.12 (ddd, J=10.0, 8.1, 5.7 Hz, 1H); MS (ESI): 335.2 (M+H)$^+$.

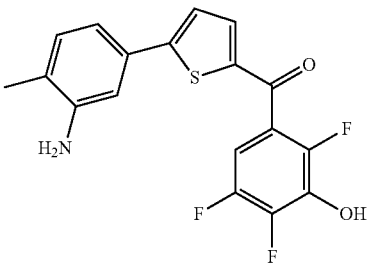

57

(5-(3-Amino-4-methylphenyl)thiophen-2-yl)(2,4,5-trifluoro-3-hydroxyphenyl)methanone (57): The title compound was prepared by reaction of (5-bromothiophen-2-yl)(2,4,5-trifluoro-3-hydroxyphenyl)methanone (1g) (94.8 mg, 0.281 mmol), 3-amino-4-methylphenylboronic acid (45.3 mg, 0.300 mmol), cesium carbonate (326 mg, 1.00 mmol) and tetrakis(triphenylphosphine) palladium (11.6 mg, 10.0 µmol) according to method C3. The product was purified by preparative HPLC (water with 0.1% formic acid/acetonitrile with 0.1% formic acid); yield: 15% (15.7 mg). $^1$H NMR (300 MHz, MeOH-$d^4$): δ 7.61 (d, J=2.2 Hz, 1H), 7.14 (d, J=3.9 Hz, 1H), 7.11-6.97 (m, 2H), 6.86 (d, J=7.8 Hz, 1H), 6.80 (d, J=7.5 Hz, 1H), 2.22 (s, 3H); MS (ESI): 364.2 (M+H)$^+$.

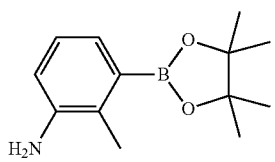

58a

2-Methyl-3-(4,4,5,5-tetramethyl-1,3,2-dioxaborolan-2-yl)aniline (58a): 3-Bromo-2-methylaniline (1.00 g, 5.37 mmol, 1.0 equiv), bis(pinacolato)diboron (1.50 g, 5.91 mmol, 1.1 equiv), potassium acetate (1.58 g, 16.1 mmol, 3.0 equiv) and Pd(dppf)Cl$_2$ (118 mg, 0.161 mmol, 0.03 equiv) were dissolved under argon atmosphere in 15 ml DMSO and the mixture was stirred at 80° C. for 48 h. Water was added and the aqueous layer was extracted with ethyl acetate three times. The combined organic layers were dried over magnesium sulfate, filtered and concentrated to dryness. The raw product was purified by flash chromatography; yield: 39% (486 mg). $^1$H NMR (300 MHz, acetone-$d^6$): δ 7.05 (dd, J=7.3, 1.3 Hz, 1H), 6.91 (t, J=7.6 Hz, 1H), 6.77 (dd, J=7.8, 1.4 Hz, 1H), 2.33 (s, 3H), 1.33 (s, 12H).

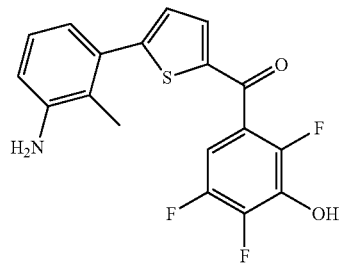

58

(5-(3-Amino-2-methylphenyl)thiophen-2-yl)(2,4,5-trifluoro-3-hydroxyphenyl)methanone (58): The title compound was prepared by reaction of (5-bromothiophen-2-yl)(2,4,5-trifluoro-3-hydroxyphenyl)methanone (1g) (94.8 mg, 0.281 mmol), 2-methyl-3-(4,4,5,5-tetramethyl-1,3,2-dioxaborolan-2-yl)aniline (58a) (69.9 mg, 0.300 mmol), cesium carbonate (326 mg, 1.00 mmol) and tetrakis(triphenylphosphine) palladium (11.6 mg, 10.0 µmol) according to method C3. The product was purified by preparative HPLC (water with 0.1% formic acid/acetonitrile with 0.1% formic acid); yield: 7% (7.60 mg).

$^1$H NMR (300 MHz, MeOH-$d^4$): δ 7.58 (dd, J=3.9, 1.8 Hz, 1H), 7.43 (d, J=4.0 Hz, 1H), 7.19-6.88 (m, 4H), 2.22 (s, 3H); MS (ESI): 364.2 (M+H)$^+$.

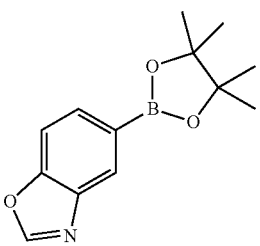

59a 5-(4,4,5,5-Tetramethyl-1,3,2-dioxaborolan-2-yl)benzo[d]oxazole (59a): 5-Bromobenzo[d]oxazole (500 mg, 2.53 mmol, 1.0 equiv), bis(pinacolato)diboron (706 mg, 2.78 mmol, 1.1 equiv), potassium acetate (745 mg, 7.59 mmol, 3.0 equiv) and Pd(dppf)Cl$_2$ (55.5 mg, 75.9 µmol, 0.03 equiv) were dissolved under argon atmosphere in 7 ml DMSO and the mixture was stirred at 80° C. for 22 h. Water was added and the aqueous layer was extracted with ethyl acetate three times. The combined organic layers were dried over magnesium sulfate, filtered and concentrated to dryness. The raw product was purified by flash chromatography; yield: 37% (229 mg). $^1$H NMR (300 MHz, acetone-$d^6$): δ 8.47 (s, 1H), 8.12 (s, 1H), 7.86-7.80 (m, 1H), 7.72-7.64 (m, 1H), 1.37 (s, 12H).

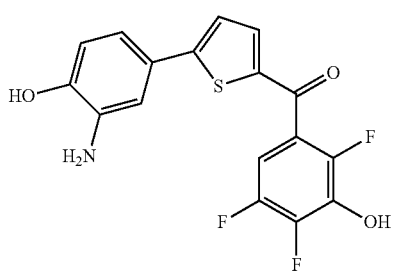

59

(5-(3-Amino-4-hydroxyphenyl)thiophen-2-yl)(2,4,5-trifluoro-3-hydroxyphenyl)methanone (59): The title compound was prepared by reaction of (5-bromothiophen-2-yl)(2,4,5-trifluoro-3-hydroxyphenyl)methanone (1g) (94.8 mg, 0.281 mmol), 5-(4,4,5,5-tetramethyl-1,3,2-dioxaborolan-2-yl)benzo[d]oxazole (59a) (73.5 mg, 0.300 mmol), cesium carbonate (326 mg, 1.00 mmol) and tetrakis(triphenylphosphine) palladium (11.6 mg, 10.0 μmol) according to method C3. The product was purified by preparative HPLC (water with 0.1% formic acid/acetonitrile with 0.1% formic acid); yield: 35% (35.7 mg).

$^1$H NMR (300 MHz, MeOH-d$^4$): δ 7.58-7.51 (m, 1H), 7.33 (d, J=3.9 Hz, 1H), 7.17 (d, J=1.5 Hz, 1H), 7.04 (dd, J=8.0, 2.1 Hz, 1H), 7.01-6.92 (m, 1H), 6.78 (d, J=8.1 Hz, 1H); MS (ESI): 366.2 (M+H)$^+$.

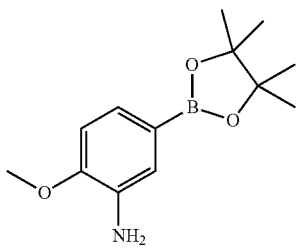

60a

2-Methoxy-5-(4,4,5,5-tetramethyl-1,3,2-dioxaborolan-2-yl)aniline (60a): 5-Bromo-2-methoxyaniline (500 mg, 2.48 mmol, 1.0 equiv), bis(pinacolato)diboron (691 mg, 2.72 mmol, 1.1 equiv), potassium acetate (730 mg, 7.44 mmol, 3.0 equiv) and Pd(dppf)Cl$_2$ (54.4 mg, 74.4 μmol, 0.03 equiv) were dissolved under Argon atmosphere in 7 ml DMSO and the mixture was stirred at 80° C. for 48 h. Water was added and the aqueous layer was extracted with ethyl acetate three times. The combined organic layers were dried over magnesium sulfate, filtered and concentrated to dryness. The raw product was purified by flash chromatography; yield: 30% (184 mg). $^1$H NMR (300 MHz, acetone-d$^6$): δ 7.11-7.02 (m, 2H), 6.81 (d, J=7.9 Hz, 1H), 3.84 (s, 3H), 1.29 (s, 12H).

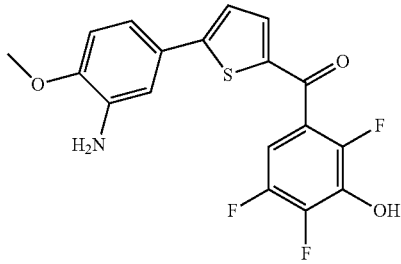

60

(5-(3-Amino-4-methoxyphenyl)thiophen-2-yl)(2,4,5-trifluoro-3-hydroxyphenyl)methanone (60): The title compound was prepared by reaction of (5-bromothiophen-2-yl)(2,4,5-trifluoro-3-hydroxyphenyl)methanone (1g) (94.8 mg, 0.281 mmol), 2-methoxy-5-(4,4,5,5-tetramethyl-1,3,2-dioxaborolan-2-yl)aniline (60a) (74.7 mg, 0.300 mmol), cesium carbonate (326 mg, 1.00 mmol) and tetrakis(triphenylphosphine) palladium (11.6 mg, 10.0 μmol) according to method C3. The product was purified by preparative HPLC (water with 0.1% formic acid/acetonitrile with 0.1% formic acid); yield: 31% (33.3 mg). $^1$H NMR (300 MHz, MeOH-d$^4$): δ 7.61-7.52 (m, 1H), 7.29 (d, J=3.9 Hz, 1H), 7.22-7.10 (m, 1H), 7.05-6.86 (m, 1H), 6.78 (d, J=8.1 Hz, 1H), 4.61 (br. s, 2H), 3.94 (s, 3H); MS (ESI): 380.3 (M+H)$^+$.

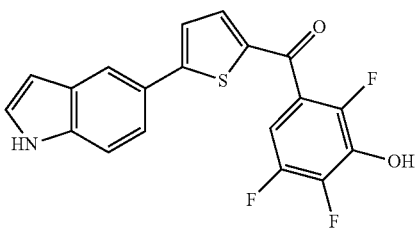

61

(5-(1H-Indol-5-yl)thiophen-2-yl)(2,4,5-trifluoro-3-hydroxyphenyl)methanone (61): The title compound was prepared by reaction of (5-bromothiophen-2-yl)(2,4,5-trifluoro-3-hydroxyphenyl)methanone (1g) (94.8 mg, 0.281 mmol), (1H-indol-5-yl)boronic acid (48.3 mg, 0.300 mmol), cesium carbonate (326 mg, 1.00 mmol) and tetrakis(triphenylphosphine) palladium (11.6 mg, 10.0 μmol) according to method C3. The product was purified by preparative HPLC (water with 0.1% formic acid/acetonitrile with 0.1% formic acid); yield: 49% (51.6 mg). $^1$H NMR (500 MHz, acetone-d$^6$): δ 8.09 (dd, J=1.9, 0.6 Hz, 1H), 7.65 (dd, J=4.1, 1.9 Hz, 1H), 7.60-7.51 (m, 3H), 7.47-7.41 (m, 1H), 7.11 (ddd, J=10.1, 8.2, 5.7 Hz, 1H), 6.63-6.57 (m, 1H); MS (ESI): 374.3 (M+H)$^+$.

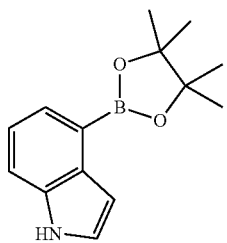

62a 4-(4,4,5,5-Tetramethyl-1,3,2-dioxaborolan-2-yl)-1H-indole (62a): 4-Bromoindole (1.00 g, 5.10 mmol, 1.0 equiv), bis(pinacolato)diboron (1.42 g, 5.61 mmol, 1.1 equiv), potassium acetate (1.50 g, 15.3 mmol, 3.0 equiv) and Pd(dppf)Cl$_2$ (112 mg, 0.153 mmol, 0.03 equiv) were dissolved under Argon atmosphere in 15 ml DMSO and the mixture was stirred at 80° C. for 24 h and afterwards at 40° C. for 72 h. Water was added and the aqueous layer was extracted with ethyl acetate three times. The combined organic layers were dried over magnesium sulfate, filtered and concentrated to dryness. The raw product was purified by flash chromatography and by preparative HPLC (water with 0.1% formic acid/acetonitrile with 0.1% formic acid); yield: 38% (470 mg). $^1$H NMR (500 MHz, acetone-d$^6$): δ 10.21 (br. s, 1H), 7.55-7.49 (m, 2H), 7.34 (dt, J=3.0, 1.3 Hz, 1H), 7.10 (dd, J=8.0, 7.1 Hz, 1H), 6.93-6.91 (m, 1H), 1.37 (s, 12H).

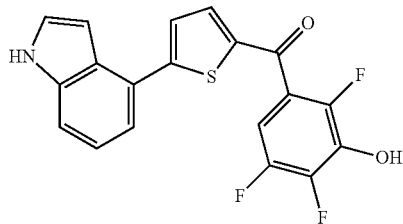

62

(5-(1H-Indol-4-yl)thiophen-2-yl)(2,4,5-trifluoro-3-hydroxyphenyl)methanone (62): The title compound was prepared by reaction of (5-bromothiophen-2-yl)(2,4,5-trifluoro-3-hydroxyphenyl)methanone (1g) (94.8 mg, 0.281 mmol), 4-(4,4,5,5-tetramethyl-1,3,2-dioxaborolan-2-yl)-1H-indole (62a) (72.9 mg, 0.300 mmol), cesium carbonate (319 mg, 0.979 mmol) and tetrakis(triphenylphosphine) palladium (11.3 mg, 9.78 μmol) according to method C3. The product was purified by preparative HPLC (water with 0.1% formic acid/acetonitrile with 0.1% formic acid); yield: 95% (99.6 mg). $^1$H-NMR (300 MHz, acetone-d$^6$): δ 10.67 (br. s, 1H), 7.73 (dd, J=4.0, 1.8 Hz, 1H), 7.67 (d, J=4.1 Hz, 2H), 7.60-7.52 (m, 2H), 7.48 (dd, J=7.4, 0.9 Hz, 1H), 7.28-7.20 (m, 1H), 7.15 (ddd, J=10.0, 8.1, 5.6 Hz, 1H), 6.96 (ddd, J=3.2, 2.0, 1.0 Hz, 1H); MS (ESI): 374.3 (M+H)$^+$.

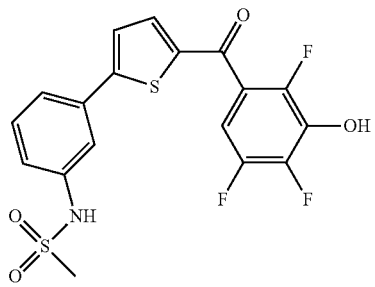

63

N-(3-(5-(2,4,5-trifluoro-3-hydroxybenzoyl)thiophen-2-yl)phenyl)methanesulfonamide (63): The title compound was prepared by reaction of (5-bromothiophen-2-yl)(2,4,5-trifluoro-3-hydroxyphenyl)methanone (1g) (94.8 mg, 0.281 mmol), 3-methylsulfonylaminophenylboronic acid (64.5 mg, 0.300 mmol), cesium carbonate (319 mg, 0.979 mmol) and tetrakis(triphenylphosphine) palladium (11.3 mg, 9.78 μmol) according to method C3. The product was purified by preparative HPLC (water with 0.1% formic acid/acetonitrile with 0.1% formic acid); yield: 53% (64.2 mg). $^1$H-NMR (500 MHz, acetone-d$^6$): δ 9.95 (br. s, 1H), 8.76 (s, 1H), 7.76 (t, J=1.9 Hz, 1H), 7.71 (dd, J=3.9, 1.7 Hz, 1H), 7.63-7.56 (m, 2H), 7.49 (t, J=7.9 Hz, 1H), 7.43 (ddd, J=8.0, 2.1, 1.0 Hz, 1H), 7.13 (ddd, J=9.9, 8.1, 5.7 Hz, 1H), 3.08 (s, 3H); MS (ESI): 428.2 (M+H)$^+$.

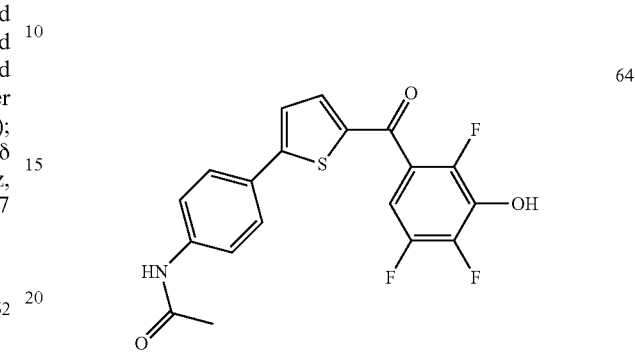

64

N-(4-(5-(2,4,5-trifluoro-3-hydroxybenzoyl)thiophen-2-yl)phenyl)acetamide (64): The title compound was prepared by reaction of (5-bromothiophen-2-yl)(2,4,5-trifluoro-3-hydroxyphenyl)methanone (1g) (94.8 mg, 0.281 mmol), 4-acetylamidophenylboronic acid (53.7 mg, 0.300 mmol), cesium carbonate (319 mg, 0.979 mmol) and tetrakis(triphenylphosphine) palladium (11.3 mg, 9.78 μmol) according to method C3. The product was purified by preparative HPLC (water with 0.1% formic acid/acetonitrile with 0.1% formic acid); yield: 12% (12.9 mg). $^1$H-NMR (300 MHz, DMSO-d6): δ 10.16 (s, 1H) 7.76 (d, J=8.9 Hz, 2H), 7.69 (d, J=8.8 Hz, 2H), 7.64 (dd, J=4.1, 1.5 Hz, 1H), 7.61-7.56 (m, 1H), 7.19-7.07 (m, 1H), 2.07 (s, 3H); MS (ESI): 392.2 (M+H)$^+$.

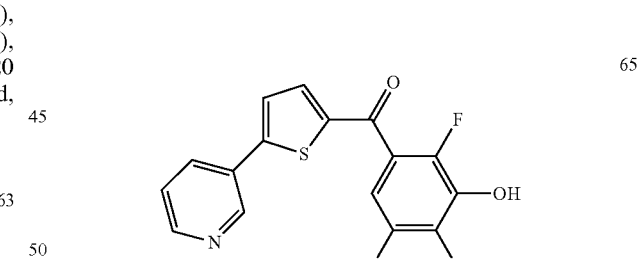

65

(5-(Pyridin-3-yl)thiophen-2-yl)(2,4,5-trifluoro-3-hydroxyphenyl)methanone (65): The title compound was prepared by reaction of (5-bromothiophen-2-yl)(2,4,5-trifluoro-3-hydroxyphenyl)methanone (1g) (94.8 mg, 0.281 mmol), pyridine-3-boronic acid (36.9 mg, 0.300 mmol), cesium carbonate (326 mg, 1.00 mmol) and tetrakis(triphenylphosphine) palladium (11.3 mg, 9.78 μmol) according to method C3. The product was purified by preparative HPLC (water with 0.1% formic acid/acetonitrile with 0.1% formic acid); yield: 15% (14.2 mg). $^1$H-NMR (500 MHz, DMSO-d$^6$): δ 9.05 (d, J=2.0 Hz, 1H), 8.63 (dd, J=4.8, 1.4 Hz, 1H), 8.22 (dt, J=8.0, 1.9 Hz, 1H), 7.81 (d, J=4.1 Hz, 1H), 7.74 (dd, J=4.1, 1.4 Hz, 1H), 7.67-7.48 (m, 1H), 7.24 (ddd, J=10.0, 8.2, 5.7 Hz, 1H); MS (ESI): 336.3 (M+H)$^+$.

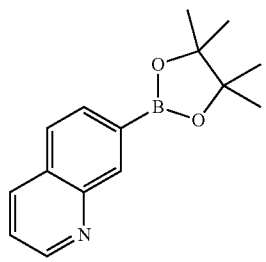

66a 7-(4,4,5,5-Tetramethyl-1,3,2-dioxaborolan-2-yl)quinoline (66a): 7-Bromoquinoline (500 mg, 2.36 mmol, 1.0 equiv), bis(pinacolato)diboron (671 mg, 2.64 mmol, 1.1 equiv), potassium acetate (707 mg, 7.20 mmol, 3.1 equiv) and Pd(dppf)Cl$_2$ (52.7 mg, 72.0 µmol, 0.03 equiv) were dissolved under Argon atmosphere in 7 ml DMSO and the mixture was stirred at 80° C. over night. Water was added and the aqueous layer was extracted with ethyl acetate three times. The combined organic layers were dried over magnesium sulfate, filtered and concentrated to dryness. The raw product was purified by flash chromatography; yield: 52% (316 mg). $^1$H NMR (300 MHz, acetone-d$^6$): δ 8.93 (dd, J=4.1, 1.7 Hz, 1H), 8.49 (s, 1H), 8.35-8.27 (m, 1H), 7.97-7.83 (m, 2H), 7.53 (dd, J=8.3, 4.2 Hz, 1H), 1.39 (s, 12H).

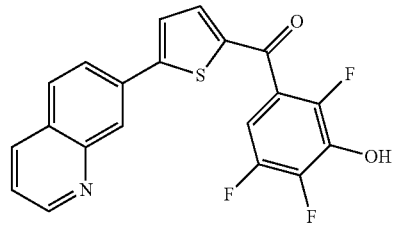

66

(5-(Quinolin-7-yl)thiophen-2-yl)(2,4,5-trifluoro-3-hydroxyphenyl)methanone (66): The title compound was prepared by reaction of (5-bromothiophen-2-yl)(2,4,5-trifluoro-3-hydroxyphenyl)methanone (1g) (7-(4,4,5,5-tetramethyl-1,3,2-dioxaborolan-2-yl)quinoline (66a) (76.5 mg, 0.300 mmol), sodium carbonate (74.2 mg, 0.700 mmol) and tetrakis(triphenylphosphine) palladium (3.24 mg, 2.80 µmol) according to method C2. The product was purified by preparative HPLC (water with 0.1% formic acid/acetonitrile with 0.1% formic acid); yield: 5% (5.9 mg). $^1$H-NMR (300 MHz, DMSO-d$^6$): δ 8.97 (dd, J=4.2, 1.7 Hz, 1H), 8.46-8.38 (m, 2H), 8.20-8.02 (m, 2H), 7.94 (d, J=4.0 Hz, 1H), 7.74 (dd, J=4.1, 1.5 Hz, 1H), 7.58 (dd, J=8.1, 4.2 Hz, 1H), 7.13 (d, J=6.2 Hz, 1H); MS (ESI): 386.2 (M+H)$^+$.

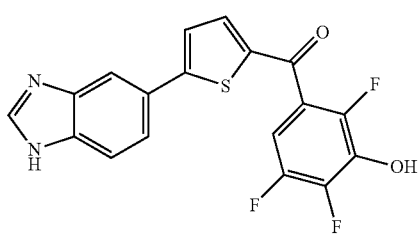

67

(5-(1H-Benzo[d]imidazol-5-yl)thiophen-2-yl)(2,4,5-trifluoro-3-hydroxyphenyl)methanone (67): The title compound was prepared by reaction of (5-bromothiophen-2-yl)(2,4,5-trifluoro-3-hydroxyphenyl)methanone (1g) (94.8 mg, 0.281 mmol), 1H-benzimidazole-5-boronic acid pinacol ester (73.2 mg, 0.300 mmol), cesium carbonate (320 mg, 0.984 mmol) and tetrakis(triphenylphosphine) palladium (40.4 mg, 35.0 µmol) according to method C3. The product was purified by preparative HPLC (water with 0.1% formic acid/acetonitrile with 0.1% formic acid); yield: 7% (7.6 mg). $^1$H-NMR (300 MHz, DMSO-d$^6$): δ 12.58 (br. s, 1H), 8.32 (s, 1H), 8.04 (br. s, 1H), 7.70-7.64 (m, 4H), 7.19-7.11 (m, 1H); MS (ESI): 375.2 (M+H)$^+$.

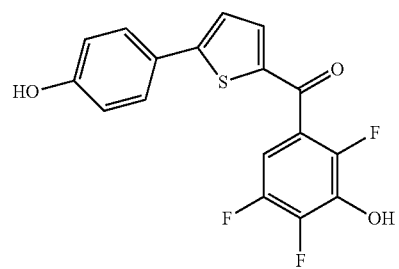

68

(5-(4-Hydroxyphenyl)thiophen-2-yl)(2,4,5-trifluoro-3-hydroxyphenyl)methanone (68): The title compound was prepared by reaction of (5-(4-methoxyphenyl)thiophen-2-yl)(2,4,5-trifluoro-3-hydroxyphenyl)methanone (51) (20.0 mg, 54.9 µmol) and boron tribromide (0.165 mmol, 3.0 equiv) according to method B. The product was purified by preparative HPLC (water with 0.1% formic acid/acetonitrile with 0.1% formic acid); yield: 18% (3.50 mg). $^1$H-NMR (300 MHz, acetone-d$^6$): δ 7.70-7.63 (m, 2H), 7.61 (dd, J=4.1, 1.9 Hz, 1H), 7.43 (d, J=4.1 Hz, 1H), 7.05-6.91 (m, 3H); MS (ESI): 351.2 (M+H)$^+$.

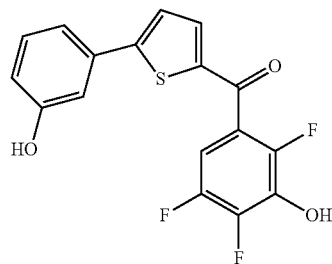

69

(5-(3-Hydroxyphenyl)thiophen-2-yl)(2,4,5-trifluoro-3-hydroxyphenyl)methanone (69): The title compound was prepared by reaction of (5-(3-methoxyphenyl)thiophen-2-yl)(2,4,5-trifluoro-3-hydroxyphenyl)methanone (52) (26.2 mg, 71.9 µmol) and boron tribromide (0.216 mmol, 3.0 equiv) according to method B. The product was purified by preparative HPLC (water with 0.1% formic acid/acetonitrile with 0.1% formic acid); yield: 83% (21.0 mg). $^1$H-NMR (500 MHz, acetone-d$^6$): δ 7.66 (dd, J=3.9, 1.7 Hz, 1H), 7.54 (d, J=4.1 Hz, 1H), 7.33-7.26 (m, 2H), 7.25-7.23 (m, 1H), 7.11 (ddd, J=10.0, 8.1, 5.5 Hz, 1H), 6.95-6.91 (m, 1H); MS (ESI): 351.3 (M+H)$^+$.

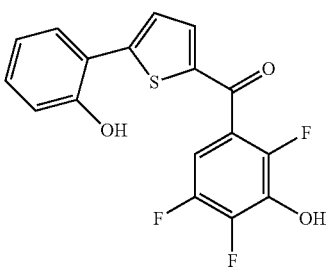

(5-(2-Hydroxyphenyl)thiophen-2-yl)(2,4,5-trifluoro-3-hydroxyphenyl)methanone (70): The title compound was prepared by reaction of (5-(2-methoxyphenyl)thiophen-2-yl)(2,4,5-trifluoro-3-hydroxyphenyl)methanone (53) (34.3 mg, 94.1 μmol) and boron tribromide (0.282 mmol, 3.0 equiv) according to method B. The product was purified by preparative HPLC (water with 0.1% formic acid/acetonitrile with 0.1% formic acid); yield: 45% (14.7 mg). $^1$H-NMR (300 MHz, acetone-d$^6$): δ 7.82 (dd, J=7.9, 1.5 Hz, 1H), 7.75 (d, J=4.2 Hz, 1H), 7.64 (dd, J=4.1, 1.6 Hz, 1H), 7.31-7.21 (m, 1H), 7.15-7.03 (m, 2H), 6.98 (t, J=7.5 Hz, 1H); MS (ESI): 351.2 (M+H)$^+$.

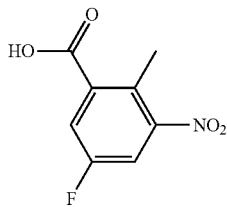
71a 5-fluoro-2-methyl-3-nitrobenzoic acid (71a): The title compound was prepared by reaction of 5-fluoro-2-methylbenzoic acid (500 mg, 3.24 mmol, 1.0 equiv) in 4 mL sulphuric acid (95%) and fuming nitric acid (245.1 mg, 3.89 mmol, 1.2 equiv) in 0.7 mL sulphuric acid (95%) at −11° C. The mixture was warmed to 0° C. and stirred for one hour at this temperature. It was poured into ice cold water, extracted with ethyl acetate three times, washed with brine and dried over magnesium sulfate, filtered and concentrated to dryness. The crude product was used in the next step without any further purification.

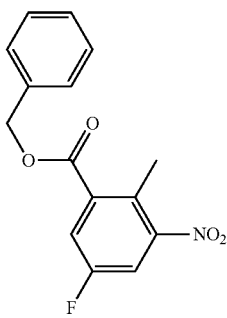
71b

Benzyl 5-fluoro-2-methyl-3-nitrobenzoate (71b): The title compound was prepared by reaction of the crude mixture of 5-fluoro-2-methyl-3-nitrobenzoic acid (71a) (591 mg, 3.24 mmol, 1.0 equiv), benzylbromide (665 mg, 3.89 mmol, 1.2 equiv) and potassium carbonate (558 mg, 3.89 mmol, 1.2 equiv) at 50° C. in 4.0 mL DMF for 1.5 hours. The reaction was stopped by the addition of water and extracted with ethyl acetate three times. The combined organic layers were washed with brine and dried with magnesium sulfate. After concentration in vacuo the crude mixture was purified by flash chromatography (dichloromethane:n-hexane) to obtain the product as an oil; yield: 35% (328.1 mg). $^1$H NMR (300 MHz, CDCl$_3$) δ 7.76 (dd, J=8.2, 2.8 Hz, 1H), 7.61 (dd, J=7.4, 2.8 Hz, 1H), 7.45-7.34 (m, 6H), 5.38 (s, 2H), 2.56 (s, 3H).

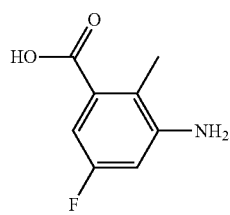
71c

3-Amino-5-fluoro-2-methylbenzoic acid (71c): The title compound was prepared by reaction of benzyl 5-fluoro-2-methyl-3-nitrobenzoate (71b) (321 mg, 1.11 mmol) and palladium on charcoal (10% Pd, 160 mg) under hydrogen atmosphere in 5.0 mL methanol at room temperature for 41.5 h. The reaction was stopped by dilution with ethyl acetate and filtered through a pad of celite fine. After drying with magnesium sulfate, evaporation of the solvent afforded the pure product as solid; yield: 90% (167.9 mg). $^1$H NMR (300 MHz, MeOH-d$^4$) δ 6.80 (dd, J=9.4, 2.5 Hz, 1H), 6.63 (dd, J=10.5, 2.3 Hz, 1H), 2.32-2.28 (m, 3H).

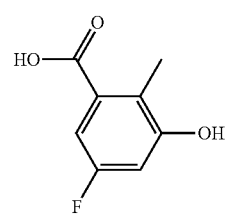
71d

5-Fluoro-3-hydroxy-2-methylbenzoic acid (71d): The title compound was prepared by reaction of 3-amino-5-fluoro-2-methylbenzoic acid (71c) (68.1 mg, 0.403 mmol, 1 equiv) in 0.5 ml water and 1.0 ml sulfuric acid (95%) and sodium nitrite (29.2 mg, 0.423 mmol, 1.05 equiv) dissolved in 0.7 mL water at 0° C. After 2 h of reaction time, the mixture was added dropwise to a boiling solution of 10.0 mL sulfuric acid (50%) and refluxed for 15 min. After cooling to room temperature, the mixture was extracted with ethyl acetate, washed with brine, dried with magnesium sulfate and purified by preparative HPLC (water with 0.1% formic acid/acetonitrile with 0.1% formic acid); yield: 40% (27.3 mg). $^1$H NMR (300 MHz, MeOH-d$^4$) δ 7.02 (dd, J=9.4, 2.3 Hz, 1H), 6.70 (dd, J=10.0, 2.2 Hz, 1H), 2.37 (s, 3H).

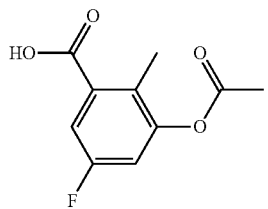

71e

3-Acetoxy-5-fluoro-2-methylbenzoic acid (71e): The title compound was prepared by reaction of 5-fluoro-3-hydroxy-2-methylbenzoic acid (71d) (39.2 mg, 0.230 mmol) in 1.0 ml of acetic anhydride in the presence of a catalytic amount of DMAP (~2 mg) at room temperature for 15 h. 1.0 ml of water was added and the mixture was stirred for another hour. After dilution with water, the crude mixture was extracted with ethyl acetate, dried with magnesium sulfate and purified by preparative HPLC (water with 0.1% formic acid/acetonitrile with 0.1% formic acid); yield: 82% (39.8 mg); $^1$H NMR (300 MHz, MeOH-$d_4$) δ 7.54 (dd, J=9.1, 2.8 Hz, 1H), 7.12 (dd, J=8.7, 2.7 Hz, 1H), 2.42-2.32 (m, 6H).

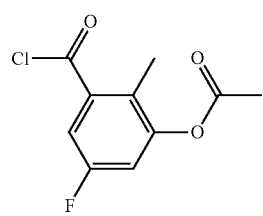

71f 3-(Chlorocarbonyl)-5-fluoro-2-methylphenyl acetate (71f): The title compound was prepared by reaction of 3-acetoxy-5-fluoro-2-methylbenzoic acid (71e) (20.0 mg, 94.3 μmol, 1 equiv) in 1.0 ml of thionyl chloride at room temperature for 14 h. The mixture was heated to 80° C. and stirred for another 1 h. Removal of excess thionyl chloride by distillation under reduced pressure yielded the crude product, which was used in the next step without further purification.

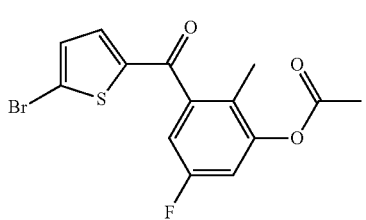

71g 3-(5-Bromothiophene-2-carbonyl)-5-fluoro-2-methylphenyl acetate (71g): The title compound was prepared by reaction of 3-(chlorocarbonyl)-5-fluoro-2-methylphenyl acetate (71f) (94.3 μmol, 1 equiv) aluminum chloride (25.1 mg, 0.188 mmol, 2 equiv) and 2-bromothiophene (15.3 mg, 93.8 μmol, 1 equiv.) at 0° C. for one hour and at room temperature for 4 h. After dilution with 1 M hydrochloric acid, the crude mixture was extracted with ethyl acetate, washed with brine, dried with magnesium sulfate and purified by flash chromatography; yield: 25% (8.5 mg). $^1$H NMR (300 MHz, CDCl$_3$) δ 7.16-7.14 (m, 1H), 7.11-7.07 (m, 1H), 7.01 (dd, J=8.0, 2.7 Hz, 1H), 6.95 (dd, J=8.7, 2.6 Hz, 1H), 2.33 (s, 3H), 2.10-2.07 (m, 3H).

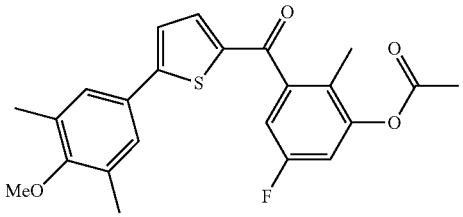

71h

5-Fluoro-3-(5-(4-methoxy-3,5-dimethylphenyl)thiophene-2-carbonyl)-2-methylphenyl acetate (71h): The title compound was prepared by reaction of (3-(5-bromothiophene-2-carbonyl)-5-fluoro-2-methylphenyl acetate (71g) (8.5 mg, 24 μmol), 4-methoxy-3,5-dimethyl phenylboronic acid (4.7 mg, 26 μmol), cesium carbonate (27.1 mg, 83.2 μmol) and tetrakis(triphenylphosphine) palladium (1.00 mg, 0.865 μmol) according to method C3. The crude product was used in the next step without further purification.

71i (5-Fluoro-3-hydroxy-2-methylphenyl)(5-(4-methoxy-3,5-dimethylphenyl)thiophen-2-yl)methanone (71i): The title compound was prepared by reaction of (5-fluoro-3-(5-(4-methoxy-3,5-dimethylphenyl)thiophene-2-carbonyl)-2-methylphenyl acetate (71h) (24 μmol) and sodium hydroxide (3.82 mg, 95.6 μmol, 4 equiv) in 4 ml THF/methanol/water 1/1/2 overnight. The mixture was diluted with water, extracted with ethyl acetate, dried with magnesium sulfate, concentrated under reduced pressure und purified by flash chromatography; yield: 82% (7.2 mg); $^1$H NMR (300 MHz, acetone-$d^6$) δ 7.51-7.41 (m, 4H), 6.80 (dd, J=10.2, 2.6 Hz, 1H), 6.73 (dd, J=8.6, 2.6 Hz, 1H), 3.76 (s, 3H), 2.32 (s, 6H), 2.15-2.09 (m, 3H).

71

(5-(4-Hydroxy-3,5-dimethylphenyl)thiophen-2-yl)(5-fluoro-3-hydroxy-2-methylphenyl)methanone (71): The title compound was prepared by reaction of (5-fluoro-3-hydroxy-2-methylphenyl)(5-(4-methoxy-3,5-dimethylphenyl)thiophen-2-yl)methanone (71i) (7.2 mg, 19.4 μmol) and boron tribromide (58.3 µmol, 3.0 equiv) according to method B. The product was purified by preparative HPLC (water with 0.1% formic acid/acetonitrile with 0.1% formic acid); yield: 97% (6.7 mg). $^1$H NMR (300 MHz, acetone-d$^6$) δ 7.44-7.37 (m, 4H), 6.79 (dd, J=10.2, 2.6 Hz, 1H), 6.72 (dd, J=8.6, 2.6 Hz, 1H), 2.30 (s, 6H), 2.13-2.10 (m, 3H); MS (ESI): 357.2 (M+H)$^+$.

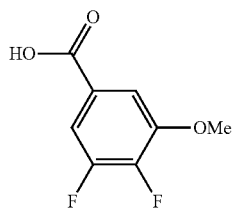

3,4-Difluoro-5-methoxybenzoic acid (72a): The title compound was prepared by reaction of 5-bromo-1,2-difluoro-3-methoxybenzene (1.03 g, 4.62 mmol, 1.0 equiv) and magnesium (112 mg, 4.61 mmol, 1.0 equiv) and iodine (~2 mg) in 13 ml diethylether under reflux for 2 h. Carbon dioxide was bubbled through the solution at 10° C. until all solvent (13 ml) was evaporated two times. The crude product was dissolved in 10 mL THF and carbon dioxide was bubbled through the solution for additional 1 h. The reaction was quenched with 1 M HCl, extracted with ethyl acetate, dried with magnesium sulfate and concentrated under reduced pressure to afford the crude product, which was purified by flash chromatography; yield: 31% (265 mg). $^1$H NMR (300 MHz, MeOH-d$^4$) δ 7.65-7.45 (m, 2H), 3.99 (s, 1H).

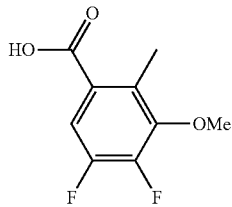

4,5-Difluoro-3-methoxy-2-methylbenzoic acid (72b): The title compound was prepared by reaction of 2,2,6,6-tetramethylpiperidine (374 mg, 2.65 mmol, 5 equiv) and n-butyllithium (2.5 M in n-hexane, 2.65 mmol, 5 equiv) in 12.5 ml THF at −78 OC for 15 min. The mixture was warmed to 0° C. and 3,4-difluoro-5-methoxybenzoic acid (72a) (100 mg, 0.532 mmol, 1 equiv) in 0.9 ml THF was added dropwise and the mixture was stirred for 1 h at 0° C. Methyliodide (331 µl, 5.31 mmol, 10 equiv) was added dropwise and the mixture was stirred for 20 min at 0° C. and for 1.5 h at 40° C., quenched with water, acidified with 1 M hydrochloric acid extracted with ethyl acetate, dried with magnesium sulfate and concentrated under reduced pressure to afford the crude product. This was purified by preparative HPLC (water with 0.1% formic acid/acetonitrile with 0.1% formic acid); yield: 45% (48.7 mg). $^1$H NMR (300 MHz, MeOH-d$^4$) δ 7.50 (dd, J=8.1, 1.9 Hz, 1H), 3.95 (s, 3H), 2.48 (d, J=2.6 Hz, 3H).

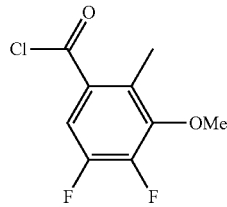

4,5-Difluoro-3-methoxy-2-methylbenzoyl chloride (72c): The title compound was prepared by reaction of 4,5-difluoro-3-methoxy-2-methylbenzoic acid (72b) (52.8 mg, 0.261 mmol) in 2 ml thionyl chloride at room temperature for 16 h, and at 80° C. for 1 h. The thionyl chloride was removed by distillation under reduced pressure to obtain the crude product, which was used in the next step without further purification.

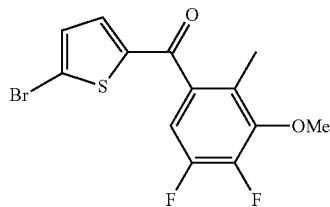

(5-Bromothiophen-2-yl)(4,5-difluoro-3-methoxy-2-methylphenyl)methanone (72d): The title compound was prepared by reaction of 4,5-difluoro-3-methoxy-2-methylbenzoyl chloride (72c) (0.261 mmol, 1 equiv), aluminum chloride (34.8 mg, 0.261 mmol, 1 equiv) and 2-bromothiophene (42.7 mg, 0.262 mmol, 1 equiv) at 0° C. for 45 min and at room temperature for 2 h. After dilution with 1 M hydrochloric acid, the crude mixture was extracted with ethyl acetate, washed with brine, dried with magnesium sulfate and purified by flash chromatography; yield: 47% (42.4 mg). $^1$H NMR (300 MHz, CDCl$_3$) δ 7.18-7.14 (m, 1H), 7.12-7.08 (m, 1H), 6.80 (dd, J=7.4, 2.0 Hz, 1H), 3.86 (s, 3H), 2.20 (d, J=2.5 Hz, 3H).

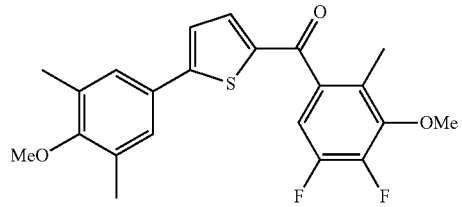

(4,5-Difluoro-3-methoxy-2-methylphenyl)(5-(4-methoxy-3,5-dimethylphenyl)thiophen-2-yl)methanone (72e): The title compound was prepared by reaction of (5-bromothiophen-2-yl)(4,5-difluoro-3-methoxy-2-methylphenyl)methanone (72d) (42.4 mg, 0.122 mmol), 4-methoxy-3,5-dimethylphenylboronic acid (24.1 mg, 0.134 mmol), cesium carbonate (139 mg, 0.427 mmol) and tetrakis (triphenylphosphine) palladium (4.93 mg, 4.27 µmol) according to method C3. The product was purified by preparative HPLC (water with 0.1% formic acid/acetonitrile with 0.1% formic acid); yield: 92% (45.4 mg). $^1$H NMR (300 MHz, CDCl$_3$) δ 7.36 (d, J=4.0 Hz, 1H), 7.31 (s, 2H), 7.22 (d, J=4.0 Hz, 1H), 6.85 (dd, J=7.5, 2.0 Hz, 1H), 3.87 (s, 3H), 3.74 (s, 3H), 2.31 (s, 6H), 2.22 (d, J=2.5 Hz, 3H).

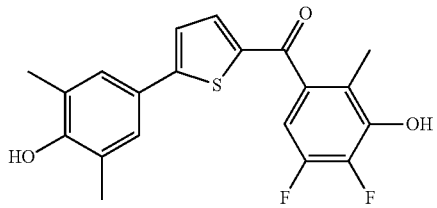

72

(4,5-Difluoro-3-hydroxy-2-methylphenyl)(5-(4-hydroxy-3,5-dimethylphenyl)thiophen-2-yl)methanone (72): The title compound was prepared by reaction of (4,5-difluoro-3-methoxy-2-methylphenyl)(5-(4-methoxy-3,5-dimethylphenyl)thiophen-2-yl)methanone (72e) (45.4 mg, 0.113 mmol) and boron tribromide (0.678 mmol, 6.0 equiv) according to method B. The product was purified by preparative HPLC (water with 0.1% formic acid/acetonitrile with 0.1% formic acid); yield: 86% (36.4 mg). $^1$H-NMR (300 MHz, acetone-d$^6$) δ 7.47-7.37 (m, 4H), 6.98 (dd, J=7.9, 2.1 Hz, 1H), 2.30 (s, 6H), 2.18 (d, J=2.5 Hz, 3H); MS (ESI): 375.2 (M+H)$^+$.

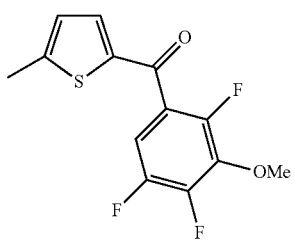

73a (5-Methylthiophen-2-yl)(2,4,5-trifluoro-3-methoxyphenyl)methanone (73a): The title compound was prepared by reaction of 2-methylthiophene (64.4 mg, 0.656 mmol), 2,4,5-trifluoro-3-methoxybenzoyl chloride (147.2 mg, 0.656 mmol) and aluminum chloride (87.5 mg, 0.656 mmol) according to method A. The product was purified by flash chromatography; yield: 69% (130 mg). $^1$H NMR (300 MHz, acetone-d$^6$) δ 7.49 (dd, J=3.8, 1.8 Hz, 1H), 7.29 (ddd, J=9.9, 8.3, 5.7 Hz, 1H), 6.98 (dd, J=3.9, 1.0 Hz, 1H), 4.04-4.14 (m, 3H), 2.57-2.62 (m, 3H).

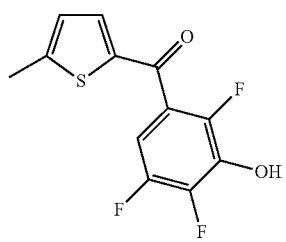

73

(5-Methylthiophen-2-yl)(2,4,5-trifluoro-3-hydroxyphenyl)methanone (73): The title compound was prepared by reaction of (5-methylthiophen-2-yl)(2,4,5-trifluoro-3-methoxyphenyl)methanone (73a) (121 mg, 0.423 mmol) and boron tribromide (1.38 mmol, 3.3 equiv) according to method B. The product was purified by preparative HPLC (water with 0.1% formic acid/acetonitrile with 0.1% formic acid); yield: 55% (63.1 mg). $^1$H-NMR (300 MHz, MeOH-d$^4$) δ 7.47-7.43 (m, 1H), 7.02-6.90 (m, 2H), 2.62 (s, 3H); MS (ESI): 273.2 (M+H)$^+$.

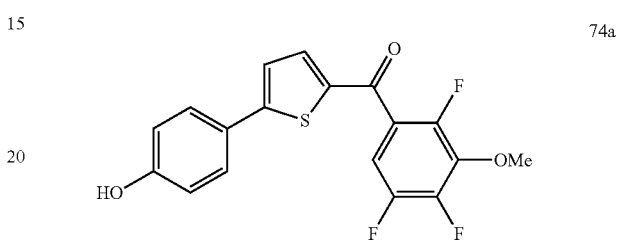

74a (5-(4-Hydroxyphenyl)thiophen-2-yl)(2,4,5-trifluoro-3-methoxyphenyl)methanone (74a): The title compound was prepared by reaction of (5-Bromo-thiophen-2-yl)(2,4,5-trifluoro-3-methoxyphenyl)methanone (1d) (176 mg, 0.500 mmol), 4-hydroxyphenylboronic acid (75.9 mg, 0.550 mmol), cesium carbonate (569 mg, 1.75 mmol) and tetrakis(triphenylphosphine) palladium (20.2 mg, 17.5 µmol) according to method C3. The product was purified by preparative HPLC (water with 0.1% formic acid/acetonitrile with 0.1% formic acid); yield: 17% (31.1 mg).

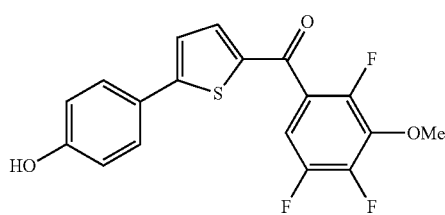

74b 4-(5-(2,4,5-Trifluoro-3-methoxybenzoyl)thiophen-2-yl)phenyl sulfamate (74b): The title compound was prepared by reaction of (5-(4-hydroxyphenyl)thiophen-2-yl)(2,4,5-trifluoro-3-methoxyphenyl)methanone (74a) (31.0 mg, 85.1 µmol) and sulfamoyl chloride (49.1 mg, 0.425 mmol) in 1.5 ml N,N-Dimethylacetamide at 0° C. for 2 h. The reaction mixture was diluted with water and extracted with ethyl acetate, dried with magnesium sulphate and concentrated under reduced pressure to afford the crude product. The product was purified by preparative HPLC (water with 0.1% formic acid/acetonitrile with 0.1% formic acid); yield: 56% (21.3 mg). $^1$H-NMR (300 MHz, MeOH-d$^4$) δ 7.86 (d, J=8.4 Hz, 2H), 7.65-7.60 (m, 1H), 7.55 (d, J=4.2 Hz, 1H), 7.45 (d, J=8.4 Hz, 2H), 7.35-7.25 (m, 1H), 4.12 (s, 3H); MS (ESI): 444.1 (M+H)$^+$.

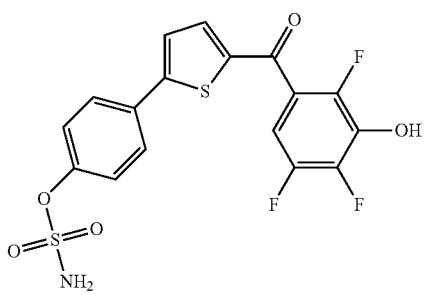

74

4-(5-(2,4,5-Trifluoro-3-hydroxybenzoyl)thiophen-2-yl)phenyl sulfamate (74): The title compound was prepared by reaction of (4-(5-(2,4,5-trifluoro-3-methoxybenzoyl)thiophen-2-yl)phenyl sulfamate (74b) (20.0 mg, 45.1 µmol) and boron tribromide (0.135 mmol, 3.0 equiv) according to method B with 3 h reaction time. The product was purified by preparative HPLC (water with 0.1% formic acid/acetonitrile with 0.1% formic acid); yield: 64% (12.4 mg). $^1$H-NMR (300 MHz, MeOH-d$^4$) δ 7.86 (d, J=8.7 Hz, 2H), 7.66-7.60 (m, 1H), 7.57-7.53 (m, 1H), 7.45 (d, J=8.1 Hz, 2H), 7.07-6.96 (m, 1H); MS (ESI): 430.2 (M+H)$^+$.

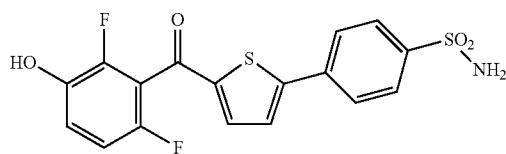

75

4-(5-(2,6-Difluoro-3-hydroxybenzoyl)thiophen-2-yl)benzenesulfonamide (75): The title compound was prepared by reaction of (5-bromo-thiophen-2-yl)-(2,6-difluoro-3-hydroxy-phenyl)-methanone (1e) (319 mg, 1.00 mmol) and (4-sulfamoylphenyl)boronic acid (241 mg, 1.20 mmol), cesium carbonate (1.30 g, 4.00 mmol) and tetrakis(triphenylphosphine) palladium (12.0 mg, 10.3 µmol) according to method C1. The product was purified by CC (dichloromethane/methanol 98:2); yield: 81% (320 mg). $^1$H NMR (500 MHz, DMSO-d$^6$) δ 10.28 (s, 1H), 8.05-8.00 (m, 2H), 7.94-7.88 (m, 2H), 7.81 (d, J=4.1 Hz, 1H), 7.71 (d, J=4.1 Hz, 1H), 7.48 (s, 2H), 7.17 (td, J=9.4, 5.6 Hz, 1H), 7.13-7.08 (m, 1H); $^{13}$C NMR (126 MHz, DMSO) δ 180.08, 152.13, 150.52 (dd, J=239.6, 5.6 Hz), 146.90 (dd, J=246.6, 7.5 Hz), 144.60, 142.38, 141.88 (dd, J=11.8, 2.8 Hz), 137.99, 135.16, 127.20, 126.80, 126.65, 119.63 (dd, J=9.3, 4.1 Hz), 116.43 (dd, J=23.5, 19.1 Hz), 111.73 (dd, J=22.2, 3.6 Hz); MS (ESI): 396.3 (M+H)$^+$.

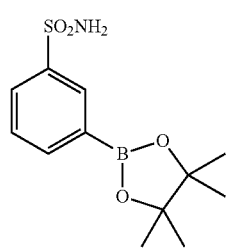

76a 3-(4,4,5,5-Tetramethyl-1,3,2-dioxaborolan-2-yl)benzenesulfonamide (76a): 3-Bromobenzenesulfonamide (580 mg, 2.46 mmol, 1.0 equiv), bis(pinacolato)diboron (1.00 g, 3.94 mmol, 1.6 equiv), potassium acetate (730 mg, 7.44 mmol, 3 equiv) and Pd(dppf)Cl2 (92.0 mg, 0.126 mmol, 0.05 equiv) were dissolved under N2 in 10 ml dioxane and the mixture was stirred for 30 minutes under reflux. The reaction was quenched with water. The mixture was used directly in the subsequent reaction without any further purification as the product is unstable.

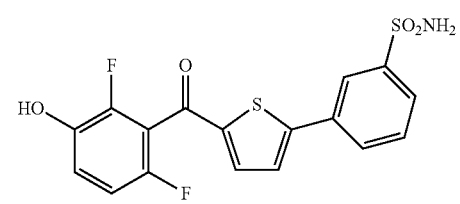

76

3-(5-(2,6-Difluoro-3-hydroxybenzoyl)thiophen-2-yl)benzenesulfonamide (76): The title compound was prepared by reaction of (5-bromo-thiophen-2-yl)(2,6-difluoro-3-hydroxyphenyl)methanone (1e) (670 mg, 2.10 mmol) and 3-(4,4,5,5-tetramethyl-1,3,2-dioxaborolan-2-yl)benzenesulfonamide (76a) (707 mg, 2.50 mmol), cesium carbonate (2.74 g, 8.41 mmol) and tetrakis(triphenylphosphine) palladium (26.0 mg, 22.5 µmol) according to method C1. The product was purified by CC (dichloromethane/methanol 98:2); yield: 24% (200 mg). $^1$H NMR (500 MHz, DMSO-d$^6$) δ 10.28 (s, 1H), 8.22 (t, J=1.7 Hz, 1H), 8.07 (ddd, J=7.8, 1.8, 0.9 Hz, 1H), 7.88 (ddd, J=7.8, 1.6, 1.0 Hz, 1H), 7.77 (d, J=4.1 Hz, 1H), 7.71 (dd, J=14.2, 6.1 Hz, 2H), 7.50 (s, 2H), 7.17 (td, J=9.4, 5.7 Hz, 1H), 7.11 (td, J=9.0, 1.2 Hz, 1H); $^{13}$C NMR (126 MHz, DMSO-d$^6$) δ 180.04, 152.19, 150.51 (dd, J=239.5, 5.6 Hz), 146.89 (dd, J=246.5, 7.7 Hz), 145.27, 142.09, 141.89 (dd, J=11.6, 2.9 Hz), 138.06, 132.90, 130.26, 129.42, 126.77, 126.38, 123.09, 119.63 (dd, J=9.0, 4.1 Hz), 116.43 (dd, J=23.4, 19.3 Hz), 111.74 (dd, J=22.3, 3.6 Hz); MS (ESI): 396.2 (M+H)$^+$.

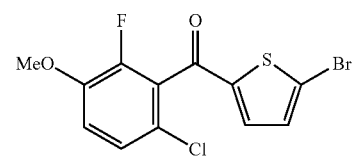

77a (5-Bromothiophen-2-yl)(6-chloro-2-fluoro-3-methoxyphenyl)methanone (77a): The title compound was prepared by reaction of 2-bromothiophene (1.22 g, 7.48 mmol), 6-chloro-2-fluoro-3-methoxybenzoyl chloride (1.12 g, 5.02 mmol) and aluminum chloride (666 mg, 4.99 mmol) according to method A. The product was purified by CC (dichloromethane/hexane 75:25); yield: 60% (1.05 g). MS (ESI): 350.5 (M+H)$^+$.

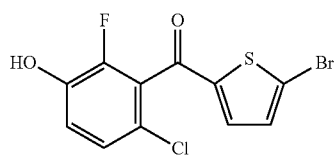

77b

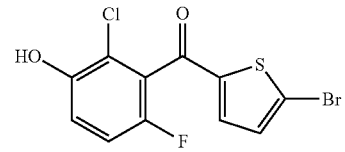

78b (5-Bromothiophen-2-yl)(6-chloro-2-fluoro-3-hydroxyphenyl)methanone (77b): The title compound was prepared by reaction of (5-bromothiophen-2-yl)(6-chloro-2-fluoro-3-methoxyphenyl)methanone (77a) (700 mg, 2.00 mmol) and boron tribromide (6.00 mmol, 3 equiv) according to method B. The product was purified by CC (dichloromethane); yield: 81% (540 mg). $^1$H NMR (300 MHz, DMSO-d$^6$) δ 10.61 (s, 1H), 7.46-7.40 (m, 2H), 7.26 (dd, J=8.8, 1.3 Hz, 1H), 7.13 (t, J=9.0 Hz, 1H); MS (ESI): 336.5 (M+H)$^+$.

(5-Bromothiophen-2-yl)(2-chloro-6-fluoro-3-hydroxyphenyl)methanone (78b): The title compound was prepared by reaction of (5-bromothiophen-2-yl)(2-chloro-6-fluoro-3-methoxyphenyl)methanone (78a) (700 mg, 2.00 mmol) and boron tribromide (6.00 mmol, 3 equiv) according to method B. The product was purified by CC (dichloromethane); yield: 78% (523 mg). $^1$H NMR (300 MHz, DMSO-d$^6$) δ 10.59 (s, 1H), 7.41 (q, J=4.1 Hz, 2H), 7.27-7.19 (m, 1H), 7.13 (dd, J=9.1, 5.3 Hz, 1H); MS (ESI): 336.5 (M+H)$^+$.

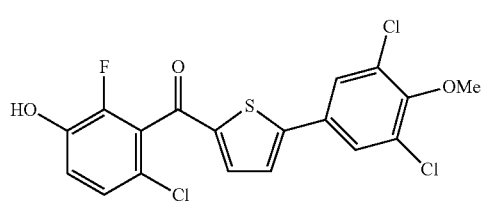

77

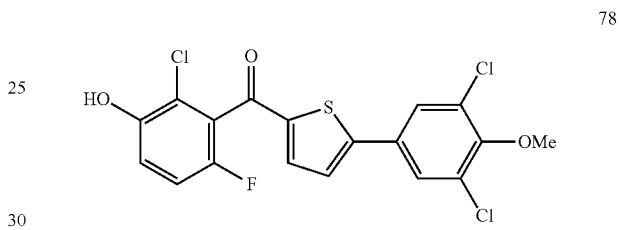

78

(6-Chloro-2-fluoro-3-hydroxyphenyl)(5-(3,5-dichloro-4-methoxyphenyl)thiophen-2-yl)methanone (77): The title compound was prepared by reaction of (5-bromothiophen-2-yl)(6-chloro-2-fluoro-3-hydroxyphenyl)methanone (77b) (335 mg, 1.00 mmol) and (3,5-dichloro-4-methoxyphenyl)boronic acid (264 mg, 1.20 mmol), cesium carbonate (1.30 g, 3.99 mmol) and tetrakis(triphenylphosphine) palladium (12.0 mg, 10.4 µmol) according to method C1. The product was purified by CC (dichloromethane/methanol 99.5:0.5) followed by washing with petroleum ether; yield: 89% (385 mg). $^1$H NMR (300 MHz, DMSO-d$^6$) δ 10.59 (s, 1H), 7.97 (s, 2H), 7.78 (d, J=4.1 Hz, 1H), 7.59 (d, J=4.0 Hz, 1H), 7.27 (dd, J=8.8, 1.4 Hz, 1H), 7.14 (t, J=9.0 Hz, 1H), 3.88 (s, 3H); $^{13}$C NMR (75 MHz, DMSO-d$^6$) δ 182.50, 152.80, 150.94, 148.14 (d, J=245.2 Hz), 145.02 (d, J=11.9 Hz), 142.31, 138.29, 130.75, 129.80, 127.91, 127.37, 127.10, 126.24 (d, J=3.3 Hz), 120.36 (d, J=3.7 Hz), 118.96 (d, J=4.1 Hz), 61.32; MS (ESI): 432.9 (M+H)$^+$.

(2-Chloro-6-fluoro-3-hydroxyphenyl)(5-(3,5-dichloro-4-methoxyphenyl)thiophen-2-yl)methanone (78): The title compound was prepared by reaction of (5-bromothiophen-2-yl)(2-chloro-6-fluoro-3-hydroxyphenyl)methanone (78b) (335 mg, 1.00 mmol) and (3,5-dichloro-4-methoxyphenyl)boronic acid (264 mg, 1.20 mmol), cesium carbonate (1.30 g, 3.99 mmol) and tetrakis(triphenylphosphine) palladium (12.0 mg, 10.4 µmol) according to method C1. The product was purified by CC (dichloromethane/methanol 99.25:0.75) followed by washing with petroleum ether; yield: 83% (360 mg). $^1$H NMR (300 MHz, DMSO-d$^6$) δ 10.58 (s, 1H), 7.96 (s, 2H), 7.77 (d, J=4.1 Hz, 1H), 7.57 (d, J=4.1 Hz, 1H), 7.24 (t, J=8.8 Hz, 1H), 7.14 (dd, J=9.1, 5.3 Hz, 1H), 3.87 (s, 3H); $^{13}$C NMR (75 MHz, DMSO-d$^6$) δ 182.59, 152.78, 151.68 (d, J=238.3 Hz), 150.82, 150.77 (d, J=2.3 Hz), 142.38, 138.10, 130.77, 129.79, 127.87, 127.35, 127.10 (d, J=23.3 Hz), 118.52 (d, J=8.5 Hz), 117.04 (d, J=6.0 Hz), 115.81 (d, J=22.3 Hz), 61.32; MS (ESI): 432.8 (M+H)$^+$.

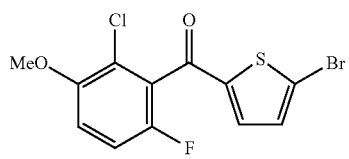

78a

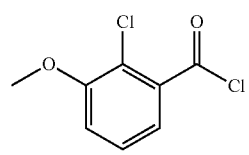

79a (5-Bromothiophen-2-yl)(2-chloro-6-fluoro-3-methoxyphenyl)methanone (78a): The title compound was prepared by reaction of 2-bromothiophene (1.22 g, 7.48 mmol), 2-chloro-6-fluoro-3-methoxybenzoyl chloride (1.12 g, 5.02 mmol) and aluminum chloride (666 mg, 4.99 mmol) according to method A. The product was purified by CC (dichloromethane/hexane 75:25); yield: 72% (1.26 g). MS (ESI): 350.5 (M+H)$^+$.

2-Chloro-3-methoxybenzoyl chloride (79a): 2-Chloro-3-methoxybenzoic acid (200 mg, 1.07 mmol, 1 equiv) was dissolved in thionyl chloride (2.16 g, 18.2 mmol, 17 equiv) and stirred under reflux for 1 h. The solution was concentrated in vacuum and the crude product was used in the next step without purification.

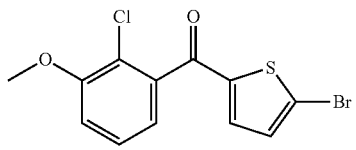

79b (5-Bromothiophen-2-yl)(2-chloro-3-methoxyphenyl)methanone (79b): The title compound was prepared by reaction of 2-chloro-3-methoxybenzoyl chloride (79a) (1.07 mmol), 2-bromothiophene (175 mg, 1.07 mmol) and aluminium trichloride (143 mg, 1.07 mmol) according to method A. In contrast, the mixture was stirred at room temperature overnight. The crude product was purified by flash chromatography ($SiO_2$, hexane/ethyl acetate 8:2); yield: 76% (270 mg). $^1$H NMR (300 MHz, acetone-$d^6$) δ 7.46 (m, 1H), 7.33-7.29 (m, 2H), 7.24 (d, J=4.1 Hz, 1H), 7.10 (dd, J=7.6, 1.4 Hz, 1H), 3.97 (s, 3H).

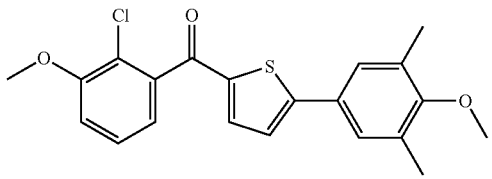

79c (2-Chloro-3-methoxyphenyl)(5-(4-methoxy-3,5-dimethylphenyl)thiophen-2-yl)methanone (79c): The title compound was prepared by reaction of (5-bromothiophen-2-yl)(2-chloro-3-methoxyphenyl)methanone (79b) (262 mg, 0.790 mmol), 3,5-dimethyl-4-methoxyphenylboronic acid (171 mg, 0.950 mmol), cesium carbonate (1.03 g, 3.16 mmol) and tetrakis(triphenylphosphine) palladium (18.0 mg, 15.6 μmol) according to method C1. The crude product was purified by flash chromatography (SiO2, hexane/ethyl acetate 9:1 to 8:2); yield: 50% (183 mg). $^1$H NMR (300 MHz, acetone-$d^6$) δ 7.51-7.43 (m, 4H), 7.38 (d, J=4.0 Hz, 1H), 7.30 (dd, J=8.3, 1.4 Hz, 1H), 7.10 (dd, J=7.5, 1.4 Hz, 1H), 3.99 (s, 3H), 3.76 (s, 3H), 2.32 (s, 6H).

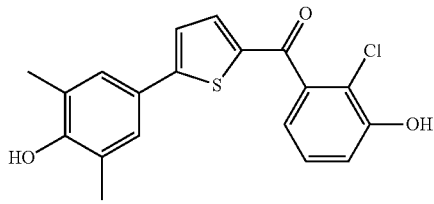

79

(2-Chloro-3-hydroxyphenyl)(5-(4-hydroxy-3,5-dimethylphenyl)thiophen-2-yl)methanone (79): The title compound was prepared by reaction of (2-Chloro-3-methoxyphenyl)(5-(4-methoxy-3,5-dimethylphenyl)thiophen-2-yl)methanone (79c) (177 mg 0.457 mmol) and boron tribromide (3.68 mmol, 8.0 equiv) according to method B with 3 h reaction time. The crude product was purified by preparative TLC (SiO2, hexane/ethyl acetate 7:3); yield: 45% (75.0 mg). 1H-NMR (300 MHz, acetone-$d^6$) δ 9.06 (s, 1H), 7.74 (s, 1H), 7.42 (m, 2H), 7.36-7.39 (m, 2H), 7.31 (dd, J=8.1, 7.5 Hz, 1H), 7.18 (dd, J=8.2, 1.5 Hz, 1H), 7.01 (dd, J=7.5, 1.5 Hz, 1H), 2.29 (s, 6H); $^{13}$C-NMR (300 MHz, acetone-$d^6$) δ 186.75, 156.01, 155.92, 154.46, 141.53, 141.03, 138.10, 128.72, 127.53, 125.85, 125.57, 123.91, 120.42, 118.77, 118.05, 16.65.

Example 2

Biological Testing

Biological methods: [2,4,6,7-$^3$H]-E1 and [2,4,6,7-$^3$H]-E2 were bought from Perkin-Elmer. Quickszint Flow 302 scintillator fluid was bought from Zinsser Analytic. Human 17β-HSD1 and human 17β-HSD2 were prepared from human placenta according to a previously described procedure (Marchais-Oberwinkler et al. S., J. Med. Chem., 56:167-181 (2013)). Fresh human placenta was homogenized, and cytosolic fraction and microsomes were separated by differential centrifugation at 1,000 g, 10,000 g and 150,000 g. For the partial purification of 17β-HSD1, the cytosolic fraction was precipitated with ammonium sulfate. 17β-HSD2 was obtained from the microsomal fraction.

1. Inhibition of human 17β-HSD1: Inhibitory activities were evaluated by an established method (Marchais-Oberwinkler et al. S., J. Med. Chem., 56:167-181 (2013)). Briefly, the cytosolic enzyme preparation was incubated with NADH [500 μM] in the presence of potential inhibitors at 37° C. in a phosphate buffer (50 mM) supplemented with 20% of glycerol and EDTA (1 mM). Inhibitor stock solutions were prepared in DMSO. The final concentration of DMSO was adjusted to 1% in all samples. The enzymatic reaction was started by addition of a mixture of unlabelled- and [2,4,6,7-$^3$H]-E1 (final concentration: 500 nM, 0.15 μCi). After 10 min, the incubation was stopped with $HgCl_2$ and the mixture was extracted with diethylether. After evaporation, the steroids were dissolved in acetonitrile. E1 and E2 were separated using acetonitrile/water (45:55) as mobile phase in a C18 reverse phase chromatography column (Nucleodur C18 125/3 100-5, Macherey-Nagel) connected to a HPLC-system (Agilent 1200 series, Agilent Technologies). Detection and quantification of the labeled steroids were performed using a radioflow detector (Ramona, raytest). The conversion rate was calculated after analysis of the resulting chromatograms according to the following equation:

% conversion=[% E2/(% E2+% E1)]×100.

2. Inhibition of human 17β-HSD2: The 17β-HSD2 inhibition assay was performed similar to the human 17β-HSD1 procedure. The microsomal fraction was incubated with $NAD^+$ [1,500 μM], test compound and a mixture of unlabelled- and [2,4,6,7-$^3$H]-E2 (final concentration: 500 nM, 0.11 μCi) for 20 min at 37° C. Further treatment of the samples and HPLC separation were carried out as indicated above. The conversion rate was calculated after analysis of the resulting chromatograms according to the following equation:

% conversion=[% E1/(% E1+% E2)]×100

3. Preparation of mouse and rat 17β-HSD1 and 2: Recombinant mouse and rat 17β-HSD1 enzymes were produced by transfection of HEK293 cells with a mouse or rat 17β-HSD1 expression plasmid. 48 hours after transfection, cells were homogenized by ultrasonication (3×10 s) in a buffer containing sucrose (40 mM Tris, 250 mM sucrose, 5 mM EDTA, 7 mM DTT, 1 mM PMSF, pH 7.5). Cell lysates were centrifuged (1,000 g, 15 min, 4° C.) and 20% glycerol was added to the supernatant before aliquots were frozen and stored at −70° C. Microsomal 17β-HSD2 fractions were obtained from mouse or rat liver. Fresh liver tissues were processed as described for the human placental 17β-HSD2 preparation. The pellet fractions containing the microsomal 17β-HSD2 were used for the determination of E1 formation.

4. Inhibition of mouse and rat 17β-HSD1: Inhibitory activities of the compounds towards mouse or rat 17β-HSD1 were evaluated by a method similar to the human 17β-HSD1 assay. The recombinant enzyme preparations were incubated with NADPH (500 μM), test compound and a mixture of unlabeled- and [2,4,6,7-$^3$H]-E1 (final concentration: 10 nM, 0.15 μCi) for 10 min at 37° C. Further treatment of the samples and HPLC separation was carried out as mentioned above.

The conversion rate was calculated after analysis of the resulting chromatograms according to the following equation:

% conversion=[% E2/(% E2+% E1)]×100

5. Inhibition of mouse and rat 17β-HSD2: The mouse and rat 17β-HSD2 inhibition assays were performed similarly to the human 17β-HSD2 procedure. The microsomal fractions were incubated with NAD$^+$ (1,500 μM), test compound and a mixture of unlabelled- and [2,4,6,7-$^3$H]-E2 (final concentration: 10 nM, 0.15 μCi) for 20 min at 37° C. Further treatment of the samples and HPLC separation was carried out as mentioned above.

The conversion rate was calculated after analysis of the resulting chromatograms according to the following equation:

% conversion=[% E1/(% E1+% E2)]×100

6. Metabolic Stability Tests in Human Liver S9 Fraction: The compound (1 g M) was incubated with 1 mg/mL pooled human liver S9 fraction (BD Gentest), 2 mM NADP, 10 mM glucose-6-phosphate, 10 U/ml glucose-6-phosphate dehydrogenase, 10 mM MgCl2, 1 mM UDPGA, and 0.1 mM PAPS at 37 dr for 0, 5, 15, and 60 min. The incubation was stopped by precipitation of S9 enzymes with 2 volumes of cold acetonitrile containing internal standard. Concentration of the remaining test compound at the different time points was analyzed by LC-MS/MS and used to determine halfound at the and Clint.

Biological Data

TABLE 1

Inhibitory effect of compounds 1-79, 1g, and 31a on human and mouse 17β-HSD1 and 17β-HSD2.

| Cpmd | IC$_{50}$ [nM][a] | | Inhibition @ 1 μM[a] | |
|---|---|---|---|---|
| | h17β-HSD1 | h17β-HSD2 | m17β-HSD1 | m17β-HSD2 |
| F1 | 8 | 384 | 18 | 22 |
| 1g | 130 | 27 | 11 | 44 |
| 1 | 10 | 25 | 30 | n.d.[b] |
| 2 | 1.7 | 17 | 71 | IC50: 67 nM |
| 3 | 3.1 | 13 | IC50: 750 nM | IC50: 54 nM |
| 4 | 2.3 | 6 | IC50: 250 nM | IC50: 7 nM |
| 5 | 4 | 3.7 | 47 | 86 |
| 6 | 5.5 | 2.7 | 10 | n.d.[b] |
| 7 | 1.8 | 6.5 | 76 | 91 |
| 8 | 27%@ 1 μM | 49%@ 1 μM | n.d.[b] | n.d.[b] |
| 9 | 57%@ 1 μM | 64%@ 1 μM | 14 | 23 |
| 10 | 3.5 | 9 | 41 | 67 |
| 11 | 1.2 | 10 | 60 | 75 |
| 12 | 1.3 | 11 | 40 | 64 |
| 13 | 5.5 | 52 | 25 | 65 |
| 15 | 0.6 | 41 | 43 | IC50: 550 nM |

TABLE 1-continued

Inhibitory effect of compounds 1-79, 1g, and 31a on human and mouse 17β-HSD1 and 17β-HSD2.

| Cpmd | IC$_{50}$ [nM][a] | | Inhibition @ 1 μM[a] | |
|---|---|---|---|---|
| | h17β-HSD1 | h17β-HSD2 | m17β-HSD1 | m17β-HSD2 |
| 16 | 0.9 | 18 | 59 | 55 |
| 17 | 7 | 36 | 47 | 74 |
| 18 | 8 | 19 | n.d.[b] | n.d.[b] |
| 19 | 79%@ 1 μM | 85%@ 1 μM | 58 | 44 |
| 20 | 0.5 | 20 | 50 | 82 |
| 21 | 0.8 | 11 | 38 | IC50: 78 nM |
| 22 | 27 | 29 | 46 | 82 |
| 23 | 2.4 | 39 | 23 | IC50: 209 nM |
| 24 | 0.4 | 7 | IC50: 397 nM | 76 |
| 25 | 3.3 | 29 | 23 | 40 |
| 26 | 0.4 | 7 | n.d.[b] | n.d.[b] |
| 27 | 0.2 | 7 | n.d.[b] | n.d.[b] |
| 28 | 1.4 | 21 | 37 | 45 |
| 29 | 2.1 | 11 | 16 | 40 |
| 30 | 4.7 | 26 | 25 | 41 |
| 31a | 28%@ 1 μM | 32%@ 1 μM | 20 | n.d.[b] |
| 31 | 2.1 | 9 | 32 | 84 |
| 32 | 37%@ 1 μM | 30%@ 1 μM | n.i.[c] | n.d.[b] |
| 33 | 4.7 | 8 | IC50: 602 nM | IC50: 122 nM |
| 34 | 5 | 20 | IC50: 513 nM | 46%@250 nM |
| 35 | 49 | 5 | 9 | 80 |
| 36 | 2.4 | 1.8 | 68 | IC50: 90 nM |
| 37 | 5.8 | 2.0 | 55 | IC50: 79 nM |
| 38 | 4.8 | 1.4 | 81 | IC50: 36 nM |
| 39 | 59 | 18 | 9 | 24 |
| 40 | 7.2 | 1.4 | 28 | IC50: 326 nM |
| 41 | 1.1 | 3.1 | 33 | 89 |
| 42 | 2.5 | 3.0 | 46 | 84 |
| 43 | 28.8 | 7.5 | IC50: 1138 nM | IC50: 113 nM |
| 44 | 22.4 | 6.8 | 10%@ 100 nM | 19%@ 100 nM |
| 45 | 0.6 | 2.6 | IC50: 1732 | IC50: 89 nM |
| 46 | 1.2 | 2.3 | 13.4 | 16%@ 100 nM |
| 47 | 5.9 | 4.4 | 13.8 | IC50: 260 nM |
| 48 | 21.0 | 4.1 | 12.1 | IC50: 155 nM |
| 49 | 9.1 | 11.2 | 13.8 | n.d.[b] |
| 50 | 0.9 | 1.3 | IC50: 650 nM | IC50: 100 nM |
| 51 | 47%@ 10 nM | 87%@ 10 nM | n.d.[b] | n.d.[b] |
| 52 | 75%@ 10 nM | 47%@ 10 nM | n.d.[b] | 15%@ 50 nM |
| 53 | 81%@ 10 nM | 96%@ 10 nM | n.d.[b] | 34%@ 50 nM |
| 54 | 31%@ 10 nM | 89%@ 10 nM | n.d.[b] | 30%@ 50 nM |
| 55 | 12%@ 10 nM | 68%@ 10 nM | n.d.[b] | 23%@ 50 nM |
| 56 | 71%@ 10 nM | 93%@ 10 nM | n.d.[b] | n.d.[b] |
| 57 | 14%@ 10 nM | 60%@ 10 nM | n.d.[b] | n.d.[b] |
| 58 | 1.1%@ 10 nM | 61%@ 10 nM | n.d.[b] | 40%@ 50 nM |
| 59 | 48%@ 10 nM | 68%@ 10 nM | n.d.[b] | 27%@ 50 nM |
| 60 | 13%@ 10 nM | 51%@ 10 nM | n.d.[b] | 23%@ 50 nM |
| 61 | 48%@ 10 nM | 68%@ 10 nM | n.d.[b] | 60%@ 50 nM |
| 62 | 93%@ 10 nM | 100%@ 10 nM | n.d.[b] | 46%@ 50 nM |
| 63 | 53%@ 10 nM | 77%@ 10 nM | n.d.[b] | 38%@ 50 nM |
| 64 | 0%@ 10 nM | 62%@ 10 nM | n.d.[b] | 28%@ 50 nM |
| 65 | 15%@ 10 nM | 62%@ 10 nM | n.d.[b] | n.d.[b] |
| 66 | 22%@ 10 nM | 83%@ 10 nM | n.d.[b] | n.d.[b] |
| 67 | 30%@ 10 nM | 86%@ 10 nM | n.d.[b] | n.d.[b] |
| 68 | 66%@ 10 nM | 96%@ 10 nM | n.d.[b] | 42%@ 50 nM |
| 69 | 72%@ 10 nM | 95%@ 10 nM | n.d.[b] | 32%@ 50 nM |
| 70 | 19%@ 10 nM | 100%@ 10 nM | n.d.[b] | n.d.[b] |
| 71 | 12.6 nM | 50 nM | n.d.[b] | 79%@ 50 nM |
| 72 | 44 nM | 159 nM | n.d.[b] | 22%@ 50 nM |
| 73 | 9.1%@ 100 nM | 56%@ 100 nM | n.d.[b] | n.d.[b] |
| 74 | 20%@ 10 nM | 72%@ 10 nM | n.d.[b] | n.d.[b] |
| 75 | 18%@ 10 nM | 54%@ 10 nM | n.d.[b] | 10%@ 50 nM |
| 76 | 34%@ 10 nM | 26%@ 10 nM | n.d.[b] | 1.8%@ 50 nM |
| 77 | 100%@ 10 nM | 45%@ 10 nM | n.d.[b] | n.d.[b] |

TABLE 1-continued

Inhibitory effect of compounds 1-79, 1g, and 31a on human and mouse 17β-HSD1 and 17β-HSD2.

| Cpmd | IC$_{50}$ [nM][a] | | Inhibition @ 1 μM[a] | |
|---|---|---|---|---|
| | h17β-HSD1 | h17β-HSD2 | m17β-HSD1 | m17β-HSD2 |
| 78 | 41%@ 10 nM | 54%@ 10 nM | n.d.[b] | 76%@ 50 nM |
| 79 | 31%@ 10 nM | 64%@ 10 nM | n.d.[b] | 70%@ 50 nM |

[a]Mean value of three determinations, standard deviation less than 15%.
[b]not determined.
[c]no inhibition

TABLE 2

Metabolic Stability of selected compounds in human liver S9 fraction

| | Human liver S9 | |
|---|---|---|
| Cmpd | t$_{1/2}$ (min) | CL$_{int}$ |
| F1 | 3.6 | 193.8 |
| 2 | 5.7 | 122.5 |
| 11 | 4.3 | 160.7 |
| 12 | 4.6 | 149.6 |
| 15 | 18.1 | 38.3 |
| 16 | 8.5 | 81.3 |
| 21 | 2.9 | 241.4 |
| 23 | 129.4 | 5.4 |
| 24 | 2.6 | 272.7 |
| 25 | 10.7 | 64.5 |
| 30 | 6.5 | 106.8 |
| 41 | 11.3 | 61.5 |
| 45 | 15.0 | n.d.[a] |
| 48 | 24.9 | 27.9 |
| 50 | 38.0 | 18.2 |
| 58 | 20.8 | 33.3 |
| 62 | 48.9 | 14.2 |
| 63 | 25.0 | 27.7 |
| 68 | 27.4 | 25.3 |
| 79 | 22.0 | 31.6 |

TABLE 3

Inhibition of rat 17β-HSD1 and 17β-HSD2 by selected compounds.

| Cmpd | Cmpd conc. | % Inhibition[a] | |
|---|---|---|---|
| | | r17β-HSD1 | r17β-HSD2 |
| F1 | 5000 nM | 48 | n.d.[b] |
| 1e | 250 nM | 5 | 60 |
| 2 | 250 nM | 56 | 86 |
| 3 | 250 nM | 70 | 74 |
| 4 | 100 nM | 59 | 70 |
| 5 | 250 nM | 32 | 28 |
| 6 | 250 nM | 29 | 31 |
| 7 | 250 nM | 51 | 49 |
| 16 | 250 nM | 39 | 27 |
| 19 | 250 nM | 26 | n.i.[c] |
| 23 | 5000 nM | 59 | n.d.[b] |
| 24 | 250 nM | 63 | 35 |
| 29 | 250 nM | n.i.[c] | n.i.[c] |
| 30 | 500 nM | 51 | 55 |
| 31 | 250 nM | 39 | n.d.[b] |
| 32 | 250 nM | n.i.[c] | 66 |
| 35 | 250 nM | 46 | 100 |
| 36 | 250 nM | 50 | 100 |
| 37 | 250 nM | 29 | 93 |
| 38 | 250 nM | 41 | 96 |
| 40 | 250 nM | 58 | 86 |

[a]Mean value of three determinations, standard deviation lessthan 15%.
[b]n.d., not determined
[c]n.i., no inhibition.

Comparative Data

The introduction of two and three fluorine atoms, respectively, on the benzoyl moiety led to a dramatic increase in potency towards murine 17beta-HSD1 and 2 by up to 100-fold; in case of the human enzymes, the achieved potencies increase 5-1000-fold. The strong beneficial effects exerted by multiple halogenation of the benzoyl moiety on human and rodent 17beta-HSD1 and 2 inhibition are documented by a direct comparison of inhibitory activities displayed by compounds with different degrees of halogenation. These examples also illustrate the fact that difluorination in general leads to a slight-to-good human 17beta-HSD1 selectivity whereas trifluorination favours human 17beta-HSD2 selectivity.

Both the strong increase in potency and the modulation of selectivity are unanticipated in light of WO2012/025638: The monofluorinated compounds 7 and 9 of WO2012/025638 show insignificant differences in potency toward human 17beta-HSD1 and are less selective compared to their non-fluorinated analogs 1 and 4 (numbering refers to WO2012/025638). Compounds with more than one fluorine atom attached to the benzoyl moiety are not described in WO2012/025638. Thus, the data did not allow the conclusion that introduction of two or three fluorine atoms increases potencies dramatically. Furthermore, due to the different architectures of the substrate binding sites (which are supposed to be the inhibitor binding sites as well) of human 17beta-HSD1/2 in comparison to murine 17beta-HSD1/2, the strong inhibition of the murine enzymes is unexpected.

TABLE 4

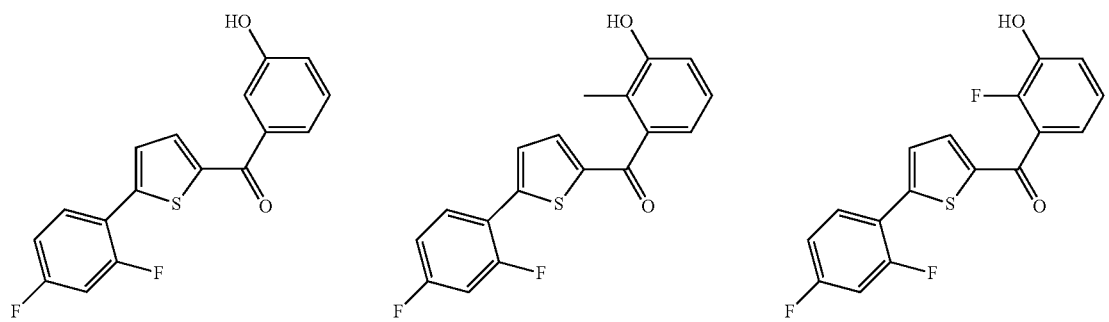

TABLE 4-continued

| | A | | B | | C | |
|---|---|---|---|---|---|---|
| | 10 | | | | 40 | |
| Compd | IC$_{50}$ [nM] or % inhibition h17β-HSD1 | IC$_{50}$ [nM] or % inhibition h17β-HSD2 | IC$_{50}$ [nM] or % inhibition m17β-HSD1 | IC$_{50}$ [nM] or % inhibition m17β-HSD2 | IC$_{50}$ [nM] or % inhibition r17β-HSD1 | IC$_{50}$ [nM] or % inhibition r17β-HSD2 |
|---|---|---|---|---|---|---|
| A | 32% @ 1 μM | 35% @ 1 μM | n.d | n.d | n.d | n.d |
| B | 3427 | 300 | 5% @ 1 μM | 18% @ 1 μM | n.d | n.d |
| C | 92% @ 100 nM | 87% @ 100 nM | 18% @ 1 μM | 75% @ 1 μM | 35% @ 250 nM | 20% @ 250 nM |
| 10 | 3.5 | 9.0 | 41 | 67.5 | 63% @ 250 nM | 66% @ 250 nM |
| 40 | 7.2 | 1.4 | 27.5 | 80 | 58% @ 250 nM | 86% @ 250 nM |

TABLE 5

| D | E | 20 |
|---|---|---|

(= compd. 17 in WO 2012/025638)

| Compd | IC$_{50}$ [nM] or % inhibition h17β-HSD1 | IC$_{50}$ [nM] or % inhibition h17β-HSD2 | IC$_{50}$ [nM] or % inhibition m17β-HSD1 | IC$_{50}$ [nM] or % inhibition m17β-HSD2 | IC$_{50}$ [nM] or % inhibition r17β-HSD1 | IC$_{50}$ [nM] or % inhibition r17β-HSD2 |
|---|---|---|---|---|---|---|
| D | 5 | 240 | 42% @ 1 μM | 9% @ 1 μM | n.d | n.d |
| E | 76% @ 1 μM | 93% @ 1 μM | 14% @ 1 μM | 92% @ 1 μM | n.d | n.d |
| 20 | 0.5 | 20 | 50% @ 1 μM | 95% @ 1 μM | 48% @ 500 nM | 98% @ 500 nM |

TABLE 6

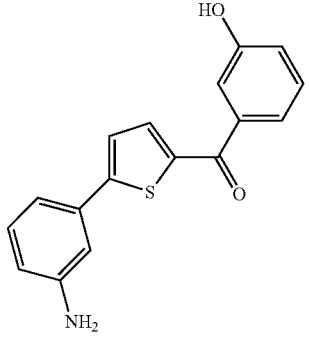 [SMILES: Nc1cccc(-c2ccc(C(=O)c3cccc(O)c3)s2)c1]

| | F | 1 | 35 |
|---|---|---|---|
| Compd | IC$_{50}$ [nM] or % inhibition h17β-HSD1 | IC$_{50}$ [nM] or % inhibition h17β-HSD1 | IC$_{50}$ [nM] or % inhibition m17β-HSD1 | IC$_{50}$ [nM] or % inhibition m17β-HSD2 | IC$_{50}$ [nM] or % inhibition r17β-HSD1 | IC$_{50}$ [nM] or % inhibition r17β-HSD2 |
| F | 77% @ 1 μM | 68% @ 1 μM | n.d | n.d | n.d | n.d |
| 1 | 10 | 25 | 30% @ 1 μM | n.d | 51% @ 250 nM | 48% @ 250 nM |
| 35 | 49 | 5 | 13 | 177 | 46% @ 250 nM | 100% @ 250 nM |

TABLE 7

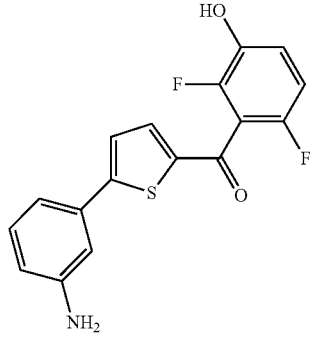 [SMILES: Nc1cccc(-c2ccc(C(=O)c3c(F)ccc(O)c3F)s2)c1]

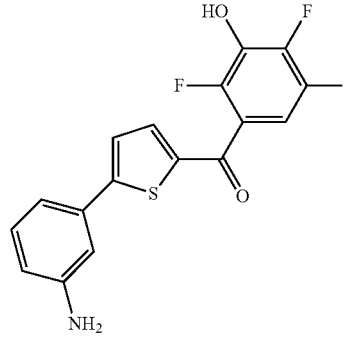

| Compd | IC$_{50}$ or % inhibition h17β-HSD1 | IC$_{50}$ or % inhibition h17β-HSD2 | IC$_{50}$ or % inhibition m17β-HSD1 | IC$_{50}$ or % inhibition m17β-HSD2 | IC$_{50}$ or % inhibition r17β-HSD1 | IC$_{50}$ or % inhibition r17β-HSD2 |
|---|---|---|---|---|---|---|
| G | 899 nM | 239 nM | 35.5 μM | 546 nM | n.d. | n.d. |
| 71 | 12.6 nM | 50 nM | n.d. | 79% @ 50 nM | n.d. | n.d. |
| 72 | 44 nM | 159 nM | n.d. | 22% @ 50 nM | n.d. | n.d. |
| 50 | 0.9 nM | 1.3 nM | 650 nM | 100 nM | n.d. | n.d. |

TABLE 8

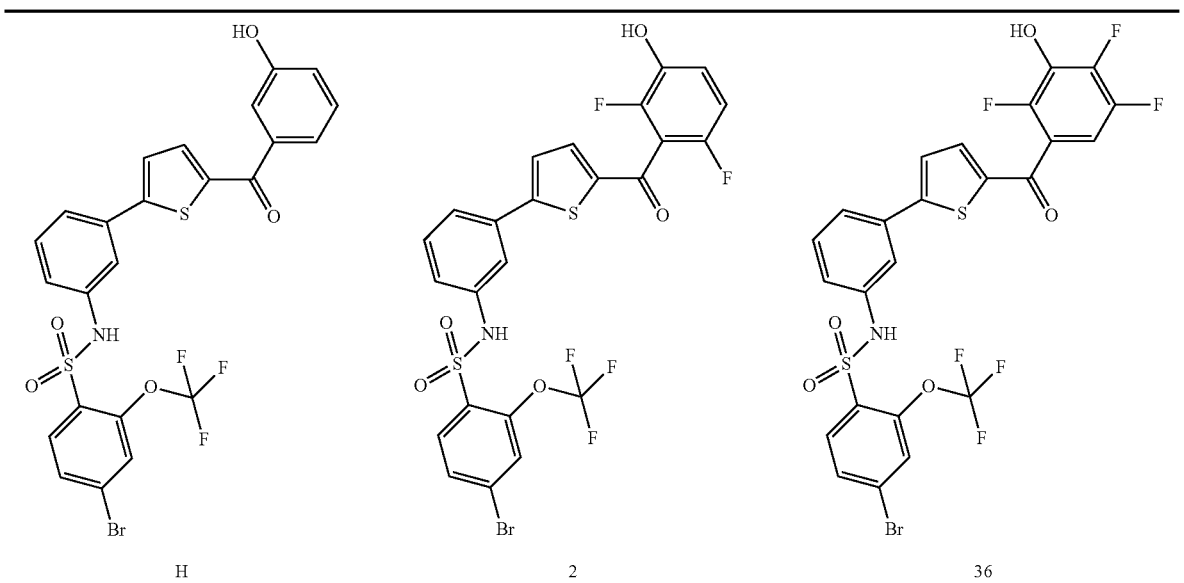

| Compd | IC$_{50}$ [nM] or % inhibition h17β-HSD1 | IC$_{50}$ [nM] or % inhibition h17β-HSD2 | IC$_{50}$ [nM] or % inhibition m17β-HSD1 | IC$_{50}$ [nM] or % inhibition m17β-HSD2 | IC$_{50}$ [nM] or % inhibition r17β-HSD1 | IC$_{50}$ [nM] or % inhibition r17β-HSD2 |
|---|---|---|---|---|---|---|
| H | 8 | 199 | 21% @ 1 μM | 36% @ 1 μM | n.d | n.d |
| 2 | 1.7 | 17 | 71% @ 1 μM | 100 | 56% @ 250 nM | 86% @ 250 nM |
| 36 | 2.4 | 1.8 | 68% @ 1 μM | 12.5 | 50% @ 250 nM | 100% @ 250 nM |

TABLE 9

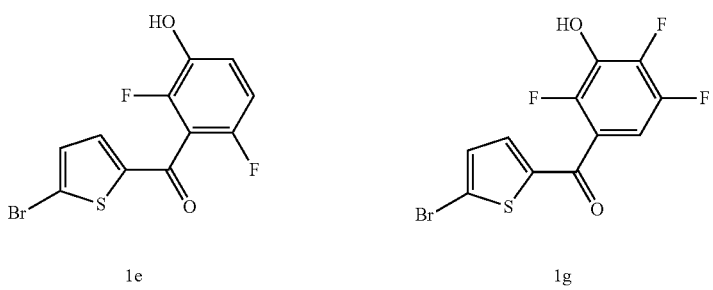

| Compd | IC$_{50}$ [nM] or % inhibition h17β-HSD1 | IC$_{50}$ [nM] or % inhibition h17β-HSD1 | IC$_{50}$ [nM] or % inhibition m17β-HSD1 | IC$_{50}$ [nM] or % inhibition m17β-HSD2 | IC$_{50}$ [nM] or % inhibition r17β-HSD1 | IC$_{50}$ [nM] or % inhibition r17β-HSD2 |
|---|---|---|---|---|---|---|
| 1e | 85% @ 100 nM | 71% @ 100 nM | 5% @ 1 μM | 80% @ 1 μM | 5% @ 250 nM | 60% @ 250 nM |
| 1g | 130 | 27 | 11% @ 1 μM | 44% @ 1 μM | n.d | n.d |

TABLE 10

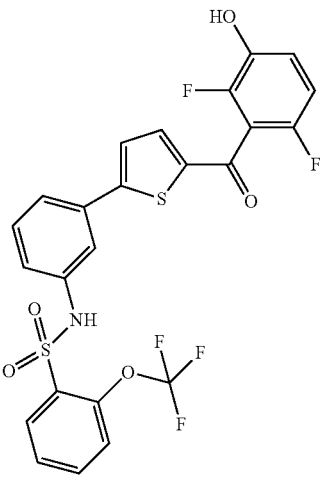 [SMILES: O=C(c1ccc(-c2cccc(NS(=O)(=O)c3ccccc3OC(F)(F)F)c2)s1)c1c(F)ccc(O)c1F]

| Compd | IC$_{50}$ [nM] or % inhibition h17β-HSD1 | IC$_{50}$ [nM] or % inhibition h17β-HSD2 | IC$_{50}$ [nM] or % inhibition m17β-HSD1 | IC$_{50}$ [nM] or % inhibition m17β-HSD2 | IC$_{50}$ [nM] or % inhibition r17β-HSD1 | IC$_{50}$ [nM] or % inhibition r17β-HSD2 |
|---|---|---|---|---|---|---|
| 3 | 3 | 13 | 746 | 33 | 70% @ 250 nM | 74% @ 250 nM |
| 37 | 5.8 | 2 | 55% @ 1 μM | 22 | 29% @ 250 nM | 93% @ 250 nM |

TABLE 11

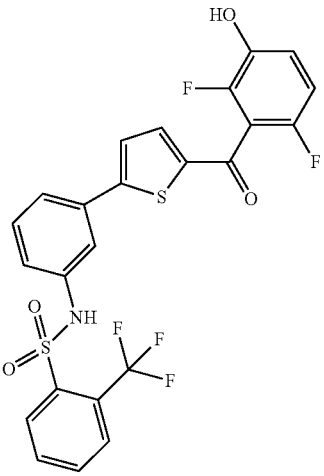 [SMILES: O=C(c1ccc(-c2cccc(NS(=O)(=O)c3ccccc3C(F)(F)F)c2)s1)c1c(F)ccc(O)c1F]

| Compd | IC$_{50}$ [nM] or % inhibition h17β-HSD1 | IC$_{50}$ [nM] or % inhibition h17β-HSD2 | IC$_{50}$ [nM] or % inhibition m17β-HSD1 | IC$_{50}$ [nM] or % inhibition m17β-HSD2 | IC$_{50}$ [nM] or % inhibition r17β-HSD1 | IC$_{50}$ [nM] or % inhibition r17β-HSD2 |
|---|---|---|---|---|---|---|
| 4 | 2.3 | 6 | 251 | 20 | 59% @ 100 nM | 70% @ 100 nM |
| 38 | 4.8 | 1.4 | 81% @ 1 μM | 36 | 41% @ 250 nM | 96% @ 250 nM |

The invention claimed is:
1. A compound having the formula (I) for use in the treatment of hormone-related diseases in a mammal

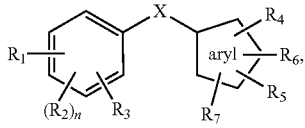
(I)

wherein
R1 represents, OH, alkoxy or acyloxy;
n represents an integer of 1 or 2;
R2 is at each occurrence independently selected from the group consisting of fluorine, chlorine, and bromine;
R3 represents alkyl, haloalkyl or halogen atom;
R4 represents H; OH; an alkyl or an alkoxy group, each of which may carry phenyl and halogen substituents, wherein said phenyl substituents may carry up to 3 substituents independently selected from —OH, alkyl, haloalkyl, alkoxy, halogen, amino, —CN and NO$_2$; a 6-membered aromatic group which may carry 1 to 3 substituents independently selected from —R, haloalkyl, halogen, —NO$_2$, OR', SR', CH$_2$R, —COR', NR'R', —CN, COOR', —NR'SO$_2$R, SO$_2$NR'R', NR'COR, CONR'R', OC(O)R', —CH$_2$NR'R', —CH$_2$OR', —SO$_2$R and —SOR, wherein R is an alkyl group, a heterocyclic ring, an aromatic or non aromatic ring that is optionally condensed or linked with a 5- or 6-membered, aliphatic or aromatic heterocyclic ring, a benzyl group, or an aliphatic or aromatic heterocyclic group that is optionally condensed or linked with a benzene ring, each of said groups may be substituted with up to 5 substituents independently selected from halogen, lower alkyl, lower haloalkyl, OH, NO$_2$, lower alkoxy, lower haloalkoxy, NH$_2$, phenyl, —CN, —COR", —NHCOR", CONHR", NHSO$_2$R" and SO$_2$NHR", wherein R" is H, lower alkyl, lower haloalkyl or phenyl, and R' at each occurrence is independently selected from the groups of R above and H, or two of said substituents, together with the adjacent carbon atoms of the 6-membered aromatic group, optionally form a 5- or 6-membered, aliphatic or aromatic, homocyclic or heterocyclic ring condensed to said 6-membered aromatic group, wherein the heterocyclic ring carries up to 3 heteroatoms independently selected from N, S and O, and the third substituent is optionally located on the 6-membered aromatic group or on the ring condensed thereto; or a 5 or 6-membered aliphatic or aromatic heterocyclic group which carries up to 3 heteroatoms independently selected from N, S and O and may carry 1 to 3 substituents independently selected from —R, haloalkyl, halogen, —NO$_2$, OR', SR', —CH$_2$R, —COR', NR'R', —CN, COOR', —NR'SO$_2$R, SO$_2$NR'R', NR'COR, NRCOR', CONR'R', —OC(O)R', —CH$_2$NR'R', —CH$_2$OR', —SO$_2$R and —SOR, wherein R and R' is as defined above, or two of said substituents, together with the adjacent carbon atoms of the 5 or 6-membered aliphatic or aromatic heterocyclic group, optionally form a 6-membered, aliphatic or aromatic ring condensed to said 5 or 6-membered aromatic group, and the third substituent is optionally present on the 5 or 6-membered aromatic group or on the ring condensed thereto;

and said substituent R4 being directly or through a phenylene group bound to the aryl ring;
R5, R6 and R7 independently represent H, —R, haloalkyl, halogen, —NO$_2$, OR', SR', —CH$_2$R', —COR', —NR'R', —CN, —COOR', —NHSO$_2$R', —NRSO$_2$R', SO$_2$NRR', NHCOR', NRCOR', CONRR', —OC(O)R', —CH$_2$NRR', —CH$_2$OR', —SO$_2$R' or —SOR', wherein R and R' is as defined above,
X represents

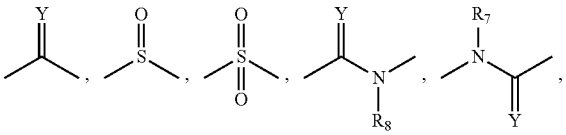

wherein Y, if present, represents O or S, and R8 represents H or lower alkyl; and
the aryl ring is a 5-membered heteroaromatic ring which carries up to 3 heteroatoms independently selected from N, S and O;
or a pharmaceutically acceptable salt thereof.

2. The compound for use in the treatment of hormone-related diseases in a mammal of claim 1, wherein the compound has the formula (II)

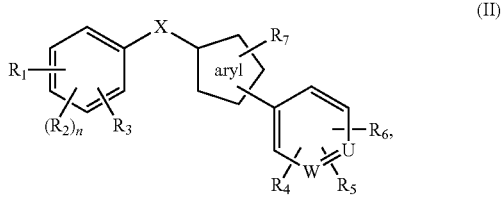
(II)

wherein R1, R2, R3, R4, R5, R6, R7, X and n have the same meaning as in claim 1, the aryl ring is a heterocyclic aromatic ring, which carries up to 3 heteroatoms independently selected from N, S and O, W and U represent independently CH or N.

3. The compound for use in the treatment of hormone-related diseases in a mammal of claim 2, wherein the compound has the formula (III)

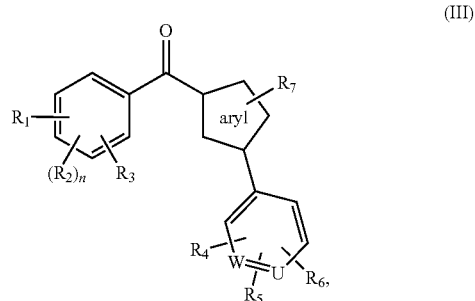
(III)

wherein all the variables are as defined in claim 2.

4. The compound for use in the treatment of hormone-related diseases in a mammal of claim 2, wherein
the aryl ring represents a thiadiazole, triazole, oxadiazole, isothiadiazole, isooxadiazole, thiazole, oxazole, imidazole, pyrazole, isoxazole, isothiazole, furane, pyrrole or thiophene;

W and U represent independently CH or N;
R1 is OH or lower alkoxy;
R3 represents lower alkyl, lower haloalkyl or halogen;
R7 represents H or lower alkyl;
R5 represent H, —R, haloalkyl, halogen, —NO$_2$, —CH$_2$R, —OR', —NR'R', —CN, —NR'SO$_2$R, —SO$_2$NR'R', —NR'COR' or —CONR'R', wherein R is alkyl, aryl, benzyl, an aliphatic or aromatic heterocyclic group, an aliphatic cyclic or heterocyclic ring, each of which may be substituted with up to 5 substituents independently selected from halogen, lower alkyl, lower haloalkyl, OH, —NO$_2$, lower alkoxy, —NH$_2$, phenyl, —CN, —COR", —NHCOR", —CONHR", —NHSO$_2$R" and SO$_2$NHR", wherein R" is —H, lower alkyl, lower haloalkyl or phenyl; and R' is R or H;
R6 is selected from H, OH, lower alkyl, lower alkoxy, lower haloalkoxy and halogen; and/or
R4 represents H, OH, an alkyl or an alkoxy group, each of which optionally carry phenyl and halogen substituents, wherein said phenyl substituents optionally carry up to 3 substituents independently selected from —OH, alkyl, haloalkyl, alkoxy, halogen, amino, —CN and —NO$_2$, —CH$_2$R, —NHSO$_2$R and —NHCOR', wherein R and R' is as defined above, a 6-membered aromatic or hetero aromatic group which optionally carry 1 to 3 substituents independently selected from —R, haloalkyl, halogen, —NO$_2$, —OR', —NR'R', —CN, —NR'SO$_2$R, —SO$_2$NR'R', —NR'COR', —CONR'R', wherein R and R' is as defined above, or two of said substituents, together with the adjacent carbon atoms of the 6-membered aromatic group, optionally form a 5- or 6-membered aliphatic or aromatic, homocyclic or heterocyclic ring condensed to said 6-membered aromatic group, wherein the heterocyclic ring carries up to 3 heteroatoms independently selected from N, S and O, and wherein the third substituent may be located on the 6-membered aromatic group or on the ring condensed thereto, or a 5 or 6-membered, aliphatic or aromatic heterocyclic group which carries up to 3 heteroatoms independently selected from N, S and O and optionally carry 1 to 3 substituents independently selected from —R, haloalkyl, halogen, —NO$_2$, —OR', —NR'R', —CN, —NR'SO$_2$R, —SO$_2$NR'R', —NR'COR', —CONR'R', wherein R and R' is as defined above or two of said substituents, together with the adjacent carbon atoms of the 5 or 6-membered aliphatic or aromatic heterocyclic group, optionally form a 6-membered, aliphatic or aromatic ring condensed to said 5 or 6-membered aromatic group.

5. The compound for use in the treatment of hormone-related diseases in a mammal of claim 4, wherein the aryl ring represents a thiophene; R1 is OH; n is 1 or 2; R2 is F; R3 is lower alkyl, lower haloalkyl or F, W and U are independently selected from CH and N; R4 represents H, OH, an alkoxy group, which optionally carry up to 3 halogen substituents, —CH$_2$R, —SO$_2$R, —NHSO$_2$R and —NRSO$_2$R', wherein R and R' is as defined above; R7 is selected from H and alkyl; and/or R5 and R6 are independently selected from H, OH, —CN, alkyl, alkoxy and halogen.

6. The compound for use in the treatment of hormone-related diseases in a mammal of claim 3, wherein in the compounds of formula (I) R1 is a hydroxy group in the meta position relative to the —CO— junction, n is 1 or 2, R2 is F and R3 is CH$_3$, CF$_3$ or F.

7. The compound for use in the treatment of hormone-related diseases in a mammal of claim 1, wherein the compound has 17β-HSD1 inhibitory activity, and wherein in formula (I) n is 1, R2 and R3 independently represent halogen atoms.

8. The compound for use in the treatment of hormone-related diseases in a mammal of claim 1, wherein the compound has 17β-HSD2 inhibitory activity, and wherein in formula (I)
(i) n is 1, R2 is selected from the group consisting of fluorine, chlorine, and bromine and R3 represents alkyl or haloalkyl; or
(ii) n is 2, R2 is at each occurrence independently selected from the group consisting of fluorine, chlorine, and bromine and R3 at each occurrence independently represents a halogen atom.

9. The compound for use in the treatment of hormone-related diseases in a mammal of claim 1, wherein the compound is selected from [5-(3aminophenyl)thiophen-2-yl](2,6-difluoro-3 -hydroxyphenyl)methanone, 4-bromo-N-{3-[5-(2,6-difluoro-3-hydroxybenzoyl)thiophen-2-yl]-phenyl}-2-trifluoromethoxybenzenesulfonamide, N-{3-[5-(2,6-difluoro-3 -hydroxybenzoyl) thiophen-2-yl]phenyl}-2-trifluoromethoxybenzene-sulfonamide, N-{3-[5-(2,6-difluoro-3-hydroxybenzoyl) thiophen-2-yl]phenyl}-2-trifluoromethylbenzene-sulfonamide, pyridine-3-sulfonic acid{3-[5-(2,6-difluoro-3-hydroxy-benzoyl)-thiophen-2-yl]-phenyl}-amide, 1-methyl-1H-imidazole-4-sulfonic acid {3-[5-(2,6-difluoro-3-hydroxyl-benzoyl)-thiophen-2-yl]-phenyl}-amide, cyclopropanesulfonic acid {3-[5-(2,6-difluoro-3-hydroxy-benzoyl)-thiophen-2-yl]-phenyl}-amide, (2,6-difluoro-3-hydroxy-phenyl)-(5-pyridin-4-yl-thiophen-2-yl)-methanone, (2,6-difluoro-3-hydroxy-phenyl)-(5-pyridin-3-yl-thiophen-2-yl)-methanone, (2,6-difluoro-3-hydroxy-phenyl)-[5-(2,4-difluoro-phenyl)-thiophen-2-yl]-methanone, [5-(3-chloro-phenyl)-thiophen-2-yl]-(2,6-difluoro-3-hydroxy-phenyl)-methanone, [5-(3-chloro-4-methoxy-phenyl)-thiophen-2-yl]-(2,6-difluoro-3-hydroxy-phenyl)-methanone, [5-(3-chloro-4-methoxy-phenyl)-4-methyl-thiophen-2-yl]-(2,6-difluoro-3-hydroxy-phenyl)-methanone, [5-(3-chloro-2-methoxy-phenyl)-thiophen-2-yl]-(2,6-difluoro-3-hydroxy-phenyl)-methanone, [5-(3,5-dichloro-4-methoxy-phenyl)-thiophen-2-yl]-(2,6-difluoro-3-hydroxy-phenyl)-methanone, (2,6-difluoro-3-hydroxy-phenyl)-[5-(4-methoxy-3,5-dimethyl-phenyl)-thiophen-2-yl]-methanone, (2,6-difluoro-3-hydroxy-phenyl)-[5-(4-difluoromethoxy-3,5-difluoro-phenyl)-thiophen-2-yl]-methanone, 5-[5-(2,6-difluoro-3-hydroxy-benzoyl)-thiophen-2-yl]-2-isopropoxy-benzonitrile, (2,6-difluoro-3-hydroxy-phenyl)-{5-[4-methoxy-3-(morpholine-4-sulfonyl)-phenyl]-thiophen-2-yl}-methanone, [5-(3-chloro-4-hydroxy-phenyl)-thiophen-2-yl]-(2,6-difluoro-3-hydroxy-phenyl)-methanone, [5-(3-chloro-4-hydroxy-phenyl)-4-methyl-thiophen-2-yl]-(2,6-difluoro-3-hydroxy-phenyl)-methanone, [5-(3-chloro-2-hydroxy-phenyl)-thiophen-2-yl]-(2,6-difluoro-3-hydroxy-phenyl)-methanone, [5-(3,5-dichloro-4-hydroxy-phenyl)-thiophen-2-yl]-(2,6-difluoro-3-hydroxy-phenyl)-methanone, (2,6-difluoro-3-hydroxy-phenyl)-[5-(4-hydroxy-3,5-dimethyl-phenyl)-thiophen-2-yl]-methanone, 5-[5-(2,6-difluoro-3-hydroxy-benzoyl)-thiophen-2-yl]-2-hydroxy-benzonitrile, [5-(3-chloro-4-methoxy-5-methyl-phenyl)-thiophen-2-yl]-(2,6-difluoro-3-hydroxy-phenyl)-methanone, [5-(3-chloro-4-hydroxy-5-methyl-phenyl)-thiophen-2-yl]-(2,6-difluoro-3-hydroxy-phenyl)-methanone, 1-(4-{3-chloro-5-[5-(2,6-difluoro-3-hydroxy-benzoyl)-thiophen-2-yl]-2-methoxy-benzyl}-piperazin-1-yl)-ethanone, 1-(4-{3-chloro-5-[5-(2,6- difluoro-3-hydroxy-benzoyl)-thiophen-2-yl]-2-hydroxy-benzyl}-piperazin-1-yl)-ethanone, [5-(3-chloro-4-methoxy-5-piperazin-1-ylmethyl-phenyl)-thiophen-2-yl]-(2,6-difluoro-3-hydroxy-phenyl)-methanone, [5-(3-chloro-4-methoxy-5-[1,2,3]triazol-1-ylmethyl-phenyl)-thiophen-2-yl]-(2,6-difluoro-3-hydroxy-phenyl)-methanone, [5-(3-chloro-4-hydroxy-5-[1,2,3]triazol-1-ylmethyl-phenyl)-thiophen-2-yl]-(2,6-difluoro-3-hydroxy-phenyl)-methanone, cyclopropanesulfonic acid {3-[5-(2,6-difluoro-3-hydroxy-benzoyl)-thiophen-2-yl]-5-methyl-phenyl}-amide, cyclopropanesulfonic acid {3-[5-(2,6-difluoro-3-hydroxy-benzoyl)-thiophen-2-yl]-5-methyl-phenyl}-methyl-amide, [5-(3-aminophenyl)thiophen-2-yl](2,4,5-trifluoro-3-hydroxyphenyl)methanone, 4-bromo-N-{3-[5-(2,4,5-trifluoro-3-hydroxybenzoyl)thiophen-2-yl]phenyl}-2-trifluoromethoxybenzenesulfonamide, N-{3-[5-(2,4,5-trifluoro-3-hydroxybenzoyl)thiophen-2-yl]phenyl}-2-trifluoromethoxybenzenesulfonamide, N-{3-[5-(2,4,5-trifluoro-3-hydroxybenzoyl)thiophen-2-yl]phenyl}-2-trifluoromethylbenzenesulfonamide, [5-(5-fluoro-pyridin-3-yl)-thiophen-2-yl]-(2,4,5-trifluoro-3-hydroxy-phenyl)-methanone, [5-(2,4-difluoro-phenyl)-thiophen-2-yl]-(2,4,5-trifluoro-3-hydroxy-phenyl)-methanone, (5-(3-chloro-4-hydroxyphenyl)thiophen-2-yl)(2,4,5-trifluoro-3-hydroxyphenyl)methanone, (5-(3-fluoro-4-hydroxyphenyl)thiophen-2-yl)(2,4,5-trifluoro-3-hydroxyphenyl)methanone, (5-(1H-indol-6-yl)thiophen-2-yl)(2,4,5-trifluoro-3-hydroxyphenyl)methanone, 3-(5-(2,4,5-trifluoro-3-hydroxybenzoyl)thiophen-2-yl)benzamide, (5-(3,5-dichloro-4-methoxyphenyl)thiophen-2-yl)(2,4,5-trifluoro-3-hydroxyphenyl)methanone, (5-(4-methoxy-3,5-dimethylphenyl)thiophen-2-yl)(2,4,5-trifluoro-3-hydroxyphenyl)methanone, (5-(3-(hydroxymethyl)phenyl)thiophen-2-yl)(2,4,5-trifluoro-3-hydroxyphenyl)methanone, 1-methyl-N-(3-(5-(2,4,5-trifluoro-3-hydroxy-benzoyl)thiophen-2-yl)phenyl)-1H-imidazole-4-sulfonamide, (5-(3,5-dichloro-4-hydroxyphenyl)thiophen-2-yl)(2,4,5-trifluoro-3-hydroxyphenyl)methanone, (5-(4-hydroxy-3,5-dimethylphenyl)thiophen-2-yl)(2,4,5-trifluoro-3-hydroxyphenyl)methanone, (5-(4-methoxyphenyl)thiophen-2-yl)(2,4,5-trifluoro-3-hydroxyphenyl)methanone, (5-(3-methoxyphenyl)thiophen-2-yl)(2,4,5-trifluoro-3-hydroxyphenyl)methanone, (5-(2-methoxyphenyl)thiophen-2-yl)(2,4,5-trifluoro-3-hydroxyphenyl)methanone, N-(3-(5-(2,4,5-trifluoro-3-hydroxybenzoyl)thiophen-2-yl)phenyl) acetamide, (5-(2-aminophenyl)thiophen-2-yl)(2,4,5-trifluoro-3-hydroxyphenyl)methanone, (5-phenylthiophen-2-yl)(2,4,5-trifluoro-3-hydroxyphenyl)methanone, (5-(3-Amino-4-methylphenyl)thiophen-2-yl)(2,4,5-trifluoro-3-hydroxyphenyl)methanone, (5-(3-amino-2-methylphenyl)thiophen-2-yl)(2,4,5-trifluoro-3-hydroxyphenyl)methanone, (5-(3-amino-4-hydroxyphenyl)thiophen-2-yl)(2,4,5-trifluoro-3-hydroxyphenyl)methanone, (5-(3-amino-4-methoxyphenyl)thiophen-2-yl)(2,4,5-trifluoro-3-hydroxyphenyl)methanone, (5-(1H-indol-5-yl)thiophen-2-yl)(2,4,5-trifluoro-3-hydroxy-phenyl)-methanone, (5-(1H-indol-4-yl)thiophen-2-yl)(2,4,5-trifluoro-3-hydroxyphenyl)methanone, N-(3-(5-(2,4,5-trifluoro-3-hydroxybenzoyl)thiophen-2-yl)phenyl)methanesulfonamide, N-(4-(5-(2,4,5-trifluoro-3-hydroxybenzoyl)thiophen-2-yl)phenyl)acetamide, (5-(pyridin-3-yl)thiophen-2-yl)(2,4,5-trifluoro-3-hydroxyphenyl)methanone, (5-(quinolin-7-yl)thiophen-2-yl)(2,4,5-trifluoro-3-hydroxyphenyl)methanone, (5-(1H-benzo[d]imidazol-5-yl)thiophen-2-yl)(2,4,5-trifluoro-3-hydroxyphenyl)methanone, (5-(4-hydroxyphenyl)thiophen-2-yl)(2,4,5-trifluoro-3-hydroxyphenyl)methanone, (5-(3-hydroxyphenyl)thiophen-2-yl)(2,4,5-trifluoro-3-hydroxyphenyl)methanone, (5-(2-hydroxyphenyl)thiophen-2-yl)(2,4,5-trifluoro -3-hydroxyphenyl)methanone, (5-(4-hydroxy-3,5-dimethylphenyl)thiophen-2-yl)(5-fluoro-3-hydroxy-2-methylphenyl)methanone, (4,5-difluoro-3-hydroxy-2-methylphenyl)(5-(4-hydroxy-3,5-dimethylphenyl)thiophen-2-yl)methanone, (5-methylthiophen-2-yl)(2,4,5-trifluoro-3-hydroxyphenyl)methanone, 4-(5-(2,4,5-trifluoro-3-hydroxybenzoyl)thiophen-2-yl)phenyl sulfamate, 4-(5-(2,6-difluoro-3-hydroxybenzoyl)thiophen-2-yl) benzenesulfonamide, 3-(5-(2,6-difluoro-3-hydroxybenzoyl) thiophen-2-yl)benzenesulfonamide, (6-chloro-2-fluoro-3-hydroxyphenyl)(5-(3,5-dichloro-4-methoxyphenyl) thiophen-2-yl)methanone, (2-chloro-6-fluoro-3-hydroxyphenyl)(5-(3,5-dichloro-4-methoxyphenyl) thiophen-2-yl)methanone, and pharmaceutically acceptable salts thereof.

10. A pharmaceutical composition comprising a compound having the formula (I)

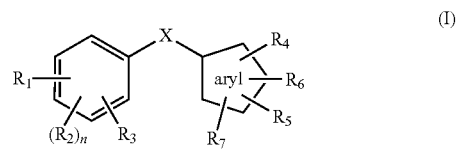

wherein
R1 represents, OH, alkoxy or acyloxy;
n represents an integer of 1 or 2;
R2 is at each occurrence independently selected from the group consisting of fluorine, chlorine, and bromine;
R3 represents alkyl, haloalkyl or halogen atom;
R4 represents H; OH; an alkyl or an alkoxy group, each of which optionally carry phenyl and halogen substituents, wherein said phenyl substituents optionally carry up to 3 substituents independently selected from —OH, alkyl, haloalkyl, alkoxy, halogen, amino, —CN and —NO$_2$; a 6-membered aromatic group which optionally carry 1 to 3 substituents independently selected from —R, haloalkyl, halogen, —NO$_2$, —OR', —SR', —CH$_2$R, —COR', —NR'R', —CN, —COOR', —NR'SO$_2$R, —SO$_2$NR'R', —NR'COR, —CONR'R', —OC(O)R', —CH$_2$NR'R', —CH$_2$OR', —SO$_2$R and —SOR, wherein R is an alkyl group, a heterocyclic ring, an aromatic or non aromatic ring that is optionally condensed or linked with a 5- or 6-membered, aliphatic or aromatic heterocyclic ring, a benzyl group, or an aliphatic or aromatic heterocyclic group that is optionally condensed or linked with a benzene ring, each of said groups is optionally substituted with up to 5 substituents independently selected from halogen, lower alkyl, lower haloalkyl, OH, —NO$_2$, lower alkoxy, lower haloalkoxy, —NH$_2$, phenyl, —CN, —COR", —NHCOR", —CONHR", —NHSO$_2$R" and SO$_2$NHR", wherein R" is H, lower alkyl, lower haloalkyl or phenyl, and R' at each occurrence is independently selected from the groups of R above and H, or two of said substituents, together with the adjacent carbon atoms of the 6-membered aromatic group, optionally form a 5- or 6-membered, aliphatic or aromatic, homocyclic or heterocyclic ring condensed to said 6-membered aromatic group, wherein the heterocyclic ring carries up to 3 heteroatoms independently selected from N, S and O, and the third substituent is optionally located on the 6-membered aromatic group or on the ring condensed thereto; or a 5 or 6-membered aliphatic or aromatic heterocyclic group which carries up to 3 heteroatoms independently selected from N, S and O and optionally carry 1 to 3 substituents independently selected from —R, haloalkyl, halogen, —NO$_2$, —OR', —SR', —CH$_2$R, —COR', —NR'R', —CN, —COOR', —NR'SO$_2$R, —SO$_2$NR'R', —NR'COR', —NRCOR', —CONR'R', —OC(O)R', —CH$_2$NR'R', —CH$_2$OR', —SO$_2$R and —SOR, wherein R and R' is as defined above, or two of said substituents, together with the adjacent carbon atoms of the 5 or 6-membered aliphatic or aromatic heterocyclic group, optionally form a 6-membered, aliphatic or aromatic ring condensed to said 5 or 6-membered aromatic group, and the third substituent may be present on the 5 or 6-membered aromatic group or on the ring condensed thereto; and said substituent R4 being directly or through a phenylene group bound to the aryl ring;

R5, R6 and R7 independently represent H, —R, haloalkyl, halogen, —NO$_2$, —OR', —SR', —CH$_2$R', —COR', —NR'R', —CN, —COOR', —NHSO$_2$R', —NRSO$_2$R'—SO$_2$NRR', —NHCOR', —NRCOR', —CONRR', —OC(O)R', —CH$_2$NRR', —CH$_2$OR', —SO$_2$R' or —SOR', wherein R and R' is as defined above, X represents

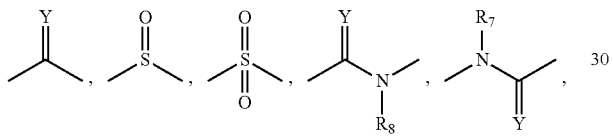

wherein Y, if present, represents O or S, and R8 represents H or lower alkyl; and the aryl ring is a 5-membered heteroaromatic ring which carries up to 3 heteroatoms independently selected from N, S and O;

provided that
(i) when in the compound of formula (I) the aryl ring is 3-amino-4-carboxamido-5-(4'-phenoxy)phenyl-pyrrol-2-yl, and X is —CO—, then the phenyl moiety carrying R1-R3 is not 2,6-difluorophenyl, 2,4,6-trifluorophenyl, 2,6-difluoro-3-methylphenyl, 2,5-difluorophenyl, 3-fluoro-2-methylphenyl, 2,3-difluorophenyl, 2,3-dichlorophenyl, 2,4-dichlorophenyl, 3,5-dichlorophenyl, 2,5-dichlorophenyl, 3-chloro-2-methylphenyl, 3,4-dichlorophenyl or 3-bromo-2-methylphenyl;
(ii) when in the compound of formula (I) the phenyl moiety carrying R1-R3 is 2,6-difluorophenyl and X is —CO—, then the aryl ring is not a 3-amino-4-carboxamido-5-(4'-substituted)phenyl-pyrrol-2-yl, in which the substituent is methoxy, 2-pyrimidinyloxy, benzyloxy, 2,6-dichlorobenzyloxy, amino, benzoylamido, benzylamino, cyclohexylmethylamino, 2,6-dichlorobenzylamino, N-(2,6-dichlorobenzyl)-N-methylamino, 2,5-dichlorobenzylamino, 2-chloro-6-methlbenzylamino, 3-phenylpropylamino, 4-trifluoromethylbenzylamino, 2-pyridylmethoxy, 2-(4-methylpiperazin-1-yl)ethyloxy, 5-tifluoromethylpyridin-2-yloxy, piperidin-2-yloxy, 4,6-dimethylpiperidin-2-yloxy, piperidin-2-yloxy, 4,6-dimethoxypiperidin-2-yloxy, 3-phenylpropionoylamido, 2-pyridinylcarbamido, 3-(3-pyridinyl)propionoylamido, 2-chloro-6-fluorobenzylamino, 2-trifluoromethylbenzylamino, 2-methylbenzylamino, 2,6-difluorobenzylamino, 2,4,6-trimethylbenzylamino, 2,3,5,6-tetramethylbenzylamino, 2,3,5,6-tetrafluorobenzylamino, 2,4,6-trichlorobenzylamino, 2,4,6-triisopropylbenzylamino, 2,4,6-trifluorobenzyl-amino, 2,6-dimethoxybenzylamino, 2,6-dichloro-3-nitrobenzylamino, 3-chloro-2,6-difluoro-benzylamino, 2-chloro-6-methylbenzylamino, 2-chloro-6-fluoro-5-methylbenzylamino, 4-bromo-2,6-fluorobenzylamino, 2-chloro-3,6-difluorobenzylamino, 2,5-dichlorobenzylamino, 2-bromo-6-methylbenzylamino, 2,6-difluoro-3-methylbenzylamino, 2-bromo-6-chloro-benzylamino, 2-fluoro-6-methoxybenzylamino, 2,6-dimethyl-4-fluorobenzylamino, 2-chloro-6-methoxybenzylamino, 2-chloro-6-fluoro-5-methylbenzylamino, 2-(2-(N,N-dimethylamino)ethyloxy)phenyloxy or 3-(2-(N,N-dimethylamino)ethyloxy)phenyloxy; and
(iii) when in the compound of formula (I) the aryl ring is N-methyl-3-amino-4-carboxamido-5-(4'-phenoxy)phenyl-pyrrol-2-yl, and X is —CO—, then the phenyl moiety carrying R1-R3 is not 2,6-dichlorophenyl;

or a pharmaceutically acceptable salt thereof.

11. A compound having the formula (I)

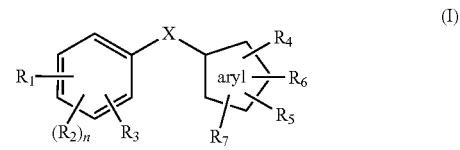

wherein
R1 represents, OH, alkoxy or acyloxy;
n represents an integer of 1 or 2;
R2 is at each occurrence independently selected from the group consisting of fluorine, chlorine, and bromine;
R3 represents alkyl, haloalkyl or halogen atom;
R4 represents H; OH; an alkyl or an alkoxy group, each of which optionally carry phenyl and halogen substituents, wherein said phenyl substituents optionally carry up to 3 substituents independently selected from —OH, alkyl, haloalkyl, alkoxy, halogen, amino, —CN and —NO$_2$; a 6-membered aromatic group which optionally carry 1 to 3 substituents independently selected from —R, haloalkyl, halogen, —NO$_2$, —OR', —SR', —CH$_2$R, —COR', —NR'R', —CN, —COOR', —NR'SO$_2$R, —SO$_2$NR'R', —NR'COR, —CONR'R', —OC(O)R', —CH$_2$NR'R', —CH$_2$OR', —SO$_2$R and —SOR, wherein R is an alkyl group, a heterocyclic ring, an aromatic or non aromatic ring that is optionally condensed or linked with a 5- or 6-membered, aliphatic or aromatic heterocyclic ring, a benzyl group, or an aliphatic or aromatic heterocyclic group that is optionally condensed or linked with a benzene ring, each of said groups is optionally substituted with up to 5 substituents independently selected from halogen, lower alkyl, lower haloalkyl, OH, —NO$_2$, lower alkoxy, lower haloalkoxy, —NH$_2$, phenyl, —CN, —COR", —NHCOR", —CONHR", —NHSO$_2$R" and SO$_2$NHR", wherein R" is H, lower alkyl, lower haloalkyl or phenyl, and R' at each occurrence is independently selected from the groups of R above and H, or two of said substituents, together with the adjacent carbon atoms of the 6-membered aromatic group, may form a 5- or 6-membered, aliphatic or aromatic, homocyclic or heterocyclic ring condensed to said 6-membered aromatic group, wherein the heterocyclic ring carries up to 3 heteroatoms independently selected from N, S and O, and the third substituent is optionally located on the 6-membered aromatic group or on the ring condensed thereto; or a 5 or 6-membered aliphatic or aromatic heterocyclic group which carries up to 3 heteroatoms independently selected from N, S and O and optionally carry 1 to 3 substituents independently selected from —R, haloalkyl, halogen, —NO$_2$, —OR', —SR', —CH$_2$R, —COR', —NR'R', —CN, —COOR', —NR'SO$_2$R, —SO$_2$NR'R', —NR'COR', —NRCOR', —CONR'R', —OC(O)R', —CH$_2$NR'R', —CH$_2$OR', —SO$_2$R and —SOR, wherein R and R' is as defined above, or two of said substituents, together with the adjacent carbon atoms of the 5 or 6-membered aliphatic or aromatic heterocyclic group, optionally form a 6-membered, aliphatic or aromatic ring condensed to said 5 or 6-membered aromatic group, and the third substituent optionally is present on the 5 or 6-membered aromatic group or on the ring condensed thereto; and said substituent R4 being directly or through a phenylene group bound to the aryl ring;

R5, R6 and R7 independently represent H, —R, haloalkyl, halogen, —NO$_2$, —OR', —SR', —CH$_2$R', —COR', —NR'R', —CN, —COOR', —NHSO$_2$R', —NRSO$_2$R'—SO$_2$NRR', —NHCOR', —NRCOR', —CONRR', —OC(O)R', —CH$_2$NRR', —CH$_2$OR', —SO$_2$R' or —SOR', wherein R and R' is as defined above, X represents

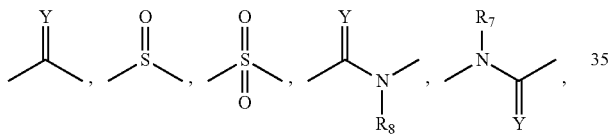

wherein Y, if present, represents O or S, and R8 represents H or lower alkyl; and the aryl ring is a 5-membered heteroaromatic ring which carries up to 3 heteroatoms independently selected from N, S and O;

provided that
(i) the compound of formula (I) is not 2,4-dichloro-6-hydroxyphenyl-furyl-ketone, 2,4-dibromo-6-hydroxyphenyl-furyl-ketone, 4-chloro-2-hydroxy-6-methylphenyl-furyl-ketone, 4-chloro-2-hydroxy-5-methylphenyl-furyl-ketone, 2,4-dichloro-6-hydroxyphenyl-thienyl-ketone or 4-chloro-2-hydroxy-6-methylphenyl-thienyl-ketone;
(ii) when in the compound of formula (I) the aryl ring is 3-amino-4-carboxamido-5-(4'-phenoxy)phenyl-pyrrol-2-yl, and X is —CO—, then the phenyl moiety carrying R1-R3 is not 2,6-difluorophenyl, 2,4,6-trifluorophenyl, 2,6-difluoro-3-methylphenyl, 2,5-difluorophenyl, 3-fluoro-2-methylphenyl, 2,3-difluorophenyl, 2,3-dichlorophenyl, 2,4-dichlorophenyl, 3,5-dichlorophenyl, 2,5-dichlorophenyl, 3-chloro-2-methylphenyl, 3,4-dichlorophenyl or 3-bromo-2-methylphenyl;
(iii) when in the compound of formula (I) the phenyl moiety carrying R1-R3 is 2,6-difluorophenyl and X is —CO—, then the aryl ring is not a 3-amino-4-carboxamido-5-(4'-substituted)phenyl-pyrrol-2-yl, in which the substituent is methoxy, 2-pyrimidinyloxy, benzyloxy, 2,6-dichlorobenzyloxy, amino, benzoylamino, benzylamino, cyclohexylmethylamino, 2,6-dichlorobenzylamino, N-(2,6-dichlorobenzyl)-N-methylamino, 2,5-dichlorobenzylamino, 2-chloro-6-methlbenzylamino, 3-phenylpropylamino, 4-trifluoromethylbenzylamino, 2-pyridylmethoxy, 2-(4-methylpiperazin-1-yl)ethyloxy, 5-tifluoromethylpyridin-2-yloxy, piperidin-2-yloxy, 4,6-dimethylpiperidin-2-yloxy, piperidin-2-yloxy, 4,6-dimethoxypiperidin-2-yloxy, 3-phenylpropionoylamido, 2-pyridinylcarbamido, 3-(3-pyridinyl)propionoylamido, 2-chloro-6-fluorobenzylamino, 2-trifluoromethylbenzylamino, 2-methylbenzylamino, 2,6-difluorobenzylamino, 2,4,6-trimethylbenzylamino, 2,3,5,6-tetramethylbenzylamino, 2,3,5,6-tetrafluorobenzylamino, 2,4,6-trichlorobenzylamino, 2,4,6-triisopropylbenzylamino, 2,4,6-trifluorobenzyl-amino, 2,6-dimethoxybenzylamino, 2,6-dichloro-3-nitrobenzylamino, 3-chloro-2,6-difluoro-benzylamino, 2-chloro-6-methylbenzylamino, 2-chloro-6-fluoro-5-methylbenzylamino, 4-bromo-2,6-fluorobenzylamino, 2-chloro-3,6-difluorobenzylamino, 2,5-dichlorobenzylamino, 2-bromo-6-methylbenzylamino, 2,6-difluoro-3-methylbenzylamino, 2-bromo-6-chlorobenzylamino, 2-fluoro-6-methoxybenzylamino, 2,6-dimethyl-4-fluorobenzylamino, 2-chloro-6-methoxybenzylamino, 2-chloro-6-fluoro-5-methylbenzylamino, 2-(2-(N,N-dimethylamino)ethyloxy)phenyloxy or 3-(2-(N,N-dimethylamino)ethyloxy)phenyloxy;
(iv) when in the compound of formula (I) the aryl ring is N-methyl-3-amino-4-carboxamido-5-(4'-phenoxy)phenyl-pyrrol-2-yl, and X is —CO—, then the phenyl moiety carrying R1-R3 is not 2,6-dichlorophenyl;
(v) when in the compound of formula (I) the aryl is a pyrrol and R4 is a phenyl residue substituted with 1 to 3 substituents independently selected from halogen, —NO$_2$, CN, $C_{1-4}$alkyl, $C_{1-4}$haloalkyl and $C_{1-4}$alkoxy, and the phenyl moiety carrying R1-R3 is a phenyl substituted with 2 to 4 substituents selected from halogen, —NO$_2$, CN, $C_{1-4}$alkyl, $C_{1-4}$haloalkyl and $C_{1-4}$alkoxy, then X is not —SO— or —SO$_2$—; and
(vi) when in the compound of formula (I) the aryl is a thiene, R4 is an aryl group, unsaturated monocyclic heterocyclic ring or unsaturated fused heterobicyclic ring, each of which may be substituted with 1 to 3 substituents independently selected from halogen, —NO$_2$, amino, cyano, hydroxy, mercapto, carboxyl, $C_{1-4}$ alkyl, $C_{1-4}$haloalkyl, $C_{1-4}$alkoxy, benzyloxy, $C_{1-4}$alkylthio, $C_{1-4}$ hydroxyalkyl, $C_{1-4}$alkyl amino, bis($C_{1-4}$alkyl)amino, $C_{1-4}$acylamino, carbamoyl, $C_{1-4}$alkoxycarbonyl, and $C_{1-4}$ alkylsulfonyl, R5 and R6 are hydrogen, and the phenyl moiety is a phenyl substituted with 2 to 3 substituents selected from halogen, hydroxy, $C_{1-4}$ alkyl, $C_{1-4}$ haloalkyl and $C_{1-4}$alkoxy, then X is not —CO—;

or a pharmaceutically acceptable salt thereof.

12. The compound of claim 11, wherein the aryl ring represents a thiophene and R1 is OH.

13. A method for the production of the compound of claim 11 or a pharmaceutically acceptable salt thereof, comprising condensing an aromatic precursor compound of the compound of formula (I).

14. The compound for use in the treatment of hormone-related diseases in a mammal of claim 2, wherein the compound has the formula (IIa)

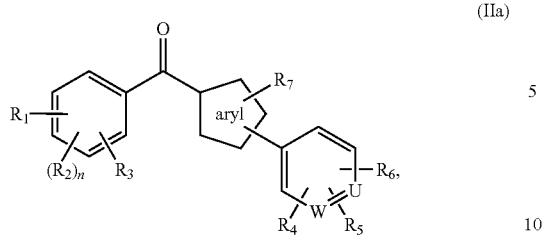
(IIa)
and wherein all the variables are as defined in claim 2.
* * * * *